US009505827B2

(12) United States Patent
Bradley et al.

(10) Patent No.: US 9,505,827 B2
(45) Date of Patent: *Nov. 29, 2016

(54) ANIMAL MODELS AND THERAPEUTIC MOLECULES

(71) Applicant: Kymab Limited, Cambridge (GB)

(72) Inventors: Allan Bradley, Cambridge (GB); E-Chiang Lee, Cambridge (GB); Qi Liang, Cambridge (GB); Wei Wang, Cambridge (GB); Glenn Friedrich, Cambridge (GB)

(73) Assignee: Kymab Limited, Cambridge (GB)

( * ) Notice: Subject to any disclaimer, the term of this patent is extended or adjusted under 35 U.S.C. 154(b) by 739 days.

This patent is subject to a terminal disclaimer.

(21) Appl. No.: 13/740,727

(22) Filed: Jan. 14, 2013

(65) Prior Publication Data

US 2013/0318643 A1    Nov. 28, 2013

Related U.S. Application Data

(60) Division of application No. 13/310,431, filed on Dec. 2, 2011, which is a continuation-in-part of application No. PCT/GB2010/051122, filed on Jul. 7, 2010, and a continuation-in-part of application No. PCT/GB2011/050019, filed on Jan. 7, 2011.

(60) Provisional application No. 61/223,960, filed on Jul. 8, 2009, provisional application No. 61/355,666, filed on Jun. 17, 2010.

(30) Foreign Application Priority Data

Jul. 8, 2009 (GB) .................................. 0911846.4
Jul. 28, 2009 (GB) .................................. 0913102.0

(51) Int. Cl.
| | | |
|---|---|---|
| *A01K 67/027* | (2006.01) | |
| *C07K 16/18* | (2006.01) | |
| *C07K 16/00* | (2006.01) | |
| *C07K 16/12* | (2006.01) | |
| *C07K 16/46* | (2006.01) | |
| *A61K 39/02* | (2006.01) | |
| *A61K 39/35* | (2006.01) | |

(52) U.S. Cl.
CPC ........... *C07K 16/18* (2013.01); *A01K 67/0275* (2013.01); *A01K 67/0278* (2013.01); *A61K 39/107* (2013.01); *A61K 39/35* (2013.01); *C07K 16/00* (2013.01); *C07K 16/1203* (2013.01); *C07K 16/1239* (2013.01); *C07K 16/462* (2013.01); *A01K 2227/105* (2013.01); *A01K 2267/01* (2013.01); *C07K 2317/24* (2013.01)

(58) Field of Classification Search
CPC ................... A01K 67/0278; A01K 2227/105; A01K 67/0275; A01K 2217/05; A01K 2217/072; A01K 2267/01; A01K 2217/15; C07K 16/00; C07K 16/462; C07K 16/28; C07K 2317/56; C07K 16/082; C07K 16/461; C07K 2317/02

See application file for complete search history.

(56) References Cited

U.S. PATENT DOCUMENTS

| | | | |
|---|---|---|---|
| 4,720,449 A | 1/1988 | Borror et al. | ................. 430/338 |
| 5,169,939 A | 12/1992 | Gefter et al. | ............. 530/387.3 |
| 5,545,807 A | 8/1996 | Surani et al. | ..................... 800/2 |
| 5,633,425 A | 5/1997 | Lonberg et al. | |
| 5,770,429 A | 6/1998 | Lonberg et al. | ........... 435/240.2 |
| 5,789,215 A | 8/1998 | Berns et al. | ............... 435/172.3 |
| 5,939,598 A | 8/1999 | Kucherlapati et al. | ......... 800/25 |
| 5,948,600 A | 9/1999 | Roschger et al. | ............ 430/348 |
| 6,162,963 A | 12/2000 | Kucherlapati et al. | ......... 800/18 |
| 6,395,487 B1 | 5/2002 | Bradley et al. | |
| 6,461,818 B1 | 10/2002 | Bradley et al. | |
| 6,596,541 B2 † | 7/2003 | Murphy | |
| 6,673,986 B1 | 1/2004 | Kucherlapati et al. | ......... 800/18 |
| 6,713,610 B1 | 3/2004 | Kucherlapati et al. | .. 530/388.23 |
| 6,833,268 B1 | 12/2004 | Green et al. | ............... 435/320.1 |
| 6,914,128 B1 | 7/2005 | Salfeld et al. | ............. 530/387.3 |
| 6,998,514 B2 | 2/2006 | Bruggemann | ................... 800/18 |
| 7,119,248 B1 | 10/2006 | Rajewsky et al. | ................ 808/6 |
| 7,205,140 B2 | 4/2007 | Gottschalk et al. | .......... 435/462 |
| 7,205,148 B2 | 4/2007 | Economides et al. | |
| 7,435,871 B2 | 10/2008 | Green et al. | ..................... 800/18 |
| 7,501,552 B2 | 3/2009 | Lonberg et al. | ................... 800/6 |
| 7,605,237 B2 | 10/2009 | Stevens et al. | ............ 530/387.9 |
| 7,910,798 B2 | 3/2011 | Tanamachi et al. | ............ 800/18 |
| 7,932,431 B2 | 4/2011 | Bruggemann | ................... 800/18 |
| 8,158,419 B2 | 4/2012 | Lonberg et al. | .............. 435/328 |

(Continued)

FOREIGN PATENT DOCUMENTS

| | | | | |
|---|---|---|---|---|
| CA | 2 307 503 A1 | 11/2001 | ............. A61K 39/42 |
| EP | 1780272 A1 | 5/2007 | ............. C12N 15/00 |

(Continued)

OTHER PUBLICATIONS

Jackson Laboratory Recourse Manual, 2007, 1-29.*
Sen and Baltimore (Cell, 1986, 46, 705-716.*
Zheng et al Mol. Cell Biol. 2000, 20, 648-655.*
Oberdoerffer et al Nucleic Acids Res. 2003, 31: e140.*
Torres and Kuhn, (Laboratory Protocols for Conditional Gene Targeting, 1997, p. 37-40.*
Featherstone et al, J. Biol. Chem. 2010, 285:9327-9338.*
Bono et al J. Mol. Biol. (2004) 342, 131-143.*
Han et al Biology of Reproduction, 2009, 80, 1001-1008.*

(Continued)

*Primary Examiner* — Anoop Singh
(74) *Attorney, Agent, or Firm* — Sunstein Kann Murphy & Timbers LLP

(57) ABSTRACT

The invention discloses methods for the generation of chimaeric human-non-human antibodies and chimaeric antibody chains, antibodies and antibody chains so produced, and derivatives thereof including fully humanized antibodies; compositions comprising said antibodies, antibody chains and derivatives, as well as cells, non-human mammals and vectors, suitable for use in said methods.

10 Claims, 57 Drawing Sheets

(56) References Cited

U.S. PATENT DOCUMENTS

| | | | | |
|---|---|---|---|---|
| 8,502,018 B2* | 8/2013 | Murphy | ............ | A01K 67/0275 435/320.1 |
| 8,642,835 B2 | 2/2014 | MacDonald et al. | ........... | 800/16 |
| 9,253,965 B2 | 2/2016 | Bradley et al. | | |
| 2002/0088016 A1 | 7/2002 | Bruggemann | ................ | 800/18 |
| 2003/0108925 A1 | 6/2003 | Dix et al. | ........................ | 435/6 |
| 2003/0217373 A1 | 11/2003 | Green et al. | ..................... | 800/6 |
| 2004/0231012 A1 | 11/2004 | Bruggemann | | |
| 2005/0048621 A1 | 3/2005 | Grasso et al. | ............... | 435/69.1 |
| 2006/0015949 A1 | 1/2006 | Lonberg et al. | .................. | 800/6 |
| 2006/0015957 A1 | 1/2006 | Lonberg et al. | ............... | 800/18 |
| 2006/0021074 A1 | 1/2006 | Kellermann et al. | ........... | 800/18 |
| 2006/0199204 A1 | 9/2006 | Dix et al. | ........................ | 435/6 |
| 2007/0280945 A1 | 12/2007 | Stevens et al. | ............ | 424/145.1 |
| 2008/0098490 A1 | 4/2008 | Jakobovits et al. | ............. | 800/13 |
| 2009/0083870 A1 | 3/2009 | Horn et al. | ...................... | 800/13 |
| 2009/0196112 A1 | 8/2009 | Cho | ............................ | 365/200 |
| 2009/0209036 A1 | 8/2009 | Reynaud et al. | ............. | 435/455 |
| 2010/0011450 A1 | 1/2010 | Garcia et al. | | |
| 2010/0069614 A1 | 3/2010 | Houtzager et al. | ........ | 530/387.1 |
| 2010/0146647 A1 | 6/2010 | Logtenberg et al. | ............. | 800/4 |
| 2010/0196367 A1 | 8/2010 | Day | .......................... | 424/133.1 |
| 2011/0138489 A1 | 6/2011 | Tanamachi et al. | .............. | 800/6 |
| 2011/0145937 A1 | 6/2011 | MacDonald et al. | ............ | 800/6 |
| 2011/0195454 A1 | 8/2011 | McWhirter et al. | ......... | 435/69.6 |
| 2011/0236378 A1 | 9/2011 | Green et al. | ................ | 424/133.1 |
| 2011/0283376 A1* | 11/2011 | Murphy | ............ | A01K 67/0275 800/18 |
| 2012/0070861 A1 | 3/2012 | Macdonald et al. | ......... | 435/91.1 |
| 2012/0073004 A1 | 3/2012 | Macdonald et al. | ............ | 800/18 |
| 2012/0167237 A1 | 6/2012 | Bradley et al. | ................... | 800/9 |
| 2012/0204278 A1 | 8/2012 | Bradley et al. | ................... | 800/18 |
| 2012/0233715 A1 | 9/2012 | Kuroiwa et al. | ................... | 800/3 |
| 2012/0322108 A1 | 12/2012 | Macdonald et al. | ......... | 435/69.6 |
| 2013/0039850 A1 | 2/2013 | Lonberg et al. | ............. | 424/1.49 |
| 2013/0102031 A1 | 4/2013 | King et al. | ................... | 435/69.6 |
| 2013/0160153 A1 | 6/2013 | Macdonald et al. | ............ | 800/18 |
| 2013/0212719 A1 | 8/2013 | Macdonald et al. | .............. | 800/6 |
| 2013/0254911 A1 | 9/2013 | Macdonald et al. | ............ | 800/18 |
| 2013/0263293 A1 | 10/2013 | Bradley et al. | ................... | 800/6 |
| 2013/0323790 A1 | 12/2013 | Macdonald et al. | ......... | 435/70.2 |
| 2013/0323791 A1 | 12/2013 | Macdonald et al. | ......... | 435/91.1 |
| 2013/0326647 A1 | 12/2013 | Macdonald et al. | ............. | 800/18 |
| 2013/0333057 A1 | 12/2013 | Macdonald et al. | .............. | 800/6 |
| 2014/0017228 A1 | 1/2014 | Macdonald et al. | ....... | 424/132.1 |
| 2014/0130193 A1 | 5/2014 | Macdonald et al. | ............. | 800/18 |
| 2014/0130194 A1 | 5/2014 | Macdonald et al. | ............. | 800/18 |
| 2014/0137275 A1 | 5/2014 | Macdonald et al. | ............. | 800/18 |
| 2014/0213773 A1 | 7/2014 | Macdonald et al. | ....... | 530/387.3 |
| 2014/0331344 A1 | 11/2014 | Friedrich et al. | ............... | 800/18 |

FOREIGN PATENT DOCUMENTS

| | | | | |
|---|---|---|---|---|
| EP | 2 421 357 | 2/2012 | ........... | A01K 67/027 |
| EP | 2550363 | 10/2012 | ............ | C12N 15/85 |
| GB | 2398784 | 9/2004 | ........... | A01K 67/027 |
| KR | 1020050042792 | 5/2005 | ............ | A01K 67/027 |
| WO | WO 90/04036 A1 | 4/1990 | ............ | C12P 21/08 |
| WO | WO 91/00906 A1 | 1/1991 | ............ | C12N 15/00 |
| WO | WO 91/10741 | 7/1991 | ............ | C12P 21/06 |
| WO | WO 93/12227 | 6/1993 | ............ | C12N 15/00 |
| WO | WO 94/02602 A1 | 2/1994 | ............ | C12N 15/00 |
| WO | WO 94/04667 A1 | 3/1994 | ............ | C12N 15/00 |
| WO | WO 96/30498 A1 | 10/1996 | ................ | C12N 5/00 |
| WO | WO 98/24884 | 6/1998 | ................ | C12N 5/00 |
| WO | WO 98/24893 A2 | 6/1998 | ............ | C12N 15/00 |
| WO | WO 99/45962 A1 | 9/1999 | ............ | A61K 39/395 |
| WO | WO 02/08409 A2 | 1/2002 | ............ | C12N 15/00 |
| WO | WO 02/36789 A2 | 5/2002 | ............ | C12N 15/85 |
| WO | WO 02/43478 | 6/2002 | ........... | A01K 67/027 |
| WO | WO 02/053596 A2 | 7/2002 | ............ | C07K 16/28 |
| WO | WO 02/059263 A2 | 8/2002 | | |
| WO | WO 02/066630 A1 | 8/2002 | ............ | C12N 15/00 |
| WO | WO 02/070648 | 9/2002 | | |
| WO | WO 03/006639 A1 | 1/2003 | ............ | C12N 5/10 |
| WO | WO 03/047336 A2 | 6/2003 | | |
| WO | WO 03/061363 A2 | 7/2003 | | |
| WO | WO 2004/050838 A2 | 6/2004 | | |
| WO | WO 2005/003364 A2 | 1/2005 | ............ | C12N 15/90 |
| WO | WO-2005004592 A2 | 1/2005 | | |
| WO | WO 2005/019463 A1 | 3/2005 | ............ | C12N 15/85 |
| WO | WO-2005058815 A2 | 6/2005 | | |
| WO | WO 2006/044492 | 4/2006 | ............ | C12N 15/52 |
| WO | WO-2006055704 A2 | 5/2006 | | |
| WO | WO-2006068953 A2 | 6/2006 | | |
| WO | WO 2006/122442 A1 | 11/2006 | ............ | C12N 9/22 |
| WO | WO 2007/096779 A2 | 8/2007 | | |
| WO | WO 2007/117410 * | 10/2007 | | |
| WO | WO 2007/117410 A2 | 10/2007 | ........... | A01K 67/027 |
| WO | WO-2007143168 A2 | 12/2007 | | |
| WO | WO 2008/022391 A1 | 2/2008 | ............ | C07K 16/28 |
| WO | WO 2008/054606 | 5/2008 | ............ | C07K 16/00 |
| WO | WO 2008/070367 A2 | 6/2008 | ............ | C12N 15/09 |
| WO | WO 2008/076379 A2 | 6/2008 | ............ | C07K 16/18 |
| WO | WO 2008/094178 A2 | 8/2008 | ............... | C12Q 1/68 |
| WO | WO 2008/103474 A1 | 8/2008 | ............ | C12N 15/13 |
| WO | WO 2008/118970 A2 | 10/2008 | ............ | A61K 48/00 |
| WO | WO 2008/122886 | 10/2008 | ............ | C12N 15/85 |
| WO | WO 2008/151081 A1 | 12/2008 | ............ | C12N 15/13 |
| WO | WO 2009/013620 | 1/2009 | | |
| WO | WO 2009/018411 | 2/2009 | ............ | C07K 16/28 |
| WO | WO 2009/023540 | 2/2009 | ........... | A61K 39/395 |
| WO | WO 2009/076464 A2 | 6/2009 | ............ | C12N 15/09 |
| WO | WO 2009/080254 A1 | 7/2009 | ............ | C07K 16/46 |
| WO | WO 2009/094178 A2 | 7/2009 | ............ | C09B 67/08 |
| WO | WO 2009/118524 A2 | 10/2009 | ............ | C12N 5/00 |
| WO | WO 2009/129247 A2 | 10/2009 | ............ | C12N 15/13 |
| WO | WO 2009/143472 A2 | 11/2009 | ............ | C07K 16/46 |
| WO | WO 2009/157771 | 12/2009 | ........... | A01K 67/027 |
| WO | 2010039900 A2 † | 4/2010 | | |
| WO | WO 2010/039900 A2 | 4/2010 | ............ | C12N 15/13 |
| WO | WO 2010/070263 | 6/2010 | ............ | C12N 15/85 |
| WO | WO-2010077854 A1 | 7/2010 | | |
| WO | WO 2010/097385 A1 | 9/2010 | ............ | C07K 16/24 |
| WO | WO 2010/113039 A1 | 10/2010 | ................ | C12N 5/00 |
| WO | WO 2011/004192 A1 | 1/2011 | ........... | A01K 67/027 |
| WO | WO 2011/008093 | 1/2011 | ............ | C07K 16/00 |
| WO | WO 2011/056864 A1 | 5/2011 | ............. | C12P 21/06 |
| WO | WO 2011/062206 A1 | 5/2011 | ............ | C12N 15/09 |
| WO | WO-2011062207 A1 | 5/2011 | | |
| WO | WO-2011071957 A1 | 6/2011 | | |
| WO | WO 2011/097603 | 8/2011 | ............ | C12N 15/85 |
| WO | WO-2011146121 A1 | 11/2011 | | |
| WO | 2011163311 † | 12/2011 | | |
| WO | WO 2011/158009 | 12/2011 | ........... | A01K 67/027 |
| WO | WO 2011/163311 | 12/2011 | ............ | C12N 15/85 |
| WO | WO 2011/163314 | 12/2011 | ............ | C12N 15/85 |
| WO | WO 2012/018764 | 2/2012 | ............ | C12N 15/85 |
| WO | WO 2012/023053 | 2/2012 | | |
| WO | WO 2012/141798 | 10/2012 | ............ | C12N 15/85 |
| WO | WO 2012/148873 A2 | 11/2012 | ........... | A01K 67/027 |
| WO | WO 2013/022782 | 2/2013 | ............ | C12N 15/85 |
| WO | WO 2013/041844 | 3/2013 | ............ | C12N 15/85 |
| WO | WO 2013/041845 A2 | 3/2013 | ............ | C12N 15/85 |
| WO | WO 2013/059230 A1 | 4/2013 | ............ | C12N 15/85 |
| WO | WO 2013/061098 A2 | 5/2013 | ............ | C12N 15/85 |
| WO | WO 2013/096142 | 6/2013 | ........... | A01K 67/027 |
| WO | WO 2013/116609 | 8/2013 | ........... | A01K 67/027 |
| WO | WO-2013176772 A1 | 11/2013 | | |
| WO | WO-2014093622 A2 | 6/2014 | | |

OTHER PUBLICATIONS

MacDonald, L. et al., Expanded Poster: "VelociGene® Technology Extended to Humanization of Several Megabases of Complex," 2006, p. 1.*

Stevens, S. et al., Expanded Poster: "VelocImmune'M: Humanization of immunoglobulin loci using VelociGene@ technology," 2006, 1 page.*

Yancopoulous et al., "Preferential utilization of the most $J_H$-proximal $V_H$ gene segments in pre-B-cell lines", Nature, vol. 311, pp. 727-733, 1984.

(56) References Cited

OTHER PUBLICATIONS

Sen et al., "Multiple Nuclear Factors Interact with the Immunoglobulin Enhancer Sequences", Cell, vol. 46, pp. 705-716, Aug. 29, 1986.
Storb et al., "Physical Linkage of Mouse Genes by Pulsed-Field Gel Electrophoresis Suggests that the Rearrangement Process Favors Proximate Target Sequences", Molecular and Cellular Biology, vol. 9, No. 2, pp. 711-718, Feb. 1989.
Gerstein et al., Isotype Switching of an Immunoglobulin Heavy Chain Transgene Occurs by DNA Recombination between Different Chromosomes, Cell, vol. 63, pp. 537-548, Nov. 2, 1990.
Kitamura et al., "A B cell-deficient mouse by targeted disruption of the membrane exon of the immunoglobulin chain gene", Nature, vol. 350, pp. 423-426, Apr. 1991.
Torres et al., "Laboratory Protocols for Conditional Gene Targeting", Institute for Genetics, University of Cologne, pp. 37-40, 1997.
Kingzette et al., "Trans-chromosomal recombination within the Ig heavy chain switch region in B lymphocytes", Proc. Natl. Acad. Sci., vol. 95, pp. 11840-11845, Sep. 1998.
Zheng et al., Engineering Mouse Chromosomes with Cre-loxP: Range, Efficiency, and Somatic Applications, Molecular and Cellular Biology, vol. 20, No. 2, pp. 648-655, Jan. 2000.
Williams et al., "Unequal $V_H$ Gene Rearrangement Frequency Within the Large Vh7183 Gene Family is not Due to Recombination Signal Sequence Variation, and Mapping of the Genes Shows a Bias of Rearrangement Base on Chromosomal Location", The Journal of Immunology, pp. 257-263, 2001.
Bruggemann, "Human Antibody Expression in Transgenic Mice", Archivum Immunologiae et Therapiae Experimentalis, vol. 49, pp. 203-208, 2001.
Mortuza et al., "Immunoglobulin heavy-chain gene rearrangement in adult acute lymphoblastic leukemia reveals preferential usage of $J_H$-proximal variable gene segments", Blood, vol. 97, No. 9, pp. 2716-2726, May 2001.
Clark et al., "A Future for Transgenic Livestock", Nature Reviews, Genetics, vol. 4, pp. 825-833, Oct. 2003.
Schnutgen et al., "A directional strategy for monitoring Cre-mediated recombination at the cellular level in the mouse", Nature Biotechnology, vol. 21, pp. 562-565, May 2003.
Oberdoerffer et al., "Unidirectional Cre-mediated genetic inversion in mice using the mutant loxP pair lox66/lox71", Nucleic Acids Research, vol. 31, No. 22, pp. 1-7, 2003.
Kuroiwa et al., "Sequential targeting of the genes encoding immunoglobulin and prion protein in cattle", Nature Genetics, vol. 36, No. 7, pp. 775-780, Jul. 2004.
Niemann et al., "Transgenic farm animals: present and future", Rev. Sci Tech Off. Int Epiz., vol. 24, pp. 285-298, 2005.
Lonberg, "Human antibodies from transgenic animals", Nature Biotechnology, vol. 23, No. 9, pp. 1117-1125, Sep. 2005.
Venken et al., "P[acman]: A BAC Transgenic Platform for Targeted Insertion of Large DNA Fragments in *D. melanogaster*", Science, vol. 314, pp. 1747-1751, Dec. 15, 2006.
Qu et al., "Gene Targeting of ErbB3 Using a Cre-Mediated Unidirectional DNA Inversion Strategy", Technology Report, Genesis, vol. 44, pp. 477-486, 2006.
Ungrin et al., "Strict control of telomerase activation using Cre-mediated inversion", BMC Biotechnology, vol. 6, pp. 1-9, 2006.
Wallace et al., "Manipulating the Mouse Genome to Engineer Precise Functional Syntenic Replacements with Human Sequence", Cell, vol. 18, pp. 197-209, Jan. 12, 2007.
"News in Brief", Nature Biotechnology, vol. 25, No. 6, p. 613, Jun. 2007.
Nagle, "Regeneron helps make Sanofi VelocImmune to its 'weak' pipeline", Outsourcing-Pharmac.com, 2 pages, Dec. 3, 2007.
Bates et al., "Chromosomal position of a $V_H$ gene segment determines its activation and inactivation as a substrate for V(D)J recombination", The Journal of Experimental Medicine, vol. 204, No. 13, pp. 3247-3256, Dec. 24, 2007.

Stevens et al., "Human Antibody Discovery, VelocImmune—A novel platform", Pharma Focus Asia, Clinical Trials Issue 8, pp. 1-5, 2008.
Statement of Fact and Arguments in Support of Opposition pertaining to Application No. 10734546.4, 41 pages, dated Oct. 22, 2013.
Opposition against EP2421357 Animal Models and Therapeutic Molecules in the name of Kymab Limited pertaining to Application No. 10734546.4, 44 pages, dated Oct. 23, 2013.
Opposition against EP2421357 B1 in the name of Kymab Limited Statement of Facts and Arguments pertaining to Application No. 10734546.4, 29 pages, dated Oct. 23, 2013.
Auerbach, et al., "Establishment and chimera analysis of 129/SvEv- and C57BL/6-derived mouse embryonic stem cell lines," Biotechniques 29: pp. 1024-1032 (Nov. 2000).
Beard, et al., "Efficient method to generate single-copy transgenic mice by site-specific integration in embryonic stem cells," Genesis (2006), vol. 44, pp. 23-28.
Billiard, et al., "Ongoing Dll4-Notch signaling is required for T-cell homeostasis in the adult thymus," European Journal of Immunology, Aug. 4, 2011, vol. 41, pp. 2207-2216.
Carstea, et al., "Germline competence of mouse ES and iPS cell lines: Chimera technologies and genetic background," World Journal of Stem Cells, Dec. 31, 2009; 1(1): pp. 22-29.
Ding, et al., "Generation of high-affinity fully human anti-interleukin-8 antibodies from its cDNA by two-hybrid screening and affinity maturation in yeast," Protein Science, Oct. 2010; vol. 19, pp. 1957-1966.
Doyle, et al., "The construction of transgenic and gene knockout/knockin mouse models of human disease," Transgenic Research, Apr. 2012; 21(2): pp. 327-349.
Hagiwara, Transgenic expression of VpreB-3 under the control of the immunoglobulin heavy chain enhancer and SV40 promoter, Kobe Journal of Medical Sciences, Feb. 1996, vol. 42, No. 1, pp. 43-59 (English Abstract).
Iglesias-Ussel, et al, "Forced expression of AID facilitates the isolation of class switch variants from hybridoma cells," Journal of Immunological Methods, Oct. 2006; 316(1-2), pp. 59-66.
Janssens, et al., "Generation of heavy-chain-only antibodies in mice," Proceedings of the National Academy of Sciences (USA), Oct. 10, 2006, vol. 103, No. 41, pp. 15130-15135.
Kaminski, et al., "Antibody class switching differs among SJL, C57BL/6 and 129 mice," International Immunology, vol. 19, No. 4, pp. 545-556 (2007).
Kellermann, et al., "Developing the XENOMOUSE® technology for evaluating immunogenicity," AntibOZ 2: An International Forum to Predict the Next Wave of Protein-based Therapies and Immunodiagnostics, AntibOZ 2 Conference, Australia, p. 1 (2004).
Laventie, et al., "Heavy chain-only antibodies and tetravalent bispecific antibody neutralizing *Staphylococcus aureus* leukotoxins," Proceedings of the National Academy of Sciences (USA), Sep. 27, 2011; vol. 108, No. 39, pp. 16404-16409.
Luby, et al., "The µ switch region tandem repeats are important, but not required, for antibody class switch recombination," The Journal of Experimental Medicine, Jan. 15, 2001; 193(2): pp. 159-168.
Scott, "Mice with a human touch," Nature Biotechnology, vol. 25, No. 10, pp. 1075-1077, Oct. 2007.
Shultz, et al., "Humanized mice in translational biomedical research," The Journal of Immunology, Feb. 2007, vol. 7, No. 2, pp. 118-130.
Te Riele, et al., "Highly efficient gene targeting in embryonic stem cells through homologous recombination with isogenic DNA constructs," Proceedings of the National Academy of Sciences (USA), vol. 89, pp. 5128-5132, Jun. 1992.
Tomizuka, et al., "Double trans-chromosomic mice: Maintenance of two individual human chromosome fragments containing Ig heavy and k loci and expression of fully human antibodies," Proceedings of the National Academy of Sciences (USA), Jan. 18, 2000, vol. 97, No. 2, pp. 722-727.
Valenzuela, et al., "High-throughput engineering of the mouse genome coupled with high-resolution expression analysis," Nature Biotechnology vol. 21, No. 6, p. 652-659 and vol. 21, No. 7, p. 822, (2003).

(56) References Cited

OTHER PUBLICATIONS

Xu, et al., "Combinatorial surrobody libraries," Proceedings of the National Academy of Sciences (USA), (2008) vol. 105, No. 31, pp. 10756-10761.
European Patent Office, Authorized Officer, Gaby Brouns, International Search Report—International Application No. PCT/GB2013/050682, dated Sep. 25, 2013, 4 pages
Intellectual Property Office, United Kingdom, International Search Report, Application No. GB1116122.1, dated Feb. 2, 2012, 1 page.
International Search Report, Application No. GB1116122.1, dated Feb. 2, 2012, 1 page, Corrected International Search Report and Opinion, Application No. GB1122047.2, dated Apr. 20, 2012, 5 pages.
European Patent Office, Munich, Germany, International Search Report, Application No. EP 12194977, dated Jul. 5, 2013, 4 pages.
European Patent Office, Munich, Germany, International Search Report, Application No. EP 12195041, dated Nov. 8, 2013, 3 pages.
Chinese Patent Office, First Office Action, Chinese Patent Application No. 201180039668.1, dated Jan. 3, 2014, 6 pages.
Chinese Patent Office (English Translation), First Office Action for Chinese Patent Application No. 201180039668.1, dated Jan. 3, 2014, 6 pages.
Chinese Patent Office, Search Report, Chinese Patent Application No. 201180039668.1, dated Jan. 3, 2014, 2 pages.
Chinese Patent Office (English Translation), Search Report, Chinese Patent Application No. 201180039668.1, dated Jan. 3, 2014, 1 page.
Briney, et al., "Human Peripheral Blood Antibodies with Long HCDR3s are Established Primarily at Original Recombination Using a Limited Subset of Germline Genes," PLoS ONE, May 2012, vol. 7, Issue 5, e36750, 13 pages.
Brüggemann, et al., "Human Antibody Production in Transgenic Mice: Expression from 100 kb of the Human IgH Locus," European Journal of Immunology, May 1991, vol. 21, Issue 5, pp. 1323-1326.
Feeney, "Genetic and Epigenetic Control of V Gene Rearrangement Frequency," V(D)J Recombination Advances in Experimental Medicine and Biology, 2009, vol. 650, 2009, pp. 73-81.
Green, "Antibody Engineering via Genetic Engineering of the Mouse: XenoMouse Strains are a Vehicle for the Facile Generation of Therapeutic Human Monoclonal Antibodies," Journal of Immunological Methods, Dec. 10, 1999, vol. 231, Issues 1-2, pp. 11-23.
Huang, et al., "Structural Basis of Tyrosine Sulfation and VH-Gene Usage in Antibodies that Recognize the HIV Type 1 Coreceptor-Binding Site on gp120," PSNA, Mar. 2, 2004, vol. 101, No. 9, pp. 2706-2711.
Jung, et al., "Mechanism and Control of V(D)J Recombination at the Immunoglobulin Heavy Chain Locus," Annual Review of Immunology, Apr. 2006, vol. 24, pp. 541-570.
Liu, et al., "Potent and Broad Anti-HIV-1 Activity Exhibited by a Glycosyl-Phosphatidylinositol-Anchored Peptide Derived from the CDR H3 of Broadly Neutralizing Antibody PG16," Journal of Virology, Sep. 2011, vol. 85, No. 17, pp. 8467-8476.
Mendez, et al., "Functional Transplant of Megabase Human Immunoglobulin Loci Recapitulates Human Antibody Response in Mice," Nature Genetics, Feb. 1997, vol. 15, pp. 146-156.
Nadel, et al., "Sequence of the Spacer in the Recombination Signal Sequence Affects V(D)J Rearrangement Frequency and Correlates with Nonrandom Vκ Usage In Vivo," J. Exp. Med., May 4, 1998, vol. 187, No. 9, pp. 1495-1503.
Nicholson, et al., "Antibody Repertoires of Four- and Five-Feature Translocus Mice Carrying Human Immunoglobulin Heavy Chain and κ and χ Light Chain Yeast Artificial Chromosomes," The Journal of Immunology, Dec. 15, 1999, vol. 163, No. 12, pp. 6898-6906.
Schroeder, et al., "Preferential utilization of conserved immunoglobulin heavy chain variable gene segments during human fetal life," Proceeding of the National Academy of Sciences of the United States of America, Aug. 1990, vol. 87, pp. 6146-6150.
Yu, et al., Differential Usage of VH Gene Segments is Mediated by cis Elements, The Journal of Immunology, Oct. 1, 1998, vol. 161, No. 7, pp. 3444-3454.
International Search Report and Written Opinion, International Application No. PCT/GB2012/052298, Jun. 13, 2013, 22 pages.
International Search Report, International Application No. PCT/GB2010/51122 dated Sep. 29, 2010.
Examiners Report re: allowability, International Application No. PT/GB2010/51122, dated.
Declaration of Andrew J. Murphy, dated Oct. 6, 2014, including Slide Presentation dated Nov. 3, 2009, at Wellcome Trust Advanced Course: Genetic Manipulation of ES Cells, in Hinxton, UK, entitled "BAC-based Modifications of the Mouse Genome: The Big and the Backward", 62 pages.
Excerpts from U.S. Appl. No. 14/682,859, filed Apr. 9, 2015, including Applicant Initiated Interview Summary; Amendments to the Claims, and Information Disclosure Statement, 14 pages.
U.S. Appl. No. 13/433,984, filed Mar. 28, 2012.
U.S. Appl. No. 14/516,461, filed Jun. 20, 2015.
Arnaout et al., "High-Resolution Description of Antibody Heavy-Chain Repertoires in Humans," Public Library of Science One, vol. 6, Issue 8, pp. 1-8, Aug. 2011.
Atlas Genetics Oncology, "Atlas of Genetics and Cytogenics in Oncology and Hematology: VPREB1," Accessed Online <http://atlasgeneticsoncology.org/Genes/GC_VPREB1.html on May 25, 2015, 5 pages.
Baker et al., "Adapation of TCR Expression Vectors for the Construction of Mouse-Human Chimeric MBP-Specific TCR Transgenes," Journal of Neuroscience Research, vol. 45, No. 4, pp. 487-491, Aug. 15, 1996.
Blankenstein et al., "Immunoglobulin $V_H$ region genes of the mouse are organized in overlapping clusters," European Journal of Immunology, vol. 17, No. 9, pp. 1351-1357, Jul. 13, 1987.
Bode et al., "The Transgeneticist's Toolbox: Novel Methods for the Targeted Modification of Eukaryotic Genomes," Biological Chemistry, vol. 381, Issue Nos. 9-10, pp. 801-813, Sep.-Oct. 2000.
Bogen et al., "A rearranged λ2 light gene chain retards but does not exclude χ and λ1 expression," vol. 21, No. 10, pp. 2391-2395, Oct. 1991.
Bransteitter et al., "Activation-induced cytidine deaminase deaminates deoxycytidine on single-stranded DNA but requires the Action of RNase," Proceedings of the National Academy of Sciences of the United States of America. vol. 100, No. 7, pp. 4102-4107, Apr. 1, 2003.
Brezinchek et al., "Analysis of the Human $V_H$ Gene Repertoire," The American Society for Clinical Investigations, Inc., vol. 99, No. 10, pp. 2488-2501, May 1997.
Brüggemann, "Human Monoclonal Antibodies from Translocus Mice," Molecular Biology of B Cells, Chapter 34, pp. 547-561, 2003.
Brüggemann et al., "Strategies for expressing human antibody repertories in transgenic mice," Immunology Today, vol. 17, No. 8, pp. 391-397, Aug. 1996.
Brüggemann et al., "The Immunogenicity of Chimeric Antibodies," The Journal of Experimental Medicine, vol. 170, No. 6, pp. 2153-2157, Dec. 1, 1989.
Butler, "Immunoglobulin diversity, B-cell and antibody repertoire development in large farm animals," Scientific and Technical Review of the Office International des Epizooties (Paris), vol. 17, No. 1, pp. 43-70, Apr. 1998.
Clark, "IgG Effector Mechanisms," Chemical Immunology, vol. 65, pp. 88-110, 1997.
Collins et al., "A Mouse for All Reasons," Cell, vol. 128, Issue 1, pp. 9-13, Jan. 2007.
Combriato et al., "Regulation of Human Igλ Light Chain Gene Expression by NF-κB1," Journal of Immunology, Issue 168, vol. 3, pp. 1259-1266, Feb. 1, 2002.
Conrath et al., "Camel Single-domain Antibodies as Modular Building Units in Bispecific and Bivalent Antibody Constructs," The Journal of Biological Chemistry, vol. 276, No. 10, pp. 7346-7350, Mar. 9, 2001.
Corbett et al., "Sequence of the Human Immunoglobulin Diversity (D) Segment Locus: A Systematic Analysis Provides No Evidence for the Use of DIR Segments, Inverted D Segments, "Minor" D Segments or D-D Recombination," Journal of Molecular Biology, vol. 270, No. 4, pp. 587-597, Jul. 25, 1997.

(56) References Cited

OTHER PUBLICATIONS

Davies et al., "Creation of Mice Expressing Human Antibody Light Chains by Introduction of a Yeast Artificial Chromosome Containing the Core Region of the Human Immunoglobulin κ Locus," Nature Biotechnology, vol. 11, pp. 911-914, Aug. 1993.
Deng et al., "Reexamination of Gene Targeting Frequency as a Function of the Extent of Homology between the Targeting Vector and the Target Locus," Molecular and Cellular Biology, vol. 12, No. 8, pp. 3365-3371, Aug. 1992.
Edwards et al., "The ADAM metalloproteinases," Molecular Aspects of Medicine, vol. 29, No. 5, pp. 258-289, Oct. 2008.
Eisener-Dorman et al., "Cautionary insights on knockout mouse studies: The gene or not the gene?," Brain, Behavior, and Immunity, vol. 23, No. 3, pp. 318-324, Sep. 2009.
Feng et al., "Site-Specific Chromosomal Integration in Mammalian Cells: Highly Efficient CRE Recombinase-mediated Cassette Exchange," Journal of Molecular Biology, vol. 292, No. 4, pp. 779-785, Oct. 1, 1999.
Fleischer et al. "Reactivity of Mouse T-Cell Hybridomas Expressing Human Vβ Gene Segments With Staphylococcal and Streptococcal Superantigens," Infection and Immunity, vol. 64, No. 3, pp. 987-994, Mar. 1996.
Fujieda et al., "Multiple Types of Chimeric Germ-Line Ig Heavy Chain Transcripts in Human B Cells: Evidence for *trans*-Splicing of Human Ig RNA," The Journal of Immunology, vol. 157, No. 8, pp. 3450-3459, Oct. 15, 1996.
Gallo et al., "The human immunoglobulin loci introduced into mice: V(D) and J gene segment usage similar to that of adult humans," European Journal of Immunology, vol. 30, pp. 534-540, Aug. 28, 2000.
Gama Sosa et al., "Animal transgenesis: an overview", Brain Structure &. Function, vol. 214, Nos. 2-3, pp. 91-109, Mar. 2010.
Gavilondo et al., "Antibody Engineering at the Millennium," Bio Techniques, vol. 29, No. 1, pp. 128-145, Jul. 2000.
GenBank, GenBank Accession No. X97051.1 S64822 29 pages, accessed Aug. 6, 2014.
GenBank, GenBank Accession No. X97051.1 S64822, 26 pages, Mar. 3, 2015 (Updated version).
GenBank, GenBank Accession No. AC111740.4 GI:24818723, 42 pages, accessed Nov. 9, 2002.
GenBank, Rattus norvegicus clone CH230-30N12, * Sequencing in Progress * Nucleotide, 42 pages, accessed Mar. 9, 2015.
GenBank, GenBank Accession No. NT_114985, 1 pages, Dec. 27, 2013.
Giallourakis et al., "Elements between the IgH variable (V) and diversity (D) clusters influence antisense transcription and lineage-specific V(D)J recombination," Proceedings of the National Academy of Science USA, vol. 107, No. 51, pp. 22207-22212, Dec. 21, 2010.
Giraldo et al., "Size matters: use of YACs, BACs and PACs in transgenic animals," Transgenic Research, vol. 10, No. 2, pp. 83-103, Apr. 2001.
Giusti et al., "Hypermutation Is Observed Only in Antibody H Chain V Region Transgenes That Have Recombined with Endogenous Immunoglobulin H DNA: implications for the Location of *cis*-acting Elements Required for Somatic Mutation," Journal of Experimental Medicine, vol. 177, pp. 797-809, Mar. 1993.
Glanville et al., "Naive antibody gene-segment frequencies are heritable and unaltered by chronic lymphocyte ablation," Proceedings of the National Academy of Sciences, USA, vol. 108, No. 50, pp. 20066-20071, Dec. 13, 2011.
Goodhardt et al., "Rearrangement and expression of rabbit immunoglobulin κ light chain gene in transgenic mice," Proceedings of the National Academy of Sciences, USA, vol. 84, No. 12, pp. 4229-4233, Jun. 1987.
Green et al., "Antigen-specific human monoclonal antibodies from mice engineered with human Ig heavy and light chain YACs," Nature Genetics, vol. 7, No. 1, pp. 13-21, May 1994.
Green et al., "Regulation of B Cell Development by Variable Gene Complexity in Mice Reconstituted with Human Immunoglobulin Yeast Artificial Chromosomes," The Journal of Experimental Medicine, vol. 188, No. 3, pp. 483-495, Aug. 3, 1998.
Harding et al., "Class Switching in Human Immunoglobulin Transgenic Mice," Annals of New York Academy of Science, vol. 764, pp. 536-546, Sep. 29, 1995.
Hendricks et al., "Organization of the variable region of the immunoglobulin heavy-chain gene locus of the rat," Immunogenetics, vol. 62, No. 7, pp. 479-486, Jul. 2010.
Houldsworth et al., "Comparative Genomic Hybridization: An Overview," American Journal of Pathology, vol. 145, No. 6, pp. 1253-1260, Dec. 1994.
Huber et al., "Distinct Contributions of Vaccine-Induced Immunoglobulin G1 (IgG1) and IgG2a Antibodies to Protective Immunity against Influenza," Clinical and Vaccine Immunology, vol. 13, No. 9, pp. 981-990, Sep. 2006.
Jakobovits, "Production of fully human antibodies by transgenic mice," Biotechnology, vol. 6, No. 5, pp. 561-566, Oct. 1995.
Jakobovits, "The long-awaited magic bullets: therapeutic human monoclonal antibodies from transgenic mice," Expert Opinion on Investigational Drugs, vol. 7, No. 4, pp. 607-614, Apr. 1998.
Janeway et al., "Structural variation in immunoglobulin constant regions," Immuobiology:The Immune System in Health and Disease, 5th edition, 5 pages, 2001.
Janeway et al., "The rearrangement of antigen-receptor gene segments controls lymphocyte development," In Immunobiology, 5th edition, 13 pages, Aug. 14, 2015 (retrieved online at <http://www.ncbi.nlm.nih.gov/book/NBK27113/>).
Jendreyko et al., "Intradiabodies, Bispecific, Tetravalent Antibodies for the Simultaneous Functional Knockout of Two Cell Surface Receptors," The Journal of Biological Chemistry, vol. 278, No. 48, pp. 47812-47819, Nov. 28, 2003.
Jessen et al., "Molecular analysis of metastasis in a poiyomavirus middle T mouse model: the role of osteopontin," Breast Cancer Research, vol. 6, No. 3, pp. R157-R169, Feb. 25, 2004.
Johnston et al., "Complete Sequence Assembly and Characterization of the C57BL/6 Mouse Ig Heavy Chain V Region," The Journal of Immunology, vol. 176, No. 7, pp. 4221-4234, Apr. 1, 2006.
Karu et al., "Recombinant Antibody Technology," Institute for Laboratory Animal Research, vol. 37, No. 3, pp. 132-141, 1995.
Kaushik et al., "Novel insight into antibody diversification from cattle," Veterinary Immunology and Immunopathology, vol. 87, Nos. 3-4, pp. 347-350, Sep. 10, 2002.
Kenter et al., "Three-dimensional architecture of the IgH locus facilitates class switch recombination," Annals of the New York Academy of Sciences, vol. 1267, No. 1, pp. 86-94, Sep. 1, 2012.
Kim et al., "Expression and Relationship of Male Reproductive ADAMS in Mouse," Biology of Reproduction, vol. 74, No. 4, pp. 744-750, Apr. 2006.
Kostenuik et al., "Denosumab, A Fully Human Monoclonal Antibody to RANKL, Inhibits Bone Resorption and Increases BMD in Knock-In Mice That Express Chimeric (Murine/Human) RANKL," Journal of Bone and Mineral Research, vol. 24, No. 2, pp. 182-195, Nov. 2, 2009.
Kouskoff et al., "Cassette vectors directing expression of T cell receptor genes in transgenic mice," Journal of Immunology Methods, vol. 180, pp. 273-280 (Mar. 27, 1995).
Lee et al., "Human C5aR knock-in mice facilitate the production and assessment of anti-infiammatory monoclonal antibodies," Nature Biotechnology, vol. 24, No. 10, pp. 1279-1284, Oct. 2006.
Lee et al., "Complete humanization of the mouse immunoglobulin loci enables efficient therapeutic antibody discovery," Nature Biotechnology, vol. 32, No. 4, pp. 356-363, Mar. 16, 2014.
Lefranc, "Nomenclature of the Human Immunoglobulin Lambda (IGL) Genes," Experimental and Clinical Immunogenetics vol. 18, pp. 242-254, 2001.
Lefranc, "Nomenclature of the Human Immunoglobulin Heavy (IGH) Genes," Experimental and Clinical Immunogenetics, vol. 18, pp. 100-116, Aug. 31, 2000.
Lefranc et al., "The Immunoglobulin Facts Book," Academic Press, ISBN:978-0-08-057447, 428 pages, May 29, 2001.
Little et al., "Generation of a large complex antibody library from multiple donors," Journal of Immunology Methods, vol. 231, Issue Nos. 1-2, pp. 3-9, Dec. 10, 1999.

(56) References Cited

OTHER PUBLICATIONS

Loveslati et al., "A study of Gm allotypes and immunoglobulin heavy gamma IGHG genes in Berbers, Arabs and sub-Saharan Africans from Jerba Island, Tunisia," Blackwell Science Ltd., European Journal of Immunogenetics, vol. 28, No. 5, pp. 531-538, Oct. 2001.
Ma et al., "Human antibody expression in transgenie rats: Comparison of chimeric IgH loci with human $V_H$, D and $J_H$ but bearing different rat C-gene regions," Journal of Immunological Methods, vol. 400-401, pp. 78-86, Dec. 31, 2013.
Macdonald et al., "Precise and in situ genetic humanization of 6 Mb of mouse immunoglobulin genes," Proceedings of the National Academy of Sciences, USA, vol. 111, No. 14, pp. 5147-5152, Apr. 8, 2014.
Macdonald et al., "Velocigene Technology Extended to Humanization of Several Megabases of Complex Gene Loci," (Abstract) 1st International MUGEN Conference on Animal Models for Human Immunological Disease, Athens Greece, 1 page, Sep. 10-13, 2006.
Maitta et al., "Immunogenicity and Efficacy of *Cryptococcus neoformans* Capsular Polysaccharide Glucuronoxylomannan Peptide Mimotope-Protein Conjugates in Human Immunoglobulin Transgenic Mice," Infection and Immunity, vol. 72, No. 1, pp. 196-208, Jan. 2004.
Manis et al., "Mechanism and control of class-switch recombination," Trends in Immunology, vol. 23. Issue 1, pp. 31-39, Jan. 2002.
Matthews et al., "A locus affecting immunoglobulin isotype selection (*Igis1*) maps to the MHC region in C57BL, BALB/c and NOD mice," Immunology and Cell Biology, vol. 79, No. 6, pp. 576-582, Dec. 2001.
Matilla et al., "Extensive allelic sequence variation in the J region of the human immunoglobulin heavy chain gene locus," European Journal of Immunology, vol. 25, No. 9, pp. 2578-2582, Sep. 1995.
McMurry et al., "Enhancer Control of Local Accessibility of V(D)J Recombinase," Molecular and Cellular Biology, vol. 17, No. 8, pp. 4553-4561, Aug. 1997.
Milner et al., "Polymorphism and Utilization of Human $V_H$ Genes[a]," Annals of the New York Academy of Sciences, vol. 764, pp. 50-61, Sep. 1995.
Monaco et al., "YACs, BAC, PACs and MACs: artificial chromosomes as research tools," Trends in Biotechnology, vol. 12, No. 7, pp. 280-286, Jul. 1994.
Moran, "Mouse platforms jostle for slice of humanized antibody market," Nature Biotechnology, vol. 31, No. 4, pp. 267-268, Apr. 2013.
Müller, "Ten years of gene targeting: targeted mouse mutants, from vector design to phenotype analysis," Mechanisms of Development, vol. 82, Issue Nos. 1-2, pp. 3-21, Apr. 1999.
Murphy et al., "Mice with megabase humanization of their immunoglobulin genes generate antibodies as efficiently as normal mice," Proceedings of the National Academy of Sciences, vol. 111, No. 14, pp. 5153-5158, Apr. 8, 2014.
Muyrers et al., "Rapid modification of bacterial artificial chromosomes by ET-recombination," Nucleic Acids Research, vol. 27, No. 6, pp. 1555-1557, Feb. 2, 1999.
Narayanan et al., "Efficient and precise engineering of a 200 kb β-globin human/bacterial artificial chromosome in *E. coil* DH10B using an inducible homologous recombination system," Gene Therapy, vol. 6, No. 3, pp. 442-447, Mar. 1999.
Neuberger et al., "Isotype exclusion and transgene down-regulation in immunoglobulinλ transgenic mice," Nature, vol. 338, No. 5213, pp. 350-352, Mar. 23, 1989.
Ohlin et al., "The human antibody repertoire to infectious agents: implications for disease pathogenesis," Molecular Immunology, vol. 40, Issue 1, pp. 1-11, Sep. 2003.
Ohm-Laursen et al., "Identification of two new alleles, *IGHV3-23\*04* and *IGHJ6\*04*, and the complete sequence of the *IGHV3-H* pseudogene in the human immunoglobulin locus and their prevalences in Danish Caucasians," Immunogenetics, vol. 57, No. 9, pp. 621-627, Oct. 2005.

Parng et al., "Gene Conversion Contributes to Ig Light Chain Diversity in Cattle," The Journal of Immunology, vol. 157, No. 12, pp. 5478-5486, Dec. 15, 1996.
Pettitt et al., "Agouti C57BL/6N embryonic stem cells for mouse genetic resources," Nature Methods, vol. 6, No. 7, pp. 493-495, Jul. 2009.
Ponsel et al., "High Affinity, Developability and Functional Size: The Holy Grail of Combinatorial Antibody Library Generation," Molecules, vol. 16, No. 5, pp. 3675-3700, 2011.
Pramanik et al., "Segmental duplication as one of the driving forces underlying the diversity of the human immunoglobolin heavy chain variable gene region," BMC Genomics, vol. 12, No. 78, Jan. 2011.
Prosser et al., "Mosaic Complementation Demonstrates a Regulatory Role for Myosin VIIa in Actin Dynamics of Stereocilia," Molecular and Cellular Biology, vol. 28, No. 5, pp. 1702-1712, Mar. 2008.
Prosser et al., "A resource of vectors and ES cells for targeted deletion of microRNAs in mice," Nature Biotechnology, vol. 29, No. 9, pp. 840-845, Sep. 2011.
Pruzina et al., "Human monoclonal antibodies to HIV-1 gp140 from mice bearing YAC-based human immunoglobulin transloci," Protein Engineering, Design & Selection, vol. 24, No. 10, pp. 791-799, Aug. 2011.
Qi et al., "A New Transgenic Rat Model of Hepatic Steatosis and the Metabolic Syndrome," Hypertension, vol. 45, No. 5, pp. 1004-1011, May 2005.
Ramirez-Solis et al., "Chromosome engineering in mice," Nature, vol. 378, No. 6558, pp. 720-724, Dec. 14, 1995.
Ramsden et al., "Conservation of sequence in recombination signal sequence spacers," Nucleic Acids Research, vol. 22, No. 10, pp. 1785-1796, Apr. 13, 1994.
Ray et al., "Ectopic expression of a $c\text{-}Kit^{W42}$ minigene in transgenic mice: recapitulation of *W* phenotypes and evidence for c-*kit* function in melanoblast progenitors," Genes & Development, vol. 5, pp. 2265-2273, 1991.
Regeneron Pharmaceuticals Inc., "Big Pharma vies for mice," Nature Biotechnology, vol. 25, No. 6, p. 613, Jun. 2007.
Ren et al., "Targeted Insertion Results in a Rhombomere 2-Specific *Hoxa2* Knockdown and Ectopic Activation of *Hoxa1* Expression," Developmental Dynamics, vol. 225, No. 3, pp. 305-315, Nov. 2002.
Ristevski, "Making Better Transgenic Models," Molecular Biotechnology, vol. 29, No. 2, pp. 153-163, Feb. 2005.
Rivera et al., "Genetic Background and the Dilemma of Translating Mouse Studies to Humans," Immunity, vol. 28, No. 1, pp. 1-4, Jan. 28, 2008.
Rodriguez et al., "High-efficiency deleter mice show that FLPe is an alternative to Cre-*loxP*," Nature Genetics, vol. 25, pp. 139-140, Jun. 2000.
Rosner et al., "Third complementarity-determining region of mutated $V_H$ immunoglobulin genes contains shorter V, D, J, P, and N components than non-mutated genes," Immunology, vol. 103, No. 2, pp. 179-187, Jun. 2001.
Rusk, "Making mice at high speed," Nature Methods, vol. 4, No. 3, pp. 196-197, Mar. 2007.
Sasso et al., "Ethnic Differences in Polymorphism of an Immunoglobulin $V_H3$ gene," Journal of Clinical Investigation, vol. 96, No. 3, pp. 1591-1600, Sep. 1995.
Scapini et al., "Myeloid cells, BAFF, and IFN-γ establish an inflammatory loop that exacerbates autoimmunity in Lyn-deficient mice," The Journal of Experimental Medicine, vol. 207, No. 8, pp. 1757-1773, Jul. 12, 2010.
Seals et al., "The ADAMs family of metalloproteases: multidomain proteins with multiple functions," Genes & Development, vol. 17, No. 1, pp. 7-30, Jan. 2003.
Seidl et al., "An expressed $neo^r$ cassette provides required functions of the 1γ2b exon for class switching," International Immunology, vol. 10, No. 11, pp. 1683-1692, Nov. 1998.
Seidl et al., "Position-dependent inhibition of class-switch recombination by PGK-$neo^r$ cassettes inserted into the immunoglobulin heavy chain constant region locus," Proceedings of the National Academy of Sciences, USA, vol. 96, No. 6, pp. 3000-3005, Mar. 16, 1999.

(56) References Cited

OTHER PUBLICATIONS

Seong et al., "To knockout in 129 or in C57BL/6: that is the question," Trends in Genetics, vol. 20, No. 2, pp. 59-62, Feb. 2004.
Shi et al., "Comparative analysis of human and mouse immunogiobulin variable heavy regions from IMGT/LIGM-DB with IMGT/HighV-QUEST," Theoretical Biology and Medical Modelling, vol. 11, pp. 1-11, Nov. 2014.
Shi et al., "The mapping of transgenes by fluorescence in situ hybridization on G-banded mouse chromosomes," Mammalian Genome, vol. 5, No. 6, pp. 337-341, Jun. 1994.
Shih, "Discovery Process for Antibody-Based Therapeutics," Development of Antibody-Based Therapeutics, Chapter 2, pp. 9-32, Apr. 24, 2012.
Sirac et al., "Role of the monoclonal κ chain V domain and reversibility of renal damage in a transgenic model of acquired Fanconi syndrome," Blood, vol. 108, No. 2, pp. 536-543, Jul. 15, 2006.
Skarnes et al., "A conditional knockout resource for the genome-wide study of mouse gene function," Nature, vol. 474, pp. 337-342, Jun. 16, 2011.
Smith, "Gene transfer in higher animals: theoretical considerations and key concepts," Journal of Biotechnology, vol. 99, No. 1, pp. 1-22, Oct. 9, 2002.
Soukharev et al., "Segmental genomic replacement in embryonic stem cells by double lox targeting," Nucleic Acids Research, vol. 27, No. 18, pp. e21-i to e21-viii, Jun. 1, 1999.
Spanopoulou et al., "Functional immunoglobulin transgenes guide ordered B-cell differentiation in Rag-1-deficient mice," Genes & Development, vol. 8, No. 9, pp. 1030-1042, May 1, 1994.
Stavnezer et al., "Mechanism and Regulation of Class Switch Recombination," Annual Review of Immunology vol. 26, pp. 261-292, Apr. 2008.
Stevens et al., "Velocimmune: Humanization of Immunoglobulin Loci Using Velocigene Technology," (Abstract) Presented at 1st International MUGEN Conference on Animal Models for Human Immunological Disease, Athens, Greece, 1 page, Sep. 10-13, 2006.
Suárez et al., "Rearrangement of only one human IGHV gene is sufficient to generate a wide repertoire of antigen specific antibody responses in transgenic mice," Molecular Immunology, vol. 43, No. 11, pp. 1827-1835, Dec. 2006.
Takeda et al., "Construction of chimaeric processed immunoglobulin genes containing mouse variable and human constant region sequences," Nature, vol. 314, pp. 452-454, Apr. 4, 1985.
Tan, "A Human-Mouse Chimeric Immunoglobulin Gene With a Human Variable Region is Expressed in Mouse Myeloma Cells," The Journal of Immunology vol. 135, No. 5, pp. 3564-3567, Nov. 1, 1985.
Taylor et al., "Human immunoglobulin transgenes undergo rearrangement, somatic mutation and class switching in mice that lack endogenous IgM," International Immunology, vol. 6, No. 4, pp. 579-591, Apr. 1994.
Thykjaer et al., "Gene targeting approaches using positive-negative selection and large flanking regions," Plant molecular Biology, vol. 35, No. 4, pp. 523-530, Nov. 1997.
Tonegawa, "Somatic generation of antibody diversity," Nature, vol. 302, No. 5909, pp. 575-581, Apr. 14, 1983.
Tucker et al., "Mouse IgA heavy chain gene sequence: Implications for evolution of immunoglobulin hinge exons," Proceedings of the National Academy of Sciences, USA, vol. 78, No. 12, pp. 7684-7688, Dec. 1981.
Van Snick et al., "Genetic Control of Rheumatoid Factor Production in the Mouse," Arthritis & Rheumatism, vol. 26, No. 9, pp. 1085-1090, Sep. 1983.
Van Spriel et al., "Immunotherapeutic perspective for bispecific antibodies," Immunology Today, vol. 21, No. 8, pp. 391-397, Aug. 1, 2000.
Vasicek et al., "Structure and Expression of the Human Immunoglobulin λ Genes," Journal of Experimental Medicine, vol. 172, pp. 609-620, Aug. 1990.
Vollmer et al., "Antigen contacts by Ni-reactive TCR: typical αβ chain cooperation versus α chain-dominated specificity," International Immunity, vol. 12, No. 12, pp. 1723-1731, May 31, 2000.
Wagner et al., "Antibodies generated from human immunoglobulin miniloci in transgenic mice," Nucleic Acids Research, vol. 22, No. 8, pp. 1389-1393, Apr. 25, 1994.
Wang et al., "Chromosomal transposition of *PiggyBac* in mouse embryonic stem cells," Proceedings of the National Academy of Sciences, USA, vol. 105, No. 27, pp. 9290-9295, Jul. 2008.
Wang et al., "Many human immunoglobulin heavy-chain IGHV gene polymorphisms have been reported in error," Immunology and Cell Biology, vol. 86, No. 2, pp. 111-115, Feb. 2008.
Waterhouse et al., "Combinatorial infection and in vivo recombination: a strategy for making large phage antibody repertoires," Nucleic Acids Research, vol. 21, No. 9, pp. 2265-2266, May 11, 1993.
Waterston et al., "Initial sequencing and comparative analysis of the mouse genome," Nature, vol. 420, No. 6915, pp. 520-562, Dec. 2002.
White et al., "Genome-wide Generation and Systematic Phenotyping of Knockout Mice Revels New Roles for Many Genes," Cell, vol. 154, Issue 2, pp. 452-464, Jul. 18, 2013.
Wilke et al., "Diagnosis of Haploidy and Triploidy Based on Measurement of Gene Copy Number By Real-Time PCR," Human Mutation, vol. 16, Issue 5, pp. 431-436, Nov. 2000.
Wuerffel et al., "S—S Synapsis during Class Switch Recombination is Promoted by Distantly Located Transcriptional Elements and Activation-Induced Deaminase," Immunity, vol. 27, Issue 5, pp. 711-722, Nov. 26, 2007.
Xu et al., "Deletion of Igκ Light Chain Intronic Enhancer/Matrix Attachment Region Impairs but Does Not Abolish VκJκ Rearrangement," Immunity, vol. 4, pp. 377-385, Apr. 1, 1996.
Yang et al., "Homologous recombination based modification in *Esherichia coli* and germline transmission in transgenic mice of a bacterial artificial chromosome," Nature Biotechnology, vol. 15, No. 9, pp. 859-865, Sep. 1997.
Zemlin et al., "Expressed Murine and Human CDR-H3 Intervals of Equal Length Exhibit Distinct Repertoires that Differ in their Amino Acid Composition and Predicted Range and Structures," Journal of Molecular Biology, vol. 334, No. 4, pp. 733-749, Dec. 5, 2003.
Zhang et al., "A new logic for DNA engineering using recombination in *Escherichia coli*," Nature Genetics, vol. 20, No. 2, pp. 123-128, Oct. 1998.
Zhao, "A comprehensive BAC resource," Nucleic Acids Research, vol. 29, No. 1, pp. 141-143, Jan. 2001.
European Patent Office, Extended European Search Report, Application No. 14196645.7, 12 pages, dated Jun. 26, 2015.
European Patent Office, Extended European Search Report, Application No. EP 14176740.0, 7 pages, dated Oct. 15, 2014.
European Patent Office, Extended European Search Report, Application No. EP 12194977.0, 9 pages, Jul. 17, 2013.
European Patent Office, Extended European Search Report, Application No. EP 12171793.8, 8 pages, dated. Jun. 21, 2013.
European Patent Office, Extended European Search Report, Application No. EP 12171791.2, 5 pages, dated Jun. 18, 2013.
France IP Office, International Search Report, Application No. FR 1359518, 3 pages, dated Aug. 20, 2014.
European Patent Office, International Search Report, Application No. PCT/GB2012/052296, 30 pages, dated May 17, 2013, together with the Written Opinion of the International Searching Authority.
European Patent Office, International Search Report, Application No. PCT/GB2012/052956, 8 pages, dated Mar. 1, 2013.
European Patent Office, International Search Report, Application No. PCT/GB2013/051280, 19 pages, dated Nov. 15, 2013, together with the Written Opinion of the International Searching Authority.
European Patent Office, Communication pursuant to Article 94(3) EPC, Application No. 12194970.5, 6 pages, dated Sep. 23, 2013.
European Patent Office, Statement of Fact and Arguments in Support of Opposition against EP2421357, pertaining to Appl. No. EP 10734546.4, 41 pages, dated Jan. 23, 2013.
United Kingdom IP Office, Combined Search and Examination Report under Sections 17 and 18(3), Application No. GB1317410.7, 8 pages, dated Nov. 21, 2013.

(56) References Cited

OTHER PUBLICATIONS

United Kingdom IP Office, Combined Search and Examination Report under Sections 17 and 18(3), Application No. GB1317447.9, 7 pages, dated Jan. 14, 2014.
Dr. Martin Grund, Third Party Observation in PCT/GB2012/052960, 3 pages, dated Apr. 2, 2014.
Dr. Martin Grund, Third-Party Observations according to Article 115 EPC regarding EP 11705964.2, 5 pages, dated Feb. 26, 2015.
Dr. Martin Grund, Third-Party Observations according to Article 115 EPC regarding EP 11705964.2, 4 pages, dated Apr. 30, 2014.
Dr. Martin Grund, Third-Party Observations according to Article 115 EPC regarding EP 11705964,2, 8 pages, dated Oct. 9, 2013.
Dr. Martin Grund, Third-Party Observations according to Article 115 EPC regarding EP 12171791.2, 9 pages, dated Feb. 26, 2014.
Dr. Martin Grund, Third-Party Observations according to Article 115 EPC regarding EP 12171791.2, 6 pages, dated Aug. 4, 2014.
Dr. Martin Grund, Third-Party Observations according to Article 115 EPC regarding EP 12171793.8, 7 pages, dated Jun. 25, 2014.
Dr. Martin Grund, Third-Party Observations according to Article 115 EPC regarding EP 12194970.5, 9 pages, dated Mar. 5, 2014.
Dr. Martin Grund, Third-Party Observations according to Article 115 EPC regarding EP 12194970.5, 5 pages, dated Aug. 12, 2014.
Dr. Martin Grund, Third-Party Observations according to Article 115 EPC regarding EP 12194977.0, 4 pages, dated Mar. 26, 2014.
Dr. Martin Grund, Third-Party Observations according to Article 115 EPC regarding EP 12194977.0, 5 pages, dated May 12, 2015.
Dr. Martin Grund, Third-Party Observations according to Article 115 EPC regarding EP 12195041.4, 5 pages, dated Jul. 30, 2014.
Dr. Martin Grund, Third-Party Observations according to Article 115 EPC regarding EP 12795606.8, 6 pages, dated Feb. 26, 2014.
Dr. Martin Grund, Third-Party Observations according to Article 115 EPC regarding EP 12795606.8, 4 pages, dated Mar. 26, 2015.
Dr. Martin Grund, Third Party Observation regarding Application No. PCT/GB2013/050682, 3 pages, dated Jul. 28, 2014.
Dr. Martin Grund, Third Party Observation regarding Application No. PCT/GB2013/050683, 2 pages, dated Jul. 28, 2014.
Dr. Martin Grund, Third Party Observation Application No. PCT/GB2012/052297, 3 pages, dated Jan. 17, 2014.
Dr. Martin Grund, Third Party Observation Application No. PCT/GB2012/052298, 4 pages, dated Jan. 17, 2014.
Dr. Martin Grund, Third Party Observation Application No. PCT/GB2012/052380, 4 pages, dated Jan. 24, 2014.
Kymab Ltd., Third Party Observation regarding Application PCT/US2012/026416, 2 pages, dated Jun. 7, 2013.
Dr. Martin Grund, Third Party Observations according to Article 115 EPC regarding EP 12171791.2, 7 pages, dated Dec. 19, 2014.
Dr. Martin Grund, Third Party Observations according to Article 115 EPC regarding EP 12194970.5, 6 pages, dated Apr. 25, 2014.
Dr. Martin Grund, Third Party Observations according to Article 115 EPC regarding EP 12194970.5, 6 pages, dated Nov. 15, 2013.
Dr. Martin Grund, Third Party Observations according to Article 115 EPC regarding EP 12772122.3, 5 pages, dated Mar. 12, 2015.
Dr. Martin Grund, Third Party Observations according to Article 115 EPC regarding EP 14176740.0, 13 pages, dated Aug. 10, 2015.
Charles E. Lyon, Third-Party Pre-Issuance Submission Under 37 CFR 1.290 in U.S. Appl. No. 14/040,405, 18 pages, dated Jan. 16, 2015.
Charles E. Lyon, Third-Party Submission Under 37 CFR 1.290 in U.S. Appl. No. 14/056,434, 6 pages, dated Dec. 15, 2014.
Charles E. Lyon, Third-Party Pre-Issuance Submission Under 37 CFR 1.290 in U.S. Appl. No. 14/056,700, 6 pages, dated Nov. 28, 2014.
Charles E. Lyon, Third-Party Pre-Issuance Submission Under 37 CFR Sec. 1.290 in U.S. Appl. No. 14/226,698, 53 pages, dated Jun. 3, 2015.
Charles E. Lyon, Third-Party Pre-Issuance Submission Under 37 CFR Sec. 1.290 in U.S. Appl. No. 14/498,685, 37 pages, dated Sep. 18, 2015.
Charles E. Lyon, Third-Party Pre-Issuance Submission Under 37 CFR 1.290 in U.S. Appl. No. 14/056,707, 10 pages, dated Nov. 28, 2014.
Charles E. Lyon Third-Party Pre-Issuance Submission Under 37 CFR Sec. 1.290 in U.S. Appl. No. 14/137,902, 9 pages, dated Nov. 13, 2014.
Charles E. Lyon, Third-Party Pre-Issuance Submission Under 37 CFR Section 1.290 in U.S. Appl. No. 13/875,892, 49 pages, dated May 5, 2015.
Brenda Herschbach Jarrell, Third-Party Pre-Issuance Submission Under 37 CFR Section 1.290 in U.S. Appl. No. 14/052,259, dated Aug. 6, 2014, 7 pages.
Kevin J. Pobursky, Third-Party Pre-Issuance Submission Under 37 CFR Section 1.290 in U.S. Appl. No. 13/843,528, 14 pages, dated Mar. 18, 2014.
Sean Avery, Third-Party Pre-Issuance Submission Under 37 CFR Section 1.290 in U.S. Appl. No. 14/517,755, 16 pages, dated Jun. 26, 2015.
European Patent Office, Invitation to Pay Additional Fees and, Where Applicable, Protest Fee, Application No. PCT/GB2012/052296, 9 pages, dated Jan. 24, 2013.
Lynn E. MacDonald, Declaration of Lynn E. MacDonald with Exhibits, dated Feb. 3, 2015 relating to International Patent Application No. PCT/US02/04500, 13 pages (Published as WO 02/066630 A1).
European Patent Office Gaby Brouns, Authorized officer, Written Opinion of the International Searching Authority, Application No. PCT/GB2013/050682, 8 pages, dated Sep. 25, 2013.
Ahmed, "Sanofi-aventis and Regeneron Extend Therapeutic Antibody Agreement," *PharmaDeals Review*, vol. 2009, Issue No. 11, p. 115, Nov. 2009.
Beerli, R. et al., "Mining Human Antibody Repertoires," *MAbs*, vol. 2, Issue No. 4, pp. 365-378, Jul./Aug. 2010.
Bhattacharya, P. et al., "Switch Region Identity Plays an Important Role in Ig Class Switch Recombination," *Journal of Immunology*, vol. 184, Issue No. 11, pp. 6242-6248, 2010.
Casrouge, A., et al., "Size Estimate of the αβ TCR Repertoire of Naïve Mouse Splenocytes," *Journal of Immunology*, vol. 164, Issue No. 11, pp. 5782-5787, 2000.
Chan, A. et al., "Therapeutic Antibodies for Autoimmunity and Inflammation," *Nature Reviews Immunology*, vol. 10, Issue No. 5, pp. 301-316, 2010.
Chen, Y. et al., "PiggyBac Transposon-Mediated, Reversible Gene Transfer in Human Embryonic Stem Cells," *Stem Cells and Development*, vol. 19, Issue No. 6, pp. 763-771, Sep. 2009.
Crouch, E. et al., "Regulation of AID expression in the immune response," *Journal of Experimental Medicine*, vol. 204, Issue No. 5, pp. 1145-1156, Apr. 2007.
Ebert, A. et al., "The Distal V(H) Gene Cluster of the *IgH* Locus Contains Distinct Regulatory Elements with Pax5 Transcription Factor-Dependent Activity in Pro-B Cells," *Immunity*, vol. 34 Issue No. 2, pp. 175-187, 2011.
Goldman, I. et al., "Transgenic animals in medicine: Integration and expression of foreign genes, theoretical and applied aspects," *Medical Science Monitor*, vol. 10, Issue No. 11, pp. RA274-RA285, 2004.
Guirouilh-Barbat J. et al., "Is homologous recombination really an error-free process?," *Frontiers in Genetics*, vol. 5, Issue No. 175, 15 pages, Jun. 2014.
Hewitt, S. et al., "Association Between the *Igk* and *Igh* immunoglobulin loci mediated by the 3' *Igk* enhancer induces 'decontraction' of the *Igh* locus in pre-B cells," *Nature Immunology*, vol. 9 Issue No. 4, pp. 396-404, 2008.
Houdebine, L., "The methods to generate transgenic animals and to control transgene expression," *Journal of Biotechnology*, vol. 98, Issue Nos. 2-3, pp. 145-160, 2002.
Houdebine, L., "Transgenic Animal Models in Biomedical Research," Chapter 10, *Methods in Molecular Biology*, vol. 360, pp. 163-202, 2007.
Kondo, S. et al., "Highly Improved Gene Targeting by Germline-Specific Cas9 Expression in *Drosophila*," *Genetics*, vol. 195, pp. 715-721, Nov. 2013.

(56) References Cited

OTHER PUBLICATIONS

Kondo, S. et al., "Highly Improved Gene Targeting by Germline-Specific Cas9 Expression in *Drosophila*," *Genetics*, vol. 195, pp. 715-721, Nov. 2013 (Abstract—1 page).
Kuraoka M., et al., "AID expression during B-cell development: searching for answers," *Immunologic Research*, vol. 49, Issue Nos. 1-3, pp. 3-13, 2011.
Laffleur, B. et al., Chapter 9, "Production of Human or Humanized Antibodies in Mice," *Methods in Molecular Biology*, vol. 901, pp. 149-159, 2012.
Lee, E. et al., Chapter 8, "The Application of Transgenic Mice for Therapeutic Antibody Discovery," *Methods in Molecular Biology*, vol. 901, pp. 137-148, 2012.
Lefranc, M., "Nomenclature of the Human Immunoglobulin Kappa (IGK) Genes," *Experimental and Clinical Immunogenetics*, vol. 18, Issue No. 3, pp. 161-174, 2001.
Li, H. et al., "Genetic diversity of the human immunoglobulin heavy chain V(H) region," *Immunological Reviews*, vol. 190, pp. 53-68, 2002.
Lonberg, N., "Fully human antibodies from transgenic mouse and phage display platforms," *Current Opinion in Immunology*, vol. 20, Issue No. 4, pp. 450-459, 2008.
MacDonald, L. et al., Poster: "VelociGene® Technology Extended to Humanization of Several Megabases of Complex," Exhibit IJR-47 to Jeffrey Rourke Declaration, 1 page, 2006.
MacDonald, L. et al., Expanded Poster: "VelociGene® Technology Extended to Humanization of Several Megabases of Complex," Exhibit IJR-49 to Jeffrey Rourke Declaration, 6 pages, 2006.
MacDonald, Lynn E., "Curriculum Vitae of Lynn E. MacDonald, Ph.D.," 3 pages.
Magadán, S. et al., "Production of Antigen-Specific Human Monoclonal Antibodies: Comparison of Mice Carrying IgH/kappa or IgH/kappa/lambda Transloci," *BioTechniques*, vol. 33, Issue No. 3, pp. 680, 682, 684 passim, Sep. 2002.
Martinez-Jean, C. et al., "Nomenclature and Overview of the Mouse (*Mus musculus* and *Mus.* sp.) Immunoglobulin Kappa (IGK) Genes," *Experimental and Clinical Immunogenetics*, vol. 18, pp. 255-279, 2001.
Regeneron Pharmaceuticals, Inc., "AstraZeneca Licenses Regeneron's VelocImmune® Technology for Discovering Human Monoclonal Antibodies—AstraZeneca is First Licensee of Novel VelocImmune Technology License Fees Total up to $120 Million Over Six Years," 2 pages, Feb. 5, 2007.
Regeneron Pharmaceuticals, Inc., "Astellas Licenses Regeneron's Velocimmune® Technology for Discovering Human Monoclonal Antibodies," 2 pages, Mar. 30, 2007.
Regeneron Pharmaceuticals, Inc., "Regeneron Initiates Major Global Collaboration with Sanofi-aventis to Develop and Commercialize Fully-Human Therapeutic Antibodies," 2 pages, Nov. 29, 2007.
Rourke, J., "Declaration of Jeffrey Rourke, Registered Patent Attorney for Regeneron Pharmaceuticals, Inc.—In the matter of Patent Acceptance 2011266843 in the Name of Kymab Limited and in the matter of Opposition thereto by Regeneron Pharmaceuticals, Inc.," 5 pages, dated Jan. 29, 2016.
Sekiguchi J. et al., "The Mechanism of V(D)J Recombination," *Molecular Biology of B Cells*, Chapter 5, pp. 61-82, 2004.
Sigmund C., "Viewpoint: Are Studies in Genetically Altered Mice Out of Control?", *Arteriosclerosis, Thrombosis and Vascular Biology*, vol. 20, Issue No. 6, pp. 1425-1429, 2000.
Stevens, S. et al., Poster: "VelocImmune$^{TM}$: Humanization of immunoglobulin loci using VelociGene® technology," Exhibit IJR-46 to Jeffrey Rourke Declaration, 1 page, 2006.
Stevens, S. et al., Expanded Poster: "VelocImmune$^{TM}$: Humanization of immunoglobulin loci using VelociGene® technology," Exhibit IJR-48 to Jeffrey Rourke Declaration, 1 page, 2006.
Tuaillon, N. et al., "Human immunoglobulin heavy-chain minilocus recombination in transgenic mice: Gene-segment use in μ and γ transcripts," *Proceedings of the National Academy of Sciences USA*, vol. 90, pp. 3720-3724, Apr. 1993.
Wasserman, R. et al., "The Pattern of Joining ($J_H$) Gene Usage in the Human IgH Chain is Established Predominantly at the B Precursor Cell Stage$^1$," *The Journal of Immunology*, vol. 149, pp. 511-516, Jul. 1992.
Weichhold, G. et al., "Megabase inversions in the human genome as physiological events," *Nature*, vol. 347, Issue No. 6288, pp. 90-92, Sep. 1990.
Weichhold, G. et al., "The Human Immunoglobulin Kappa Locus Consists of Two Copies That are Organized in Opposite Polarity," *Genomics*, vol. 16 (2), pp. 503-511, 1993.
Weiner, L., "Fully Human Therapeutic Monoclonal Antibodies," *Journal of Immunology*, vol. 29, Issue No. 1, pp. 1-9, Jan./Feb. 2006.
Yamada, M. et al., "Preferential Utilization of Specific Immunoglobulin Heavy Chain Diversity and Joining Segments in Adult Human Peripheral Blood B Lymphocytes," *Journal of Experimental Medicine*, vol. 173, pp. 395-407, Feb. 1991.
Yu, Y. et al., "Engineering Chromosomal Rearrangements in Mice," *Nature Reviews Genetics*, vol. 2, Issue No. 10, pp. 780-790, 2001.
Zheng, J. et al., "Immunoglobulin Gene Transcripts Have Distinct $V_HDJ_H$ Recombination Characteristics in Human Epithelial Cancer Cells," *Journal of Biological Chemistry*, vol. 284, Issue No. 20, pp. 13610-13619, May 2009.
Zou, X. et al., "Removal of the BiP-retention domain in Cμ permits surface deposition and developmental progression without L-chain," *Molecular Immunology*, vol. 45, Issue No. 13, pp. 3573-3579, 2008.
Genbank, Accession No. KF698731.1, 1 page, accessed Nov. 18, 2013.
NCBI Blast, Accession No. Y55HBK1W114, 2 pages, accessed Aug. 6, 2014.
Grund, Martin, European Patent Attorney, Grund Intellectual Property Group, Third-Party Observations according to Article 115 EPC regarding 12762377.5, 7 pages, dated May 22, 2015.
Grund, Martin, European Patent Attorney, Grund Intellectual Property Group, Third-Party Observations according to Article 115 EPC regarding 12762377.5, 8 pages, dated Feb. 12, 2016.
Grund, Martin, European Patent Attorney, Grund Intellectual Property Group, Third-Party Observations according to Article 115 EPC regarding 13711119.1, 7 pages, dated Dec. 9, 2015.
Urquhart-Dykes & Lord LLP, Third-Party Observation for Application No. EP20140772198, 8 pages, dated Dec. 14, 2015.
European Patent Office, Laurent Deleu, Authorized Officer, Written Opinion of the International Searching Authority for Application No. PCT/GB2010/051122, 6 pages, mailed Sep. 29, 2010.
European Patent Office, Laurent Deleu, Authorized Officer, International Preliminary Report on Patentability for Application No. PCT/GB2010/051122, 33 pages, mailed Nov. 2, 2011.
European Patent Office, Laurent Deleu, Authorized Officer, International Search Report and Written Opinion of the International Searching Authority for Application No. PCT/GB2011/050019, 12 pages, mailed May 16, 2011.
European Patent Office, Alessandro Brero, Authorized Officer, International Search Report and Written Opinion of the International Searching Authority for Application No. PCT/GB2012/052297, 24 pages, mailed Jun. 19, 2013.
European Patent Office, Written Opinion of the International Searching Authority for PCT/GB2012/052956, 6 pages, mailed on Mar. 1, 2013.
European Patent Office, International Search Report and Written Opinion of the International Searching Authority for Application No. PCT/GB2012/052960, 19 pages, mailed Apr. 29, 2013.
European Patent Office, International Search Report and Written Opinion of the International Searching Authority for Application No. PCT/GB2013/050683, 11 pages, mailed Jul. 9, 2013.
European Patent Office, Laurent Deleu, Authorized Officer, Extended European Search for Application No. EP12194970, 9 pages, mailed Jan. 23, 2013.
European Patent Office, Laurent Deleu, Authorized Officer, Extended European Search Report for Application No. 12195041.4, 8 pages, mailed Nov. 18, 2013.

(56) References Cited

OTHER PUBLICATIONS

European Patent Office, Laurent Deleu, Authorized Officer, Extended European Search Report for Application No. EP14170196, 8 pages, mailed Oct. 8, 2014.
European Patent Office, Extended European Search Report for Application No. 15188522.5, 15 pages, mailed Feb. 2, 2016.
European Patent Office, Gaby Brouns, Authorized Officer, Examination Report for Application No. EP 13711119.1, 6 pages, mailed Dec. 17, 2015.
European Patent Office, Gaby Brouns, Authorized Officer, Examination Report for Application No. EP 12795841.1, 5 pages, mailed Feb. 12, 2016.
European Patent Office, Laurent Deleu, Authorized Officer, Communication pursuant to Article 94(3) EPC for Application No. 14176740.0, 5 pages, mailed Oct. 23, 2015.
New Zealand Patent Office, Simon Maguire, Authorized Officer, Further Examination Report for Patent No. 623756, 3 pages, mailed on Sep. 9, 2015.
Lyon, Charles E., Attorney for Applicant, Third Party Pre-Issuance Submission Under 37 CFR 1.290 in U.S. Appl. No. 13/846,672, 32 pages, dated Mar. 17, 2015.
Lyon, Charles E., Attorney for Applicant, Third Party Pre-Issuance Submission Under 37 CFR 1.290 in U.S. Appl. No. 13/886,511, 18 pages, dated May 5, 2015.
Lyon, Charles E., Attorney for Applicant, Third Party Pre-Issuance Submission Under 37 CFR 1.290 in U.S. Appl. No. 14/040,427, 20 pages, dated Jan. 16, 2015.
Lyon, Charles E., Attorney for Applicant, Third Party Pre-Issuance Submission Under 37 CFR 1.290 in U.S. Appl. No. 14/080,630, 8 pages, dated Oct. 31, 2014.
Lyon, Charles E., Attorney for Applicant, Third Party Pre-Issuance Submission Under 37 CFR 1.290 in U.S. Appl. No. 14/220,080, 28 pages, dated Jul. 28, 2015.
Lyon, Charles E., Attorney for Applicant, Third Party Pre-Issuance Submission Under 37 CFR 1.290 in U.S. Appl. No. 14/220,095, 19 pages, dated Aug. 4, 2015.
Lyon, Charles E., Attorney for Applicant, Third Party Pre-Issuance Submission Under 37 CFR 1.290 in U.S. Appl. No. 14/220,099, 43 pages, dated Apr. 29, 2015.
Lyon, Charles E., Attorney for Applicant, Third Party Pre-Issuance Submission Under 37 CFR 1.290 in U.S. Appl. No. 14/226,706, 53 pages, dated Jul. 28, 2015.
Lyon, Charles E., Attorney for Applicant, Third Party Pre-Issuance Submission Under 37 CFR 1.290 in U.S. Appl. No. 14/263,158, 16 pages, dated Apr. 29, 2015.
Lyon, Charles E., Attorney for Applicant, Third Party Pre-Issuance Submission Under 37 CFR 1.290 in U.S. Appl. No. 14/263,176, 16 pages, dated Apr. 29, 2015.
Lyon, Charles E., Attorney for Applicant, Third Party Pre-Issuance Submission Under 37 CFR 1.290 in U.S. Appl. No. 14/497,054, 81 pages, dated Oct. 21, 2015.
Lyon, Charles E., Attorney for Applicant, Third Party Pre-Issuance Submission Under 37 CFR 1.290 in U.S. Appl. No. 14/516,461, 27 pages, dated Aug. 4, 2015.
Pobursky, Kevin J, Attorney for Applicant, Third-Party Pre-Issuance Submission Under 37 CFR 1.290 in U.S. Appl. No. 13/433,084, 15 pages, dated Apr. 1, 2014.
Pobursky, Kevin J, Attorney for Applicant, Third-Party Pre-Issuance Submission Under 37 CFR 1.290 in U.S. Appl. No. 13/434,361, 15 pages, dated Apr. 1, 2014.
U.S. Appl. No. 13/310,431, filed Dec. 2, 2011.
U.S. Appl. No. 13/416,684, filed Mar. 9, 2012.
U.S. Appl. No. 13/433,084, filed Mar. 28, 2012.
U.S. Appl. No. 13/846,672, filed Mar. 18, 2013.
U.S. Appl. No. 13/843,528, filed Mar. 15, 2013.
U.S. Appl. No. 13/875,892, filed May 2, 2013.
U.S. Appl. No. 13/886,511, filed May 3, 2013.
U.S. Appl. No. 13/890,147, filed May 8, 2013.
U.S. Appl. No. 14/040,427, filed Sep. 27, 2013.
U.S. Appl. No. 14/040,405, filed Sep. 27, 2013.
U.S. Appl. No. 14/052,259, filed Oct. 11, 2013.
U.S. Appl. No. 14/056,434, filed Oct. 17, 2013.
U.S. Appl. No. 14/056,700, filed Oct. 17, 2013.
U.S. Appl. No. 14/056,707, filed Oct. 17, 2013.
U.S. Appl. No. 14/080,630, filed Nov. 14, 2013.
U.S. Appl. No. 14/137,902, filed Dec. 20, 2013.
U.S. Appl. No. 14/543,359, filed Nov. 17, 2014.
U.S. Appl. No. 14/220,074, filed Mar. 19, 2014.
U.S. Appl. No. 14/220,095, filed Mar. 19, 2014.
U.S. Appl. No. 14/220,099, filed Mar. 19, 2014.
U.S. Appl. No. 14/220,080, filed Mar. 19, 2014.
U.S. Appl. No. 14/226,698, filed Mar. 26, 2014.
U.S. Appl. No. 14/226,706, filed Mar. 26, 2014.
U.S. Appl. No. 14/263,158, filed Apr. 28, 2014.
U.S. Appl. No. 14/263,176, filed Apr. 28, 2014.
U.S. Appl. No. 14/498,685, filed Sep. 26, 2014.
U.S. Appl. No. 14/497,054, filed Sep. 25, 2014.
U.S. Appl. No. 14/516,461, filed Oct. 16, 2014.
U.S. Appl. No. 14/750,870, filed Jun. 25, 2015.
U.S. Appl. No. 14/818,162, filed Aug. 4, 2015.
U.S. Appl. No. 14/935,010, filed Nov. 6, 2015.
U.S. Appl. No. 15/016,211, filed Feb. 4, 2016.
U.S. Appl. No. 15/018,670, filed Feb. 8, 2016.
Adams et al., "A genome-wide, end-sequenced 129Sv BAC library resource for targeting vector construction", Genomics 86, pp. 753-759, 2005.
Askew et al., Site-Directed Point Mutations in Embryonic Stem Cells: a Gene-Targeting Tag-and-Exchange Strategy, Molecular and Cellular Biology, vol. 13, No. 7, pp. 4115-4124, Jul. 1993.
Baker et al., "Homologous Recombination between Transferred and Chromosomal Immunoglobulin k Genes", Mol. Cell. Biology, pp. 4041-4047, Oct. 1988.
Barreto et al., "AID from bony fish catalyzes class switch recombination", Journal of Experimental Medicine, pp. 1-6, Sep. 12, 2005.
Beck et al., "Nucleotide sequence and exact localization of the neomycin phosphotransferase gene from transposon Tn5". Gene, vol. 19, pp. 327-336, Oct. 1982.
Berg et al., "Inverted repeats of Tn5 are transposable elements". PNAC USA, Genetics, Vo. 79, pp. 2632-2635, Apr. 1982.
Betke et al., "Segmental genomic replacement by Cre-mediated recombination: genotoxic stress activation of the p53 promoter in single-copy transformants", Nucleic Acids Research, vol. 25, No. 14, pp. 2828-2834, 1997.
Bolland et al., "Antisense Intergenic Transcription Precedes IghD-to-J Recombination and is Controlled by the Intronic Enhancer Eμ", Mol. Cell. Biology, vol. 27, No. 15, pp. 5523-5533, Aug. 2007.
Bonin et al., "Isolation, Microinjection, and Transfer of Mouse Blastocysts" Methods in Molecular Biology, vol. 158, Gene Knock-out Protocols, pp. 121-134.
Bottaro et al., "Deletion of the IgH intronic enhancer and associated matrix-attachment regions decreases, but does not abolish, class switching at the μ locus", Int. Immunol. Vo. 10, No. 6, pp. 799-806, 1998.
Bradley et al., "Formation of germ-line chimaeras from embryo-derived teratocarcinoma cell lines", Nature Publishing Group, pp. 255-256, vol. 309, 1984.
Breden et al., "Comparison of Antibody Repertoires Produced by HIV-1 Infection, Other Chronic and Acute Infections, and Systemic Autoimmune Disease", PLoS One. vol. 6, Issue 3, pp. 1-11, Mar. 2011.
Brocker et al., "Evolutionary divergence and functions of the ADAM and ADAMTS gene families" Human Genomics, vol. 4, No. 2, pp. 43-55, Oct. 2009.
Bruggemann et al., "Immunoglobulin heavy chain locus of the rat: Striking homology to mouse antibody genes", Proc. Natl. Acad. Sci. USA, Immunology, vol. 83, pp. 6075-6079, Aug. 1986.
Bruggemann et al., "A repertoire of monoclonal antibodies with human heavy chains from transgenic mice", Proc. Natl. Acad. Sci. USA, Immunology, vol. 86, pp. 6709-6713, Sep. 1989.
Buehr et al., "Capture of Authentic Embryonic Stem Cells from Rat Blastocysts", Cell, vol. 135, pp. 1287-1298, Dec. 26, 2008.

(56) References Cited

OTHER PUBLICATIONS

Cadinanos et al., "Generation of an inducible and optimized piggyBac transposon system", Nucleic Acids Research, vol. 35, No. 12, Jun. 18, 2007.
Chen et al., "B cell development in mice that lack one or both immunoglobulin χ light chain genes", The EMBO Journal, Vo. 12, No. 3, pp. 821-830, 1993.
Chen et al., "Immunoglobulin Heavy Chain Gene Replacement: A Mechanism of Receptor Editing" Immunity, vol. 3, pp. 747-755, Dec. 1995.
Cho, "Testicular and epididymal ADAMs: expression and function during fertilization", Nature, vol. 9, pp. 550-560, Oct. 2012.
Choi et al., "Characterization and comparative genomic analysis of intronless Adams with testicular gene expression", Genomics 83, pp. 636-646, Aug. 2003.
Clark et al., "Trends in Antibody Sequence Changes During the Somatic Hypermutation Process", The Journal of Immunology, vol. 177, pp. 333-340, 2006.
Colbere_Garapin et al., "A New Dominant Hybrid Selective Marker for Higher Eukaryotic Cells". J Mol. Biol., vol. 150, No. 1, pp. 1-14, Jul. 25, 1981.
Copeland et al., "Recombineering: A Powerful New Tool for Mouse Functional Genomic", Nature Reviews, Genetics, vol. 2, pp. 769-869, Oct. 2001(10):769-79.
Corti et al., "A Neutralizing Antibody Selected from Plasma Cells That Binds to Group 1 and Group 2 Influenza A Hemagglutinins" Science, vol. 333, pp. 850-856, 2011.
Cuesta et al., "Multivalent antibodies: when design surpasses evolution", Trends Biotechnology, vol. 28, pp. 355-362, 2010.
De Saint Vincent et al., "Homologous recombination in mammalian cells mediates formation of a functional gene from two overlapping gene fragments", Proc. Natl. Acad. Sci., USA, Genetics, vol. 80, pp. 2002-2006, Apr. 1983.
DeChiara et al., "Producing Fully ES Cell-Derived Mice From Eight-Cell Stage Embryo Injections", Methods in Enzymology, vol. 476, Chapter 16, pp. 285-294.
DeChiara et al., "VelociMouse: Fully ES Cell-Derived FO-Generation Mice Obtained from the Injection of ES Cells into Eight-Cell-Stage Embryos", Gene Knockout Protocols: Second Edition, vol. 530, pp. 311-324, 2009.
Denome et al., "Patterns of polyadenylation site selection in gene constructs containing multiple polyadenylation signals", Mol. Cell Biol., vol. 8, No. 11, pp. 4829-4839, Nov. 1988.
Diez-Roux et al., "A High-Resolution Anatomical Atlas of the Transcriptome in the Mouse Embryo", PLoS Biology, vol. 9, Issue 1, pp. 1-13, Jan. 2011.
DiNoia et al., "Molecular Mechanism of Antibody Somatic Hypermutation", Annu. Rev. Biochem, vol. 76, No. 1, pp. 1-22, 2007.
Doetschman et al., "Establishment of Hamster Blastocyst-Derived Embryonic Stem (ES) Cells", Developmental Biology, vol. 127, pp. 224-227, 1988.
Doetschman et al., "Targeted mutation of the H*prt* gene in mouse embryonic stem cells" Proc. Natl. Acad. Sci., vol. 85, pp. 8583-8587, Nov. 1988.
Durbin, "A map of human genome variation from population-scale sequencing", Nature, vol. 467, pp. 1061-1074, Oct. 28, 2012.
Durdik et al., "Isotype switching by a microinjected μ immunoglobulin heavy chain gene in transgenic mice", PNAS USA Immunol, vol. 86, pp. 2346-2350, Apr. 1989.
Ekiert et al., "A Highly Conserved Neutralizing Epitope on Group 2 Influenza A Viruses", Science, vol. 333, pp. 843-850, Aug. 12, 2011.
Evans, "Fertilin B and other ADAMs as integrin ligands: insights into cell adhesion and fertilization", BioEssays 23.7, pp. 628-639, 2001.
Featherstone et al., "The Mouse Immunoglobulin heavy Chain V-D Intergenic Sequence Contains Insulators That May Regulate Ordered V(D)J Recombination", The Journal of Biological Chemistry, vol. 285, No. 13, pp. 9327-9338, Mar. 26, 2010.
Fell et al., "Homologous recombination in hybridoma cells: heavy chain chimeric antibody produced by gene targeting", PNAS USA Immunology, vol. 86, pp. 8507-8511, Nov. 1989.
Feschotte et al., "DNA Transposons and the Evolution of Eukaryotic Genomes.", Annu Rev Genet., vol. 41, pp. 331-368, 2007.
Folger et al., "Patterns of Integration of DNA Microinjected into Cultured Mammalian Cells: Evidence for Homologous Recombination Between Injected Plasmid DNA Molecules", Mol. Cell Biol., vol. 2, No. 11, pp. 1372-1387, 1982.
Forconi et al., "The normal IGHV1-69-derived B-cell repertoire contains stereotypic patterns characteristic of unmutated CLL", vol. 115, pp. 71-77, 2010.
Fukita et al., "Somatic Hypermutation in the Heavy Chain Locus Correlates with Transcription", Immunity, vol. 9, pp. 106-114, Jul. 1998.
Gefter et al., "Expression of a VHC kappa chimaeric protein in mouse myeloma cells", Nature, pp. 364-367, May 24-30, 1984 (Abstract only).
Gerdes et al., "Physical Map of the mouse λ light chain and related loci", Immunogenetics, vol. 54, pp. 62-65, 2002.
Geurts et al., "Knockout Rats via Embryo Microinjection of Zinc-Finger Nucleases", Science, vol. 325, p. 433, Jul. 24, 2009.
Gluzman, "SV40-Transformed Simian Cells Support the Replication of Early SV40 Mutants". Cell, vol. 23, pp. 175-182, Jan. 1981.
Gorman et al., "The Igκ 3' enhancer influences the ratio of Ig? versus Ig? B lymphocytes" Immunity, vol. 5, pp. 241-252, Sep. 1996.
Gorny et al., "Human Anti-V3 HIV-1 Monoclonal Antibodies Encoded by the VH5-51/VL Lambda Genes Define a Conserved Antigenic Structure", PLoSone, vol. 6, Issue 12, pp. 1-10, Dec. 2011.
Goyenechea et al., "Cells strongly expressing Ig(kappa) transgenes show clonal recruitment of hypermutation: a role for both MAR and the enhancers" The EMBO Journal, vol. 16, No. 13., pp. 3987-3994, 1997.
Gu et al., Independent Control of Immunoglobulin Switch Recombination at Individual Switch Regions Evidenced through Cre-loxP-Mediated Gene Targeting. Cell, vol. 73, pp. 1155-1164, Jun. 18, 1993.
Guerrero et al., "The bleomycin resistance gene of transposon Tn5 is an excellent marker for transformation of corynebacteria", Applied Microbiology Biotechnology, vol. 36, pp. 759-762, 1992.
Guntaka, "Transcription Termination and Polyadenylation in Retroviruses" Microbiological Reviews, vol. 57, No. 3, pp. 511-521, Sep. 1993.
Han et al., "Comprehensive Analysis of Reproductive ADAMs: Relationship of ADAM4 and ADAM6 with an ADAM Complex Required for Fertilization in Mice", Biology of Reproduction 80, pp. 1001-1008, Jan. 7, 2009.
Hasty et al., "Target frequency and integration pattern for insertion and replacement vectors in embryonic stem cells", Molecular Cellular Biology, vol. 11, No. 9, pp. 4509-4517, Sep. 1991.
Houvila et al., "Shedding light on ADAM metalloproteinases", Trends in Biochemical Sciences, vol. 30, No. 7, pages, Jul. 2005.
Hudziak et al., "Establishment of Mammalian Cell Lines Containing Multiple Nonsense Mutations and Functional Suppressor tRNA Genes", Cell, vol. 31, pp. 137-146, Nov. 1982.
Ivics et al., "The expanding universe of transposon technologies for gene and cell engineering", Mobile DNA, pp. 1-25, 2010.
Ivics et al., "The Sleeping Beauty Transposable Element: Evolution, Regulation and Genetic Applications", Curr. Issues Mol. Biol., vol. 6, pp. 43-56, 2004.
Izsvak et al., "Sleeping Beauty Transposition: Biology and Applications for Molecular Therapy", Molecular Therapy, vol. 9, No. 2, pp. 147-156, Feb. 2, 2004.
Jacob et al., "Gene targeting in the rat: advances and opportunities", Trends in Genetics, vol. 26, No. 12, pp. 510-518, Dec. 2010.
Jakobovits, "From XenoMouse Technology to Panitumumab, the First Fully Human Antibody Product from Transgenic Mice", Nature Biotechnology, vol. 25, No. 10, pp. 1134-1143, Oct. 2007.
Kim et al., "CHO cells in biotechnology for production of recombinant proteins: current state and further potential" Appl. Microbiology Biotechnology, vol. 93, pp. 917-930, Dec. 9, 2011.

(56) References Cited

OTHER PUBLICATIONS

Kohrer et al., "Import of amber and ochre suppressor tRNAs into mammalian cells: A general approach to site-specific insertion of amino acid analogues into proteins", PNAS USA, vol. 98, No. 25, pp. 214310-214315, Dec. 4, 2001.

Kotzamaris et al., Recombining overlapping BACs into a single larger BAC, BMC Biotechnology, pp. 1-10, 2004.

Krause, Epitope-Specific Human Influenza Antibody Repertoires Diversify by B Cell Intraclonal Sequence Divergence and Interclonal Convergence, The Journal of Immunology, pp. 3704-3711, Aug. 31, 2011.

Kruif et al., "Human Immunoglobulin Repertoires against Tetanus Toxoid Contain a Large and Diverse Fraction of High-Affinity Promiscuous Vh Genes", Journal of Molecular Biology, vol. 387, pp. 548-558, Feb. 11, 2009.

Krutskikh et al., "Epididymal protein Rnase10 is required for post-testicular sperm maturation and male fertility", The FASEB Journal, pp. 4198-4209, 2012.

Kucherlapati et al., "Homologous recombination between plasmids in mammalian cells can be enhanced by treatment of input DNA", PNAS USA Genetics, vol. 81, pp. 3135-3157, May 1984.

Li et al., "Transgenic mice with a diverse human T cell antigen receptor repertoire", Nature Medicine, vol. 16, No. 9, pp. 1029-1035, Sep. 2010.

Li et al., "The minimum Internal and external sequence requirements for transposition of the eukaryotic transformation vector piggyBAC", Mol. Genet. Genomics, vol. 266, pp. 190-198, 2001.

Li et al., "Crafting rat genomes with zinc fingers", Nature Biotechnology, vol. 29, No. 1, pp. 39-41, Jan. 2011.

Li et al., "Germline Competent Embryonic Stem Cells Derived from Rat Blastocysts", Cell, vol. 135, pp. 1299-1310, Dec. 26, 2008.

Liao et al., "Generation of Induced Pluripotent Stem Cell Lines from Adult Rat Cells", Cell Stem Cell Brief Report, vol. 4, pp. 11-15, Jan. 9, 2009.

Luciw et al., "Location and Function of Retroviral and SV40 Sequences that Enhance Biochemical Transformation after Microinjection of DNA", Cell., vol. 33, pp. 705-176, Jul. 1983.

Luo et al., "Chromosomal transposition of a Tc1/mariner-like element in mouse embryonic stem cells", Proc. Natl. Acad. Sci. USA, Genetics, vol. 95, pp. 10769-10773, Sep. 1998.

Mack et al., "A small bispecific antibody construct expressed as a functional single-chain molecule with high tumor cell cytotoxicity", Proc. Natl. Acad. Sci. USA, Immunology, vol. 92, pp. 7021-7025, Jul. 1995.

Makris et al., "Mutational analysis of insertion sequence 50 (IS50) and transposon 5 (Tn5) ends", Proc. Natl. Acad. Sci. USA, Genetics, vol. 85, pp. 2224-2228, Apr. 1988 1998.

Mallender et al., "Construction, Expression, and Activity of a Bivalent Bispecific Single-chain Antibody", The Journal of Biological Chemistry, vol. 269, No. 1, pp. 199-206, 1994.

Marcello et al., Lack of Tyrosylprotein Sulfotransferase-2 Activity Results in Altered Sperm-Egg Interactions and Loss of ADAM3 and ADAM6 in Epididymal Sperm, The Journal of Biological Chemistry, vol. 286, No. 15, pp. 13060-13070, Apr. 15, 2011.

Martensson et al., "Role of the surrogate light chain and the pre-B-cell receptor in mouse B-cell development", Immunology, vol. 101, pp. 435-441, 2000.

Maul et al., "AID and Somatic Hypermutation", Advances in Immunology, vol. 105, pp. 159-191, 2010.

McCreath et al., "Production of gene-targeted sheep by nuclear transfer from cultured somatic cells", Nature, vol. 405, pp. 1066-1070, Jul. 29, 2000.

Mejia et al., "The Assembly of Large BACs by in Vivo Recombination", Genomics, vol. 70, pp. 165-170, 2000.

Mir, "Sequencing Genomes: From Individuals to Populations", Briefings in Functional Genomics Proteomics, vol. 8, No. 5, pp. 367-378, 2009.

Moreau et al., "The SV40 72 base repair repeat has a striking effect on gene expression both in SV40 and other chimeric recombinants", Nuclear Acids Research, vol. 9, No. 22, pp. 6047-6068, 1981.

Moreno et al., "The emerging role of matrix metalloproteases of the ADAM family in male germ cell apoptosis", Spermatogenesis, vol. 1, No. 3, pp. 195-208, Jul./Aug./Sep. 2011.

Mouellic et al., "Pattern of transcription of the homeo gene Hox-3.1 in the mouse embryo", Denes Dev., vol. 2, pp. 125-135, 1988.

Murphy, "VelocImmune: Immunoglobulin Variable Region Humanized Mice", Recombinant Antibodies for Immunotherapy. 1st ed. Cambridge: Cambridge University Press, pp. 100-108, 2009.

Nandi et al., "Regulated expression of genes inserted at the human chromosomal B-globin locus by homologous recombination", Proc. Natl. Sci. USA, Cell Biology, vol. 85, pp. 3845-3849, Jun. 1998.

Narayanan et al., "Bacterial Artificial Chromosome Mutagenesis Using Recombineering" Journal of Biomedicine and Biotechnology, vol. 2011, Article ID 971296, 10 pages, Dec. 9, 2010.

Nelson et al., "Development trends for human monoclonal antibody therapeutics", Nature Reviews, Drug Discovery, vol. 9, pp. 767-774, Oct. 2010.

Neuberger et al., "Somatic hypermutation", Current Opinion in Immunology, vol. 7, pp. 248-254, 1995.

Oancea et al., "Expression of the (Recombinant) Endogenous Immunoglobulin Heavy-Chain Locus requires the Intronic Matrix Attachment Regions", Molecular and Cellular Biology, vol. 17, No. 5, pp. 2658-2668, May 1997.

Osborn et al., "High-Affinity IgG Antibodies Develop Naturally in Ig-Knockout Rats Carrying Germline Human IgH/Ig k/Ig? Loci Bearing the Rat Ch Region", The Journal of Immunology, pp. 1481-1491.

Osoegawa et al., "Bacterial Artificial Chromosome Libraries for Mouse Sequencing and Functional Analysis", Genome Research, pp. 16-28, 2000.

Pavlicek et al., "Ancient Transposable Elements, Processed Pseudogenes, and Endogenous Retroviruses", Genomic Disorders, pp. 57-72, 2006.

Pelham et al., "Expression of a *Drosophila* Heat Shock Protein in Mammalian Cells: Transient Association with Nucleoli after Heat Shock", Philosophical Transactions of the Royal Society, pp. 301-307, 1984.

Perlot et al., "Antisense transcripts from immunoglobulin heavy-chain locus V(D)J and switch regions", PNAS, vol. 105, No. 10, pp. 3843-3848, Mar. 11, 2008.

Perlot et al., "Cis-Regulatory Elements and Epigenetic Changes Control Genomic Rearrangements of the IgH Locus", Advances in Immunology, vol. 99, pp. 1-32, 2008.

Plasterk et al., "Resident aliens: The Tc1/mariner superfamily of transposable elements", YIG, vol. 15, No. 8, pp. 326-333, Aug. 1999.

Popov et al., "A Human Immunoglobulin λ Locus is Similarly Well Expressed in Mice and Humans", Journal of Experimental Medicine, vol. 189, No. 10, pp. 1611-1619, May 17, 1999.

Primakoff et al., "Penetration, Adhesion, and Fusion in Mammalian Sperm-Egg Interaction", Science, vol. 296, pp. 2183-2185, Jun. 21, 2002.

Primakoff et al., "The ADAM Gene Family: surface proteins with adhesion and protease activity", Trends in Genetics, vol. 16, No. 2, pp. 83-87, Feb. 2000.

Puente et al., "Comparative genomic analysis of human and chimpanzee proteases", Genomics, vol. 86, pp. 638-647, 2005.

Raynard et al., "Cis-acting regulatory sequences promote high-frequency gene conversion between repeated sequences in mammalian cells", Nucleic Acids Research, vol. 32, No. 19, pp. 5916-5927, Nov. 4, 2004.

Reddy et al., "Monoclonal antibodies isolated without screening by analyzing the variable-gene repertoire of plasma cells", Nature Biotechnology, vol. 28, No. 9, pp. 965-971, Sep. 2010.

Retter, "Sequence and Characterization of the Ig Heavy Chain Constant and Partial Variable Region of the Mouse Strain 129S1", The Journal of Immunology, vol. 179, pp. 2419-2427, 2007.

Rogozin et al., "Cutting Edge: DGYW/WRCH is a Better Predictor of Mutability at G:c Bases in Ig Hypermutation Than the Widely Accepted RGYW/WRCY Motif and Probably Reflects a Two-Step Activation-Induced Cytidine Deaminase-Triggered Process", Journal of Immunology, vol. 172, pp. 3382-3384, 2004.

(56) References Cited

OTHER PUBLICATIONS

Sakai et al., "Recombination and transcription of the endogenous Ig heavy chain locus is effected by the Ig heavy chain intronic enhancer core region in the absence of the matrix attachment regions", Proc. Natl. Acad. Sci., vol. 96, pp. 1526-1531, Feb. 1999.
Sarkar et al., "Molecular evolutionary analysis of the widespread *piggyBac* transposon family and related "domesticated" sequences", Mol. Gen. Genomics, vol. 270, pp. 173-180, 2003.
Sasso et al., "Expression of the Immunoglobulin Vh Gene 51p1 is Proportional to Its Germline Gene Copy Number", J. Clin. Invest., vol. 97, No. 9, pp. 2074-2080, May 1996.
Sauer, "Functional Expression of the cre-lox Site-Specific Recombination System in the Yeast *Saccharomyces cerevisiae*", Molecular and Cellular Biology, vol. 7, No. 6, pp. 2087-2096, Jun. 1987.
Sauer et al., "Cre-stimulated recombination at loxP-containing DNA sequences placed into the mammalian genome", Nucleic Acids Research, vol. 17, No. 1, pp. 147-161, 1989.
Sauer et al., "Site-specific DNA recombination in mammalian cells by the Cre recombinase of bacteriophage P1", Proc. Natl. Acad. Sci. USA, Genetics, vol. 85, pp. 5166-5170, 1988.
Schlake et al., "Use of Mutated FLP Recognition Target (FRT) Sites for the Exchange of Expression Cassettes at Defined Chromosomal Loci", Biochemistry, vol. 33, pp. 12746-12751, 1994.
Schrock et al., "Comparative Genomic Hybridization (CGH)-Detection of Unbalanced Genetic Aberrations Using Conventional Micro-Array Techniques", Molecular Cytogenetics, Unit 8.12.1, Supplement 18, 30 pages, 2001.
Schweinfest et al., "A heat-shock-inducible eukaryotic expression vector", Gene. 71, pp. 207-210, 1988.
Seed et al., "Purification of genomic sequences from bacteriophage libraries by recombination and selection in vivo", Nucleic Acids Research, vol. 11, No. 8, pp. 2427-2445, 1983.
Serwe et al., "V(D)J recombination in B cells is impaired but not blocked by targeted deletion of the immunoglobulin heavy chain intron enhancer", The EMBO Journal, vol. 12, No. 6, pp. 2321-2327, 1993.
Shaul et al., "Homologous recombination between a virus and a chromosomal sequence in mammalian cells", PNAS, Genetics, vol. 82, pp. 3781-3784, Jun. 1985.
Shimizu et al., "Immunoglobulin double-isotype expression by trans-mRNA in a human immunoglobulin transgenic mouse", Proc. Natl. Acad. Sci. USA, Immunology, vol. 86, pp. 8020-8023, Oct. 1989.
Simpson et al., "Gene variation among 129 substrains and its importance for targeted mutagenesis in mice", Nature Genetics, vol. 16, pp. 19-27, May 16, 1997.
Skoultchi et al., "Expression of Genes Inserted at the Human B-Globin Locus by Homologous Recombination", Developmental Control of Globin Gene Expression, pp. 581-594, 1987.
Smithies, "Direct Alteration of a Gene in the Human Genome" J. inher. Metab., Dis. 9, Suppl. 1, pp. 92-97, 1986.
Smithies et al., "Insertion of DNA sequences into the human chromosomal B-globin locus by homologous recombination", Nature, vol. 317, No. 19, pp. 230-234, Sep. 1985.
Sohn et al., "Somatic Hypermutation of an Immunoglobulin μ Heavy Chain Transgene", J. Exp. Med., vol. 177, pp. 493-504, Feb. 1993.
Song et al., "Accurate modification of a chromosomal plasmid by homologous recombination in human cells", Proc. Natl. Acad. Sci. USA, Genetics, vol. 84, pp. 6820-6824, Oct. 1987.
Sonoda et al., "B Cell Development under the Condition of Allelic Inclusion", Immunology, vol. 6, pp. 225-233, Mar. 1997.
Taki et al., "Targeted Insertion of a Variable Region Gene into the Immunoglobulin Heavy Chain Locus", Science, vol. 262, pp. 1268-1271, Nov. 19, 1993.
Talbot et al., "Cell Adhesion and Fertilization: Steps in Oocyte Transport, Sperm-Zona Pellucida Interactions, and Sperm-Egg Fusion", Biology of Reproduction 68, pp. 1-9, 2003.
Thomas et al., "High Frequency Targeting of Genes to Specific Sites in the Mammalian Genome", Cell, vol. 44, pp. 419-428, Feb. 14, 1986.
Thomas et al., "Introduction of homologous DNA sequences into mammalian cells induces mutations in the cognate gene" Nature, vol. 324, Nov. 1986.
Thomas et al., "Site-Directed Mutagenesis by Gene Targeting in Mouse Embryo-Derived Stem Cells", Cell, vol. 51, pp. 503-512, Nov. 6, 1987.
Vassilieva et al., "Establishment of SSEA-1- and Oct-4 Expressing Rat Embryonic Stem-like Cell Lines and Effects of Cytokines of the IL-6 Family on Clonal Growth", Experimental Cell Research, vol. 258, pp. 361-373, 2000.
Vora et al., "Altering the Antibody Repertoire via Transgene Homologous Recombination: Evidence for Global and Clone-autonomous Regulation of Antigen-driven B Cell Differentiation", J. Exp. Med., vol. 181, pp. 271-281, Jan. 1995.
Wang et al., "AID upmutants isolated using a high-throughput screen highlight the immunity/cancer balance limiting DNA deaminase activity", Nature Structural & Molecular Biology, vol. 16, No. 7, Jul. 2009.
Wang et al., "Altering the spectrum of immunoglobulin V gene somatic hypermutation by modifying the active site of AID", J. Exp. Med., vol. 207, No. 1, pp. 141-153, 2010.
Wang et al., "Catching a Moving Target", Science, Biochemistry, vol. 333, pp. 834-835, Aug. 21, 2011.
Wilkie et al., "Analysis of the Integrant in MyK-103 Transgenic Mice in which Males Fail to Transmit the Integrant", Molecular and Cellular Biology, pp. 1646-1655, May 1987.
Zou et al., "Cre-loxP-mediated gene replacement: a mouse strain producing humanized antibodies", Current Biology, vol. 4, No. 12, pp. 1099-1104, 1994.
Martinez-Jean et al., (2001) Nomenclature and overview of the mouse (*Mus musculus* and *Mus* sp.) immunoglobulin kappa (IGK) genes, Exp. Clin. Immunogenet. 18(4):255-279.†

\* cited by examiner
† cited by third party

Distribution of JH Usage Within Each VHs

|      | JH1 | JH2 | JH3 | JH4 | JH5 | JH6 |
|------|-----|-----|-----|-----|-----|-----|
| V2-5 |     | 1   | 5   | 5   | 2   | 1   |
| V4-4 |     | 1   | 1   | 1   |     | 8   |
| V1-3 | 1   | 6   | 6   | 49  | 13  | 40  |
| V1-2 | 1   |     |     | 1   |     | 1   |
| V6-1 |     | 1   | 4   | 18  | 1   | 29  |
| Total| 2   | 9   | 16  | 74  | 16  | 79  |

The data includes 196 independent sequences.

Distribution of DH Usage Within Each VHs

The data includes 196 independent sequences.

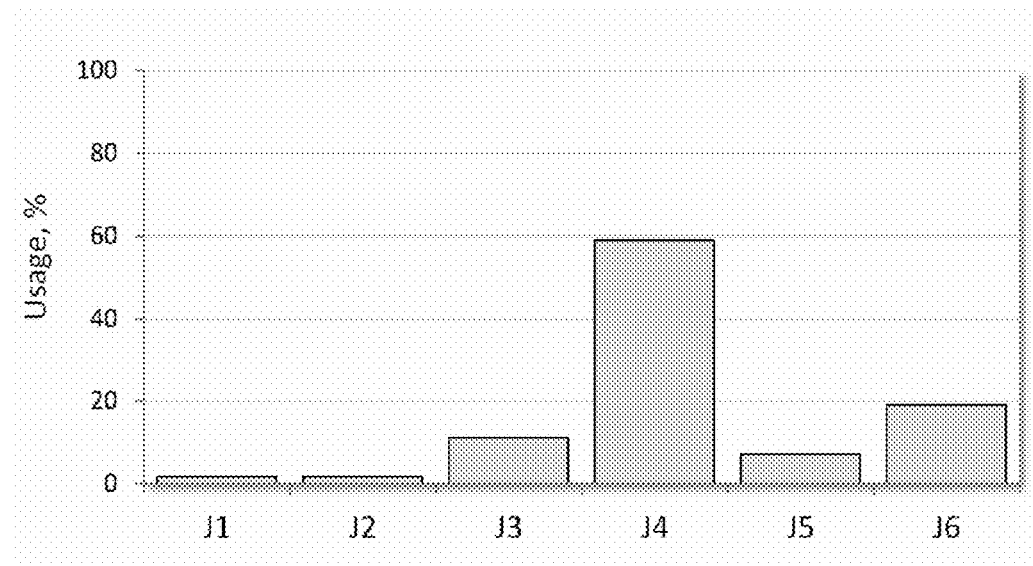
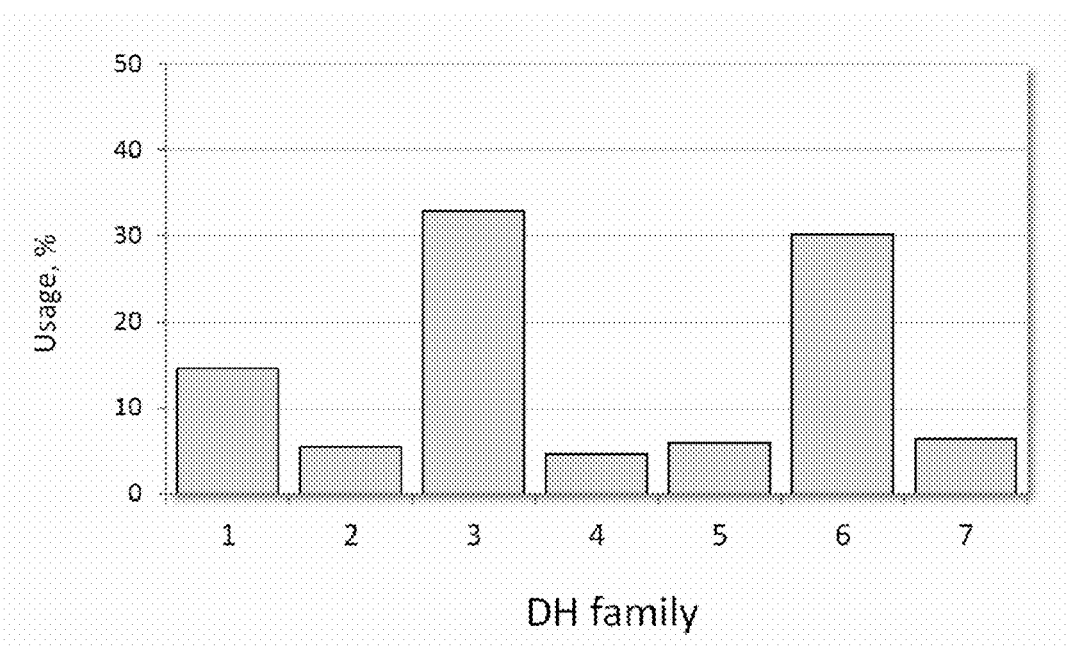
Fig. 49

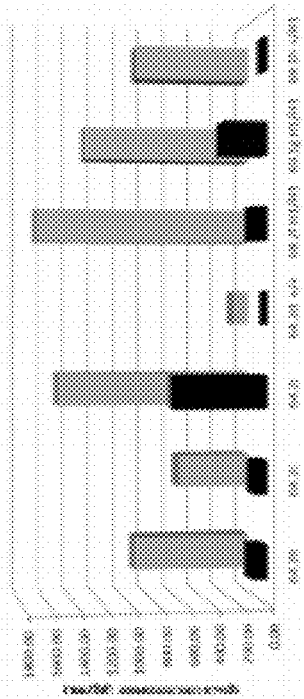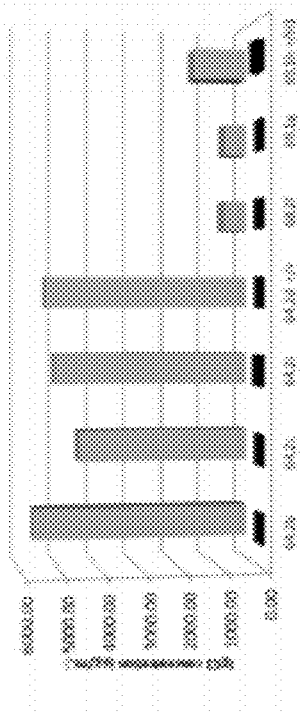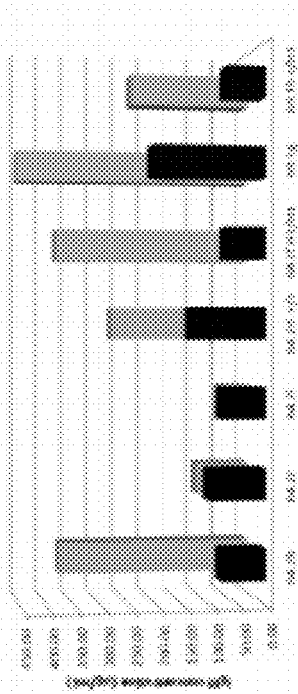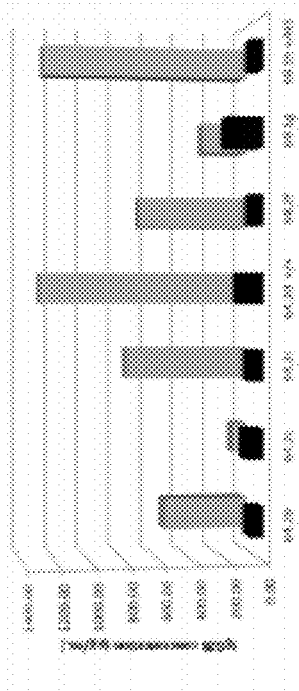

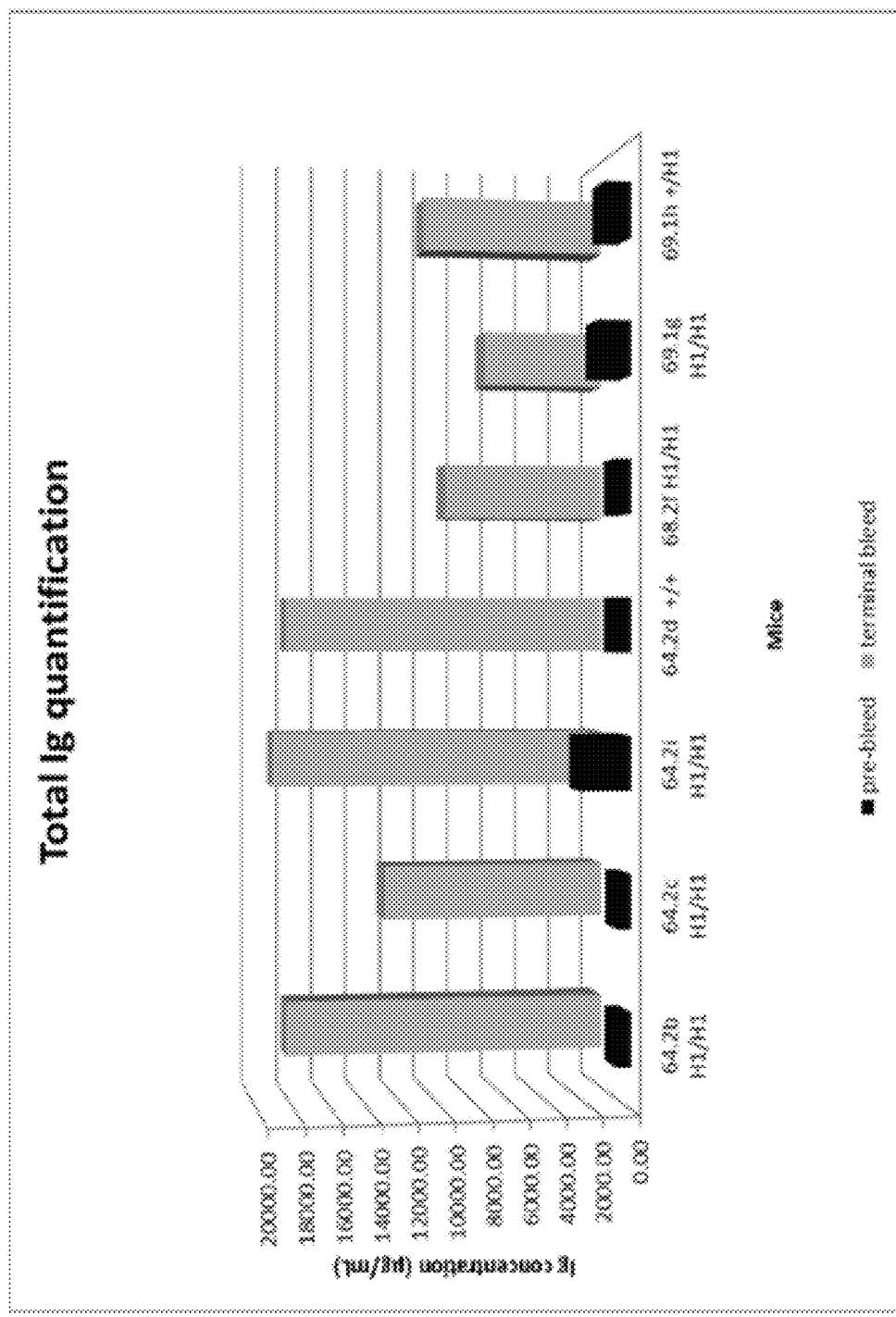

SEQUENCE LISTING

```
<160> NUMBER OF SEQ ID NOS: 68

<210> SEQ ID NO 1
<211> LENGTH: 4272
<212> TYPE: DNA
<213> ORGANISM: Rattus norvegicus

<400> SEQUENCE: 1
agatctgccc atctcaggct agttaaatta gttcatccca gtttggccca acttacccca      60
tctagagtag cgaaactaat ctgagcctag ctaagtccca tttagtttaa tgtagcccag     120
cttggcacag gctaatacat actgctacag tttggtctag cctaccctaa ttaagctgat     180
ccaggcctgg gtagacctag ctcatctcag cccagttaag gttatccagt acatctcttt     240
ccagttcagc tcaggttacc ataccttatc tcaattcagc tcagctagtg taattcatct     300
tagttcatcc cctaccccte tagactccct gttgatctta actcagttta gacatggcca     360
acaaagcctg gcccaactca ggccaggtta gtgtagctca gcataagcag tctagccttg     420
ctcagtctag ctcacccttc ctcatctaaa ttcaactcag ctatgccggc cctgcagcag     480
gtcccctcag ctcacccaag tccaaccagt tcagtctggc tcatttaagt cttgacaatc     540
cccaattcat cccagctcag cttagcataa ctcaggcagt ccattcttag cccaacccag     600
tttagcccag tttatcccag ttcatcctgg ctgtactcag tgcaactcga ttcatgttct     660
cccaggccac ctcagcccag ttcatggtag ctcatctgag cccaacttat cccagctcat     720
cccaaaccac ctcacctaag ccctgctcag cctagctcat ctgagcctag ttcaacctct     780
ctcatcctgc cagctagccc agtttagtcc acatcatctt gcaaagctca accagcccaa     840
```

```
gtcagccggg tccagctcat tcatgtccaa accagctcag tcatgctcat cctaactcag    900
cctcaccatc atccacatca gctagcccag ttcagctgag ctcatcccag cccacttcaa    960
tcacagctca tttaagtaca gctcaccccc gctctattta gctcaagcta gcttatttag   1020
cctacttcat cccagctcag cccagccaac tcaactcatc ctagctcagc taaaccctgc   1080
tcagctcacc caagcaaagc tgactccaac ccagatcctt tcagctcagc tcacccagct   1140
caggccagct cacccatccc agctcaccca gcttagctca cccagcccag ctcagcccag   1200
ctcacccagc ccagctcagc ccagctcacc cagcccagct cagcccagct cagctcagct   1260
cagctcagct cagctcagct cacccagctc agctcagcca gctcagctca ccccagctca   1320
gtccagctca gttcagctca ccccagctca gctcacccaa ctcagctcac tcaactcagc   1380
tcacccaact cagctcagct cagttcaccc agctcagctc acccagccca gcacagctca   1440
tctcacccag ctcagctcac ccagcccagc tcacccagc tcaccccagc tcagctcagc    1500
tcaccccagc tcagcccagc tcagctcacc cagctcagct cacccaactc agctcagctc   1560
agttcaccca gctcagctca cccagcccag cacagctcat ctcacccagc ccagctcacc   1620
ccagctcacc ccagctcagc tcagctcagc ccagctcacc cagctcagct cagctcaccc   1680
cagctcagct cacccagctc agctcaccca gcccagctca gctcagctca ccccagctca   1740
gcccagctca gctcacccag ctcagctcac ccagcccagc tcaccccagc tcaccccagc   1800
tcagtccagc tcagttcagc tcacccagct cagctcaccc aactcaactc agctcagttc   1860
acccagctca gctcagctca ccccagctca ccccagctca cccagctcag ttcagctcac   1920
cccagctcag ttcacccagc tcagctcacc cagcccagct cagcccagct cacccccagct  1980
cagctcaacc agatcagctc agcccagctc acctagtttt agttcaccca gcccagctca   2040
ccccagctca gctcaccca actcagctca cccagctcat cccagctcag ccagctaatc    2100
ccagctcagc tcaccccagc tcagctcacc cagctcagct cacccaactc agctcacccc   2160
agctcacccc agctcatccc agctcatccc agttcagacc tgttcagctc atctcacccc   2220
agctcagctc accccagttc agctcaccta gcccaactca ccccagctca gtccagctca   2280
gttcagctca cccaactca tctcacccag ctcagctcac cccagctcat cccagctcag   2340
ctcaccccag ttcagccctg ttcagctcat ctcacccagc tcagctcatc cagcccagct   2400
caccccagct caccccagct cagtccagct cagttcagct cacccagctc agctcaccca   2460
actcaactca gctcagttca cccagctcag ctcagctcac cccagctcac ccagctcagt   2520
tcagctcacc ccagctcagt tcacccagct cagctcaccc agcccagctc aaccagatca   2580
gctcagccca gctcacccta gtttagttca cccagcccag ctcaccccag ctcagctcac   2640
cccaactcag ctcacctagc tcatcccagc tcagctcacc ccagctcagc tcaccccagc   2700
tcatctcacc ccagctcagc tcacccagct catcccagct cagctcagcc agctcatcc    2760
cagccctgct catcccagct cagctcagct cagcccagct cagcccagct cagcccagct   2820
cagcccagct cagcccagct cagctcaacc cagctcagct cacccagccc agctcagccc   2880
agctcaccca gctcagctca ccccagctca gctcacccca gctcatctca cccagctcag   2940
ctcacccagc tcagcccagc tcagctcagc tcacccagct catctcaccc agctcagctc   3000
accccagctc atcccagctc agctcacccc agttcagccc tgttcagctc atctcacccc   3060
agctcagctc accagttca gctcatccca gccatcccag ctcagctcag cccagctca    3120
gcccagctca gcccagccca gcccagccca gctcagctca gcccagctca gcccagctca   3180
gtccagctca gcttagccca gcccagctca gctcagccca gctcagccca gctcagccca   3240
```

```
gctcagctca cccagctcac cccagctcag cccagctcag cccagctcag ctcacccagc    3300
tcacccacc ccagctcacc ccagttcagc ccagctcagc ccagctcagc ccagcccagc    3360
ccagcccagc ccagcccagc tcagcccagc tcagctcagc ccagcccagc tcagctcagc    3420
ccagctcagc ccagctcatc ccagctcagc tcaccccagc tcagcccagc tcagcccagc    3480
tcagctcacc cagctcaccc caccccagct caccccagtt cagcccagct catccagctc    3540
agctcacccc cagctctgct cacccagctc agctcagctt acccagctca gctcaactca    3600
cccagctcag ctcacccagc tcagctcagc tcaccccagc ccagctcagc tcagctcacc    3660
ccagctctgc tcacccagct cagctcagct cacctcagct ctgctcaccc agctcagctc    3720
aaccacctca ggtcagccca gctcaccccca gcttacccca gctcacccag ctcagctcag    3780
ctcacccagc tcagctcacc cagctcagct caccccagct acccccagct cacccccagct    3840
cagctaaccc agctcagctc acccagctca gctcacccag ctcagctcat cccagctcac    3900
cccagctacc acagagtagc tcatgctagc tcagctcacc ccagcacaac acagcccaac    3960
acagctcagt tcagagcagt ccagtagagt ttagctccaa tcagcccaga tcaagacaat    4020
tcattccaat ttggctatct tggttaagtc agcctagttt agcttagccg gcctagctca    4080
attcagctca ttgcagtcta cctcgttcct gctcaagtcc agctttggct acctcagagt    4140
aatcatctca gcttagcaca tttttgaagg gctcagggaa gcctacacat ctcagtccaa    4200
ctgtgcttaa ctagagccta gcttcctagc caggctgtca accttgttca ctaaattttg    4260
ctcagcaagc tt                                                      4272

<210> SEQ ID NO 2
<211> LENGTH: 22190
<212> TYPE: DNA
<213> ORGANISM: Artificial Sequence
<220> FEATURE:
<223> OTHER INFORMATION: Tragetting Vector (long version)

<400> SEQUENCE: 2
gcggccgcaa cctgggcaaa tgggagctta gcaacaatgt aggggggctgg acctagactt      60
cctacacatt tgtagcagat gtgcagcttg gtcttcatgt gtgtattacc ctaacatttg     120
gagcaggagc tgtctctgac tctgttgcct gccattggat cccttcccc tgcttgggct     180
gccttgtttg gccttagtag gaaaggatgt gcttagtcct gctgtgactt gatgtcccta     240
ggcagaatga taccccaggg gggctcccca tctctgagga gatgggcaaa gggtaatggt     300
tggagggact tgtgaggctg ggactgggag gagagaaagg agacagctgt aactggaatg     360
atgttaagtg aacaaatgaa tggatagatt agatagacag atagacagac agacagacag     420
acagacagac agacagacag acagatagaa agatagatag ataagggga aaagaaacgt     480
agctgagcaa gccagagaga gcaagccaaa taagcagcat tcctccatga cttttccttc     540
agctcctgcc tatgagtctg ccttgacttc cctcagtgat tggttgtaag ttaaaaggtg     600
aaataaaccc tttctttgac aagttgcttt tggttctgat ttttatcaca gcaagagaaa     660
atcaaactag aacaaacatg tattttttcct ggcacatgtc catagtaagg cagaaatgat     720
cttcagacct agaccataga tactacagag agcagaagtg tagataggtg gacttactgt     780
atgattgtaa tccaagtaaa tctacatagc tagagagcta gaggaaaggc caaagcttcc     840
tctgggaggt cagatcctgt cgcactgtag ccaataaggc atattgcatc acaggaaagg     900
actaagaccc aggctggcaa tagtgtctgt atcttaacta gacctctcta gtgagtgagg     960
```

```
aaggaagttt gtgagagccc agactgtggg ctcggaaggt acctgccatg cccctgttag      1020
taactgagta ctacagcagg agcaggtgtt ctctagaaag cctgagacaa ctctacttct      1080
tctctcaaga gaccacctaa tacaggcctg agagaacaga ctctggaaat agatgggact      1140
taaggagcta agatctagag ctcatctaca gagcagaatc ccagccaaga gaacaaagaa      1200
tactggctct ctctcctgtt ccctactcct agagttctaa acacactat agggaaggga      1260 gcctctagac ctccgtccat tccccatctt gctcattcca tcttcccatg tccccaggtc      1320
tccaagccac agacactacc tttcctattc acccaccttt ctgtgtccct aggtccccag      1380
gccatagtca cctccccccca cacacacccc actcaccctg ccccatctat gccctagat       1440 gcttacttac cagagtcttt tgtctgacgt ggggctacaa gcatctatgc tccctaagca      1500
cctactgctg acctgtagga cccagctctg aaccaactca tataagtaaa tacagactct      1560
cccctgtctt aggatggcct cctggatcag gaggagacca ctgccaaaga accttctctc      1620
agagcactga actcctcccc tgtaccactt aggacagacc tgagacctat tattactgat      1680
taccagagct ctggcagtga ccacggagga gataggtcca ccctggacac aggaaacaca      1740
gcagcagaga tactgctcca tcacaacagt agagtgacac tttagacttt aatttgggtc      1800
actttcctgc tgcagaggtg ggatcagaaa gcaaagagca gtatgagtgc ctgataggca      1860
cccaagtaca ctatagagta ctcatggtga ataaggtacc tccatggctt cccagggagg      1920
ggcactgccc caccccacc atcacagacc tttctccata gttgataact cagacacaag       1980
tgaatgacag atggacctcc atctactctt attttaaaaa gaagacaaac cccacaggct      2040
cgagaacttt agcgactgtt ttgagagaaa tcattggtcc ctgactcaag agatgactgg      2100
cagattgggg atcagaatac ccatactctg tggctagtgt gaggtttaag cctcagagtc      2160
cctgtggtct ctgactggtg caaggttttg actaagcgga gcaccacagt gctaactggg      2220
accacggtga cacgtggctc aacaaaaacc ttctgtttgg agctctccag gggcagcctg      2280
agctatgagg aagtagagag gcttgagaaa tctgaggaag aaaagagtag atctgagagg      2340
aaaggtagct ttctggaggt caggagacag tgcagagaag aacgagttac tgtggacagg      2400
tcttagatgg ggaaagaatg agcaaatgca agcatcagaa gggtggatgc aatgtcctgc      2460
caaggactta ccaagaggat ccccggacag agcaggcagg tggagttgac tgagaggaca      2520
gggtaggtgc aggtccctct ctcgtttcct ttctccttct cctgtttcct tcctctcttg      2580
tcacaggtct cactatgcta gccaaggcta gcctgaaaga ttaccatcct acagatgggc      2640
ccatccagtt gagttaaggt ggagatctct ccaaacatct gagtttctga ggcttggatg      2700
ccactgggga cgccaaggga ctttgggctg ggtttggttg gccccagatg aagggctact      2760
tcactgggtc tataattact ctgatgtcta ggaccagggg gctcaggtca ctcaggtcag      2820
gtgagtcctg catctgggga ctgtggggtt caggtgtcct aaggcaggat gtggagagag      2880
ttttagtata ggaacagagg cagaacagag actgtgctac tggtacttcg atgtctgggg      2940
cgcagggacc acggtcaccg tctcctcagg taagctggct ttttctttc tgcacattcc       3000 attctgaaat gggaaaagat attctcagat ctccccatgt caggccatct gccacactct      3060
gcatgctgca gaagcttttc tgtaaggata gggtcttcac tcccaggaaa agaggcagtc      3120
agaggctagc tgcctgtgga acagtgacaa tcatggaaaa taggcattta cattgttagg      3180
ctacatgggt agatgggttt ttgtacaccc actaaagggg tctatgatag tgtgactact      3240
ttgactactg gggccaaggc accactctca cagtctcctc aggtgagtcc ttacaacctc      3300
tctcttctat tcagcttaaa tagatttac tgcatttgtt ggggggaaa tgtgtgtatc        3360
```

```
tgaatttcag gtcatgaagg actagggaca ccttgggagt cagaaagggt cattgggagc    3420
cctggctgat gcagacagac atcctcagct cccagacttc atggccagag atttataggg    3480
atcctggcca gcattccgc taggtccctc tcttctatgc tttctttgtc cctcactggc     3540
ctccatctga gatcatcctg gagccctagc caaggatcat ttattgtcag gggtctaatc    3600
attgttgtca caatgtgcct ggtttgctta ctggggccaa gggactctgg tcactgtctc    3660
tgcaggtgag tcctaacttc tcccattcta aatgcatgtt ggggggattc tgagccttca    3720
ggaccaagat tctctgcaaa cgggaatcaa gattcaaccc ctttgtccca agttgagac     3780 atgggtctgg gtcagggact ctctgcctgc tggtctgtgg tgacattaga actgaagtat    3840
gatgaaggat ctgccagaac tgaagcttga agtctgaggc agaatcttgt ccagggtcta    3900
tcggactctt gtgagaatta ggggctgaca gttgatggtg acaatttcag ggtcagtgac    3960
tgtctggttt ctctgaggtg aggctggaat ataggtcacc ttgaagacta agagggggtc    4020
caggggcttc tgcacaggca gggaacagaa tgtggaacaa tgacttgaat ggttgattct    4080
tgtgtgacac caggaattgg cataatgtct gagttgccca ggggtgattc tagtcagact    4140
ctggggtttt tgtcgggtat agaggaaaaa tccactattg tgattactat gctatggact    4200 actgggggtca aggaacctca gtcaccgtct cctcaggtaa aatgcctc tccaggtctt     4260 tattttttaac ctttgttatg gagttttctg agcattgcag actaatcttg gatatttgtc   4320
cctgagggag ccggctgaga aagttgggga aataaactgt ctagggatct cagagccttt    4380
aggacagatt atctccacat ctttgaaaaa ctaagaatct gtgtgatggt gttggtggag    4440
tccctggatg atgggatagg gactttggag gctcatttga gggagatgct aaaacaatcc    4500
tatggctgga gggatagttg gggctacgcg ttttttaaccc tagaaagata gtctgcgtaa    4560
aattgacgca tgcattcttg aaatattgct ctctcttct aaatagcgcg aatccgtcgc     4620
tgtgcattta ggacatctca gtcgccgctt ggagctcccg tgaggcgtgc ttgtcaatgc    4680
ggtaagtgtc actgattttg aactataacg accgcgtgag tcaaaatgac gcatgattat    4740
cttttacgtg acttttaaga tttaactcat acgataatta tattgttatt tcatgttcta    4800
cttacgtgat aacttattat atatatattt tcttgttata gatatcgcta gtggatccgg    4860
ctggttcttt ccgcctcaga aggtactttt tttttttttt ttttttttt ttttttttt      4920 tttttttttt ttttttttt tttttaaat ttttgggaat ttattgattt gcatttaaaa      4980
gggaactgct gacaaagatt cactggtaat aatttgaaca agttggaaaa tacagtcaac    5040
attactgaaa cactactaaa ataattccag gacagaacaa aacttcttag atgctgtctt    5100
tgatgtgaaa attgactgct tcttactttt ctaacacacg gtggtataat taacaatatt    5160
caatcacttc tattctttcc tgcatatata aaaattaaaa taccaattaa aaaactaata    5220
tatcttctct ttatttctta cagatatgag ttcaatgttt cactcaatag tgctgtggtt    5280
taagagaatt ttttcattta caagttaaac aacaatccgc ccaaagggaa ctgatagtct    5340
ataggctcat agtgcaaata aacagtttag gaatgcagca actgacattt ctaaagtaca    5400
aaacagataa aattcttaga agatacatgc aaaaagctct actaagcaga tggccacaga    5460
actagaacat tgataatttt actggcgatg tcaataggac tccagatgtt tccaaactca    5520
acttgaactc tcatcttagg ctttgtattt tgcttttcca gtttcactaa tgacacaaac    5580
atgattcaaa tccctgaagt attcattata gtcaagggca tatcctacaa caaacttgtc    5640
tggaatttca aatccaacaa agtctggctt atatccaaca cttcgtgggg tccttttcac    5700
```

```
cagcaagctt gcgaccttga ccatctttgg attatactgc ctgaccaagg aaagcaaagt    5760
ctgcattgtt ttgccagtgt caattatatc ttccacaatc aagacattct ttccagttaa    5820
agttgagaga tcatctccac caattacttt tatgtcccct gttgactggt cattacaata    5880
gctcttcagt ctgataaaat ctacagtcat aggaatggat ctatcactat ttctattcag    5940
tgctttgatg taatccagca ggtcagcaaa gaatttatag ccccccttga gcacacagag    6000
ggctacaatg tgatggcctc ccatctcctt catcacatct cgagcaagac gttcagtcct    6060
acagaaataa aatcaggaat ttaatagaaa gtttcataca ttaaacttta taacaaacac    6120
ctcttagtca ttaaacttcc acaccaacct gggcaatata gtgagacccc atgcctgcaa    6180
aaaaaaaaaa attagccagg catggtagca tgtacctgta gtcccagcta cttgagaggt    6240
gaggtgggaa atcacttta gtgcaggatg ttgaggctgg agtgaactgt gattgtgcca    6300
ctgcactcca gcctggacaa tagagcaaga ccttgtctca aaaaaatgca ttaaaaattt    6360 ttttaaatc ttccacgtaa cacatccttt gccctcatgt ttcataaggt aaaaaatttg    6420
ataccttcaa aaaaccaag cataccacta tcataatttt ttttaaatgc aaataaaaac    6480
aagataccat tttcacctat cagactggca ggttctgatt aaatgaaatt tcttggataa    6540
tatacaatat taagagagac tgtagaaact gggccagtgg ctcatgcctg taatcccagc    6600
actttgggag ctgggtaac atggcgaacc ctgtttctac aaaataaaaa tattagctgg    6660
gagtggtggc gcacacctat agtcccagct actcaggagg ctgaggtgga aggatcgctt    6720
gaacccagga ggttgagact gcagtgaact gtgatcattc tgctgcactg caccccagcc    6780
tgggcaacag agaccttgtc tcaaaaaaaa aaaaaaaga gacaaattgt gaagagaaag    6840
gtactctcat ataacatcag gagtataaaa tgattcaact tcttagagga aaatttggca    6900
ataccaaaat attcaataaa ctctttcccc ttgacccaga aattccactt gaataaagct    6960
gaacaagtac caaacatgta aaagaatgtt tcttctagta cagtcggtaa gaacaaaata    7020
gtgtctatca atagtggact ggttaaatca gttatggtat ctccataaga cagaatgcta    7080
tgcaaccttt aaaatatatt agatagctct agacagtgga tcccctcgag ggacctaata    7140
acttcgtata gcatacatta tacgaagtta tattaagggt tattgaatat gtcgactaga    7200
cacactaata ttaaagtgt ccaataacat ttaaaactat actcatacgt taaaatataa    7260
atgtatatat gtacttttgc atatagtata catgcatagc cagtgcttga aagaaatgt    7320 gtacagaagg ctgaaaggag agaactttag tcttcttgtt tatggcctcc atagttagaa    7380 tatttataa cacaaatatt ttgatattat aattttaaaa taaaacaca gaatagccag    7440 acatacaatg caagcattca ataccaggta aggtttttca ctgtaattga cttaacagaa    7500
aattttcaag ctagatgtgc ataataataa aaatctgacc ttgccttcat gtgattcagc    7560
cccagtccat taccctgttt aggactgaga aatgcaagac tctggctaga gttccttctt    7620
ccatctccct tcaatgttta ctttgttctg gtccctacag agtccactat accacaact    7680 gatactaagt aattagtaag gccctcctct tttattttta ataaagaaga ttttagaaag    7740
catcagttat ttaataagtt ggcctagttt atgttcaaat agcaagtact cagaacagct    7800
gctgatgttt gaaattaaca caagaaaaag taaaaaacct cattttaaga tcttacttac    7860
ctgtccataa ttagtccatg gggaataaac accctttcca aatcctcagc ataatgatta    7920
ggtatgcaaa ataaatcaag gtcataacct ggttcatcat cactaatcac gacgccaggg    7980
ctgcgggtcg ccataacgga gccggccggc gcgcgggctg aataacttcg tataatgtgt    8040
actatacgaa gttatttgtt caggaggagg aagccggtgg cggagcagag gaggaggcgg    8100
```

```
aggcgcagca agaccccccc ccccctgcag gtcgaaaggc ccggagatga ggaagaggag    8160
aacagcgcgg cagacgtgcg cttttgaagc gtgcagaatg ccgggcctcc ggaggacctt    8220
cgggcgcccg ccccgcccct gagcccgccc ctgagcccgc cccggacccc acccccttccc   8280 agcctctgag cccagaaagc gaaggagcaa agctgctatt ggccgctgcc ccaaaggcct    8340
acccgcttcc attgctcagc ggtgctgtcc atctgcacga gactagtgag acgtgctact    8400
tccatttgtc acgtcctgca cgacgcgagc tgcggggcgg gggggaactt cctgactagg    8460
ggaggagtag aagtggcgc gaaggggcca ccaaagaacg gagccggttg gcgcctaccg     8520
gtggatgtgg aatgtgtgcg aggccagagg ccacttgtgt agcgccaagt gcccagcggg    8580
gctgctaaag cgcatgctcc agactgcctt gggaaaagcg cctcccctac ccggtagata    8640
tctataacaa gaaatatat atataataag ttatcacgta agtagaacat gaaataacaa     8700
tataattatc gtatgagtta aatcttaaaa gtcacgtaaa agataatcat gcgtcatttt    8760
gactcacgcg gtcgttatag ttcaaaatca gtgacactta ccgcattgac aagcacgcct    8820
cacgggagct ccaagcggcg actgagatgt cctaaatgca cagcgacgga ttcgcgctat    8880
ttagaaagag agagcaatat ttcaagaatg catgcgtcaa ttttacgcag actatctttc    8940
tagggttaaa agaattcgat atcaagctta tcgatgtagt tggagatttt cagttttag    9000 aataaaagta ttagttgtgg aatatacttc aggaccacct ctgtgacagc atttatacag    9060
tatccgatgc atagggacaa agagtggagt ggggcacttt ctttagattt gtgaggaatg    9120
ttccgcacta gattgtttaa aacttcattt gttggaagga gagctgtctt agtgattgag    9180
tcaagggaga aaggcatcta gcctcggtct caaaagggta gttgctgtct agagaggtct    9240
ggtggagcct gcaaaagtcc agctttcaaa ggaacacaga agtatgtgta tggaatatta    9300
gaagatgttg cttttactct taagttggtt cctaggaaaa atagttaaat actgtgactt    9360
taaaatgtga gagggtttc aagtactcat ttttttaaat gtccaaaatt tttgtcaatc    9420
aatttgaggt cttgtttgtg tagaactgac attacttaaa gtttaaccga ggaatgggag    9480
tgaggctctc tcatacccta ttcagaactg acttttaaca ataataaatt aagtttaaaa    9540
tatttttaaa tgaattgagc aatgttgagt tggagtcaag atggccgatc agaaccagaa    9600
cacctgcagc agctggcagg aagcaggtca tgtggcaagg ctatttgggg aagggaaaat   9660
aaaaccacta ggtaaacttg tagctgtggt ttgaagaagt ggttttgaaa cactctgtcc    9720
agccccacca aaccgaaagt ccaggctgag caaaacacca cctgggtaat ttgcatttct    9780
aaaataagtt gaggattcag ccgaaactgg agaggtcctc ttttaactta ttgagttcaa    9840
ccttttaatt ttagcttgag tagttctagt ttccccaaac ttaagtttat cgacttctaa    9900
aatgtattta gaattcattt tcaaaattag gttatgtaag aaattgaagg actttagtgt    9960
ctttaatttc taatatattt agaaaacttc ttaaaattac tctattattc ttccctctga   10020
ttattggtct ccattcaatt cttttccaat acccgaagca tttacagtga ctttgttcat   10080
gatctttttt agttgtttgt tttgccttac tattaagact ttgacattct ggtcaaaacg   10140
gcttcacaaa tcttttcaa gaccactttc tgagtattca ttttaggaga aatactttt    10200 ttttaaatga atgcaattat ctagacttat ttcagttgaa catgctggtt ggtggttgag   10260
aggacactca gtcagtcagt gacgtgaagg gcttctaagc cagtccacat gctctgtgtg   10320
aactccctct ggccctgctt attgttgaat gggccaaagg tctgagacca ggctgctgct   10380
gggtaggcct ggactttggg tctcccaccc agacctggga atgtatggtt gtggcttctg   10440
```

```
ccacccatcc aacctggctgc tcatggacca gccagcctcg gtggctttga aggaacaatt    10500
ccacacaaag actctggacc tctccgaaac caggcaccgc aaatggtaag ccagaggcag    10560
ccacagctgt ggctgctgct cttaaagctt gtaaactgtt tctgcttaag agggactgag    10620
tcttcagtca ttgctttagg gggagaaaga gacatttgtg tgtcttttga gtaccgttgt    10680
ctgggtcact cacatttaac tttccttgaa aaactagtaa aagaaaaatg ttgcctgtta    10740
accaataatc atagagctca tggtattttg aggaaatctt agaaaacgtg tatacaattg    10800
tctggaatta tttcagttaa gtgtattagt tgaggtactg atgctgtctc tacttcagtt    10860
atacatgtgg gtttgaattt tgaatctatt ctggctcttc ttaagcagaa aatttagata    10920
aaatggatac ctcagtggtt tttaatggtg ggtttaatat agaaggaatt taaattggaa    10980
gctaatttag aatcagtaag gagggaccca ggctaagaag gcaatcctgg gattctggaa    11040 gaaagatgt ttttagtttt tatagaaaac actactacat tcttgatcta caactcaatg    11100
tggtttaatg aatttgaagt tgccagtaaa tgtacttcct ggttgttaaa gaatggtatc    11160
aaaggacagt gcttagatcc aaggtgagtg tgagaggaca ggggctgggg tatggatacg    11220
cagaaggaag gccacagctg tacagaattg agaaagaata gagacctgca gttgaggcca    11280
gcaggtcggc tggactaact ctccagccac agtaatgacc cagacagaga aagccagact    11340
cataaagctt gctgagcaaa atttagtgaa caaggttgac agcctggcta ggaagctagg    11400
ctctagttaa gcacagttgg actgagatgt gtaggcttcc ctgagccctt caaaaatgtg    11460
ctaagctgag atgattactc tgaggtagcc aaagctggac ttgagcagga acgaggtaga    11520
ctgcaatgag ctgaattgag ctaggccggc taagctaaac taggctgact taaccaagat    11580
agccaaattg gaatgaattg tcttgatctg ggctgattgg agctaaactc tactggactg    11640
ctctgaactg agctgtgttg ggctgtgttg tgctggggtg agctgagcta gcatgagcta    11700
ctctgtggta gctggggtga gctgggatga gctgagctgg gtgagctgag ctgggtgagc    11760
tgagctgggt tagctgagct ggggtgagct ggggtaagct ggggtgagct gagctgggtg    11820
agctgagctg ggtgagctga gctgagctgg gtgagctggg gtaagctggg gtgagctggg    11880
ctgacctgag gtggttgagc tgagctgggt gagcagagct gaggtgagct gagctgagct    11940
gggtgagcag agctggggtg agctgagctg agctgggctg gggtgagctg agctgagctg    12000
ggtgagctga gctgggtgag ttgagctgag ctgggtaagc tgagctgagc tgggtgagca    12060
gagctggggg tgagctgagc tggatgagct gggctgaact ggggtgagct ggggtggggt    12120
gagctgggtg agctgagctg ggctgagctg ggctgagctg gggtgagctg agctgggatg    12180
agctgggctg agctgggctg agctgagctg ggctgggctg agctgagctg ggctgagctg    12240
ggctgggctg ggctgggctg ggctgggctg agctgggctg agctgggctg aactggggtg    12300
agctggggtg gggtgagctg ggtgagctga gctgggctga gctgggctga gctggggtga    12360
gctgggtgag ctgagctggg ctgagctggg ctgagctggg ctgagctgag ctgggctggg    12420
ctaagctgag ctgactgag ctgggctgag ctgggctgag ctgagctggg ctgggctggg    12480
ctgggctgag ctgggctgag ctgggctgag ctgagctggg atgggctggg atgagctgaa    12540
ctgggtgagc tgagctgggg tgagatgagc tgaacagggc tgaactgggg tgagctgagc    12600
tgggatgagc tggggtgagc tgagctgggt gagatgagct gggtgagctg agctgagctg    12660
ggctgagctg ggtgagctga gctgggtgag atgagctggg gtgagctgag ctggggtgag    12720
ctgagctggg tgagctgggc tgagctgggc tgggtgagct gagctgggtt gagctgagct    12780
gggctgagct gggctgagct gggctgagct gggctgagct gggctgagct gagctgagct    12840
```

-continued

```
gggatgagca gggctgggat gagctgggct gagctgagct gggatgagct gggtgagctg    12900
agctggggtg agatgagctg gggtgagctg agctggggtg agctgagctg ggatgagcta    12960
ggtgagctga gttggggtga gctgagctgg ggtgagctgg gctgggtgaa ctaaactagg    13020
gtgagctggg ctgagctgat ctggttgagc tgggctgggt gagctgagct gggtgaactg    13080
agctggggtg agctgaactg agctgggtga gctggggtga gctgagctga gctgggtgaa    13140
ctgagctgag ttgagttggg tgagctgagc tgggtgagct gaactgagct ggactgagct    13200
ggggtgagct ggggtgagct gggctggatg agctgagctg ggtgagatga gctgaacagg    13260
gctgaactgg ggtgagctga gctgggatga gctggggtga gctgagctgg gtgagatgag    13320
ttggggtgag ctgaactgag ctggactgag ctggggtgag ttgggctagg tgagctgaac    13380
tggggtgagc tgagctgggg tgagatgagc tgaacaggtc tgaactggga tgagctggga    13440
tgagctgggg tgagctgggg tgagctgagt tgggtgagct gagctgggtg agctgagctg    13500
gggtgagctg agctgggatt agctggctga gctgggatga gctgggtgag ctgagttggg    13560
gtgagctgag ctggggtgag ctgggctggg tgaactaaac tagggtgagc tgggctgagc    13620
tgatctggtt gagctgagct ggggtgagct gggctgagct gggctgggtg agctgagctg    13680
ggtgaactga gctggggtga gctgaactga gctgggtgag ctggggtgag ctggggtgag    13740
ctgagctgag ctgggtgaac tgagctgagt tgagttgggt gagctgagct gggtgagctg    13800
aactgagctg gactgagctg gggtgagctg ggtgagctgg gctgggtga gctgagctgg    13860 gtgagctgag ctgggctgag ctggggtgag ctgagctgag ctgggctggg tgagctgagc    13920
tgggtgagct gagctggggt gagctgagct gagctgggtg agctgggctg agctgagctg    13980
agctggggtg agctggggtg agctgggctg ggtgagatga gctgtgctgg gctgggtgag    14040
ctgagctggg tgaactgagc tgagctgagt tgggtgagct gagctgggtg agctgagctg    14100
ggctgagctg gggtgagctg agctgagctg ggtgagctg gggtgagctg ggctgggtga    14160
gctgagctgg gtgagatgag ctgtgctggg ctgggtgagc tgagctgggt gaactgagct    14220
gagctgagtt gggtgagctg agttgagtga ctgagttgg gtgagctgag ctggggtgag    14280
ctgaactgag ctggactgag ctggggtgag ctgagctggc tgagctgagc tgggtgagct    14340
gagctgagct gagctgagct gagctgagct gggctgagct gggctgggtg agctgggctg    14400
agctgggctg ggtgagctgg gctgagctgg gctgggtgag ctaagctggg tgagctggga    14460
tgggtgagct ggcctgagct gggtgagctg agctgaaagg atctgggttg gagtcagctt    14520
tgcttgggtg agctgagcag ggtttagctg agctaggatg agttgagttg gctgggctga    14580
gctgggatga agtaggctaa ataagctagc ttgagctaaa tagagctggg gtgagctgta    14640
cttaaatgag ctgtgattga agtgggctgg gatgagctca gctgaactgg gctagctgat    14700
gtggatgatg gtgaggctga gttaggatga gcatgactga gctggtttgg acatgaatga    14760
gctggacccg gctgacttgg gctggttgag ctttgcaaga tgatgtggac taaactgggc    14820
tagctggcag gatgagagag gttgaactag gctcagatga gctaggctga gcagggctta    14880
ggtgaggtgg tttgggatga gctgggataa gttgggctca gatgagctac catgaactgg    14940
gctgaggtgg cctgggagaa catgaatcga gttgcactga gtacagccag gatgaactgg    15000
gataaactgg gctaaactgg gttgggctaa gaatggactg cctgagttat gctaagctga    15060
gctgggatga attggggatt gtcaagactt aaatgagcca gactgaactg gttgacttg    15120 ggtgagctga ggggacctgc tgcagggccg gcatagctga gttgaattta gatgaggaag    15180
```

```
ggtgagctag actgagcaag gctagactgc ttatgctgag ctacactaac ctggcctgag    15240
ttgggccagg ctttgttggc catgtctaaa ctgagttaag atcaacaggg agtctagagg    15300
ggtaggggat gaactaagat gaattacact agctgagctg aattgagata aggtatggta    15360
acctgagctg aactggaaag agatgtactg gataaccttg actgggctga gatgagctag    15420
gtctacccag gcctggatca gcttaattag ggtaggctag accaaactgt agcagtatgt    15480
attagcctgt gccaagctgg gctacattaa actaaactgg acttagctag gctcagatta    15540
gtttcgctac tctagatggg gtaagttggg ccaaactggg atgaactaat ttaactagcc    15600
tgagatgggc agatctgaat gagcagagct gggatgaact gaatgagttt caccaggcct    15660
ggaccagtta ggctaggacc tcgttctata gaggcagact gtgtgctaca gtggagtttc    15720
aagatgattc catgagtcct ccccgccccc aacataaccc accttcctcc taccctacaa    15780
gcctgtctgg tgtgtaaatc ccagctttgt gtgctgatac agaagcctga gcccctcccc    15840
cacctccacc tacctattac tttgggatga aatagttct cccagccagt gtctcagagg     15900
gaagccaagc aggacaggcc caaggctact tgagaagcca ggatctaggc ctctccctga    15960
gaacgggtgt tcatgcccct agagttggct gaagggccag atccacctac tctagaggca    16020
tctctccctg tctgtgaagg cttccaaagt cacgttcctg tggctagaag gcagctccat    16080
agccctgctg cagtttcgtc ctgtatacca ggttcaccta ctaccatatc tagccctgcc    16140
tgccttaaga gtagcaacaa ggaaatagca gggtgtagag ggatcctg tctgacagga     16200 ggcaagaaga cagattctta cccctccatt tctctttat ccctctctgg tcctcagaga     16260
gtcagtcctt cccaaatgtc ttccccctcg tctcctgcga gagcccctg tctgataaga     16320 atctggtggc catgggctgc ctggcccggg acttcctgcc cagcaccatt tccttcacct    16380
ggaactacca gaacaacact gaagtcatcc agggtatcag aaccttccca acactgagga    16440 caggggcaa gtacctagcc acctcgcagg tgttgctgtc tcccaagagc atccttgaag     16500
gttcagatga atacctggta tgcaaaatcc actacgagg caaaaacaaa gatctgcatg     16560
tgcccattcc aggtaagaac caaaccctcc cagcaggggt gcccaggccc aggcatggcc    16620
cagagggagc agcggggtgg ggcttaggcc aagctgagct cacaccttga cctttcattc    16680
cagctgtcgc agagatgaac cccaatgtaa atgtgttcgt cccaccacgg gatggcttct    16740 ctggcccctgc accacgcaag tctaaactca tctgcgaggc cacgaacttc actccaaaac    16800
cgatcacagt atcctggcta aaggatggga agctcgtgga atctggcttc accacagatc    16860
cggtgaccat cgagaacaaa ggatccacac cccaaaccta caggtcata agcacactta     16920 ccatctctga aatcgactgg ctgaacctga atgtgtacac ctgccgtgtg atcacaggg     16980 gtctcacctt cttgaagaac gtgtcctcca catgtgctgc cagtgagtgg cctgggataa    17040
gcccaatgcc tagccctccc agattaggga agtcctccta caattatggc caatgccacc    17100
cagacatggc catttgctcc ttgaactttg gctccccaga gtggccaagg acaagaatga    17160
gcaataggca gtagaggggt gagaatcagc tggaaggacc agcatcttcc cttaagtagg    17220
tttgggggat ggagactaag cttttttcca acttcacaac tagatatgtc ataacctgac    17280
acagtgttct cttgactgca ggtccctcca cagacatcct aaccttcacc atccccccct    17340
cctttgccga catcttcctc agcaagtccg ctaacctgac ctgtctggtc tcaaacctgg    17400
caacctatga aaccctgaat atctcctggg cttctcaaag tggtgaacca ctggaaacca    17460
aaattaaaat catggaaagc catcccaatg gcaccttcag tgctagggt gtggctagtg      17520 tttgtgtgga agactggaat aacaggaagg aatttgtgtg tactgtgact cacagggatc    17580
```

```
tgccttcacc acagaagaaa ttcatctcaa aacccaatgg taggtatccc cccttcccctt   17640 cccctccaat tgcaggaccc ttcctgtacc tcatagggag ggcaggtcct cttccaccct   17700
atcctcacta ctgtcttcat ttacagaggt gcacaaacat ccacctgctg tgtacctgct   17760
gccaccagct cgtgagcaac tgaacctgag ggagtcagcc acagtcacct gcctggtgaa   17820
gggcttctct cctgcagaca tcagtgtgca gtggcttcag agagggcaac tcttgcccca   17880
agagaagtat gtgaccagtg ccccgatgcc agagcctggg gccccaggct tctactttac   17940
ccacagcatc ctgactgtga cagaggagga atggaactcc ggagagacct atacctgtgt   18000
tgtaggccac gaggccctgc cacacctggt gaccgagagg accgtggaca agtccactgg   18060
taaacccaca ctgtacaatg tctccctgat catgtctgac acaggcggca cctgctattg   18120
accatgctag cgctcaacca ggcaggccct gggtgtccag ttgctctgtg tatgcaaact   18180
aaccatgtca gagtgagatg ttgcattta taaaaattag aaataaaaaa aatccattca   18240
aacgtcactg gttttgatta tacaatgctc atgcctgctg agacagttgt gttttgcttg   18300
ctctgcacac accctgcata cttgcctcca ccctggccct tcctctacct tgccagtttc   18360
ctccttgtgt gtgaactcag tcaggcttac aacagacaga gtatgaacat gcgattcctc   18420
cagctacttc tagatatatg gctgaaagct tgcctaacct ggtgcaggca gcattcaggc   18480
acatatatag acacacatgc atttatacat agatatatag gtacacatgt gtagacacat   18540
acatgaatgt gtattcatgg acacacagac aaaggtacac atatatacac atgagttcat   18600
gcgcacacac atgcatggac acttacaaac gccttcagag acaaataggc atagacacac   18660
aaccactcac agaaacagat accaatatgc atggtcctgt gtacacagaa acagactata   18720
ggcaaatata cacaaataaa ctatatagat acaaagatat gcatatacac acatgtacag   18780
aaacatcttc acatgtgtac actaacatgt ggacaggtat agcacacaga tacacctgga   18840
ctctgaccag ggctgtaatc tccaaggctc acggctcaga gagcctacac taggctgggt   18900
cactgatact cctcaggagc ccactctatg attgggagag ataaccccag gtacaaagta   18960
tgcctatctg tctcaacacc atggggcaga agatactcca ctaaccaccc atgcagaaaa   19020
gttagccttg gctgtgtctc cattaataga acacctcaga agaccaatgt gaaattgcct   19080
aacccactca cacccaccct gatctccagt tcaaaatgca gaaaacataa tgcagttgtc   19140
caaaagatgc cccaaccaca cacacacaca cacacacaca cacacacaca cacacacaca   19200
cacacataca cacacacaca ccatcaagga gcctctgtaa ggagtcacca cccaataaca   19260
ctgcctcttt gggctcatat cctggacatt cttcatattc atatccattt ggggcctagg   19320
ctttagatat ccccaagggc tcatctttac agggatcaga gatcccaata aatgccctgg   19380
tcccacagcc tccctcaggt atctgtctgt ttatctcttg gtacctttct tagacgttag   19440
gtggcacttt tcggggaaat gtgcgcggaa ccctatttg tttattttc taaatacatt   19500 caaatatgta tccgctcatg agacaataac cctgataaat gcttcaataa tattgaaaaa   19560
ggaagagtat gagtattcaa catttccgtg tcgcccttat tcccttttt gcggcatttt   19620 gccttcctgt ttttgctcac ccagaaacgc tggtgaaagt aaaagatgct gaagatcagt   19680
tgggtgcacg agtgggttac atcgaactgg atctcaacag cggtaagatc cttgagagtt   19740
ttcgccccga agaacgtttt ccaatgatga gcactttaa agttctgcta tgtggcgcgg   19800
tattatcccg tgttgacgcc gggcaagagc aactcggtcg ccgcatacac tattctcaga   19860
atgacttggt tgagtactca ccagtcacag aaaagcatct tacggatggc atgacagtaa   19920
```

```
gagaattatg cagtgctgcc ataaccatga gtgataacac tgcggccaac ttacttctga   19980
caacgatcgg aggaccgaag gagctaaccg cttttttgca caacatgggg gatcatgtaa   20040
ctcgccttga tcgttgggaa ccggagctga atgaagccat accaaacgac gagcgtgaca   20100
ccacgatgcc tgcagcaatg gcaacaacgt tgcgcaaact attaactggc gaactactta   20160
ctctagcttc ccggcaacaa ttaatagact ggatggaggc ggataaagtt gcaggaccac   20220
ttctgcgctc ggcccttccg gctggctggt ttattgctga taaatctgga gccggtgagc   20280
gtgggtctcg cggtatcatt gcagcactgg ggccagatgg taagccctcc cgtatcgtag   20340
ttatctacac gacggggagt caggcaacta tggatgaacg aaatagacag atcgctgaga   20400
taggtgcctc actgattaag cattggtaac tgtcagacca agtttactca tatatacttt   20460
agattgattt aaaacttcat ttttaattta aaaggatcta ggtgaagatc ctttttgata   20520
atctcatgac caaaatccct taacgtgagt tttcgttcca ctgagcgtca gaccccgtag   20580
aaaagatcaa aggatcttct tgagatcctt ttttctgcg cgtaatctgc tgcttgcaaa   20640
caaaaaaacc accgctacca gcggtggttt gtttgccgga tcaagagcta ccaactcttt   20700
ttccgaaggt aactggcttc agcagagcgc agataccaaa tactgtcctt ctagtgtagc   20760
cgtagttagg ccaccacttc aagaactctg tagcaccgcc tacatacctc gctctgctaa   20820
tcctgttacc agtggctgct gccagtggcg ataagtcgtg tcttaccggg ttggactcaa   20880
gacgatagtt accggataag gcgcagcggt cgggctgaac ggggggttcg tgcacacagc   20940
ccagcttgga gcgaacgacc tacaccgaac tgagatacct acagcgtgag ctatgagaaa   21000
gcgccacgct tcccgaaggg agaaaggcgg acaggtatcc ggtaagcggc agggtcggaa   21060
caggagagcg cacgagggag cttccagggg gaaacgcctg gtatctttat agtcctgtcg   21120
ggtttcgcca cctctgactt gagcgtcgat ttttgtgatg ctcgtcaggg gggcggagcc   21180
tatggaaaaa cgccagcaac gcggcctttt tacggttcct ggccttttgc tggccttttg   21240
ctcacatgtt ctttcctgcg ttatcccctg attctgtgga taaccgtatt accgcctttg   21300
agtgagctga taccgctcgc cgcagccgaa cgaccgagcg cagcgagtca gtgagcgagg   21360
aagcggaaga gcgcctgatg cggtattttc tccttacgca tctgtgcggt atttcacacc   21420
gcatatggtg cactctcagt acaatctgct ctgatgccgc atagttaagc cagtatacac   21480
tccgctatcg ctacgtgact gggtcatggc tgcgccccga cacccgccaa cacccgctga   21540
cgcgccctga cgggcttgtc tgctcccggc atccgcttac agacaagctg tgaccgtctc   21600
cgggagctgc atgtgtcaga ggttttcacc gtcatcaccg aaacgcgcga ggcagctgcg   21660
gtaaagctca tcagcgtggt cgtgaagcga ttcacagatg tctgcctgtt catccgcgtc   21720
cagctcgttg agtttctcca gaagcgttaa tgtctggctt ctgataaagc gggccatgtt   21780
aagggcggtt ttttcctgtt tggtcactga tgcctccgtg taagggggat ttctgttcat   21840
gggggtaatg ataccgatga aacgagagag gatgctcacg atacgggtta ctgatgatga   21900
acatgcccgg ttactggaac gttgtgaggg taaacaactg gcggtatgga tgcggcggga   21960
ccagagaaaa atcactcagg gtcaatgcca gcgcttcgtt aatacagatg taggtgttcc   22020
acagggtagc cagcagcatc ctgcgatgca gatccggaac ataatggtgc agggcgctga   22080
cttccgcgtt tccagacttt acgaaacacg gaaaccgaag accattcatg ttgttgctca   22140
ggtcgcagac gttttgcagc agcagtcgct tcacgttcgc tcgcgtatcg             22190
```

<210> SEQ ID NO 3
<211> LENGTH: 14130

```
<212> TYPE: DNA
<213> ORGANISM: Artificial Sequence
<220> FEATURE:
<223> OTHER INFORMATION: Targetting vector (short version)

<400> SEQUENCE: 3
gcggccgcaa cctgggcaaa tgggagctta gcaacaatgt aggggggctgg acctagactt      60
cctacacatg tgtaacagat gtgcagcttg tcttcatgt gtgtattacc ctaacatttg       120
gagcaggagc tgtctctgac tctgttgcct gccattggat ccccttcccc tgcttgggct      180
gccttgtttg gccttagtag gaaaggatgt gcttagtcct gctgtgactt gatgtcccta     240
ggcagaatga tacccagggg gggctcccca tctctgagga gatgggcaaa gggtaatggt      300
tggagggact tgtgaggctg ggactgggag gagagaaagg agacagctgt aactggaatg     360
atgttaagtg aacaaatgaa tggatagatt agatagacag atagacagac agacagacag      420
acagacagac agacagacag acagacagat agaaagatag atagataagg ggaaaaagaa     480
acgtagctga gcaagccaga gagagcaagc caaataagca gcattcctcc atgactttc       540
cttcagctcc tgcctatgag tctgccttga cttccctcag tgattggttg taagttaaaa     600
ggtgaaataa acccttcttt tgacaagttg cttttggttc tgattttat cacagcaaga      660
gaaaatcaaa ctagaacaaa catgtatttt tcctggcaca tgtccatagt aaggcagaaa    720
tgatcttcag acctagacca tagatactac agagagcaga agtgtagata ggtggactta    780
ctgtatgatt gtaatccaag taaatctaca tagctagaga gctagaggaa aggccaaagc     840
ttcctctggg aggtcagatc ctgtcgcact gtagccaata aggcatattg catcacagga     900
aaggactaag acccaggctg gcaatagtgt ctgtatctta actagatctc tctagtgagt     960
gaggaagtaa atttgtgaga gcccagactg tgggctcgga aggtacctgc catgcccctg    1020
ttagtaactg agtactacag caggagcagg tgttctctag aaagcctgag acaactctac    1080
ttcttctctc aagagaccac ctaatacagg cctgagagaa cagactctgg aaatagatgg    1140
gacttacgga gctaagatct agagctcatc tacagagcag aatcccagcc aagagaacaa    1200
agaatactga ctctctcctg ttccctactc ctagagttct aaaacacact atagggaagg     1260
gagcctctag acctccgtcc attccccatc ttgctcattc catcttccca tgtccccagg     1320
tctccaagcc acagacacca cctttcctat tcacccacct ttctgtgtcc ctaggtcccc    1380
aggccatagt cacctccccc cacacccgc tcaccctgcc ccatctatgc ccctagatgc     1440
ttacttacca gagtcttttg tctgacgtgg ggctacaagc atctatgctc cctaagcacc    1500
tactgctgac ctgtaggacc cagctctgaa ccaactcata taagtaaata cagactctcc    1560
cctgtcttag gatggcccccc tgggtcagga ggagaccact gccaaggaac cttctcttag    1620
agcactgaac tcctcccctg taccacttag gacagacctg agacctatta ttactgatta   1680
ccagagctct ggcagtgacc acggaggaga tagatccacc ctggacacag gaaacacagc    1740
accagagata ctgcttcatc acaacagtag agtgacactt tagactttaa tttgggtcac   1800
tttcctgctg tagaggtggg atcagaaagc aaagagcagt atgagtgcct gataggcacc    1860
caagtacact atagagtact catggtgaat aaggtacctc catggcttcc cagggagggg    1920
cactgcccca cccccaccat cacagacctt tctccatagt tgataactca gacacaagtg    1980
aatgacagat ggacctccat ctgctcttat tttaaaaaga agacaaaccc cacaggctcg   2040
agaactttag cgactgtttt gagagaaatc attggtccct gactcaagag atgactggca   2100
gattggggat cagaataccc atactctgtg gctagtgtga ggtttaagcc tcagagtccc   2160
```

```
tgtggtctct gactggtgca aggttttgac taagcggagc accacagtgc taactgggac    2220
cacggtgaca cgtggctcaa caaaaacctt ctgtttggag ctctccaggg gcagcctgag    2280
ctatgaggaa gtagagaggc ttgagaaatc tgaggaagaa aagagtagat ctgagaggaa    2340
aggtagcttt ctggaggtca ggagacagtg cagagaagaa cgagttactg tggacaggtc    2400
ttagatgggg aaagaatgag caaatgcaag catcagaagg gtggatgcaa tgtcctgcca    2460
aggacttacc aagaggatcc ccggacagag caggcaggtg gagttgactg agaggacagg    2520
ataggtgcag gtccctctct tgtttccttt ctccttctcc tgtttccttc ttctcttgtc    2580
acaggtctca ctatgctagc caaggctagc ctgaaagatt accatcctac agatgggccc    2640
atccagttga attaaggtgg agatctctcc aaacatctga gtttctgagg cttggatgcc    2700 actgggacg ccaagggact ttgggatggg tttggttggc cccagatgaa gggctacttc    2760
actgggtcta taattactct gatgtctagg accagggggc tcaggtcact caggtcaggt    2820
gagtcctgca tctggggact gtggggttca ggtggcctaa ggcaggatgt ggagagagtt    2880
ttagtatagg aacagaggca gaacagagac tgtgctactg gtacttcgat gtctgggca    2940 cagggaccac ggtcaccgtc tcctcaggta agctggcttt tttctttctg cacattccat    3000
tctgaaacgg gaaagatat tctcagatct ccccatgtca ggccatctgc cacactctgc    3060
atgctgcaga agcttttctg taaggatagg gtcttcactc ccaggaaaag aggcagtcag    3120
aggctagctg cctgtggaac agtgacaatc atggaaaata ggcatttaca ttgttaggct    3180
acatgggtag atgggttttt gtacacccac taaaggggtc tatgatagtg tgactacttt    3240
gactactggg gccaaggcac cactctcaca gtctcctcag gtgagtcctt acaacctctc    3300
tcttctattc agcttaaata gattttactg catttgttgg ggggaaatg tgtgtatctg    3360 aatttcaggt catgaaggac tagggacacc ttgggagtca gaaagggtca ttgggagccc    3420
tggctgacgc agacagacat cctcagctcc catacttcat ggccagagat ttatagggat    3480 cctgccagc attgccgcta ggtccctctc ttctatgctt tctttgtccc tcactggcct    3540
ccatctgaga tcatcctgga gccctagcca aggatcattt attgtcaggg gtctaatcat    3600
tgttgtcaca atgtgcctgg tttgcttact ggggccaagg gactctggtc actgtctctg    3660
caggtgagtc ctaacttctc ccattctaaa tgcatgttgg ggggattctg ggccttcagg    3720
accaagattc tctgcaaacg ggaatcaaga ttcaaccct ttgtcccaaa gttgagacat    3780
gggtctgggt cagggactct ctgcctgctg gtctgtggtg acattagaac tgaagtatga    3840
tgaaggatct gccagaactg aagcttgaag tctgaggcag aatcttgtcc agggtctatc    3900
ggactcttgt gagaattagg ggctgacagt tgatggtgac aatttcaggg tcagtgactg    3960
tctggtttct ctgaggtgag gctggaatat aggtcacctt gaagactaaa gaggggtcca    4020
ggggcttctg cacaggcagg gaacagaatg tggaacaatg acttgaatgg ttgattcttg    4080
tgtgacacca ggaattggca taatgtctga gttgcccagg ggtgattcta gtcagactct    4140 ggggttttg tcgggtatag aggaaaaatc cactattgtg attactatgc tatgggactac    4200 tggggtcaag gaacctcagt caccgtctcc tcaggtaaga atggcctctc caggtctttta    4260 tttttaacct ttgttatgga gttttctgag cattgcagac taatcttgga tatttgtccc    4320
tgagggagcc ggctgagaga agttgggaaa taaactgtct agggatctca gagcctttag    4380
gacagattat ctccacatct ttgaaaaact aagaatctgt gtgatggtgt tggtggagtc    4440 cctgatgat gggataggga ctttggaggc tcatttgaag aagatgctaa aacaatccta    4500
tggctggagg gatagttggg gctacgcgtt tttaaccta gaaagatagt ctgcgtaaaa    4560
```

```
ttgacgcatg cattcttgaa atattgctct ctctttctaa atagcgcgaa tccgtcgctg   4620
tgcatttagg acatctcagt cgccgcttgg agctcccgtg aggcgtgctt gtcaatgcgg   4680
taagtgtcac tgattttgaa ctataacgac cgcgtgagtc aaaatgacgc atgattatct   4740
tttacgtgac ttttaagatt taactcatac gataattata ttgttatttc atgttctact   4800
tacgtgataa cttattatat atatattttc ttgttataga tatcgctagt ggatcctggt   4860
tctttccgcc tcagaaggta cttttttttt tttttttttt tttttttttt tttttttttt   4920
tttttttttt tttttttttt taaatttttg ggaatttatt gatttgcatt taaaagggaa   4980
ctgctgacaa agattcactg gtaataattt gaacaagttg gaaaatacag tcaacattac   5040
tgaaacacta ctaaaataat tccaggacag aacaaaactt cttagatgct gtctttgatg   5100
tgaaaattga ctgcttctta ctttctaac acacggtggt ataattaaca atattcaatc   5160
acttctattc tttcctgcat atataaaaat taaaatacca attaaaaaac taatatatct   5220
tctctttatt tcttacagat atgagttcaa tgtttcactc aatagtgctg tggtttaaga   5280
gaatttttc atttacaagt taaacaacaa tccgcccaaa gggaactgat agtctatagg   5340
ctcatagtgc aaataaacag tttaggaatg cagcaactga catttctaaa gtacaaaaca   5400
gataaaattc ttagaagata catgcaaaaa gctctactaa gcagatggcc acagaactag   5460
aacattgata atttttactgg cgatgtcaat aggactccag atgtttccaa actcaacttg   5520
aactctcatc ttaggctttg tattttgctt ttccagtttc actaatgaca caaacatgat   5580
tcaaatccct gaagtattca ttatagtcaa gggcatatcc tacaacaaac ttgtctggaa   5640
tttcaaatcc aacaaagtct ggcttatatc caacacttcg tggggtcctt ttcaccagca   5700
agcttgcgac cttgaccatc tttggattat actgcctgac caaggaaagc aaagtctgca   5760
ttgttttgcc agtgtcaatt atatcttcca caatcaagac attctttcca gttaaagttg   5820
agagatcatc tccaccaatt acttttatgt cccctgttga ctggtcatta caatagctct   5880
tcagtctgat aaaatctaca gtcataggaa tggatctatc actatttcta ttcagtgctt   5940
tgatgtaatc cagcaggtca gcaaagaatt tatagccccc cttgagcaca cagagggcta   6000
caatgtgatg gcctcccatc tccttcatca catctcgagc aagacgttca gtcctacaga   6060
aataaaatca ggaatttaat agaaagtttc atacattaaa ctttataaca aacacctctt   6120
agtcattaaa cttccacacc aacctgggca atatagtgag accccatgcc tgcaaaaaaa   6180
aaaaaattag ccaggcatgg tagcatgtac ctgtagtccc agctacttga gaggtgaggt   6240
gggaaaatca ctttagtgca ggatgttgag gctggagtga actgtgattg tgccactgca   6300
ctccagcctg gacaatagag caagaccttg tctcaaaaaa atgcattaaa aatttttttt   6360
aaatcttcca cgtaacacat cctttgccct catgtttcat aaggtaaaaa atttgatacc   6420
ttcaaaaaaa ccaagcatac cactatcata atttttttta aatgcaaata aaaacaagat   6480
accatttca cctatcagac tggcaggttc tgattaaatg aaatttcttg gataatatac   6540
aatattaaga gagactgtag aaactgggcc agtggctcat gcctgtaatc ccagcacttt   6600
gggaggctgg gtaacatggc gaaccctgtt tctacaaaat aaaaatatta gctgggagtg   6660
gtggcgcaca cctatagtcc cagctactca ggaggctgag gtggaaggat cgcttgaacc   6720
caggaggttg agactgcagt gaactgtgat cattctgctg cactgcaccc cagcctgggc   6780
aacagagacc ttgtctcaaa aaaaaaaaaa aagagacaa attgtgaaga gaaaggtact   6840
ctcatataac atcaggagta taaatgatt caacttctta gaggaaaatt tggcaatacc   6900
```

```
aaaatattca ataaactctt tccccttgac ccagaaattc cacttgaata aagctgaaca   6960
agtaccaaac atgtaaaaga atgtttcttc tagtacagtc ggtaagaaca aaatagtgtc   7020
tatcaatagt ggactggtta aatcagttat ggtatctcca taagacagaa tgctatgcaa   7080
cctttaaaat atattagata gctctagaca gtggatcccc tcgagggacc taataacttc   7140
gtatagcata cattatacga agttatatta agggttattg aatatgtcga ctagacacac   7200
taatattaaa agtgtccaat aacatttaaa actatactca tacgttaaaa tataaatgta   7260
tatatgtact tttgcatata gtatacatgc atagccagtg cttgagaaga aatgtgtaca   7320
gaaggctgaa aggagagaac tttagtcttc ttgtttatgg cctccatagt tagaatattt   7380
tataacacaa atattttgat attataattt taaaataaaa acacagaata gccagacata   7440
caatgcaagc attcaatacc aggtaaggtt tttcactgta attgacttaa cagaaaattt   7500
tcaagctaga tgtgcataat aataaaaatc tgaccttgcc ttcatgtgat tcagccccag   7560
tccattaccc tgtttaggac tgagaaatgc aagactctgg ctagagttcc ttcttccatc   7620
tcccttcaat gtttactttg ttctggtccc tacagagtcc cactatacca caactgatac   7680
taagtaatta gtaaggccct cctctttat ttttaataaa gaagatttta gaaagcatca   7740
gttatttaat aagttggcct agtttatgtt caaatagcaa gtactcagaa cagctgctga   7800
tgtttgaaat taacacaaga aaagtaaaa aacctcattt taagatctta cttacctgtc   7860
cataattagt ccatggggaa taaacaccct ttccaaatcc tcagcataat gattaggtat   7920
gcaaaataaa tcaaggtcat aacctggttc atcatcacta atcacgacgc cagggctgcg   7980
ggtcgccata acggagccgg ccggcgcgcg ggctgaataa cttcgtataa tgtgtactat   8040
acgaagttat tgttcagga ggaggaagcc ggtggcggag cagaggagga ggcggaggcg   8100
cagcaagacc cccccccccc tgcaggtcga aaggcccgga gatgaggaag aggagaacag   8160
cgcggcagac gtgcgctttt gaagcgtgca gaatgccggg cctccggagg accttcgggc   8220
gcccgccccg cccctgagcc cgcccctgag cccgcccccg gacccacccc ttcccagcct   8280
ctgagcccag aaagcgaagg agccaaagct gctattggcc gctgccccaa aggcctaccc   8340
gcttccattg ctcagcggtg ctgtccatct gcacgagact agtgagacgt gctacttcca   8400
tttgtcacgt cctgcacgac gcgagctgcg gggcggggg gaacttcctg actaggggag   8460
gagtagaagg tggcgcgaag gggccaccaa agaacggagc cggttggcgc ctaccggtgg   8520
atgtggaatg tgtgcgaggc cagaggccac ttgtgtagcg ccaagtgccc agcggggctg   8580
ctaaagcgca tgctccagac tgccttggga aaagcgcctc ccctacccgg tagatatcta   8640
taacaagaaa atatatatat aataagttat cacgtaagta gaacatgaaa taacaatata   8700
attatcgtat gagttaaatc ttaaaagtca cgtaaaagat aatcatgcgt cattttgact   8760
cacgcggtcg ttatagttca aaatcagtga cacttaccgc attgacaagc acgcctcacg   8820
ggagctccaa gcggcgactg agatgtccta aatgcacagc gacggattcg cgctatttag   8880
aaagagagag caatatttca agaatgcatg cgtcaatttt acgcagacta tctttctagg   8940
gttaaaagaa ttcgtagttg agattttca gtttttagaa taaaagtatt agctgcggaa   9000
tatacttcag gaccacctct gtgacagcat ttatacagta tccgatgcat agggacaaag   9060
agtggagtgg ggcactttct ttagatttgt gaggaatgtt ccacactaga ttgtttaaaa   9120
cttcatttgt tggaaggaga gctgtcttag tgattgagtc aagggagaaa ggcatctagc   9180
ctcggtctca aaagggtagt tgctgtctag agaggtctgg tggagcctgc aaaagtccag   9240 cttttcaaagg aacacagaag tatgtgtatg gaatattaga agatgttgct tttactctta   9300
```

```
agttggttcc taggaaaaat agttaaatac tgtgactttα aaatgtgaga gggttttcaa    9360
gtactcattt ttttaaatgt ccaaaatttt tgtcaatcaa tttgaggtct tgtttgtgta    9420
gaactgacat tacttaaagt ttaaccgagg aatgggagtg aggctctctc atacccctatt   9480
cagaactgac ttttaacaat aataaattaa gtttaaaata tttttaaatg aattgagcaa    9540
tgttgagttg gagtcaagat ggccgatcag aaccagaaca cctgcagcag ctggcaggaa    9600
gcaggtcatg tggcaaggct atttggggaa gggaaaataa aaccactagg taaacttgta    9660
gctgtggttt gaagaagtgg ttttgaaaca ctctgtccag ccccaccaaa ccgaaagtcc    9720
aggctgagca aaacaccacc tgggtaattt gcatttctaa aataagttga ggattcagcc    9780
gaaactggag aggtcctctt ttaacttatt gagttcaacc ttttaatttt agcttgagta    9840
gttctagttt ccccaaactt aagtttatcg acttctaaaa tgtatttaga attcattttc    9900
aaaattaggt tatgtaagaa attgaaggac tttagtgtct ttaatttcta atatatttag    9960
aaaacttctt aaaattactc tattattctt ccctctgatt attggtctcc attcaattct   10020
tttccaatac ccgaagcatt tacagtgact ttgttcatga tcttttttag ttgtttgttt   10080
tgccttacta ttaagacttt gacattctgg tcaaaacggc ttcacaaatc ttttcaaga    10140
ccactttctg agtattcatt ttaggagaaa tactttttttt ttaaatgaat gcaattatct   10200
agacttattt cggttgaaca tgctggttgg tggttgagag gacactcagt cagtcagtgg   10260
cgtgaagggc ttctaagcca gtccacatgc tctgtgtgaa ctccctctgg ccctgcttat   10320
tgttgaatgg gccaaaggtc tgagaccagg ctgctgctgg gtaggcctgg actttgggtc   10380
tcccacccag acctgggaat gtatggttgt ggcttctgcc acccatccac ctggctgctc   10440
atggaccagc cagcctcggt ggctttgaag gaacaattcc acacaaagac tctggacctc   10500
tccgaaacca ggcaccgcaa atggtaagcc agaggcagcc acagctgtgg ctgctgctct   10560
taaagcttgt aaactgtttc tgcttaagag ggactgagtc ttcagtcatt gctttagggg   10620
gagaaagaga catttgtgtg tcttttgagt accgttgtct gggtcactca catttaactt   10680
tccttgaaaa actagtaaaa gaaaaatgtt gcctgttaac caataatcat agagctcatg   10740
gtattttgag gaaatcttag aaaacgtgta tacaattgtc tggaattatt tcagttaagt   10800
gtattagttg aggtactgat gctgtctcta cttcagttat acatgtgggt ttgaattttg   10860
aatctattct ggctcttctt aagcagaaaa tttagataaa atggatacct cagtggtttt   10920
taatggtggg tttaatatag aaggaattta aattggaagc taatttagaa tcagtaagga   10980
gggacccagg ctaagaaggc aatcctggga ttctggaaga aaagatgttt ttagttttta   11040
tagaaaacac tactacattc ttgatctaca actcaatgtg gtttaatgaa tttgaagttg   11100
ccagtaaatg tacttcctgg ttgttaaaga atggtatcaa aggacagtgc ttagatccaa   11160
ggtgagtgtg agaggacagg ggctggggta tggatacgca gaaggaaggc cacagctgta   11220
cagaattgag aaagaataga gacctgcagt tgaggccagc aggtcggctg gactaactct   11280
ccagccacag taatgaccca gacagagaag gccagactca taaagcttta tcgataccgt   11340
cgacctcgag gggggcccg gtacctttct tagacgtcag gtggcacttt tcggggaaat    11400
gtgcgcggaa cccctatttg ttattttttc taaatacatt caaatatgta tccgctcatg   11460
agacaataac cctgataaat gcttcaataa tattgaaaaa ggaagagtat gagtattcaa   11520
catttccgtg tcgcccttat tcccttttttt gcggcatttt gccttcctgt ttttgctcac   11580
ccagaaacgc tggtgaaagt aaaagatgct gaagatcagt tgggtgcacg agtgggttac   11640
```

```
atcgaactgg atctcaacag cggtaagatc cttgagagtt ttcgccccga agaacgtttt    11700
ccaatgatga gcactttttaa agttctgcta tgtggcgcgg tattatcccg tgttgacgcc    11760
gggcaagagc aactcggtcg ccgcatacac tattctcaga atgacttggt tgagtactca    11820
ccagtcacag aaaagcatct tacggatggc atgacagtaa gagaattatg cagtgctgcc    11880
ataaccatga gtgataacac tgcggccaac ttacttctga caacgatcgg aggaccgaag    11940
gagctaaccg cttttttgca caacatgggg gatcatgtaa ctcgccttga tcgttgggaa    12000
ccggagctga atgaagccat accaaacgac gagcgtgaca ccacgatgcc tgcagcaatg    12060
gcaacaacgt tgcgcaaact attaactggc gaactactta ctctagcttc ccggcaacaa    12120
ttaatagact ggatggaggc ggataaagtt gcaggaccac ttctgcgctc ggcccttccg    12180
gctggctggt ttattgctga taaatctgga gccggtgagc gtgggtctcg cggtatcatt    12240
gcagcactgg ggccagatgg taagccctcc cgtatcgtag ttatctacac gacggggagt    12300
caggcaacta tggatgaacg aaatagacag atcgctgaga taggtgcctc actgattaag    12360
cattggtaac tgtcagacca agtttactca tatatacttt agattgattt aaaacttcat    12420
ttttaattta aaaggatcta ggtgaagatc ctttttgata atctcatgac caaaatccct    12480
taacgtgagt tttcgttcca ctgagcgtca gaccccgtag aaaagatcaa aggatcttct    12540
tgagatcctt ttttctgcg cgtaatctgc tgcttgcaaa caaaaaaacc accgctacca    12600
gcggtggttt gtttgccgga tcaagagcta ccaactcttt ttccgaaggt aactggcttc    12660
agcagagcgc agataccaaa tactgtcctt ctagtgtagc cgtagttagg ccaccacttc    12720
aagaactctg tagcaccgcc tacatacctc gctctgctaa tcctgttacc agtggctgct    12780
gccagtggcg ataagtcgtg tcttaccggg ttggactcaa gacgatagtt accggataag    12840
gcgcagcggt cgggctgaac ggggggttcg tgcacacagc ccagcttgga gcgaacgacc    12900
tacaccgaac tgagatacct acagcgtgag ctatgagaaa gcgccacgct tcccgaaggg    12960
agaaaggcgg acaggtatcc ggtaagcggc agggtcggaa caggagagcg cacgagggag    13020
cttccagggg gaaacgcctg gtatctttat agtcctgtcg ggtttcgcca cctctgactt    13080
gagcgtcgat ttttgtgatg ctcgtcaggg gggcggagcc tatggaaaaa cgccagcaac    13140
gcggcctttt tacggttcct ggccttttgc tggccttttg ctcacatgtt ctttcctgcg    13200
ttatcccctg attctgtgga taaccgtatt accgcctttg agtgagctga taccgctcgc    13260
cgcagccgaa cgaccgagcg cagcgagtca gtgagcgagg aagcggaaga gcgcctgatg    13320
cggtattttc tccttacgca tctgtgcggt atttcacacc gcatatggtg cactctcagt    13380
acaatctgct ctgatgccgc atagttaagc cagtatacac tccgctatcg ctacgtgact    13440
gggtcatggc tgcgccccga cacccgccaa cacccgctga cgcgccctga cgggcttgtc    13500
tgctcccggc atccgcttac agacaagctg tgaccgtctc cgggagctgc atgtgtcaga    13560
ggttttcacc gtcatcaccg aaacgcgcga ggcagctgcg gtaaagctca tcagcgtggt    13620
cgtgaagcga ttcacagatg tctgcctgtt catccgcgtc cagctcgttg agtttctcca    13680
gaagcgttaa tgtctggctt ctgataaagc gggccatgtt aagggcggtt ttttcctgtt    13740
tggtcactga tgcctccgtg taagggggat tctgttcat gggggtaatg ataccgatga    13800
aacgagagag gatgctcacg atacgggtta ctgatgatga acatgcccgg ttactggaac    13860
gttgtgaggg taaacaactg gcggtatgga tgcggcggga ccagagaaaa atcactcagg    13920
gtcaatgcca gcgcttcgtt aatacagatg taggtgttcc acagggtagc cagcagcatc    13980
ctgcgatgca gatccggaac ataatggtgc agggcgctga cttccgcgtt tccagacttt    14040
```

```
acgaaacacg gaaaccgaag accattcatg ttgttgctca ggtcgcagac gttttgcagc   14100
agcagtcgct tcacgttcgc tcgcgtatcg                                    14130

<210> SEQ ID NO 4
<211> LENGTH: 3551
<212> TYPE: DNA
<213> ORGANISM: Mus musculus
<220> FEATURE:
<221> NAME/KEY: misc_feature
<222> LOCATION: (1399)..(1498)
<223> OTHER INFORMATION: n is a, c, g, or t

<400> SEQUENCE: 4
aagcttgctg agcaaaatta agggaacaag gttgagagcc ctagtaagcg aggctctaaa      60
aagcatggct gagctgagat gggtgggctt ctctgagcgc ttctaaaatg cgctaaactg     120
aggtgattac tctgaggtaa gcaaagctgg gcttgagcca aaatgaagta gactgtaatg     180
aactggaatg agctgggccg ctaagctaaa ctaggctggc ttaaccgaga tgagccaaac     240
tggaatgaac ttcattaatc taggttgaat agagctaaac tctactgcct acactggact     300
gttctgagct gagatgagct ggggtgagct cagctatgct acgctgtgtt ggggtgagct     360
gatctgaaat gagctactct ggagtagctg agatggggtg agatggggtg agctgagctg     420
ggctgagctg gactgagctg agctagggtg agctgagctg ggtgagctga gctaagctgg     480
ggtgagctga gctgagcttg actgagctag ggtgagctgg actgagctgg ggtgagctga     540
gctgagctgg ggtaagctgg gatgagctgg ggtgagctga gctgagctgg agtgagctga     600
gctgggctga gctggggtga gctgggctgg gctgagctgg ggtgagctgg gctgagctgg     660
ggtgagctga gctggggtga gctgagctga gctggggtga gctgagctga gctggggtga     720
gctgagctgg ggtgagctga gctgagctgg gctgagctga ggtgagctga gctggggtga     780
gctgagctgg ggtgagctga gctgagctgg ggtaagctgg gatgagctgg ggtgagctga     840
gctgagctgg agtgagctga gctgggctga gctgggctga gctggggtga gctgagctgg     900
ggtgagctga gctgagctgg gctgagctga ggtgagctga gctggggtga gctgagctga     960
gctggggtga gctgagctga gctggggtga gctgagctgg ggtgagctga gctggggtga    1020
gctgagctga gctggggtga gctgagctgg ggtgagctga gctgagctgg ggtgagctga    1080
gctgagctgg ggtgagctga gctgagctga gctggggtga gctgagctga gctggggtga    1140
gctgagctga gctggggtga gctgagctgg ggtgagctgg gctgagctga gctgggctga    1200
gctgagctga gctgagctga gctggggtga gctgagctgg gctgagctgg ggtgagctgg    1260
gctgagctgg ggtgagctga gctggggtga gctgagctga gctggggtga gctgagctga    1320
gctggggtga gctgagctgg ggtgagctga gctgagctgg gctgagctga gctgagctgg    1380
ggtgagctga gctgagctnn nnnnnnnnnn nnnnnnnnnn nnnnnnnnnn nnnnnnnnnn    1440
nnnnnnnnnn nnnnnnnnnn nnnnnnnnnn nnnnnnnnnn nnnnnnnnnn nnnnnnnnag    1500
ctgagctgag ctgagctgag ctgagctggg gtgagctggg gtgagctgag ctggggtgag    1560
ctgagctgag ctggggtgag ctgagctgag ctgagctgag ctgagctgag ctgggtgagc    1620
tgagctgagc tgagctgggg tgagctgagc tggggtgagc tgagctgagc tggggtgagc    1680
tgagctgggg tgagctgagc tgagctgggg tgagctgggg tgagctgggg tgagctgggg    1740
tgagctgagc tgaactgggg tgagctgggc tgagctgggg tgagctgagc tgagctgggc    1800
tgagctgggg tgagctgggg tgagctgggg tgagctgagc tgagctaggg tgagctgagc    1860
```

```
tgagctaggg tgagctgagc tgagctgggg tgagctgagc tgagctgggg tgagctgagc    1920
tgagctgggg tgagctgagc tgagctgggg tgagctgagc tgagctgggg tgagcttggc    1980
tgagctgggg tgagctgggg tgagctgggg tgagctgagc tggggtgagc tgagctgagc    2040
tggggtgagc tgagctgagc tggggtgagc tggggtgagc tgagctgagc tgagctgggt    2100
gatctgagct gagctgagct gggtgagctg agctgagctg agctgggtga gctgagctga    2160
gctgagctga gctgggtgag ctgagctgag ctgagctgag ctgagctgag ctggggtgag    2220
ctgggctgag ctgagctgag ctggggtgag ctgagctgag ctgagctgag ctggggtgag    2280
ctgggctgag ctggggtgag ctgggctgag ctgagctggg tgagctgagc tgaactgagc    2340
tgagctgggt gagctgagct gagctgagct gggtgagctg agctgggctg agctgagctg    2400
ggtgagctga gctgaactga gctgagctgg gtgagctgag ctgagctgag ctgggtgagc    2460
tgagctgggg tgagctgagc tgagctgggg tgagctgagc tgagctgagc tgggtgagct    2520
gagctggggt gagctgagct gagctggggt gagctgagct gagctggggt gagctgagct    2580
gagctggggt gagctgagct gagctggggt gagctgagct agggtgaact gggctgggtg    2640
agctggagtg agctgagctg aggtgaactg gggtgagccg gatgttttg agttgagctg    2700 gggtaagatg agctgaactg gggtaagatg ggatgagctg tggtgagggg agctggattg    2760
aactgagctg tgtgagctga gctggggtca gctgagcaag agtgagtaga gctggctggc    2820
cagaaccaga atcaattagg ctaagtgagc cagattgcgc tgggatcagc tgtactcaga    2880
tgagctggga tgaggtaggc tgggatgagc tgggctagct gacatggatt atgtgaggct    2940
gagctagcat gggctggcct agctgatgag ctaagcttga atgaacgggg ctgagctgga    3000
ctcagatgtg ctagactgag ctgtactgga tgatctggtg tagggtgatc tggactcaac    3060
tgggctggct gatgggatgc cccaggttga actaggctca gataagttag gctgagtagg    3120
gcctggttga gatggttcgg gatgagctgg gaaaagatgg actgggacca tgaactgggc    3180
tgagctgggt tgggagacca tgaattgagc tgaactgagt gcagctggga taaactgggt    3240
tgagctaaga atagactacc tgaattgtgc caaactgggc tgggatcaat tggaaattat    3300
caggatttag atgagccgga ctaaactatg ctgagctgga ctggttggat gtgttgaact    3360
ggcctgctgc tgggctggca tagctgagtt gaacttaaat gaggaaggat gagcaaggct    3420
agcctgcttg catagagctg aactttagcc tagcctgagc tggaccagcc tgagctgagt    3480
aggtctaaac tgagttaaaa atcaacaggg ataatttaac agctaattta acaagcctga    3540
ggtctgagat t                                                          3551

<210> SEQ ID NO 5
<211> LENGTH: 2484
<212> TYPE: DNA
<213> ORGANISM: Mus musculus

<400> SEQUENCE: 5
aagcttgctg agcaaaatta agggaacaag gttgagagcc ctagtaagcg aggctctaaa     60
aagcacagct gagctgagat gggtgggctt ctctgagtgc ttctaaaatg cgctaaactg    120
aggtgattac tctgaggtaa gcaaagctgg gcttgagcca aaatgaagta gactgtaatg    180
aactggaatg agctgggccg ctaagctaaa ctaggctggc ttaaccgaga tgagccaaac    240
tggaatgaac ttcattaatc taggttgaat agagctaaac tctactgcct acactggact    300
gttctgagct gagatgagct ggggtgagct cagctatgct acgctgtgtt ggggtgagct    360
gatctgaaat gagatactct ggagtagctg agatggggtg agatggggtg agctgagctg    420
```

```
ggctgagcta gactgagctg agctagggtg agctgagctg ggtgagctga gctaagctgg      480
ggtgagctga gctgagcttg gctgagctag ggtgagctgg gctgagctgg ggtgagctga      540
gctgagctgg ggtaagctgg gatgagctgg ggtgagctga gctgagctgg agtgagctga      600
gctgggctga gctggggtga gctgggctga gctgggctga gctgggctga gctggggtga      660
gctgagctgg ggtgagctga gctgagctgg ggtgagctga gctgagctgg ggtgagctgg      720
ggtgagctga gctggggtga gctgagctga gctggggtga gctgagctgg ggtgagctga      780
gctgagctgg ggtgagctga gctgagctga gctggggtga gctgagctga      840
gctgagctgg ggtgagctgg ggtgagctga gctgagctgg agtgagctga gctgggctga      900
gctggggtga gctgggctga gctggggtga gctgagctga gctgagctga gctggggtga      960
gctgagctga gctggggtga gctgagctgg ggtgagctgg gctgagctga gctgagctga     1020
gctgagctga gctgagctga gctgagctga gctgagctga gctgagctga gctgagctga     1080
gctgagctgg ggtgagctga gctgagctgg gctgagctgg ggtgagctgg gctgagctgg     1140
gctgagctgg gctgagctgg ggtgagctga gctggggtga gctgagctga gctgggctga     1200
gctgagctga gctggggtga gctgagctga gctggggtga gctgagctga gctgagctgg     1260
ggtgagctga gctgggctga gcagggctga gctggggtga gctgagctga gctggggtga     1320
gctgggctga gctgggctga gctgagctga gctgggctga gctgggctga gctgggctga     1380
gctgggctga gctgggctga gctggggtga gctgagctga gctggggtga gctggggtga     1440
gctgagctgg ggtgagctga gctggggtga gctgagctga gctggggtga gctgagctgg     1500
ggtgagctga gctgagctgg ggtgagctga gctgagctgg ggtgagctga gctagggtga     1560
actgggctgg gtgagctgga gtgagctgag ctgaggtgaa ctggggtgag ccggatgtt      1620 ttgagttgag ctggggtaag atgagctgaa ctggggtaaa ctgggatgag ctgtggtgag     1680
cggagctgga ttgaactgag ctgtgtgagc tgagctgggg tcagctgagc aagagtgagt     1740
agagctggct ggccagaacc agaatcaatt aggctaagtg agccagattg tgctgggatc     1800
agctgtactc agatgagctg ggatgaggta ggctgggatg agctgggcta gctgacatgg     1860
attatgtgag gctgagctag catgggctgg cctagctgat gagctaagct tgaatgagcg     1920
gggctgagct ggactcagat gtgctagact gagctgtact ggatgatctg tgtagggtg      1980 atctggactc aactgggctg gctgatggga tgcgccaggt tgaactaggc tcagataagt     2040
taggctgagt agggcctggt tgagatggtt cgggatgagc tgggaaaaga tggactcgga     2100
ccatgaactg ggctgagctg ggttgggaga ccatgaattg agctgaactg agtgcagctg     2160
ggataaactg ggttgagcta agaatagact acctgaattg tgccaaactc ggctgggatc     2220
aattggaaat tatcaggatt tagatgagcc ggactaaact atgctgagct ggactggttg     2280
gatgtgttga actggcctgc tgctgggctg gcatagctga gttgaactta aatgaggaag     2340
gctgagcaag gctagcctgc ttgcatagag ctgaacttta gcctagcctg agctggacca     2400
gcctgagctg agtaggtcta aactgagtta aaaatcaaca gggataattt aacagctaat     2460
ttaacaagcc tgaggtctga gatt                                            2484
```

<210> SEQ ID NO 6
<211> LENGTH: 4515
<212> TYPE: DNA
<213> ORGANISM: Artificial Sequence
<220> FEATURE:
<223> OTHER INFORMATION: 5' homology arm of targetting vector

<400> SEQUENCE: 6

```
aacctgggca aatgggagct tagcaacaat gtaggggggct ggacctagac ttcctacaca      60
tgtgtaacag atgtgcagct tggtcttcat gtgtgtatta ccctaacatt tggagcagga     120
gctgtctctg actctgttgc ctgccattgg atccccttcc cctgcttggg ctgccttgtt     180
tggccttagt aggaaaggat gtgcttagtc ctgctgtgac ttgatgtccc taggcagaat     240
gatacccccag gggggctccc catctctgag gagatgggca aagggtaatg gttggaggga     300
cttgtgaggc tgggactggg aggagagaaa ggagacagct gtaactggaa tgatgttaag     360
tgaacaaatg aatggataga ttagatagac agatagacag acagacagac agacagacag     420
acagacagac agacagacag atagaaagat agatagataa ggggaaaaag aaacgtagct     480
gagcaagcca gagagagcaa gccaaataag cagcattcct ccatgacttt tccttcagct     540
cctgcctatg agtctgcctt gacttccctc agtgattggt tgtaagttaa aaggtgaaat     600
aaacccttttc tttgacaagt tgcttttggt tctgattttt atcacagcaa gagaaaatca     660
aactagaaca aacatgtatt tttcctggca catgtccata gtaaggcaga aatgatcttc     720
agacctagac catagatact acagagagca gaagtgtaga taggtggact tactgtatga     780
ttgtaatcca agtaaatcta catagctaga gagctagagg aaaggccaaa gcttcctctg     840
ggaggtcaga tcctgtcgca ctgtagccaa taaggcatat tgcatcacag gaaaggacta     900
agacccaggc tggcaatagt gtctgtatct taactagatc tctctagtga gtgaggaagt     960
aaatttgtga gagcccagac tgtgggctcg gaaggtacct gccatgcccc tgttagtaac    1020
tgagtactac agcaggagca ggtgttctct agaaagcctg agacaactct acttcttctc    1080
tcaagagacc acctaataca ggcctgagag aacagactct ggaaatagat gggacttacg    1140
gagctaagat ctagagctca tctacagagc agaatcccag ccaagagaac aaagaatact    1200
gactctctcc tgttccctac tcctagagtt ctaaaacaca ctatagggaa gggagcctct    1260
agacctccgt ccattcccca tcttgctcat tccatcttcc catgtcccca ggtctccaag    1320
ccacagacac caccctttcct attcacccac ctttctgtgt ccctaggtcc ccaggccata    1380
gtcacctccc cccacacccc gctcaccctg ccccatctat gccccctagat gcttacttac    1440
cagagtcttt tgtctgacgt ggggctacaa gcatctatgc tccctaagca cctactgctg    1500
acctgtagga cccagctctg aaccaactca tataagtaaa tacagactct cccctgtctt    1560
aggatggccc cctgggtcag gaggagacca ctgccaagga accttctctt agagcactga    1620
actcctcccc tgtaccactt aggacagacc tgagacctat tattactgat taccagagct    1680
ctggcagtga ccacggagga gatagatcca ccctggacac aggaaacaca gcaccagaga    1740
tactgcttca tcacaacagt agagtgacac tttagacttt aatttgggtc actttcctgc    1800
tgtagaggtg ggatcagaaa gcaaagagca gtatgagtgc ctgataggca cccaagtaca    1860
ctatagagta ctcatggtga ataaggtacc tccatggctt cccagggagg ggcactgccc    1920
cacccccacc atcacagacc tttctccata gttgataact cagacacaag tgaatgacag    1980
atggacctcc atctgctctt atttttaaaaa gaagacaaac cccacaggct cgagaactt t    2040
agcgactgtt ttgagagaaa tcattggtcc ctgactcaag agatgactgg cagattgggg    2100
atcagaatac ccatactctg tggctagtgt gaggtttaag cctcagagtc cctgtggtct    2160
ctgactggtg caaggttttg actaagcgga gcaccacagt gctaactggg accacggtga    2220
cacgtggctc aacaaaaacc ttctgtttgg agctctccag gggcagcctg agctatgagg    2280
aagtagagag gcttgagaaa tctgaggaag aaaagagtag atctgagagg aaaggtagct    2340
```

-continued

```
ttctggaggt caggagacag tgcagagaag aacgagttac tgtggacagg tcttagatgg   2400
ggaaagaatg agcaaatgca agcatcagaa gggtggatgc aatgtcctgc caaggactta   2460
ccaagaggat ccccggacag agcaggcagg tggagttgac tgagaggaca ggataggtgc   2520
aggtccctct cttgtttcct ttctccttct cctgtttcct tcttctcttg tcacaggtct   2580
cactatgcta gccaaggcta gcctgaaaga ttaccatcct acagatgggc ccatccagtt   2640
gaattaaggt ggagatctct ccaaacatct gagtttctga ggcttggatg ccactgggga   2700
cgccaaggga ctttgggatg ggtttggttg ccccagatg aagggctact tcactgggtc    2760
tataattact ctgatgtcta ggaccagggg gctcaggtca ctcaggtcag gtgagtcctg   2820
catctgggga ctgtggggtt caggtggcct aaggcaggat gtggagagag ttttagtata   2880
ggaacagagg cagaacagag actgtgctac tggtacttcg atgtctgggg cacagggacc   2940
acggtcaccg tctcctcagg taagctggct ttttctttc tgcacattcc attctgaaac    3000
gggaaaagat attctcagat ctccccatgt caggccatct gccacactct gcatgctgca   3060
gaagcttttc tgtaaggata gggtcttcac tcccaggaaa agaggcagtc agaggctagc   3120
tgcctgtgga acagtgacaa tcatggaaaa taggcattta cattgttagg ctacatgggt   3180
agatgggttt ttgtacaccc actaaagggg tctatgatag tgtgactact ttgactactg   3240
gggccaaggc accactctca cagtctcctc aggtgagtcc ttacaacctc tctcttctat   3300
tcagcttaaa tagattttac tgcatttgtt ggggggaaa tgtgtgtatc tgaatttcag    3360
gtcatgaagg actagggaca ccttgggagt cagaaagggt cattgggagc cctggctgac   3420
gcagacagac atcctcagct cccatacttc atggccagag atttataggg atcctggcca   3480
gcattgccgc taggtccctc tcttctatgc tttctttgtc cctcactggc tccatctga    3540 gatcatcctg gagccctagc caaggatcat ttattgtcag gggtctaatc attgttgtca   3600
caatgtgcct ggtttgctta ctggggccaa gggactctgg tcactgtctc tgcaggtgag   3660
tcctaacttc tcccattcta aatgcatgtt gggggattc tgggccttca ggaccaagat    3720
tctctgcaaa cgggaatcaa gattcaaccc ctttgtccca agttgagac atgggtctgg    3780 gtcagggact ctctgcctgc tggtctgtgg tgacattaga actgaagtat gatgaaggat   3840
ctgccagaac tgaagcttga agtctgaggc agaatcttgt ccagggtcta tcggactctt   3900
gtgagaatta ggggctgaca gttgatggtg acaatttcag ggtcagtgac tgtctggttt   3960
ctctgaggtg aggctggaat ataggtcacc ttgaagacta agagggggtc caggggcttc   4020
tgcacaggca gggaacagaa tgtggaacaa tgacttgaat ggttgattct tgtgtgacac   4080
caggaattgg cataatgtct gagttgccca ggggtgattc tagtcagact ctggggtttt   4140
tgtcgggtat agaggaaaaa tccactattg tgattactat gctatggact actggggtca   4200
aggaacctca gtcaccgtct cctcaggtaa gaatggcctc tccaggtctt tattttttaac  4260 ctttgttatg gagttttctg agcattgcag actaatcttg gatatttgtc cctgaggag    4320 ccggctgaga gaagttggga aataaactgt ctagggatct cagagccttt aggacagatt   4380
atctccacat ctttgaaaaa ctaagaatct gtgtgatggt gttggtggag tccctggatg   4440
atgggatagg gactttggag gctcatttga agaagatgct aaaacaatcc tatggctgga   4500
gggatagttg gggct                                                    4515
```

<210> SEQ ID NO 7
<211> LENGTH: 25
<212> TYPE: DNA

```
<213> ORGANISM: Artificial Sequence
<220> FEATURE:
<223> OTHER INFORMATION: Oligonucleotide HV2-5

<400> SEQUENCE: 7
agatcacctt gaaggagtct ggtcc                                        25

<210> SEQ ID NO 8
<211> LENGTH: 25
<212> TYPE: DNA
<213> ORGANISM: Artificial Sequence
<220> FEATURE:
<223> OTHER INFORMATION: Oligonucleotide HV4-4

<400> SEQUENCE: 8
tggtgaagcc ttcggagacc ctgtc                                        25

<210> SEQ ID NO 9
<211> LENGTH: 25
<212> TYPE: DNA
<213> ORGANISM: Artificial Sequence
<220> FEATURE:
<223> OTHER INFORMATION: Oligonucleotide HV1-3

<400> SEQUENCE: 9
cactagctat gctatgcatt gggtg                                        25

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide HV1-2

<400> SEQUENCE: 10
atggatcaac cctaacagtg gtggc                                        25

<210> SEQ ID NO 11
<211> LENGTH: 25
<212> TYPE: DNA
<213> ORGANISM: Artificial Sequence
<220> FEATURE:
<223> OTHER INFORMATION: Oligonucleotide HV6-1

<400> SEQUENCE: 11
ggaaggacat actacaggtc caagt                                        25

<210> SEQ ID NO 12
<211> LENGTH: 25
<212> TYPE: DNA
<213> ORGANISM: Artificial Sequence
<220> FEATURE:
<223> OTHER INFORMATION: Oligonucleotide C

<400> SEQUENCE: 12
taggtacttg cccctgtcc tcagt                                         25

<210> SEQ ID NO 13
<211> LENGTH: 25
<212> TYPE: DNA
<213> ORGANISM: Artificial Sequence
<220> FEATURE:
<223> OTHER INFORMATION: Oligonucleotide KV1-9

<400> SEQUENCE: 13
agcccagtgt gttccgtaca gcctg                                        25
```

<210> SEQ ID NO 14
<211> LENGTH: 25
<212> TYPE: DNA
<213> ORGANISM: Artificial Sequence
<220> FEATURE:
<223> OTHER INFORMATION: Oligonucleotide KV1-8

<400> SEQUENCE: 14
atcctcattc tctgcatcta cagga                                              25

<210> SEQ ID NO 15
<211> LENGTH: 25
<212> TYPE: DNA
<213> ORGANISM: Artificial Sequence
<220> FEATURE:
<223> OTHER INFORMATION: Oligonucleotide KV1-6

<400> SEQUENCE: 15
ggtaaggatg gagaacactg gcagt                                              25

<210> SEQ ID NO 16
<211> LENGTH: 25
<212> TYPE: DNA
<213> ORGANISM: Artificial Sequence
<220> FEATURE:
<223> OTHER INFORMATION: Oligonucleotide KV1-5

<400> SEQUENCE: 16
ttagtagctg gttggcctgg tatca                                              25

<210> SEQ ID NO 17
<211> LENGTH: 25
<212> TYPE: DNA
<213> ORGANISM: Artificial Sequence
<220> FEATURE:
<223> OTHER INFORMATION: Oligonucleotide Ck

<400> SEQUENCE: 17
ctttgctgtc ctgatcagtc caact                                              25

<210> SEQ ID NO 18
<211> LENGTH: 10
<212> TYPE: DNA
<213> ORGANISM: Artificial Sequence
<220> FEATURE:
<223> OTHER INFORMATION: Rat Switch
<220> FEATURE:
<221> NAME/KEY: repeat_region
<222> LOCATION: (1)..(10)
<223> OTHER INFORMATION: Repeated 148 times

<400> SEQUENCE: 18
gagctgagct                                                               10

<210> SEQ ID NO 19
<211> LENGTH: 10
<212> TYPE: DNA
<213> ORGANISM: Artificial Sequence
<220> FEATURE:
<223> OTHER INFORMATION: Rat Switch
<220> FEATURE:
<221> NAME/KEY: repeat_region
<222> LOCATION: (1)..(10)
<223> OTHER INFORMATION: Repeat 25 times

<400> SEQUENCE: 19
ggggtggggt 10

<210> SEQ ID NO 20
<211> LENGTH: 10
<212> TYPE: DNA
<213> ORGANISM: Artificial Sequence
<220> FEATURE:
<223> OTHER INFORMATION: Rat Switch
<220> FEATURE:
<221> NAME/KEY: repeat_region
<222> LOCATION: (1)..(5)
<223> OTHER INFORMATION: Repeat 82 times

<400> SEQUENCE: 20
gggctgggct 10

<210> SEQ ID NO 21
<211> LENGTH: 6
<212> TYPE: PRT
<213> ORGANISM: Artificial Sequence
<220> FEATURE:
<223> OTHER INFORMATION: Antibody Sequence
<220> FEATURE:
<221> NAME/KEY: MISC_FEATURE
<222> LOCATION: (1)..(2)
<223> OTHER INFORMATION: Xaa Xaa = PR, RT, or PW

<400> SEQUENCE: 21

Xaa Xaa Thr Phe Gly Gln
1               5

<210> SEQ ID NO 22
<211> LENGTH: 17
<212> TYPE: PRT
<213> ORGANISM: Artificial Sequence
<220> FEATURE:
<223> OTHER INFORMATION: Antibody Sequence
<220> FEATURE:
<221> NAME/KEY: MISC_FEATURE
<222> LOCATION: (1)..(2)
<223> OTHER INFORMATION: Xaa Xaa= PR, RT, or PW

<400> SEQUENCE: 22

Xaa Xaa Thr Phe Gly Gln Gly Thr Lys Val Glu Ile Lys Arg Ala Asp
1               5                   10                  15

Ala

<210> SEQ ID NO 23
<211> LENGTH: 6
<212> TYPE: PRT
<213> ORGANISM: Artificial Sequence
<220> FEATURE:
<223> OTHER INFORMATION: Antibody Sequence
<220> FEATURE:
<221> NAME/KEY: MISC_FEATURE
<222> LOCATION: (1)..(2)
<223> OTHER INFORMATION: Xaa Xaa = PR or PW

<400> SEQUENCE: 23

Xaa Xaa Thr Phe Gly Gln
1               5

<210> SEQ ID NO 24
<211> LENGTH: 17
<212> TYPE: PRT
<213> ORGANISM: Artificial Sequence
<220> FEATURE:
<223> OTHER INFORMATION: Antibody Sequence
<220> FEATURE:

```
<221> NAME/KEY: MISC_FEATURE
<222> LOCATION: (1)..(2)
<223> OTHER INFORMATION: Xaa Xaa = PR or PW

<400> SEQUENCE: 24

Xaa Xaa Thr Phe Gly Gln Gly Thr Lys Val Glu Ile Lys Arg Ala Asp
1               5                  10                  15

Ala

<210> SEQ ID NO 25
<211> LENGTH: 24
<212> TYPE: DNA
<213> ORGANISM: Artificial Sequence
<220> FEATURE:
<223> OTHER INFORMATION: Primer E1554

<400> SEQUENCE: 25
atgacttcag tgttgttctg gtag                                              24

<210> SEQ ID NO 26
<211> LENGTH: 19
<212> TYPE: DNA
<213> ORGANISM: Artificial Sequence
<220> FEATURE:
<223> OTHER INFORMATION: Primer E1555

<400> SEQUENCE: 26
caccagattc ttatcagac                                                    19

<210> SEQ ID NO 27
<211> LENGTH: 35
<212> TYPE: DNA
<213> ORGANISM: Artificial Sequence
<220> FEATURE:
<223> OTHER INFORMATION: ELP1352_Cy1

<400> SEQUENCE: 27
agagcggccg ctgggcaacg ttgcaggtga cggtc                                  35

<210> SEQ ID NO 28
<211> LENGTH: 34
<212> TYPE: DNA
<213> ORGANISM: Artificial Sequence
<220> FEATURE:
<223> OTHER INFORMATION: ELP1353_Cy2b

<400> SEQUENCE: 28
agagcggccg ctttgtccac cgtggtgctg ctgg                                   34

<210> SEQ ID NO 29
<211> LENGTH: 33
<212> TYPE: DNA
<213> ORGANISM: Artificial Sequence
<220> FEATURE:
<223> OTHER INFORMATION: ELP1354_Cy2a

<400> SEQUENCE: 29
agagcggccg cacattgcag gtgatggact ggc                                    33

<210> SEQ ID NO 30
<211> LENGTH: 35
<212> TYPE: DNA
<213> ORGANISM: Artificial Sequence
<220> FEATURE:
<223> OTHER INFORMATION: ELP1356_VH4-4
```

<400> SEQUENCE: 30
aggacgcgtg aaacacctgt ggttcttcct cctgc    35

<210> SEQ ID NO 31
<211> LENGTH: 33
<212> TYPE: DNA
<213> ORGANISM: Artificial Sequence
<220> FEATURE:
<223> OTHER INFORMATION: ELP1357_VH1-2,3

<400> SEQUENCE: 31
aggacgcgtc accatggact ggacctggag gat    33

<210> SEQ ID NO 32
<211> LENGTH: 34
<212> TYPE: DNA
<213> ORGANISM: Artificial Sequence
<220> FEATURE:
<223> OTHER INFORMATION: ELP1358_VH6-1

<400> SEQUENCE: 32
aggacgcgta tgtctgtctc cttcctcatc ttcc    34

<210> SEQ ID NO 33
<211> LENGTH: 21
<212> TYPE: DNA
<213> ORGANISM: Artificial Sequence
<220> FEATURE:
<223> OTHER INFORMATION: mIgG1_2 rev

<400> SEQUENCE: 33
ggggccagtg gatagacaga t    21

<210> SEQ ID NO 34
<211> LENGTH: 18
<212> TYPE: DNA
<213> ORGANISM: Artificial Sequence
<220> FEATURE:
<223> OTHER INFORMATION: mIgG2b rev

<400> SEQUENCE: 34
cagtggatag actgatgg    18

<210> SEQ ID NO 35
<211> LENGTH: 18
<212> TYPE: DNA
<213> ORGANISM: Artificial Sequence
<220> FEATURE:
<223> OTHER INFORMATION: mIgG2a_2 rev

<400> SEQUENCE: 35
cagtggatag accgatgg    18

<210> SEQ ID NO 36
<211> LENGTH: 20
<212> TYPE: DNA
<213> ORGANISM: Artificial Sequence
<220> FEATURE:
<223> OTHER INFORMATION: mCH1 unirev
<220> FEATURE:
<221> NAME/KEY: misc_feature
<222> LOCATION: (1)..(1)
<223> OTHER INFORMATION: K = G or T

<400> SEQUENCE: 36
kcaggggcca gtggatagac    20

<210> SEQ ID NO 37
<211> LENGTH: 20
<212> TYPE: DNA
<213> ORGANISM: Artificial Sequence
<220> FEATURE:
<223> OTHER INFORMATION: mCH1 unirev_2
<220> FEATURE:
<221> NAME/KEY: misc_feature
<222> LOCATION: (3)..(3)
<223> OTHER INFORMATION: R = A or G
<220> FEATURE:
<221> NAME/KEY: misc_feature
<222> LOCATION: (6)..(6)
<223> OTHER INFORMATION: Y = C or T
<220> FEATURE:
<221> NAME/KEY: misc_feature
<222> LOCATION: (12)..(12)
<223> OTHER INFORMATION: M = A or C

<400> SEQUENCE: 37
tarccyttga cmaggcatcc          20

<210> SEQ ID NO 38
<211> LENGTH: 24
<212> TYPE: PRT
<213> ORGANISM: Artificial Sequence
<220> FEATURE:
<223> OTHER INFORMATION: 16C9

<400> SEQUENCE: 38

Gln Glu Val Ile Asn Tyr Tyr Tyr Gly Met Asp Val Trp Gly Gln
1               5                   10                  15

Gly Thr Thr Val Thr Val Ser Ser
            20

<210> SEQ ID NO 39
<211> LENGTH: 24
<212> TYPE: PRT
<213> ORGANISM: Artificial Sequence
<220> FEATURE:
<223> OTHER INFORMATION: 20B5

<400> SEQUENCE: 39

Gln Glu Val Ile Asn Tyr Tyr Tyr Gly Met Asp Val Trp Gly Gln
1               5                   10                  15

Gly Thr Thr Val Thr Val Ser Ser
            20

<210> SEQ ID NO 40
<211> LENGTH: 26
<212> TYPE: PRT
<213> ORGANISM: Artificial Sequence
<220> FEATURE:
<223> OTHER INFORMATION: 19F4

<400> SEQUENCE: 40

Leu Glu Met Ala Thr Ile Asn Tyr Tyr Tyr Gly Met Asp Val Trp
1               5                   10                  15

Gly Gln Gly Thr Met Val Thr Val Ser Ser
            20                  25

<210> SEQ ID NO 41
<211> LENGTH: 24
<212> TYPE: PRT
<213> ORGANISM: Artificial Sequence
<220> FEATURE:

-continued

<223> OTHER INFORMATION: 19E1

<400> SEQUENCE: 41

Gln Glu Phe Gly Asn Tyr Tyr Tyr Gly Met Asp Val Trp Gly Gln
1               5                   10                  15

Gly Thr Thr Val Thr Val Ser Ser
            20

<210> SEQ ID NO 42
<211> LENGTH: 24
<212> TYPE: PRT
<213> ORGANISM: Artificial Sequence
<220> FEATURE:
<223> OTHER INFORMATION: 19G8

<400> SEQUENCE: 42

Gln Glu Asp Gly Asn Pro Tyr Tyr Phe Gly Met Asp Phe Trp Gly Gln
1               5                   10                  15

Gly Thr Thr Val Thr Val Ser Ser
            20

<210> SEQ ID NO 43
<211> LENGTH: 22
<212> TYPE: PRT
<213> ORGANISM: Artificial Sequence
<220> FEATURE:
<223> OTHER INFORMATION: 20H10

<400> SEQUENCE: 43

Gly Ser Ser Tyr Tyr Tyr Asp Gly Met Asp Val Trp Gly Gln Gly Thr
1               5                   10                  15

Thr Val Thr Val Ser Ser
            20

<210> SEQ ID NO 44
<211> LENGTH: 25
<212> TYPE: PRT
<213> ORGANISM: Artificial Sequence
<220> FEATURE:
<223> OTHER INFORMATION: 18D10

<400> SEQUENCE: 44

Leu Glu Asn Asp Tyr Gly Tyr Tyr Tyr Gly Met Asp Val Trp Gly
1               5                   10                  15

Gln Gly Thr Thr Val Thr Val Ser Ser
            20                  25

<210> SEQ ID NO 45
<211> LENGTH: 23
<212> TYPE: PRT
<213> ORGANISM: Artificial Sequence
<220> FEATURE:
<223> OTHER INFORMATION: 16F2

<400> SEQUENCE: 45

Arg Gly Gly Leu Ser Pro Leu Tyr Gly Met Asp Val Trp Gly Gln Gly
1               5                   10                  15

Thr Thr Val Thr Val Ser Ser
            20

<210> SEQ ID NO 46
<211> LENGTH: 15
<212> TYPE: DNA
<213> ORGANISM: Artificial Sequence

```
<220> FEATURE:
<223> OTHER INFORMATION: Rat Switch

<400> SEQUENCE: 46
gggctgggct gggct                                                        15

<210> SEQ ID NO 47
<211> LENGTH: 20
<212> TYPE: DNA
<213> ORGANISM: Artificial Sequence
<220> FEATURE:
<223> OTHER INFORMATION: Rat Switch

<400> SEQUENCE: 47
gggctgggct gggctgggct                                                   20

<210> SEQ ID NO 48
<211> LENGTH: 25
<212> TYPE: DNA
<213> ORGANISM: Artificial Sequence
<220> FEATURE:
<223> OTHER INFORMATION: Rat Switch

<400> SEQUENCE: 48
gggctgggct gggctgggct gggct                                             25

<210> SEQ ID NO 49
<211> LENGTH: 30
<212> TYPE: DNA
<213> ORGANISM: Artificial Sequence
<220> FEATURE:
<223> OTHER INFORMATION: Rat Switch

<400> SEQUENCE: 49
gggctgggct gggctgggct gggctgggct                                        30

<210> SEQ ID NO 50
<211> LENGTH: 10
<212> TYPE: DNA
<213> ORGANISM: Artificial Sequence
<220> FEATURE:
<223> OTHER INFORMATION: Rat Switch
<220> FEATURE:
<221> NAME/KEY: repeat_region
<222> LOCATION: (1)..(5)
<223> OTHER INFORMATION: Repeat 6 to 81 times

<400> SEQUENCE: 50
gggctgggct                                                              10

<210> SEQ ID NO 51
<211> LENGTH: 6
<212> TYPE: PRT
<213> ORGANISM: Artificial Sequence
<220> FEATURE:
<223> OTHER INFORMATION: IGHV4-4*02 CDR1

<400> SEQUENCE: 51

Ser Ser Asn Trp Trp Ser
1               5

<210> SEQ ID NO 52
<211> LENGTH: 6
<212> TYPE: PRT
<213> ORGANISM: Artificial Sequence
<220> FEATURE:
<223> OTHER INFORMATION: 12D10 CDR1
```

<400> SEQUENCE: 52

Ser Gly Asn Trp Trp Ser
1               5

<210> SEQ ID NO 53
<211> LENGTH: 6
<212> TYPE: PRT
<213> ORGANISM: Artificial Sequence
<220> FEATURE:
<223> OTHER INFORMATION: 1283 CDR1

<400> SEQUENCE: 53

Arg Ser Asn Trp Trp Ser
1               5

<210> SEQ ID NO 54
<211> LENGTH: 7
<212> TYPE: PRT
<213> ORGANISM: Artificial Sequence
<220> FEATURE:
<223> OTHER INFORMATION: IGHV6-1*01 CDR1

<400> SEQUENCE: 54

Ser Asn Ser Ala Ala Trp Asn
1               5

<210> SEQ ID NO 55
<211> LENGTH: 7
<212> TYPE: PRT
<213> ORGANISM: Artificial Sequence
<220> FEATURE:
<223> OTHER INFORMATION: 4A12 CDR1

<400> SEQUENCE: 55

Ser Asn Ser Ala Ala Trp Asn
1               5

<210> SEQ ID NO 56
<211> LENGTH: 16
<212> TYPE: PRT
<213> ORGANISM: Artificial Sequence
<220> FEATURE:
<223> OTHER INFORMATION: IGHV4-4*02 CDR2

<400> SEQUENCE: 56

Glu Ile Tyr His Ser Gly Ser Thr Asn Tyr Asn Pro Ser Leu Lys Ser
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: 12D10 CDR2

<400> SEQUENCE: 57

Glu Ile Tyr His Ser Gly Asn Thr Asn Tyr Asn Pro Ser Leu Lys Ser
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: 1283 CDR2

```
<400> SEQUENCE: 58

Glu Ile Tyr His Ser Gly Ser Thr Asn Tyr Asn Pro Ser Leu Lys Ser
1               5                   10                  15

<210> SEQ ID NO 59
<211> LENGTH: 18
<212> TYPE: PRT
<213> ORGANISM: Artificial Sequence
<220> FEATURE:
<223> OTHER INFORMATION: IGHV6-1*01 CDR2

<400> SEQUENCE: 59

Arg Thr Tyr Tyr Arg Ser Lys Trp Tyr Asn Asp Tyr Ala Val Ser Val
1               5                   10                  15

Lys Ser

<210> SEQ ID NO 60
<211> LENGTH: 18
<212> TYPE: PRT
<213> ORGANISM: Artificial Sequence
<220> FEATURE:
<223> OTHER INFORMATION: 4A12 CDR2

<400> SEQUENCE: 60

Arg Thr Tyr Tyr Arg Ser Lys Trp Tyr Asn Asp Tyr Lys Val Ser Val
1               5                   10                  15

Lys Ser

<210> SEQ ID NO 61
<211> LENGTH: 12
<212> TYPE: PRT
<213> ORGANISM: Artificial Sequence
<220> FEATURE:
<223> OTHER INFORMATION: 12D10 CDR3

<400> SEQUENCE: 61

Gly Pro Leu Thr Gly Glu Lys Tyr Tyr Phe Asp Leu
1               5                   10

<210> SEQ ID NO 62
<211> LENGTH: 8
<212> TYPE: PRT
<213> ORGANISM: Artificial Sequence
<220> FEATURE:
<223> OTHER INFORMATION: 1283 CDR3

<400> SEQUENCE: 62

Ile Gly Asp Trp Tyr Phe Asp Leu
1               5

<210> SEQ ID NO 63
<211> LENGTH: 16
<212> TYPE: PRT
<213> ORGANISM: Artificial Sequence
<220> FEATURE:
<223> OTHER INFORMATION: 4A12 CDR3

<400> SEQUENCE: 63

Glu Gly Ser His Ser Gly Ser Gly Trp Tyr Leu Asp Ala Phe Asp Ile
1               5                   10                  15

<210> SEQ ID NO 64
<211> LENGTH: 17
<212> TYPE: PRT
<213> ORGANISM: Artificial Sequence
```

```
<220> FEATURE:
<223> OTHER INFORMATION: IGHJ2*01 J-region

<400> SEQUENCE: 64

Tyr Trp Tyr Phe Asp Leu Trp Gly Arg Gly Thr Leu Val Thr Val Ser
1               5                   10                  15

Ser

<210> SEQ ID NO 65
<211> LENGTH: 16
<212> TYPE: PRT
<213> ORGANISM: Artificial Sequence
<220> FEATURE:
<223> OTHER INFORMATION: 12D10 J-region

<400> SEQUENCE: 65

Tyr Tyr Phe Asp Leu Trp Gly Arg Gly Thr Leu Val Thr Val Ser Ser
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: 1283 J-Region

<400> SEQUENCE: 66

Trp Tyr Phe Asp Leu Trp Gly Arg Gly Thr Leu Val Thr Val Ser Ser
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: IGHJ3*01 J-Region

<400> SEQUENCE: 67

Asp Ala Phe Asp Val Trp Gly Gln Gly Thr Met Val Thr Val Ser Ser
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: 4A12 J-region

<400> SEQUENCE: 68

Asp Ala Phe Asp Ile Trp Gly Gln Gly Thr Lys Val Thr Val Ser Ser
1               5                   10                  15
```

ANIMAL MODELS AND THERAPEUTIC MOLECULES

CROSS-REFERENCE TO RELATED APPLICATIONS

This application is a Divisional application of U.S. Ser. No. 13/310,431, filed Dec. 2, 2011, which is a Continuation-in-Part of PCT/GB2010/051122, filed Jul. 7, 2010, which claims the benefit of U.S. Provisional Application No. 61/223,960 filed Jul. 8, 2009; U.S. Provisional Application No. 61/355,666, filed Jun. 17, 2010; GB Patent Application No. 0911846.4, filed Jul. 8, 2009; and GB Patent Application No. 0913102.0, filed Jul. 28, 2009. U.S. Ser. No. 13/310,431 is also a Continuation-in-Part of PCT/GB2011/050019, filed Jan. 7, 2011. The entire contents of the above-referenced applications are incorporated herein by reference.

BACKGROUND

The present invention relates inter alia to non-human animals and cells that are engineered to contain exogenous DNA, such as human immunoglobulin gene DNA, their use in medicine and the study of disease, methods for production of non-human animals and cells, and antibodies and antibody chains produced by such animals and derivatives thereof.

In order to get around the problems of humanizing antibodies a number of companies set out to generate mice with human immune systems. The strategy used was to knockout the heavy and light chain loci in ES cells and complement these genetic lesions with transgenes designed to express the human heavy and light chain genes. Although fully human antibodies could be generated, these models have several major limitations:
(i) The size of the heavy and light chain loci (each several Mb) made it impossible to introduce the entire loci into these models. As a result the transgenic lines recovered had a very limited repertoire of V-regions, most of the constant regions were missing and important distant enhancer regions were not included in the transgenes.
(ii) The very low efficiency of generating the large insert transgenic lines and the complexity and time required to cross each of these into the heavy and light chain knockout strains and make them homozygous again, restricted the number of transgenic lines which could be analysed for optimal expression.
(iii) Individual antibody affinities rarely reached those which could be obtained from intact (non-transgenic) animals.

WO2007117410 discloses chimaeric constructs for expressing chimaeric antibodies.

WO2010039900 discloses knock in cells and mammals having a genome encoding chimaeric antibodies.

The present invention provides, inter alia, a process for the generation in non-human mammals of antibodies that comprise a human Ig variable region, and further provides non-human animal models for the generation of such antibodies.

SUMMARY OF THE INVENTION

All nucleotide co-ordinates for the mouse are those corresponding to NCBI m37 for the mouse C57BL/6J strain, e.g. April 2007 ENSEMBL Release 55.37h, e.g. NCBI37 July 2007 (NCBI build 37) (e.g. UCSC version mm9 see World Wide Web (www) genome.ucsc.edu and World Wide Web (www) genome.ucsc.edu/FAQ/FAQreleases.html) unless otherwise specified. Human nucleotides coordinates are those corresponding to GRCh37 (e.g. UCSC version hg 19, World Wide Web (www) genome.ucsc.edu/FAQ/FAQreleases.html), February 2009 ENSEMBL Release 55.37, or are those corresponding to NCBI36, Ensemble release 54 unless otherwise specified. Rat nucleotides are those corresponding to RGSC 3.4 December 2004 ENSEMBL release 55.34w, or Baylor College of Medicine HGSC v3.4 November 2004 (e.g., UCSC rn4, see World Wide Web (www) genome.ucsc.edu and World Wide Web (www) genome.ucsc.edu/FAQ/FAQreleases.html) unless otherwise specified.

In the present invention, methods are disclosed for constructing a chimaeric human heavy and light chain loci in a non-human mammal, for example a mouse. Reference to work in mice herein is by way of example only, and reference to mice is taken to include reference to all non-human mammals unless otherwise apparent from the disclosure, with mice being preferred as the non-human mammal.

In one aspect the invention relates to a non-human mammal whose genome comprises:
  (a) a plurality of human IgH V regions, one or more human D regions and one or more human J regions upstream of the host non-human mammal constant region; and
  (b) optionally one or more human Ig light chain kappa V regions and one or more human Ig light chain kappa J regions upstream of the host non-human mammal kappa constant region and/or one or more human Ig light chain lambda V regions and one or more human Ig light chain lambda J regions upstream of the host non-human mammal lambda constant region;
wherein the non-human mammal is able to produce a repertoire of chimaeric antibodies, or chimaeric light or heavy chains, having a non-human mammal constant region and a human variable region.

In one aspect the invention relates to non-human mammal whose genome comprises
  (a) a plurality of human Ig light chain kappa V regions and one or more human Ig light chain kappa J regions upstream of the host non-human mammal kappa constant region and/or a plurality of human Ig light chain lambda V regions and one or more human Ig light chain lambda J regions upstream of the host non-human mammal lambda constant region; and
  (b) optionally one or more human IgH V regions, one or more human D regions and one or more human J regions upstream of the host non-human mammal constant region;
wherein the non-human mammal is able to produce a repertoire of chimaeric antibodies, or chimaeric light or heavy chains, having a non-human mammal constant region and a human variable region.

In one aspect the invention relates to non-human mammalian cell whose genome comprises
  (a) a plurality of human IgH V regions, one or more human D regions and one or more human J regions upstream of the host non-human mammal constant region and
  (b) optionally one or more human Ig light chain kappa V regions and one or more human Ig light chain kappa J regions upstream of the host non-human mammal kappa constant region and/or one or more human Ig light chain lambda V regions and one or more human Ig light chain lambda J regions upstream of the host non-human mammal lambda constant region.

In one aspect the invention relates to a non-human mammalian cell whose genome comprises
  (a) a plurality of human Ig light chain kappa V regions and one or more human Ig light chain kappa J regions upstream of the host non-human mammal kappa constant region and/or a plurality of human Ig light chain lambda V regions and one or more human Ig light chain lambda J regions upstream of the host non-human mammal lambda constant region; and
  (b) optionally one or more human IgH V regions, one or more human D regions and one or more human J regions upstream of the host non-human mammal constant region;

In a further aspect the invention relates to a method for producing a non-human cell or mammal comprising inserting into a non-human mammal cell genome, such as an ES cell genome;
  (a) a plurality of human IgH V regions, one or more human D regions and one or more human J regions upstream of the host non-human mammal constant region; and
  (b) optionally one or more human Ig light chain kappa V regions and one or more human Ig light chain kappa J regions upstream of the host non-human mammal kappa constant region and/or one or more human Ig light chain lambda V regions and one or more human Ig light chain lambda J regions upstream of the host non-human mammal lambda constant region;
respectively, the insertion being such that the non-human cell or mammal is able to produce a repertoire of chimaeric antibodies having a non-human mammal constant region and a human variable region, wherein steps (a) and (b) can be carried out in either order and each of steps (a) and (b) can be carried out in a stepwise manner or as a single step. Insertion may be by homologous recombination.

In a further aspect the invention relates to a method for producing an antibody or antibody chain specific to a desired antigen the method comprising immunizing a transgenic non-human mammal as disclosed herein with the desired antigen and recovering the antibody or antibody chain.

In a further aspect the invention relates to a method for producing a fully humanised antibody comprising immunizing a transgenic non-human mammal as disclosed herein with the desired antigen, recovering the antibody or cells producing the antibody and then replacing the non-human mammal constant region with a human constant region, for example by protein or DNA engineering.

In a further aspect the invention relates to humanised antibodies and antibody chains produced according to the present invention, both in chimaeric (for example, mouse-human) and fully humanised form, as well as fragments and derivatives of said antibodies and chains, and use of said antibodies, chains and fragments in medicine, including diagnosis.

In a further aspect the invention relates to use of a non-human mammal as described herein as a model for the testing of drugs and vaccines.

In one aspect the invention relates to a non-human mammal whose genome comprises:
  (a) a plurality of human IgH V regions, one or more human D regions and one or more human J regions upstream of the host non-human mammal constant region; and
  (b) optionally one or more human Ig light chain kappa V regions and one or more human Ig light chain kappa J regions upstream of the host non-human mammal kappa constant region and/or one or more human Ig light chain lambda V regions and one or more human Ig light chain lambda J regions upstream of the host non-human mammal lambda constant region;
wherein the non-human mammal is able to produce a repertoire of chimaeric antibodies or antibody chains having a non-human mammal constant region and a human variable region.

In a further aspect the invention relates to a non-human mammal whose genome comprises:
  (a) a plurality of human Ig light chain kappa V regions and one or more human Ig light chain kappa J regions upstream of the host non-human mammal kappa constant region and/or a plurality of human Ig light chain lambda V regions and one or more human Ig light chain lambda J regions upstream of the host non-human mammal lambda constant region; and
  (b) optionally one or more human IgH V regions, one or more human D regions and one or more human J regions upstream of the host non-human mammal constant;
wherein the non-human mammal is able to produce a repertoire of chimaeric antibodies having a non-human mammal constant region and a human variable region.

Optionally the non-human mammal genome is modified to prevent expression of fully host-species specific antibodies.

In one aspect the inserted human DNA comprises at least 50% of the human heavy chain variable (V) genes, such as at least 60%, at least 70%, at least 80%, at least 90%, and in one aspect all of the human V genes.

In one aspect the inserted human DNA comprises at least 50% of the human heavy chain diversity (D) genes, such as at least 60%, at least 70%, at least 80%, at least 90%, and in one aspect all of the human D genes.

In one aspect the inserted human DNA comprises at least 50% of the human heavy chain joining (J) genes, such as at least 60%, at least 70%, at least 80%, at least 90%, and in one aspect all of the human J genes.

In one aspect the inserted human DNA comprises at least 50% of the human light chain Variable (V) genes, such as at least 60%, at least 70%, at least 80%, at least 90%, and in one aspect all of the human light chain V genes.

In one aspect the inserted human DNA comprises at least 50% of the human light chain joining (J) genes, such as at least 60%, at least 70%, at least 80%, at least 90%, and in one aspect all of the human light chain J genes.

The inserted human genes may be derived from the same individual or different individuals, or be synthetic or represent human consensus sequences.

Although the number of V D and J regions is variable between human individuals, in one aspect there are considered to be 51 human V genes, 27 D and 6 J genes on the heavy chain, 40 human V genes and 5 J genes on the kappa light chain and 29 human V genes and 4 J genes on the lambda light chain (Janeway and Travers, Immunobiology, Third edition)

In one aspect the human heavy chain locus inserted into the non-human mammal contains the full repertoire of human V, D and J regions, which in the genome is in functional arrangement with the non-human mammal constant regions such that functional chimaeric antibodies can be produced between the human variable and non-human mammal constant regions. This total inserted human heavy chain genetic material is referred to herein as the human IgH VDJ region, and comprises DNA from a human genome that encodes all the exons encoding human V, D and J portions and suitably also the associated introns. Similarly, reference to the human Ig light chain kappa V and J regions herein refers to human DNA comprising all the exons encoding V and J regions and suitably also the associated introns of the human genome. Reference to the human Ig light chain lambda V and J regions herein refers to human DNA comprising all the exons encoding V and J regions and suitably also the associated introns of the human genome.

Human variable regions are suitably inserted upstream of a non-human mammal constant region, the latter comprising all of the DNA required to encode the full constant region or a sufficient portion of the constant region to allow the formation of an effective chimaeric antibody capable of specifically recognising an antigen.

In one aspect the chimaeric antibodies or antibody chains have a part of a host constant region sufficient to provide one or more effector functions seen in antibodies occurring naturally in a host mammal, for example that they are able interact with Fc receptors, and/or bind to complement.

Reference to a chimaeric antibody or antibody chain having a host non mammal constant region herein therefore is not limited to the complete constant region but also includes chimaeric antibodies or chains which have all of the host constant region, or a part thereof sufficient to provide one or more effector functions. This also applies to non-human mammals and cells and methods of the invention in which human variable region DNA may be inserted into the host genome such that it forms a chimaeric antibody chain with all or part of a host constant region. In one aspect the whole of a host constant region is operably linked to human variable region DNA.

The host non-human mammal constant region herein is preferably the endogenous host wild-type constant region located at the wild type locus, as appropriate for the heavy or light chain. For example, the human heavy chain DNA is suitably inserted on mouse chromosome 12, suitably adjacent the mouse heavy chain constant region.

In one aspect the insertion of the human DNA, such as the human VDJ region is targeted to the region between the J4 exon and the Cµ locus in the mouse genome IgH locus, and in one aspect is inserted between co-ordinates 114,667,090 and 114,665,190, or at co-ordinate 114,667,091, after 114,667,090. In one aspect the insertion of the human DNA, such as the human light chain kappa VJ is targeted into mouse chromosome 6 between co-ordinates 70,673,899 and 70,675,515, suitably at position 70,674,734, or an equivalent position in the lambda mouse locus on chromosome 16.

In one aspect the host non-human mammal constant region for forming the chimaeric antibody may be at a different (non endogenous) chromosomal locus. In this case the inserted human DNA, such as the human variable VDJ or VJ region(s) may then be inserted into the non-human genome at a site which is distinct from that of the naturally occurring heavy or light constant region. The native constant region may be inserted into the genome, or duplicated within the genome, at a different chromosomal locus to the native position, such that it is in a functional arrangement with the human variable region such that chimaeric antibodies of the invention can still be produced.

In one aspect the human DNA is inserted at the endogenous host wild-type constant region located at the wild type locus between the host constant region and the host VDJ region.

Reference to location of the variable region upstream of the non-human mammal constant region means that there is a suitable relative location of the two antibody portions, variable and constant, to allow the variable and constant regions to form a chimaeric antibody or antibody chain in vivo in the mammal. Thus, the inserted human DNA and host constant region are in functional arrangement with one another for antibody or antibody chain production.

In one aspect the inserted human DNA is capable of being expressed with different host constant regions through isotype switching. In one aspect isotype switching does not require or involve trans switching. Insertion of the human variable region DNA on the same chromosome as the relevant host constant region means that there is no need for trans-switching to produce isotype switching.

As explained above, the transgenic loci used for the prior art models were of human origin, thus even in those cases when the transgenes were able to complement the mouse locus so that the mice produced B-cells producing fully human antibodies, individual antibody affinities rarely reached those which could be obtained from intact (non-transgenic) animals. The principal reason for this (in addition to repertoire and expression levels described above) is the fact that the control elements of the locus are human. Thus, the signalling components, for instance to activate hyper-mutation and selection of high affinity antibodies are compromised.

In contrast, in the present invention, host non-human mammal constant regions are maintained and it is preferred that at least one non-human mammal enhancer or other control sequence, such as a switch region, is maintained in functional arrangement with the non-human mammal constant region, such that the effect of the enhancer or other control sequence, as seen in the host mammal, is exerted in whole or in part in the transgenic animal.

This approach above is designed to allow the full diversity of the human locus to be sampled, to allow the same high expression levels that would be achieved by non-human mammal control sequences such as enhancers, and is such that signalling in the B-cell, for example isotype switching using switch recombination sites, would still use non-human mammal sequences.

A mammal having such a genome would produce chimaeric antibodies with human variable and non-human mammal constant regions, but these could be readily humanized, for example in a cloning step. Moreover the in vivo efficacy of these chimaeric antibodies could be assessed in these same animals.

In one aspect the inserted human IgH VDJ region comprises, in germline configuration, all of the V, D and J regions and intervening sequences from a human.

In one aspect 800-1000 kb of the human IgH VDJ region is inserted into the non-human mammal IgH locus, and in one aspect a 940, 950 or 960 kb fragment is inserted. Suitably this includes bases 105,400,051 to 106,368,585 from human chromosome 14.

In one aspect the inserted IgH human fragment consists of bases 105,400,051 to 106,368,585 from chromosome 14. In one aspect the inserted human heavy chain DNA, such as DNA consisting of bases 105,400,051 to 106,368,585 from chromosome 14, is inserted into mouse chromosome 12 between the end of the mouse J4 region and the Eµ region, suitably between co-ordinates 114,667,090 and 114,665,190, or at co-ordinate 114,667,091, after 114,667,090. In one aspect the insertion is between co-ordinates 114,667,089 and 114,667,090 (co-ordinates refer to NCBI m37, for the mouse C57BL/6J strain), or at equivalent position in another non-human mammal genome.

In one aspect the inserted human kappa VJ region comprises, in germline configuration, all of the V and J regions and intervening sequences from a human. Suitably this includes bases 88,940,356 to 89,857,000 from human chromosome 2, suitably approximately 917 kb. In a further aspect the light chain VJ insert may comprise only the proximal clusters of V segments and J segments. Such an insert would be of approximately 473 kb. In one aspect the human light chain kappa DNA, such as the human IgK fragment of bases 88,940,356 to 89,857,000 from human chromosome 2, is suitably inserted into mouse chromosome 6 between co-ordinates 70,673,899 and 70,675,515, suitably at position 70,674,734. These co-ordinates refer to NCBI36 for the human genome, ENSEMBL Release 54 and NCBIM37 for the mouse genome, relating to mouse strain C57BL/6J.

In one aspect the human lambda VJ region comprises, in germline configuration, all of the V and J regions and intervening sequences from a human.

Suitably this includes analogous bases to those selected for the kappa fragment, from human chromosome 2.

A cell or non-human mammal of the invention, in one embodiment, comprises an insertion of human heavy chain variable region DNA between co-ordinates 114, 666, 183 and 114, 666, 725, such as between 114 666 283 and 114 666 625, optionally between co-ordinates 114,666,335 and 114,666,536, optionally between 114,666,385 and 114,666,486, or between 114,666,425 and 114,666,446, or between 114,666,435 and 114,666,436 of mouse chromosome 12 with reference to NCBIM37 for the mouse genome, relating to mouse strain C57BL/6J or an equivalent position of mouse chromosome 12 from a different mouse strain or an equivalent position in the genome of another non-human vertebrate, e.g., a rat. The insertion between co-ordinates 114, 666,435 and 114,666,436 relating to mouse strain C57BL/6J is equivalent to an insertion between co-ordinates 1207826 and 1207827 on chromosome 12 with reference to the 129/SvJ genomic sequence of the GenBank® access number NT114985.2. An insertion may be made at equivalent position in another genome, such as another mouse genome. In an example of this embodiment, the cell or mammal of the invention comprises a human IgH VDJ region which comprises or consists of nucleotides 106,328,851-107,268,544, such as nucleotides 106,328,901-107,268,494, such as nucleotides 106,328,941-107,268,454, such as nucleotides 106,328,951-107,268,444 of human Chromosome 14, with reference to the GRCH37/hg19 sequence database, or insertion of equivalent nucleotides relating to chromosome 14 from a different human sequence or database. The human insertion may be made between the regions indicated above.

A cell or mammal of the invention, in one embodiment, comprises an insertion of the human kappa VJ region, suitably comprising or consisting of, in germline configuration, all of the V and J regions and intervening sequences from a human, the insertion of the human DNA being made between co-ordinates 70,673,918-70,675,517, such as between co-ordinates 70,674,418 and 70 675,017, such as between co-ordinates 70,674,655-70,674,856, such as between co-ordinates 70,674,705-70,674,906, such as between co-ordinates 70,674,745-70,674,766, such as between co-ordinates 70,674,755 and 70,674,756 of mouse chromosome 6, numbering with reference to NCBIM37 for the mouse genome, relating to mouse strain C57BL/6J, or an insertion at an equivalent position in another genome, such as another mouse genome. In an example of this embodiment, a cell or mammal of the invention comprises an insertion of nucleotides 89,159,079-89,630,437 and/or 89,941,714-90,266,976 of human chromosome 2 with reference to the GRCH37/hg19 sequence database (or equivalent nucleotides relating to chromosome 2 from a different human sequence or database), such as an insertion of these 2 discrete fragments without the intervening sequence, or an insertion of the complete 89,159,079-90,266,976 region.

The insertion may comprise, or consist, of:
(i) nucleotides 89,158,979-89,630,537, such as 89,159, 029-89,630,487, such as 89,159,069-89,630,447, such as 89,159,079-89,630,437, optionally in addition to fragment (ii) below
(ii) nucleotides 89,941,614-90,267,076, such as 89,941, 664-90,267,026, such as 89, 941,704-90,266,986, such as 89,941,714-90,266,976; optionally in addition to fragment (i)
(iii) nucleotides 89,158,979-90,267,076, such as nucleotides 89,159,079-90,266,976.

The human insertion may be made between the regions indicated above.

In an embodiment, a cell or mammal of the invention comprises an insertion of a human lambda region which comprises at least one human J$\lambda$ region (eg, a germline region) and at least one human C$\lambda$ region (eg, a germline region), optionally $C_\lambda 6$ and/or $C_\lambda 7$. For example, the cell or mammal comprises a plurality of human J$\lambda$ regions, optionally two or more of $J_\lambda 1$, $J_\lambda 2$, $J_\lambda 6$ and $J_\lambda 7$, optionally all of $J_\lambda 1$, $J_\lambda 2$, $J_\lambda 6$ and $J_\lambda 7$. In an example, the cell or mammal comprises at least one human $J_\lambda$-$C_\lambda$ cluster, optionally at least $J_\lambda 7$-$C_\lambda 7$.

In one aspect the human JC cluster is inserted 3' of the last endogenous J lambda or is inserted 3' of the last endogenous J kappa region, suitably immediately 3' of these sequences, or substantially immediately 3' of these sequences.

In one aspect the insertion into the mouse lambda locus is made downstream of the endogenous C1 gene segment, for example where there is a 3' J1C1 cluster, suitably immediately 3' of the C1 segment, or substantially immediately 3' of the segment.

In one aspect (e.g. cell or non-human mammal) a human JC cluster is inserted into a kappa locus and any resulting cell or animal is heterozygous at that locus, such that the cell has one chromosome with human lambda DNA inserted into the kappa locus, and another chromosome with human kappa DNA at the endogenous kappa locus.

In an embodiment, a cell or mammal of the invention comprises a human EA enhancer.

A cell or mammal may of the invention comprise an inserted human lambda VJ region, suitably comprising or consisting of, in germline configuration, all of the V and J regions and intervening sequences from a human, the inserted region comprises or consisting of nucleotides 22,375,509-23,327,984, such as nucleotides 22,375,559-23,327,934, such as nucleotides 22,375,599-23,327,894, such as nucleotides 22,375,609-23,327,884 from human Chromosome 22, with reference to the GRCH37/hg19 sequence database, or equivalent DNA from another human sequence or database. The insertion into the mouse genome may be made between co-ordinates 19,027,763 and 19,061,845, such as between co-ordinates 19,037,763 and 19,051,845, such as between co-ordinates 19,047,451 and 19,047,652, such as between co-ordinates 19,047,491 and 19,047,602, such as between co-ordinates 19,047,541 and 19,047,562, such as between co-ordinates 19,047,551 and 19,047,552 of mouse Chromosome 16 (with reference to NCBIM37 for the mouse genome, relating to mouse strain C57BL/6J, equivalent to co-ordinates 1,293,646-1,293,647 of the 129 SvJ genomic sequence in the sequence file of NT_039630.4), or may be an insertion at an equivalent position in other genome, such as another mouse genome. The insertion of the human lambda nucleic acid into the mouse genome may alternatively be made between co-ordinates 70,673,918 and 70,675,517, such as between co-ordinates 70, 674,418 and 70 675, 017, such as between co-ordinates 70,674,655 and 70,674,856, such as between co-ordinates 70,674,705 and 70,674,806, such as between co-ordinates 70,674,745 and 70,674,766, such as between co-ordinates 70,674,755 and 70,674,756 of mouse Chromosome 6 (with reference to NCBIM37 for the mouse genome, relating to mouse strain C57BL/6J) or equivalent in another genome. The human insertion may be made between the regions indicated above.

All specific human fragments described above may vary in length, and may for example be longer or shorter than defined as above, such as 500 bases, 1 KB, 2K, 3K, 4K, 5 KB, 10 KB, 20 KB, 30 KB, 40 KB or 50 KB or more, which suitably comprise all or part of the human V(D)J region, whilst preferably retaining the requirement for the final insert to comprise human genetic material encoding the complete heavy chain region and light chain region, as appropriate, as described above.

In one aspect the 5' end of the human insert described above is increased in length. Where the insert is generated in a stepwise fashion then the increase in length is generally in respect of the upstream (5') clone.

In one aspect the 3' end of the last inserted human gene, generally the last human J gene to be inserted is less than 2 kb, preferably less than 1 KB from the human-mouse join region.

In one aspect the non-human mammal comprises some or all of the human light chain kappa VJ region as disclosed herein but not the human light chain lambda VJ region.

In one aspect the cell or non-human mammal comprises a fully human lambda locus (lambda VJC regions from a human), a chimaeric kappa locus (human kappa VJ regions operatively linked to a host kappa constant region) and a chimaeric heavy chain locus, having a human VDJ region operatively linked to a host heavy chain constant region.

In a further aspect the genome comprises an insertion of V, D (heavy chain only) and J genes as described herein at the heavy chain locus and one light chain locus, or at the heavy chain locus and both light chain loci. Preferably the genome is homozygous at one, or both, or all three loci.

In another aspect the genome may be heterozygous at one or more of the loci, such as heterozygous for DNA encoding a chimaeric antibody chain and native (host cell) antibody chain. In one aspect the genome may be heterozygous for DNA capable of encoding 2 different antibody chains of the invention, for example, comprising 2 different chimaeric heavy chains or 2 different chimaeric light chains.

In one aspect the invention relates to a non-human mammal or cell, and methods for producing said mammal or cell, as described herein, wherein the inserted human DNA, such as the human IgH VDJ region and/or light chain V, J regions are found on only one allele and not both alleles in the mammal or cell. In this aspect a mammal or cell has the potential to express both an endogenous host antibody heavy or light chain and a chimaeric heavy or light chain.

In a further aspect of the invention the human VDJ region, or light chain VJ region, is not used in its entirety, but parts of the equivalent human VDJ or VJ region, such as the exons, from other species may be used, such as one or more V, D, or J exons from other species, or regulatory sequences from other species. In one aspect the sequences used in place of the human sequences are not human or mouse. In one aspect the sequences used may be from rodent, or, primate such as chimp. For example, 1, 2, 3, 4, or more, or all of the J regions from a primate other than a human may be used to replace, one, 2, 3, 4, or more or all of the human J exons in the VDJ/VJ region of the cells and animals of the invention.

In a further aspect the inserted human DNA, such as the human IgH VDJ region, and/or light chain VJ regions, may be inserted such that they are operably linked in the genome with a mu constant region from a non-human, non-mouse species, such as a rodent or primate sequence, such as a rat sequence.

Other non-human, non-mouse species from which DNA elements may be used in the present invention include rabbits, lamas, dromedary, alpacas, camels and sharks.

In one aspect the inserted human DNA, such as the human VDJ or VJ region, is not operably linked to the endogenous host mu sequence but rather to a non-host mu sequence.

Operable linkage suitably allows production of an antibody heavy or light chain comprising the human variable region.

In one aspect the inserted human DNA, such as the human IgH VDJ region (and/or light chain VJ regions) may be inserted into the host chromosome together with mu constant region nucleic acid which is not host mu constant region nucleic acid, and preferably is a mu constant region from a non-mouse, non-human species. Suitably the inserted human DNA, such as the human VDJ region (and/or light chain VJ regions) is operably linked to a non-human, non-mouse mu, and is able to form a chimaeric antibody heavy or light chain. In another aspect a non-mouse, non-human mu may be inserted into the host chromosome on a separate genetic element to that of the human variable region, or at a different location in the genome, suitably operably linked to the variable region such that a chimaeric antibody heavy or light can be formed.

In an additional aspect the invention relates to a non-human mammal or a cell whose genome comprises a plurality of human IgH V regions, one or more human D regions and one or more human J regions upstream of a host non-human mammal light chain constant region, arranged such that the cell or mammal is able to express a chimaeric antibody chain. The invention also relates to a non-human mammal or a cell whose genome additionally or alternatively comprises a plurality of human Ig light chain V regions, and one or more human J regions upstream of a host non-human mammal heavy chain constant region, such that the cell or mammal is able to express a chimaeric antibody chain. The cell or mammal may be able to express an antibody having both heavy and light chains, including at least one chimaeric antibody chain, as disclosed above.

The inserted human heavy chain variable regions may be any of those described herein, and may be inserted at the positions described above for insertion 5' of the lambda and kappa constant regions. Likewise the inserted human light chain variable regions may be those described above, and may be inserted at the positions described above for insertion 5' of the heavy chain constant region.

For example, the genome or the cell or non-human mammal of the invention may encode an antibody comprising an antibody chain having a human heavy chain variable region upstream of a mouse light chain constant region, or an antibody chain having a human light chain variable region upstream of a mouse heavy chain constant region, in combination with one of:

a fully human antibody light chain;
a fully human antibody heavy chain;
a non-human vertebrate (e.g., mouse or rat) antibody light chain;
a non-human vertebrate (e.g., mouse or rat) antibody heavy chain;
a chimaeric non-human vertebrate (e.g., mouse or rat)-human antibody chain;

an antibody chain having a human heavy chain variable region upstream of a non-human vertebrate (e.g., mouse or rat) light chain constant region;

an antibody chain having a human light chain variable region upstream of a non-human vertebrate (e.g., mouse or rat) heavy chain constant region.

The invention also relates to a transgene encoding a plurality of human IgH V regions, one or more human D regions and one or more human J regions upstream of a host non-human mammal light chain constant region, optionally comprised within a vector.

The invention also relates to a transgene encoding a plurality of human Ig light chain V regions, and one or more human light chain J regions upstream of a host non-human mammal heavy chain constant region, optionally comprised within a vector.

In one aspect the invention relates to a cell, or non-human mammal, the genome of which comprises: one or more human Ig light chain kappa V regions and one or more human Ig light chain kappa J regions upstream of all or part of the human kappa constant region.

In another aspect the invention relates to a cell, or non-human mammal, the genome of which comprises: one or more human Ig light chain lambda V regions and one or more human Ig light chain lambda J regions upstream of all or part of the human lambda constant region.

Suitably the light chain VJ and C regions are able to form antibody chains in vivo capable of specifically reacting with an antigen.

In one aspect of the invention there is no non-human coding sequence in the inserted light chain region.

In such aspects a human kappa and/or lambda region is inserted into the genome, in combination with insertion of the heavy chain VDJ region or part thereof, upstream of the host heavy chain constant region as disclosed herein.

The cell or non-human mammal of the invention may comprise:
  (a) a plurality of human IgH V regions, one or more human D regions and one or more human J regions upstream of the host non-human mammal constant region; and
  (b) one or more human Ig light chain kappa V regions and one or more human Ig light chain kappa J regions upstream of all or part of the non-human kappa constant region,
wherein the non-human mammal is able to produce a repertoire of antibodies having an antibody chain comprising non-human mammal constant region and a human variable region.

The cell or non-human mammal of the invention may comprise
  (a) a plurality of human IgH V regions, one or more human D regions and one or more human J regions upstream of the host non-human mammal constant region; and
  one or more human Ig light chain lambda V regions and one or more human Ig light chain lambda J regions upstream of the host non-human mammal lambda constant region;
wherein the non-human mammal is able to produce a repertoire of antibodies having an antibody chain comprising a non-human mammal constant region and a human variable region.

Suitably the insertion of the human VJC light chain DNA, or part thereof as disclosed above, is made at the equivalent mouse locus. In one aspect the human light chain kappa VJC DNA, or part thereof, is inserted immediately upstream or downstream of the mouse kappa VJC region. In one aspect, the human light chain lambda VJC region or part thereof is inserted immediately upstream or downstream of the mouse lambda VJC region. In one aspect only the human kappa VJC locus is inserted and not the human lambda VJC locus. In one aspect only the human lambda VJC locus is inserted and not the human kappa VJC locus. Insertions may be made using the techniques disclosed herein, and suitably do not remove the host sequences from the genome. In one aspect the non-human mammal host VJC sequences may be inactivated in some way, by mutation, or inversion, or by insertion of the human variable region DNA, or by any other means. In one aspect the cell or non-human mammal of the invention may comprise an insertion of the complete VJC human region.

The human kappa variable region DNA might be inserted into the genome in functional arrangement with a lambda constant region, for example inserted upstream of a lambda constant region. Alternatively human lambda region variable DNA might be inserted in functional arrangement with a kappa constant region, for example inserted upstream of a kappa constant region.

In one aspect one or more non-human mammal control sequences such as the enhancer sequence(s) is maintained upstream of the nonhuman mammal Mu constant region, suitably in its native position with respect to the distance from the constant region.

In one aspect one or more non-human mammal control sequences such as an enhancer sequence(s) are maintained downstream of the nonhuman mammal Mu constant region, suitably in its native position with respect to the distance from the constant region.

In one aspect a non-human mammal switch sequence, suitably the endogenous switch sequence, is maintained upstream of the non-human mammal Mu constant region, suitably in its native position with respect to distance from the constant region.

In such location the host enhancer or switch sequences are operative in vivo with the host constant region sequence(s).

In one aspect a switch sequence is neither human, nor native in the non-human mammal, for example in one aspect a non-human mammal switch sequence is not a mouse or human switch sequence. The switch sequence may be, for example, a rodent or primate sequence, or a synthetic sequence. In particular the switch sequence may be a rat sequence where the non-human mammal is a mouse. By way of example, a mouse or human constant mu sequence may be placed under the control of a switch sequence from a rat, or chimp, or other switch sequence, suitably capable of allowing isotype switching to occur in vivo.

In one aspect the switch sequence of the invention is a switch sequence comprising 3, 4, 5, 6 or more (up to 82) contiguous repeats of the repeat sequence GGGCT (SEQ ID no 46-50), such as a rat switch sequence. By "rat switch" herein it is meant that the switch is a wild-type switch corresponding to a switch from a rat genome or derived from such a switch.

In one aspect the switch sequence of the invention is a rat switch sequence comprising the following repeats: GAGCT (296 repeats; SEQ ID No 18), GGGGT (50 repeats; SEQ ID No 19), and GGGCT (83 repeats; SEQ ID No 20).

In one example the rat switch sequence comprises or consists of the sequence of SEQ ID no 1.

In these embodiments, and where the non-human mammal is a mouse or the cell is a mouse cell, the switch is optionally a rat switch as described herein.

Alternatively, the switch sequence present in cells or mammal of the invention is a mouse switch, eg, is from a mouse such as a mouse 129 strain or mouse $C_{5-7}$ strain, or from a strain derived therefrom, optionally comprising or consisting of the sequence of SEQ ID no 4 or 5. By "mouse switch" herein it is meant that the switch is a wild-type switch corresponding to a switch from a mouse genome or derived from such a switch. In this embodiment, and where the non-human mammal is a mouse or the cell is a mouse cell, the mouse switch sequence is optionally the endogenous switch or is a mouse switch from another mouse strain.

The cell or mammal of the invention may therefore comprise a human or non-human mammal switch sequence and a human or non-human mammal enhancer region or regions. They may be upstream of a human or non-human mammal constant region. Preferably the control sequences are able to direct expression or otherwise control the production of antibodies comprising a constant region with which they are associated. One combination envisaged is a rat switch with mouse enhancer sequences and mouse constant regions in a mouse cell.

In one aspect the invention relates to a cell, preferably a non-human cell, or non-human mammal comprising an immunoglobulin heavy chain or light chain locus having DNA from 3 or more species. For example, the cell or animal may comprise host cell constant region DNA, one or more human V, D or J coding sequences and one or more non-human, non-host DNA regions that are able to control a region of the immunoglobulin locus, such as a switch sequence, promoter or enhancer which are able to control expression or isotype switching in vivo of the Ig DNA. In one aspect the cell or animal is a mouse and comprises additionally human DNA from the human Ig locus and additionally a non-mouse DNA sequence, such as a rat DNA sequence, capable of regulation of the mouse or human DNA.

In another aspect the invention relates to a cell, preferably non-human cell, or non-human mammal comprising an immunoglobulin heavy chain or light chain locus having DNA from 2 or more different human genomes. For example, it could comprise heavy chain V(D)J sequences from more than one human genome within a heavy or light chain, or heavy chain VDJ DNA from one genome and light chain VJ sequences from a different genome.

In one aspect the invention relates to a DNA fragment or cell or non-human mammal comprising an immunoglobulin heavy chain or light chain locus, or part thereof, having DNA from 2 or more species, where one species contributes a non-coding region such as a regulatory region, and the other species coding regions such as V, D, J or constant regions.

In one aspect the human promoter and/or other control elements that are associated with the different human V, D or J regions are maintained after insertion of the human VDJ into the mouse genome.

In a further aspect one or more of the promoter elements, or other control elements, of the human regions, such as the human V regions, are optimised to interact with the transcriptional machinery of a non-human mammal.

Suitably a human coding sequence may be placed under the control of an appropriate non-human mammal promoter, which allows the human DNA to be transcribed efficiently in the appropriate non-human animal cell. In one aspect the human region is a human V region coding sequence, and a human V region is placed under the control of a non-human mammal promoter.

The functional replacement of human promoter or other control regions by non-human mammal promoter or control regions may be carried out by use of recombineering, or other recombinant DNA technologies, to insert a part of the human Ig region (such as a human V region) into a vector (such as a BAC) containing a non-human Ig region. The recombineering/recombinant technique suitably replaces a portion of the non-human (e.g. mouse) DNA with the human Ig region, and thus places the human Ig region under control of the non-human mammal promoter or other control region. Suitably the human coding region for a human V region replaces a mouse V region coding sequence. Suitably the human coding region for a human D region replaces a mouse D region coding sequence. Suitably the human coding region for a human J region replaces a mouse J region coding sequence. In this way human V, D or J regions may be placed under the control of a non-human mammal promoter, such as a mouse promoter.

In one aspect the only human DNA inserted into the non-human mammalian cell or animal are V, D or J coding regions, and these are placed under control of the host regulatory sequences or other (non-human, non-host) sequences. In one aspect reference to human coding regions includes both human introns and exons, or in another aspect simply exons and no introns, which may be in the form of cDNA.

It is also possible to use recombineering, or other recombinant DNA technologies, to insert a non-human-mammal (e.g. mouse) promoter or other control region, such as a promoter for a V region, into a BAC containing a human Ig region. A recombineering step then places a portion of human DNA under control of the mouse promoter or other control region.

The approaches described herein may also be used to insert some or all of the V, D and J regions from the human heavy chain upstream of a light chain constant region, rather than upstream of the heavy chain constant region. Likewise some or all of the human light chain V and J regions may be inserted upstream of the heavy chain constant region. Insertion may be at the endogenous constant region locus, for example between the endogenous constant and J region, and may be of some, or all, of the V, D or J genes alone, excluding promoter or enhancer sequences, or may be of some, or all, of the V, D or J genes with one or more or all respective promoter or enhancer sequences. In one aspect the full repertoire of V, D or J fragments in germline orientation may be inserted upstream and in functional arrangement with a host constant region.

Thus the present invention allows V and/or D and/or J regions from a human, or any species, to be inserted into a chromosome of a cell from a different species that comprises a constant region, allowing a chimaeric antibody chain to be expressed.

In one aspect the invention requires only that some human variable region DNA is inserted into the genome of a non-human mammal in operable arrangement with some, or all, of the human heavy chain constant region at the region of the endogenous heavy chain constant region locus such that an antibody chain can be produced. In this aspect of the invention and where human light chain DNA is additionally inserted, the light chain DNA insertion can be in the form of a completely human construct, having both human variable DNA and human constant region DNA, or have human variable region DNA and constant region DNA from a non-human, non-host species. Other variations are also possible, such as insertion of both of the light chain human variable region and host genome constant region. In addition the insertion of said light chain transgenes need not be at the equivalent endogenous locus, but may be anywhere in the genome. In such a scenario the cell or mammal may produce chimaeric heavy chains (comprising human variable region DNA and mouse constant region DNA) and light chains comprising human variable and human constant region DNA. Thus in one aspect of the invention the lambda and or kappa human variable region DNA can be inserted upstream of the endogenous locus, or downstream, or indeed on a different chromosome to the endogenous locus, and inserted with or without constant region DNA.

As well insertion of human light chain DNA upstream of the host non-human mammal constant region, a further aspect of the invention relates to insertion of one or both light chain human variable regions downstream of the equivalent endogenous locus constant region, or elsewhere in the genome.

Generally, insertion of human variable region DNA at or close to the equivalent endogenous locus in the recipient genome is preferred, for example within 1, 2, 3, 4, 5, 6, 7, 8, 9, or 10 kb of the boundary (upstream or downstream) of a host immunoglobulin locus.

Thus in one aspect the invention can relate to a cell or non-human mammal whose genome comprises:
(a) a plurality of human IgH V regions, one or more human D regions and one or more human J regions upstream of the host non-human mammal constant region; and
(b) one or more human Ig light chain kappa V regions and one or more human Ig light chain kappa J regions, and/or, one or more human Ig light chain lambda V regions and one or more human Ig light chain lambda J regions;
wherein the non-human mammal is able to produce a repertoire of chimaeric antibodies, or chimaeric light or heavy chains, having a non-human mammal constant region and a human variable region.

In one particular aspect the genome of the cell or non-human mammal comprises:
a plurality of human IgH V regions, one or more human D regions and one or more human J regions upstream of the host non-human mammal constant region;
one or more human Ig light chain kappa V regions and one or more human Ig light chain kappa J regions upstream of the host non-human mammal kappa constant region, and
one or more human Ig light chain lambda V regions and one or more human Ig light chain lambda J regions downstream of the host non-human mammal lambda constant region,
optionally in which the human lambda variable region may be inserted upstream or downstream of the endogenous host lambda locus in operable linkage with a human lambda constant region, such that the non-human mammal or cell can produce fully human antibody light chains and chimaeric heavy chains.

In a further, different, aspect of the invention, the use of the methods of the invention allows a locus to be built up in a stepwise manner by sequential insertions, and thus allows for the insertion of human variable DNA together with human or non-human constant region DNA at any suitable location in the genome of a non-human host cell. For example, methods of the invention can be used to insert human immunoglobulin variable region DNA together with constant region DNA from the host genome anywhere in the genome of a non-human host cell, allowing a chimaeric antibody chain to be produced from a site other than the endogenous heavy region. Any human heavy chain or light chain DNA construct contemplated above can be inserted into any desired position into the genome of a non-human host cell using the techniques described herein. The present invention thus also relates to cells and mammals having genomes comprising such insertions.

The invention also relates to a vector, such as a BAC, comprising a human V, D or J region in a functional arrangement with a non-human mammal promoter, or other control sequence, such that the expression of the human V, D or J region is under the control of the non-human mammal promoter in a cell of the non-human mammal, such as an ES cell, in particular once inserted into the genome of that cell.

The invention also relates to cells and non-human mammals containing said cells, which cells or mammals have a human V, D or J region in a functional arrangement with a non-human mammal promoter, or other control sequence, such that the expression of the human V, D or J region is under the control of the non-human mammal promoter in the cells or mammal.

Generally, one aspect of the invention thus relates to a non-human mammal host cell capable of expression of a human V, D or J coding sequence under the control of a host promoter or control region, the expression capable of producing a humanised antibody having a human variable domain and non-human mammal constant region.

In one aspect the invention relates to a cell, such as a non mammalian cell, such as an ES cell, the genome of which comprises
(a) a plurality of human IgH V regions, one or more human D regions and one or more human J regions upstream of the host non-human mammal constant region; and
(b) optionally one or more human Ig light chain kappa V regions and one or more human Ig light chain kappa J regions upstream of the host non-human mammal kappa constant region and/or one or more human Ig light chain lambda V regions and one or more human Ig light chain lambda J regions upstream of the host non-human mammal lambda constant region;

In another aspect the invention relates to a cell, such as a non-human mammal cells, such as ES cells whose genome comprises
(a) a plurality of human Ig light chain kappa V regions and one or more human Ig light chain kappa J regions upstream of the host non-human mammal kappa constant region and/or a plurality of human Ig light chain lambda V regions and one or more human Ig light chain lambda J regions upstream of the host non-human mammal lambda constant region; and
(b) optionally one or more human IgH V regions, one or more human D regions and one or more human J regions upstream of the host non-human mammal constant region In one aspect the cell is an ES cell is capable of developing into a non-human mammal able to produce a repertoire of antibodies which are chimaeric, said chimaeric antibodies having a non-human mammal constant region and a human variable region. Optionally the genome of the cell is modified to prevent expression of fully host-species specific antibodies.

In one aspect the cell is an induced pluripotent stem cell (iPS cell).

In one aspect cells are isolated non-human mammalian cells.

In one aspect a cell as disclosed herein is preferably a non-human mammalian cell.

In one aspect the cell is a cell from a mouse strain selected from C57BL/6, M129 such as 129/SV, BALB/c, and any hybrid of C57BL/6, M129 such as 129/SV, or BALB/c.

The invention also relates to a cell line which is grown from or otherwise derived from cells as described herein, including an immortalised cell line. The cell line may comprise inserted human V, D or J genes as described herein, either in germline configuration or after rearrangement following in vivo maturation. The cell may be immortalised by fusion (eg, electrofusion or using PEG according to standard procedures.) to a tumour cell (eg, P3×63-Ag8.653 (obtainable from LGC Standards; CRL-1580), SP2/0-Ag14 (obtainable from ECACC), NSI or NS0), to provide an antibody producing cell and cell line, or be made by direct cellular immortalisation.

The present invention also relates to vectors for use in the invention. In one aspect such vectors are BACs (bacterial artificial chromosomes). It will be appreciated that other cloning vectors may be used in the invention, and therefore reference to BACs herein may be taken to refer generally to any suitable vector.

In one aspect BACs used for generation of human DNA to be inserted, such as the VDJ or VJ regions are trimmed so that in the final human VDJ or VJ region or part thereof in the non-human mammal, no sequence is duplicated or lost when compared to the original human genomic sequence.

In one aspect the invention relates to a vector comprising an insert, preferably comprising a region of human DNA from some of the human VDJ or VJ locus, flanked by DNA which is not from that locus. The flanking DNA may comprise one or more selectable markers or one or more site specific recombination sites. In one aspect the vector comprises 2 or more, such as 3, heterospecific and incompatible site specific recombination sites. In one aspect the site specific recombination sites may be loxP sites, or variants thereof, or FRT sites or variants thereof. In one aspect the vector comprises one or more transposon ITR (inverted terminal repeat) sequences.

In one aspect the non-human animals of the invention suitably do not produce any fully humanised antibodies. In one aspect this is because there is no DNA inserted from the human constant region. Alternatively there is no human constant region DNA in the genome capable of forming an antibody in conjunction with the inserted human variable region DNA component, for example due to mutation within any human constant region DNA or distance from any constant region human DNA and human variable region DNA.

In one aspect human light chain constant region DNA may be included in the cell genome, such that a fully human lambda or kappa human antibody chain might be generated, but this would only be able to form an antibody with a chimaeric heavy chain, and not produce a fully human antibody having human variable and constant regions.

In one aspect the non-human mammal genome is modified to prevent expression of fully host-species specific antibodies. Fully host species specific antibodies are antibodies that have both variable and constant regions from the host organism. In this context the term 'specific' is not intended to relate to the binding of the antibodies produced by the cells or animals of the invention but rather to the origin of the DNA which encodes those antibodies.

In one aspect the non-human mammal genome is modified to prevent expression of the native (fully host species specific) antibodies in the mammal by inactivation of all or a part of the host non-human mammal Ig loci. In this context, inactivation or prevention of endogenous antibody or gene segment usage (using any inactivation technique described herein) is, for example, substantially complete inactivation or prevention (substantially 100%, ie, essentially none (eg, less than 10, 5, 4, 3, 2, 1 or 0.5%) of the endogenous antibody chain (eg, no endogenous heavy chains) is expressed). This can be determined, for example, at the antibody chain (protein) level by assessing the antibody repertoire produced by the non-human vertebrate, mammal or at the nucleotide level by assessing mRNA transcripts of antibody chain loci, eg, using RACE. In an embodiment, inactivation is more than 50% (ie, 50% or less of the antibodies or transcripts are of an endogenous antibody chain), 60%, 70%, 80%, 85%, 90%, 95%, 96%, 97%, 98% or 99%. For example, in an embodiment, endogenous heavy chain expression is substantially inactivated such that no more than 85%, 90%, 95%, 96%, 97%, 98% or 99% of the heavy chain repertoire of the vertebrate (mammal) is provided by endogenous heavy chains. For example, endogenous heavy chain expression is substantially inactivated such that substantially none of the heavy chain repertoire of the vertebrate (mammal) is provided by endogenous heavy chains. For example, in an embodiment, endogenous heavy chain expression is substantially inactivated such that no more than 85%, 90%, 95%, 96%, 97%, 98% or 99% of the kappa chain repertoire of the vertebrate (mammal) is provided by endogenous kappa chains. For example, endogenous kappa chain expression is substantially inactivated such that substantially none of the kappa chain repertoire of the vertebrate (mammal) is provided by endogenous kappa chains. For example, in an embodiment, endogenous heavy chain expression is substantially inactivated such that no more than 85%, 90%, 95%, 96%, 97%, 98% or 99% of the lambda chain repertoire of the vertebrate (mammal) is provided by endogenous lambda chains. For example, endogenous lambda chain expression is substantially inactivated such that substantially none of the lambda chain repertoire of the vertebrate (mammal) is provided by endogenous lambda chains.

In one aspect this is achieved by inversion of all or part of the non-human mammal VDJ region, or VJ region, optionally by insertion of one or more site specific recombinase sites into the genome and then use of these sites in recombinase-mediated excision or inversion of all or a part of the non-human mammal Ig locus. In one aspect a double inversion, may be employed, the first to move the V(D)Js away from the endogenous locus and then a more local inversion which puts them in the correct orientation. In one aspect a single loxP site is used to invert the non-human mammal VDJ region to a centromeric locus or telomeric locus.

In one example, a mouse or mouse cell of the invention comprises inverted endogenous heavy chain gene segments (eg, VH, D and JH, such as the entire endogenous heavy chain VDJ region) that are immediately 3' of position 119753123, 119659458 or 120918606 on an endogenous mouse chromosome 12. Optionally, the genome of the mouse or cell is homozygous for said chromosome 12.

The invention also provides:—

A cassette for inversion and inactivation of endogenous non-human vertebrate (eg, mouse or rat) antibody chain gene segments, the segments being part of an antibody chain locus sequence on a chromosome of a non-human vertebrate (eg, mouse or rat) cell (eg, ES cell) wherein the sequence is flanked at its 3' end by a site-specific recombination site (eg, lox, rox or frt), the cassette comprising a nucleotide sequence encoding an expressible label or selectable marker and a compatible site-specific recombination site (eg, lox, rox or frt) flanked by a 5' and a 3' homology arm, wherein the homology arms correspond to or are homologous to adjacent stretches of sequence in the cell genome on a different chromosome or on said chromosome at least 10, 15, 20, 25, 30, 35, 40, 45 or 50 mb away from the endogenous gene segments.

The invention also provides:—

A cassette for inversion and inactivation of endogenous mouse antibody heavy chain gene segments, the segments being part of a heavy chain locus sequence on chromosome 12 of a mouse cell (eg, ES cell) wherein the sequence is flanked at its 3' end by a site-specific recombination site (eg, lox, rox or frt), the cassette comprising a nucleotide sequence encoding an expressible label or selectable marker and a compatible site-specific recombination site (eg, lox, rox or frt) flanked by a 5' and a 3' homology arm, wherein the homology arms correspond to or are homologous to adjacent stretches of sequence in the mouse cell genome on a different chromosome or on chromosome 12 at least 10, 15, 20, 25, 30, 35, 40, 45 or 50 mb away from the endogenous gene segments.

The invention provides:—

A cassette for inversion and inactivation of endogenous mouse antibody heavy chain gene segments, the segments being part of a heavy chain locus sequence on chromosome 12 of a mouse cell (eg, ES cell) wherein the sequence is flanked at its 3' end by a site-specific recombination site (eg, lox, rox or frt), the cassette comprising a nucleotide sequence encoding an expressible label or selectable marker and a compatible site-specific recombination site (eg, lox, rox or frt) flanked by a 5' and a 3' homology arm, wherein (i) the 5' homology arm is mouse chromosome 12 DNA from coordinate 119753124 to coordinate 119757104 and the 3' homology arm is mouse chromosome 12 DNA from coordinate 119749288 to 119753123; or (ii) the 5' homology arm is mouse chromosome 12 DNA from coordinate 119659459 to coordinate 119663126 and the 3' homology arm is mouse chromosome 12 DNA from coordinate 119656536 to 119659458; or (iii) the 5' homology arm is mouse chromosome 12 DNA from coordinate 120918607 to coordinate 120921930 and the 3' homology arm is mouse chromosome 12 DNA from coordinate 120915475 to 120918606.

Embodiment (i) results in an inversion of mouse chromosome 12 from coordinate 119753123 to coordinate 114666436.

Embodiment (ii) results in an inversion of mouse chromosome 12 from coordinate 119659458 to coordinate 114666436

Embodiment (iii) results in an inversion of mouse chromosome 12 from coordinate 12091806 to coordinate 114666436.

Thus, the invention provides a mouse or mouse cell whose genome comprises an inversion of a chromosome 12, wherein the inversion comprises inverted endogenous heavy chain gene segments (eg, VH, D and JH, such as the entire endogenous heavy chain VDJ region); wherein the mouse comprises a transgenic heavy chain locus comprising a plurality of human VH gene segments, a plurality of human D segments and a plurality of human JH segments operably connected upstream of an endogenous constant region (eg, C mu) so that the mouse or cell (optionally following differentiation into a B-cell) is capable of expressing an antibody comprising a variable region comprising sequences derived from the human gene segments; and wherein the inversion is (i) an inversion of mouse chromosome 12 from coordinate 119753123 to coordinate 114666436; (ii) an inversion of mouse chromosome 12 from coordinate 119659458 to coordinate 114666436; or (iii) an inversion of mouse chromosome 12 from coordinate 12091806 to coordinate 114666436.

In one embodiment, the endogenous gene segments are from a 129-derived mouse cell (eg, segments from an AB2.1 cell) and the homology arms are isogenic DNA (ie, identical to 129-derived endogenous sequences demarcated by the respective coordinates stated in (i) to (iii) above). Thus, no new sequence is created by homologous recombination using these homology arms. In another embodiment, the arms are from a mouse strain that is different from the endogenous strain. The site-specific recombination sites are mutually compatible and mutually inverted such that, on expression of an associated recombinase enzyme (eg, Cre, Dre or Flp), recombination between the site in the inserted inversion cassette and the site flanking the endogenous gene segments is carried out, thereby inverting and moving the endogenous gene segments far upstream (5') of their original location in the heavy chain locus. This inactivates endogenous heavy chain expression. Similarly, light chain inactivation can be performed by choosing the homology arms of the inversion cassette with reference to a chromosomal region spaced at least 10, 15, 20, 25, 30, 35, 40, 45 or 50 mb away from the endogenous light chain locus, the latter comprising a site-specific recombination site that is compatible with the site in the inversion cassette.

In one embodiment, the expressible label is a fluorescent label, eg, GFP or a variant thereof (eg, YFP, CFP or RFP). Thus, a label is used instead of a selection marker, such as one that confers resistance to allow for selection of transformants.

The invention provides a method of inactivating gene segments of an endogenous antibody locus, the method comprising
(i) Providing a non-human vertebrate cell (eg, an ES cell, eg, a mouse ES cell) whose genome comprises an antibody chain locus comprising endogenous variable region gene segments;
(ii) Targeting a site-specific recombination site to flank the 3' of the 3'-most of said endogenous gene segments;
(iii) Targeting a second site-specific recombination site at least 10 mb away from said endogenous gene segments, the second site being compatible with the first site inverted with respect to the first site;
(iv) Expressing a recombinase compatible with said sites to effect site-specific recombination between said sites, thereby inverting and moving said gene segments away from said locus, wherein the endogenous gene segments are inactivated; and
(v) Optionally developing the cell into a progeny cell or vertebrate (eg, mouse or rat) whose genome is homozygous for the inversion.

The genome of the progeny cell or vertebrate can comprise transgenic heavy and/or light chain loci, each capable of expressing antibody chains comprising human variable regions. Optionally, endogenous heavy and kappa light chain expression is inactivated by inverting endogenous heavy and kappa variable region gene segments according to the method of the invention. Optionally, endogenous lambda chain expression is also inactivated in this way.

In an alternative to the method and inversion cassettes of the invention, instead of inverting and moving variable region gene segments only, other parts of the endogenous locus can alternatively or additionally be inverted and moved to effect inactivation. For example, one or more endogenous regulatory elements (eg, Smu and/or Emu)

and/or one or more endogenous constant regions (eg, Cmu and/or Cgamma) can be inverted and moved.

Sites that "flank" in the above contexts of the invention can be provided such that a site-specific recombination site immediately flanks the endogenous sequence or is spaced therefrom, eg, by no more than 250, 200, 250, 100, 50 or 20 kb in the 3' direction.

In one aspect the non-human mammal genome into which human DNA is inserted comprises endogenous V, (D) and J regions, and the endogenous sequences have not been deleted.

The invention comprises a method for insertion of multiple DNA fragments into a DNA target, suitably to form a contiguous insertion in which the inserted fragments are joined together directly without intervening sequences. The method is especially applicable to the insertion of a large DNA fragment into a host chromosome which can be carried out in a stepwise fashion.

In one aspect the method comprises insertion of a first DNA sequence into a target, the sequence having a DNA vector portion and a first sequence of interest (X1); insertion of a second DNA sequence into the vector portion of the first sequence, the second DNA sequence having a second sequence of interest (X2) and a second vector portion; and then excising any vector sequence DNA separating X1 and X2 to provide a contiguous X1X2, or X2X1 sequence within the target. There is optionally insertion of a further one or more DNA sequences, each DNA sequence having a further sequence of interest (X3, . . . ) and a further vector portion, into the vector portion of the preceding DNA sequence, to build up a contiguous DNA fragment in the target.

The DNA target for insertion of the first DNA sequence may be a specific site or any point in the genome of a particular cell.

The general method is described herein in relation to the insertion of elements of the human VDJ region, but is applicable to insertion of any DNA region, from any organism, and in particular insertion of large DNA fragments of >100 kB, such as 100-250 kb, or even larger, such as that of the TCR or HLA. Features and approaches described herein in respect of the VDJ insertion may be equally applied to the any of the methods disclosed In one aspect the inserted DNA is human DNA, such as the human VDJ or VJ region, is built up in the genome of a cell, such as an ES cell, in a stepwise manner using 2, 3, 4, 5, 6, 7, 8, 9, 10, 11, 12, 13, 14, 15, 20 or more separate insertions for each heavy chain or light chain region. Fragments are suitably inserted at the same or substantially the same cell locus, e.g. ES cell locus, one after another, to form the complete VDJ or VJ region, or part thereof. The present invention also relates to cells and non-human animals comprising intermediates in the process whose genomes may comprise only a partial VDJ region, such as only human variable region DNA.

In a further aspect the method for producing a transgenic non-human mammal comprises the insertion of human VDJ or VJ regions upstream of the host non-human mammal constant region by step-wise insertion of multiple fragments by homologous recombination, preferably using an iterative process. Suitably fragments of approximately 100 KB from the human VDJ and VJ locus are inserted, suitably to form part of, or a complete, VDJ or VJ region after the final iteration of the insertion process, as disclosed herein.

In one aspect the insertion process commences at a site where an initiation cassette has been inserted into the genome of a cell, such as an ES cell, providing a unique targeting region. In one aspect the initiation cassette is inserted in the non-human mammal heavy chain locus, for use in insertion of human heavy chain DNA. Similarly an initiation cassette may be inserted in the non-human mammal light chain locus, for use in insertion of human light chain VJ DNA The initiation cassette suitably comprises a vector backbone sequence with which a vector having a human DNA fragment in the same backbone sequence can recombine to insert the human DNA into the cell (e.g. ES) cell genome, and suitably a selection marker, such as a negative selection marker. Suitably the vector backbone sequence is that of a BAC library, to allow BACs to be used in the construction of the ES cells and mammals. The vector backbone sequence may however be any sequence which serves as a target site into which a homologous sequence can insert, for example by homologous recombination, for example RMCE, and is preferably not DNA encoding any of the VDJ or constant region.

In one aspect the insertion of the first DNA fragment into an initiation cassette is followed by insertion of a second DNA fragment into a portion of the first DNA fragment, suitably a part of the vector backbone of the second DNA fragment. In one aspect an inserted DNA fragment comprises a part of the human VDJ region flanked by 5' and/or 3' sequences that are not from the human VDJ region. In one aspect the 5' and/or 3' flanking sequences may each contain one or more selectable markers, or be capable of creating a selectable system once inserted into the genome. In one aspect one or both flanking sequences may be removed from the genome in vitro, or in vivo, following insertion. In one aspect the method comprises insertion of a DNA fragment followed by selection of both 5' and 3' ends of the inserted fragment flanking the human VDJ DNA. In one aspect the iterative insertion is made by insertion of DNA fragments at the 5' end of the previous inserted fragment, and in this aspect there may be deletion in vivo of the vector DNA which separates the inserted human DNA sequences, to provide a contiguous human DNA sequence.

In one aspect insertion of human VDJ DNA into a genome may be achieved without leaving any flanking DNA in the genome, for example by transposase mediate DNA excision. One suitable transposase is the Piggybac transposase.

In one aspect the first human variable region fragment is inserted by homologous recombination at the initiation cassette backbone sequence and then the DNA of any negative selection marker and initiation cassette are subsequently removed by recombination between recombinase target sequences, such as FRT using in this example, FLPase expression. Generally repeated targeted insertions at the (e.g. BAC) backbone initiation sequence and subsequent removal by rearrangement between recombinase target sequences are repeated to build up the entire human VDJ region upstream of the host non-mammal constant region.

In one aspect a selectable marker or system may be used in the method. The marker may be generated upon insertion of a DNA fragment into a genome, for example forming a selectable marker in conjunction with a DNA element already present in the genome.

In one aspect the cell (e.g. ES) cell genome does not contain 2 identical selectable markers at the same time during the process. It can be seen that the iterative process of insertion and selection can be carried out using only 2 different selection markers, as disclosed in the examples herein, and for example the third selectable marker may be identical to the first marker, as by the time of insertion of the third vector fragment the first vector fragment and the first marker has been removed.

In one aspect a correct insertion event, is confirmed before moving to the next step of any multistep cloning process, for example by confirmation of BAC structure using high density genomic arrays to screen ES cells to identify those with intact BAC insertions, sequencing and PCR verification.

Initiation Cassette (Also Called a "Landing Pad")

The invention also relates to a polynucleotide 'landing pad' sequence, the polynucleotide comprising nucleic acid regions homologous to regions of a target chromosome to allow for insertion by homologous recombination into the target chromosome, and comprising a nucleic acid site which permits recombinase-driven insertion of nucleic acid into the landing pad. The invention also relates to vectors, cells and mammals of the invention comprising a landing pad as disclosed herein inserted into the genome of the cell.

The landing pad optionally comprises a non-endogenous S-mu, e.g. a rat S-mu switch The landing pad optionally comprises (in 5' to 3' orientation) a mouse Eμ sequence, a non-human, non-mouse (e.g. rat) Switch μ and at least a portion of a mouse Cμ or the entire mouse Cμ.

The rat switch sequence optionally comprises or consists of SEQ ID NO 1.

The landing pad optionally comprises the 5' homology arm of SEQ ID NO 6.

The landing pad optionally has the sequence of SEQ ID 2 or SEQ ID NO 3.

In one embodiment, the landing pad comprises an expressible label. For example the label is a fluorescent label, eg, GFP or a variant thereof (eg, YFP, CFP or RFP). Thus, a label is used instead of a selection marker (such as one that confers resistance to allow for selection of transformants).

In an embodiment, the landing pad comprises 5' and 3' homology arms for insertion into the cell genome using homologous recombination. The homology arms can be isogenic DNA (eg, identical to 129-derived endogenous sequences of when a 129-derived ES cell is used). Thus, no new sequence is created by homologous recombination using these homology arms. In another embodiment, the arms are from a mouse strain that is different from the endogenous strain (ES cell strain).

The methods of the invention include methods wherein the landing pad sequence comprises any of the configurations or sequences as disclosed herein.

Another method of the invention comprises the step of insertion of the landing pad into a mouse chromosome by homologous recombination between mouse J1-4 and mouse C mu sequences.

Another method of the invention comprises the step of insertion of the landing pad into the mouse chromosome 12 by homologous recombination between mouse J1-4 and E mu.

In one aspect the method uses site specific recombination for insertion of one or more vectors into the genome of a cell, such as an ES cell. Site specific recombinase systems are well known in the art and may include Cre-lox, and FLP/FRT or combinations thereof, in which recombination occurs between 2 sites having sequence homology.

Additionally or alternatively to any particular Cre/Lox or FLP/FRT system described herein, other recombinases and sites that may be used in the present invention include Dre recombinase, rox sites, and PhiC31 recombinase.

Suitable BACs are available from the Sanger centre, see "A genome-wide, end-sequenced 129Sv BAC library resource for targeting vector construction". Adams D J, Quail M A, Cox T, van der Weyden L, Gorick B D, Su Q, Chan W I, Davies R, Bonfield J K, Law F, Humphray S, Plumb B, Liu P, Rogers J, Bradley A. Genomics. 2005 December; 86(6):753-8. Epub 2005 Oct. 27. The Wellcome Trust Sanger Institute, Hinxton, Cambridgeshire CB10 1SA, UK. BACs containing human DNA are also available from, for example, Invitrogen™. A suitable library is described in Osoegawa K et al, Genome Research 2001. 11: 483-496.

In one aspect a method of the invention specifically comprises:

(1) insertion of a first DNA fragment into a non-human ES cell, the fragment containing a first portion of human VDJ or VJ region DNA and a first vector portion containing a first selectable marker;

(2) optionally deletion of the a part of the first vector portion;

(3) insertion of a second DNA fragment into a non-human ES cell containing the first DNA fragment, the insertion occurring within the first vector portion, the second DNA fragment containing a second portion of the human VDJ or VJ region and a second vector portion containing a second selectable marker, (4) deletion of the first selectable marker and first vector portion, preferably by a recombinase enzyme action;

(5) insertion of a third DNA fragment into a non-human ES cell containing the second DNA fragment, the insertion occurring within the second vector portion, the third DNA fragment containing a third portion of the human VDJ or VJ region and a third vector portion containing third selectable marker, (6) deletion of the second selectable marker and second vector portion; and (7) iteration of the steps of insertion and deletion, as necessary, for fourth and further fragments of the human VDJ or VJ human regions, as necessary, to produce an ES cell with a part or all of the human VDJ or VJ region inserted as disclosed herein, and suitably to remove all the vector portions within the ES cell genome.

In another aspect the invention comprises (1) insertion of DNA forming an initiation cassette into the genome of a cell;

(2) insertion of a first DNA fragment into the initiation cassette, the first DNA fragment comprising a first portion of a human DNA and a first vector portion containing a first selectable marker or generating a selectable marker upon insertion;

(3) optionally removal of part of the vector DNA (4) insertion of a second DNA fragment into the vector portion of the first DNA fragment, the second DNA fragment containing a second portion of human DNA and a second vector portion, the second vector portion containing a second selectable marker, or generating a second selectable marker upon insertion;

(5) optionally, removal of any vector DNA to allow the first and second human DNA fragments to form a contiguous sequence; and (6) iteration of the steps of insertion of human VDJ DNA and vector DNA removal, as necessary, to produce a cell with all or part of the human VDJ or VJ region sufficient to be capable of generating a chimaeric antibody in conjunction with a host constant region, wherein the insertion of one, or more, or all of the DNA fragments uses site specific recombination.

In one aspect the non-human mammal is able to generate a diversity of at least $1 \times 10^6$ different functional chimaeric immunoglobulin sequence combinations.

In one aspect the targeting is carried out in ES cells derived from the mouse C57BL/6N, C57BL/6J, 129S5 or 129Sv strain.

In one aspect non-human animals, such as mice, are generated in a RAG-1-deficient or a RAG-2-deficient background, or other suitable genetic background which prevents the production of mature host B and T lymphocytes.

In one aspect the non-human mammal is a rodent, suitably a mouse, and cells of the invention, are rodent cells or ES cells, suitably mouse ES cells.

The ES cells of the present invention can be used to generate animals using techniques well known in the art, which comprise injection of the ES cell into a blastocyst followed by implantation of chimaeric blastocystys into females to produce offspring which can be bred and selected for homozygous recombinants having the required insertion. In one aspect the invention relates to a chimeric animal comprised of ES cell-derived tissue and host embryo derived tissue. In one aspect the invention relates to genetically-altered subsequent generation animals, which include animals having a homozygous recombinants for the VDJ and/or VJ regions.

In a further aspect the invention relates to a method for producing an antibody specific to a desired antigen the method comprising immunizing a transgenic non-human mammal as above with the desired antigen and recovering the antibody (see e.g. Harlow, E. & Lane, D. 1998, $5^{th}$ edition, Antibodies: A Laboratory Manual, Cold Spring Harbor Lab. Press, Plainview, N.Y.; and Pasqualini and Arap, Proceedings of the National Academy of Sciences (2004) 101:257-259). Suitably an immunogenic amount of the antigen is delivered. The invention also relates to a method for detecting a target antigen comprising detecting an antibody produced as above with a secondary detection agent which recognises a portion of that antibody.

In a further aspect the invention relates to a method for producing a fully humanised antibody comprising immunizing a transgenic non-human mammal as above with the desired antigen, recovering the antibody or cells expressing the antibody, and then replacing the non-human mammal constant region with a human constant region. This can be done by standard cloning techniques at the DNA level to replace the non-human mammal constant region with an appropriate human constant region DNA sequence—see e.g. Sambrook, J and Russell, D. (2001, 3' d edition) Molecular Cloning: A Laboratory Manual (Cold Spring Harbor Lab. Press, Plainview, N.Y.).

In a further aspect the invention relates to humanised antibodies and antibody chains produced according to the present invention, both in chimaeric and fully humanised form, and use of said antibodies in medicine. The invention also relates to a pharmaceutical composition comprising such an antibodies and a pharmaceutically acceptable carrier or other excipient.

Antibody chains containing human sequences, such as chimaeric human-non-human antibody chains, are considered humanised herein by virtue of the presence of the human protein coding regions region. Fully humanised antibodies may be produced starting from DNA encoding a chimaeric antibody chain of the invention using standard techniques.

Methods for the generation of both monoclonal and polyclonal antibodies are well known in the art, and the present invention relates to both polyclonal and monoclonal antibodies of chimaeric or fully humanised antibodies produced in response to antigen challenge in non-human mammals of the present invention.

In a yet further aspect, chimaeric antibodies or antibody chains generated in the present invention may be manipulated, suitably at the DNA level, to generate molecules with antibody-like properties or structure, such as a human variable region from a heavy or light chain absent a constant region, for example a domain antibody; or a human variable region with any constant region from either heavy or light chain from the same or different species; or a human variable region with a non-naturally occurring constant region; or human variable region together with any other fusion partner. The invention relates to all such chimaeric antibody derivatives derived from chimaeric antibodies identified according to the present invention.

In a further aspect, the invention relates to use of animals of the present invention in the analysis of the likely effects of drugs and vaccines in the context of a quasi-human antibody repertoire.

The invention also relates to a method for identification or validation of a drug or vaccine, the method comprising delivering the vaccine or drug to a mammal of the invention and monitoring one or more of: the immune response, the safety profile; the effect on disease.

The invention also relates to a kit comprising an antibody or antibody derivative as disclosed herein and either instructions for use of such antibody or a suitable laboratory reagent, such as a buffer, antibody detection reagent.

The invention also relates to a method for making an antibody, or part thereof, the method comprising providing:
(i) a nucleic acid encoding an antibody, or a part thereof, obtained according to the present invention; or
(ii) sequence information from which a nucleic acid encoding an antibody obtained according to the present invention, or part thereof, can be expressed to allow an antibody to be produced.

The present invention also relates to a chimaeric antibody comprising a human variable region and a non-human vertebrate or mammal (optionally a rat or mouse) constant region (optionally a C gamma or C mu), wherein the antibody is encoded by a nucleotide sequence corresponding to the nucleotide sequence of a chimaeric heavy chain locus of a cell (optionally a B-cell, ES cell or hybridoma), the locus comprising a non-human vertebrate constant region nucleotide sequence and a rearranged VDJ nucleotide sequence produced by the in vivo rearrangement of a human V region, a human D region and a human J region, the V region being selected from one of a V1-3 region, V2-5 region, V4-4 region, V1-2 region or V6-1 region, and optionally a V1-3 or V6-1 segment. Optionally, the J region is any of JH1, JH2, JH3, JH4, JH5 or JH6, and in one aspect is JH4 or JH6. The D region is, in one aspect, any D3-9, D3-10, D6-13 or D6-19. In one example, rearranged VDJ nucleotide sequence is produced by the in vivo rearrangement of human V1-3 and JH4 (optionally with D3-9, D3-10, D6-13 or D-19); or V1-3 and JH6 (optionally with D3-9, D3-10, D6-13 or D-19); or V6-1 and JH4 (optionally with D3-9, D3-10, D6-13 or D-19); or V6-1 and JH6 (optionally with D3-9, D3-10, D6-13 or D-19). In one example the rearranged VDJ nucleotide sequence is produced by the in vivo rearrangement of human V6-1 DH3-10, V1-3 DH3-10, V1-3 DH6-19, V1-3 Dh3-9 or V6-1 DH6-19. In one aspect the antibody comprises any combination exemplified in the Examples and Figures herein. Optionally, the in vivo rearrangement is in a cell (eg, B cell or ES cell) derived from the same non-human vertebrate species as the constant region sequence (eg, a mouse B cell or ES cell). The invention also relates to a non-human vertebrate or mammal cell (eg, a B-cell or ES cell or hybridoma) whose genome comprises a chimaeric heavy chain locus as described above in this paragraph. The invention also relates to a non-human vertebrate or mammal (eg, a mouse or rat) whose genome comprises a chimaeric heavy chain locus as described above in this paragraph.

The present invention also relates to a non-human vertebrate or mammal having a genome encoding a chimaeric antibody, the chimaeric antibody comprising a human variable region and a non-human vertebrate or mammal (optionally a rat or mouse) constant region (optionally a C gamma or C mu), the mammal:
- expressing more V1-3 antibodies than V2-5, V4-4, V1-2 or V6-1 antibodies; and/or
- expressing more V1-3 JH4 or V1-3 JH6 antibodies than any of, individually, V1-3 JH1, V1-3 JH2, V1-3 JH3 or V1-3 JH5 antibodies, and/or
- expressing more V6-1 JH4 or V6-1 JH6 antibodies than any of, individually, V6-1 JH1, V6-1 JH2, V6-1 JH3 or V6-1 JH5 antibodies and/or
- expressing a greater number of V1-3 DH3-10 antibodies than antibodies V1-3 with any other D region. Expression of antibodies can be assessed by methods readily available to the skilled person and as conventional in the art. For example, expression can be assessed at the mRNA level as shown in the examples below.

The invention also relates to a chimaeric antibody comprising a human variable region and a non-human vertebrate or mammal (optionally a rat or mouse) constant region (optionally a light chain constant region), wherein the antibody is obtainable from a mammal (optionally a rat or mouse) whose genome comprises an antibody chain locus comprising a germline human kappa V1-8 and germline human kappa J1 sequence, and wherein the antibody is obtainable by in vivo recombination in said mammal of the V1-8 and J1 sequences and wherein the antibody has a variable region sequence which is different from that which is encoded by germline human kappa V1-8 and germline human kappa J1 sequences. Thus, in this aspect of the invention the human germline sequences are able to undergo productive rearrangement to form a coding sequence which, in conjunction with the non-human constant region sequence, can be expressed as a chimaeric antibody chain having at least a complete human variable region and a non-human constant region. This is in contrast (as the examples show below) to the combination of the germline human kappa V1-8 and germline human kappa J1 sequences per se, which do not provide for an antibody coding sequence (due to the inclusion of stop codons). In one aspect the rearranged sequence of the chimaeric antibody is a result of somatic hypermutation. In one aspect the antibody is a kappa antibody; in another aspect the antibody comprises a non-human heavy chain constant region (eg, a rat or mouse C gamma or C mu). The antibody sequence optionally comprises a $X_1X_2$ T F G Q, where $X_1X_2$=PR, RT, or PW (SEQ ID No 21); optionally a $X_1X_2$ T F G Q G T K V E I K R A D A (SEQ ID No 22) motif. Such motifs are not found in the equivalent position in the germline sequence as shown in the examples. The invention also relates to a non-human vertebrate or mammal cell (eg, a B-cell or ES cell or hybridoma) whose genome comprises a chimaeric antibody chain locus as described above in this paragraph. The invention also relates to a non-human vertebrate or mammal (eg, a mouse or rat) whose genome comprises a chimaeric antibody chain locus as described above in this paragraph.

The invention also relates to a chimaeric antibody comprising a human variable region and a non-human vertebrate or mammal (optionally a rat or mouse) constant region (optionally a light chain constant region), wherein the antibody is obtainable from a mammal (optionally a rat or mouse) whose genome comprises an antibody chain locus comprising a germline human kappa V1-6 and germline human kappa J1 sequence, and wherein the antibody is obtainable by in vivo recombination in said mammal of the V1-6 and J1 sequences and wherein the antibody has a variable region sequence which is different from that which is encoded by germline human kappa V1-6 and germline human kappa J1 sequences. Thus, in this aspect of the invention the human germline sequences are able to undergo productive rearrangement to form a coding sequence which, in conjunction with the non-human constant region sequence, can be expressed as a chimaeric antibody chain having at least a complete human variable region and a non-human constant region. This is in contrast (as the examples show below) to the combination of the germline human kappa V1-6 and germline human kappa J1 sequences per se, which do not provide for an antibody coding sequence (due to the inclusion of stop codons). In one aspect the rearranged sequence of the chimaeric antibody is a result of somatic hypermutation. In one aspect the antibody is a kappa antibody; in another aspect the antibody comprises a non-human heavy chain constant region (eg, a rat or mouse C gamma or C mu). The antibody sequence optionally comprises a $X_3X_4$ T F G Q, where $X_3X_4$=PR or PW (SEQ ID No 23); optionally a $X_3X_4$ T F G Q G T K V E I K R A D A (SEQ ID No 24) motif. Such motifs are not found in the equivalent position in the germline sequence as shown in the examples. The invention also relates to a non-human vertebrate or mammal cell (eg, a B-cell or ES cell or hybridoma) whose genome comprises a chimaeric antibody chain locus as described above in this paragraph. The invention also relates to a non-human vertebrate or mammal (eg, a mouse or rat) whose genome comprises a chimaeric antibody chain locus as described above in this paragraph.

The invention also relates to a chimaeric antibody comprising a human variable region and a non-human (optionally a rat or mouse) constant region (optionally a C gamma or C mu or a C kappa), wherein the antibody is obtainable from a mammal (optionally a rat or mouse) whose genome comprises an antibody chain locus comprising a germline human kappa V1-5 and germline human kappa J1 sequence, and wherein the antibody is obtainable by in vivo recombination in said mammal of the V1-5 and J1 sequences. The invention also relates to a non-human vertebrate or mammal cell (eg, a B-cell or ES cell or hybridoma) whose genome comprises a chimaeric antibody chain locus as described above in this paragraph. The invention also relates to a non-human vertebrate or mammal (eg, a mouse or rat) whose genome comprises a chimaeric antibody chain locus as described above in this paragraph.

The invention also relates to a chimaeric antibody comprising a human variable region and a non-human (optionally a rat or mouse) constant region (optionally a C gamma or C mu or a C kappa), wherein the antibody is obtainable from a mammal (optionally a rat or mouse) whose genome comprises an antibody chain locus comprising a germline human kappa V1-5 and germline human kappa J4 sequence, and wherein the antibody is obtainable by in vivo recombination in said mammal of the V1-5 and J4 sequences. The invention also relates to a non-human vertebrate or mammal cell (eg, a B-cell or ES cell or hybridoma) whose genome comprises a chimaeric antibody chain locus as described above in this paragraph. The invention also relates to a non-human vertebrate or mammal (eg, a mouse or rat)

whose genome comprises a chimaeric antibody chain locus as described above in this paragraph.

Antibodies of the invention may be isolated, in one aspect being isolated from the cell or organism in which they are expressed.

A non-human mammal whose genome comprises:
(a) the human IgH VDJ region upstream of the host non-human mammal constant region; and
(b) the human Ig light chain kappa V and J regions upstream of the host non-human mammal kappa constant region and/or the human Ig light chain lambda V and J regions upstream of the host non-human mammal lambda constant region;

wherein the non-human mammal is able to produce a repertoire of chimaeric antibodies having a non-human mammal constant region and a human variable region, and optionally wherein the non-human mammal genome is modified to prevent expression of fully host-species specific antibodies.

A non-human mammal ES cell whose genome comprises:
(a) the human IgH V, D and J region upstream of a non-human mammal constant region; and
(b) the human Ig locus light chain kappa V and J regions upstream of the host non-human mammal kappa constant region, and/or the human Ig locus light chain lambda V and J regions upstream of the host non-human mammal lambda constant region wherein the ES cell is capable of developing into a non-human mammal, being able to produce a repertoire of antibodies which are chimaeric, having a non-human mammal constant region and a human variable region.

A method for producing a transgenic non-human mammal able to produce a repertoire of chimaeric antibodies, the antibodies having a non-human mammal constant region and a human variable region, the method comprising inserting by homologous recombination into a non-human mammal ES cell genome
(a) the human IgH VDJ region upstream of the host non-human mammal heavy chain constant region, and
(b) the human IgL VJ region for lambda or kappa chains upstream of the host non-human mammal lambda or kappa chain constant region, respectively such that the non-human mammal is able to produce a repertoire of chimaeric antibodies having a non-human mammal constant region and a human variable region, wherein steps (a) and (b) can be carried out in either order and each of steps (a) and (b) can be carried out in a stepwise manner or as a single step.

In one aspect the insertion of human VDJ or VJ regions upstream of the host non-human mammal constant region is accomplished by step-wise insertion of multiple fragments by homologous recombination.

In one aspect the step-wise insertions commence at a site where an initiation cassette has been inserted into the genome of an ES cell providing a unique targeting region consisting of a BAC backbone sequence and a negative selection marker.

In one aspect the first human variable region fragment is inserted by homologous recombination at the initiation cassette BAC backbone sequence and said negative selection marker and initiation cassette are subsequently removed by recombination between recombinase target sequences.

In one aspect repeated targeted insertions at the BAC backbone initiation sequence and subsequent removal of the backbone by rearrangement between recombinase target sequences is repeated to build up the entire human VDJ region upstream of the host non-mammal constant region.

Insertion of Human Variable Region Gene Segments Precisely within the Endogenous Mouse JH4-Cmu Intron There is further provided a cell or non human mammal according to the invention wherein the mammal is a mouse or the cell is a mouse cell and wherein the insertion of the human heavy chain DNA is made in a mouse genome between coordinates 114,667,091 and 114,665,190 of mouse chromosome 12.

There is further provided a cell or non human mammal according to the invention wherein the insertion of the human heavy chain DNA is made at coordinate 114,667,091.

There is further provided a cell or non human mammal according to the invention wherein the human IgH VDJ region comprises nucleotides 105,400,051 to 106,368,585 from human chromosome 14 (coordinates refer to NCBI36 for the human genome).

There is further provided a method, cell or non human mammal according to the invention wherein a human coding region DNA sequence is in a functional arrangement with a non-human mammal control sequence, such that transcription of the human DNA is controlled by the non-human mammal control sequence. In one example, the initiation cassette is inserted between the mouse J4 and C alpha exons. There is further provided an initiation cassette suitable for use in the method comprising a vector backbone sequence and a selection marker.

The invention provides the following aspects (starting at aspect number 103):—

103. A cell or non human mammal according to any one of the above configurations, examples, embodiments or aspects, wherein the mammal is a mouse or the cell is a mouse cell and wherein the insertion of the human heavy chain DNA is made in a mouse genome between coordinates 114,667,091 and 114,665,190 of mouse chromosome 12.

104. A cell or non human mammal according to any one of the above configurations, examples, embodiments or aspects, wherein the insertion of the human heavy chain DNA is made at coordinate 114,667,091.

105. A cell or mammal according to any one of the above configurations, examples, embodiments or aspects, wherein the human IgH VDJ region comprises nucleotides 105,400,051 to 106,368,585 from human chromosome 14 (coordinates refer to NCBI36 for the human genome).

106. A method, cell or mammal according to any one of the above configurations, examples, embodiments or aspects, wherein a human coding region DNA sequence is in a functional arrangement with a non-human mammal control sequence, such that transcription of the human DNA is controlled by the non-human mammal control sequence.

107. A method according to aspect 106 wherein the initiation cassette is inserted between the mouse J4 and C alpha exons.

108. An initiation cassette suitable for use in the method of aspect 107 comprising a vector backbone sequence and a selection marker.

Inactivation of Endogenous Antibody Chain Expression by Insertion of Human Antibody Variable Region Gene Segments 109. A non-human vertebrate (optionally a mouse or rat) or non-human vertebrate cell (optionally a mouse or rat cell) having a genome that (i) comprises a transgenic antibody chain locus capable of expressing an antibody chain comprising a human variable region (optionally following antibody gene rearrangement); and
(ii) is inactivated for endogenous non-human vertebrate antibody chain expression;
wherein the transgenic locus comprises
(iii) a DNA sequence comprising a plurality of human antibody variable region gene segments inserted between endogenous antibody variable region gene segments and an endogenous antibody constant region, whereby endogenous antibody chain expression is inactivated.

The transgenic locus is a heavy chain or light chain locus.

Inactivation of endogenous heavy chain expression in non-human vertebrates such as mice and rats has involved the deletion of all or part of the endogenous heavy chain VDJ region (including sequences between gene segments). The ADAM6 genes are present in the endogenous mouse VDJ region. In mouse, there are two copies of ADAM6 (ADAM6a, ADAM6b) located between the VH and D gene segments in the IgH locus of chromosome 12 (in the intervening region between mouse VH5-1 and D1-1 gene segments). These two adjacent intronless ADAM6 genes have 95% nucleotide sequence identity and 90% amino acid identity. In human and rat, there is only one ADAM6 gene. Expression pattern analysis of mouse ADAM6 shows that it is exclusively expressed in testis [1]. Although ADAM6 transcripts can be detected in lymphocytes, it is restricted to the nucleus, suggesting that the transcription of ADAM6 gene in particular was due to transcriptional read-through from the D region rather than active messenger RNA production [2]. In rat, ADAM6 is on chromosome 6.

Mature ADAM6 protein is located on the acrosome and the posterior regions of sperm head. Notably, ADAM6 forms a complex with ADAM2 and ADAM3, which is required for fertilization in mice [3]. Reference [4] implicates ADAM6 in a model where this protein interacts with ADAM3 after ADAM6 is sulphated by TPST2, sulphation of ADAM6 being critical for stability and/or complex formation involving ADAM6 and ADAM3, and thus ADAM6 and ADAM3 are lost from Tpst2-null sperm. The study observes that Tpst2-deficient mice have male infertility, sperm mobility defects and possible abnormalities in sperm-egg membrane interactions.

Thus, the maintenance of ADAM6 expression in sperm is crucial for fertility. Thus, it is thought that transgenic male mice and rats in which ADAM6 genes have been deleted are not viably fertile. This hampers breeding of colonies and hampers the utility of such mice as transgenic antibody-generating platforms. It would be desirable to provide improved non-human transgenic antibody-generating vertebrates that are fertile.

[1]. Choi I, et. al., Characterization and comparative genomic analysis of intronless Adams with testicular gene expression. Genomics. 2004 April; 83(4):636-46.

[2]. Featherstone K, Wood A L, Bowen A J, Corcoran A E. The mouse immunoglobulin heavy chain V-D intergenic sequence contains insulators that may regulate ordered V(D)J recombination. J Biol. Chem. 2010 Mar. 26; 285 (13):9327-38. Epub 2010 Jan. 25.

[3]. Han C, et. al., Comprehensive analysis of reproductive ADAMs: relationship of ADAM4 and ADAM6 with an ADAM complex required for fertilization in mice. Biol Reprod. 2009 May; 80(5):1001-8. Epub 2009 Jan. 7.

[4]. Marcello et al, Lack of tyrosylprotein sulfotransferase-2 activity results in altered sperm-egg interactions and loss of ADAM3 and ADAM6 in epididymal sperm, J Biol. Chem. 2011 Apr. 15; 286(15):13060-70. Epub 2011 Feb. 21.

According to aspect 109 of the invention, inactivation does not involve deletion of the VDJ region or part thereof including endogenous ADAM6, but instead inactivation by insertion allows for the preservation of endogenous ADAM6 and thus does not risk infertility problems.

The final mouse resulting from the method (or a mouse derived from a cell produced by the method) is in one embodiment a male, so that the invention improves upon the prior art male transgenic mice that are infertile as a result of genomic manipulation. Fertile mice produce sperm that can fertilise eggs from a female mouse. Fertility is readily determined, for example, by successfully breeding to produce an embryo or child mouse. In another embodiment, the method of the invention makes a final female mouse. Such females are, of course, useful for breeding to create male progeny carrying ADAM6 and which are fertile.

In one embodiment of aspect 109, the genome is homozygous for the transgenic locus. For example, the genome is homozygous for endogenous ADAM6 genes.

In one embodiment of the vertebrate of aspect 109, the genome is inactivated for expression of endogenous heavy and kappa (and optionally also lambda) chains.

In one embodiment, in part (iii) of aspect 109 said DNA comprises human VH, D and JH gene segments or human VL and JL gene segments (eg, VK and JK gene segments). In an example, the DNA comprises a landing pad having a selectable marker, eg, a HPRT gene, neomycin resistance gene or a puromycin resistance gene; and/or a promoter.

In one embodiment, in part (iii) of aspect 109 the endogenous gene segments are the entire endogenous VDJ region of a heavy chain locus and/or the endogenous constant region is a Cmu or Cgamma.

In one embodiment, in part (iii) of aspect 109 the endogenous gene segments are the entire endogenous VJ region of a kappa chain locus and/or the endogenous constant region is a Ckappa In one embodiment, in part (iii) of aspect 109 the endogenous gene segments are the entire endogenous VJ region of a lambda chain locus and/or the endogenous constant region is a Clambda.

The non-human vertebrate cell can be a hybridoma, B-cell, ES cell or an IPS cell. When the cell is an ES cell or IPS cell, the endogenous antibody chain expression is inactivated following differentiation of the cell into a progeny B-cell (eg, in a B-cell in a non-human vertebrate).

The invention further provides:—

110. The vertebrate or cell according to aspect 109, wherein said plurality of human antibody gene segments comprises at least 11 human V segments and/or at least 6 human J segments, eg at least 11 human VH gene segments and at least 6 human JH segments and optionally also at least 27 human D segments; optionally with the human inter-gene segment intervening sequences. In an embodiment, the human antibody gene segments are provided by a stretch of DNA sequence of human chromosome 14, comprising the gene segments and intervening sequences in germline configuration.

111. The vertebrate or cell according to aspect 109 or 110, wherein said inserted DNA sequence comprises a human nucleotide sequence comprising said antibody gene segments, wherein the nucleotide sequence is at least 110, 130, 150, 170, 190, 210, 230, 250, 270 or 290 kb. In an embodiment, the nucleotide sequence corresponds to a stretch of DNA sequence of human chromosome 14, comprising the gene segments and intervening sequences in germline configuration, eg, at least a sequence corresponding to the nucleotide sequence from coordinate 106328951 to coordinate 106601551 of a human chromosome 14, eg, a sequence in the GRCH37/hg19 sequence database.

112. The vertebrate or cell according to aspect 109, wherein the transgenic locus is a light chain kappa locus and the human antibody gene segments are between the 3'-most endogenous Jk gene segment and endogenous Ck; optionally wherein the human antibody gene segments comprise five functional human Jλ-Cλ clusters and at least one human Vλ gene segment, eg, at least a sequence corresponding to the nucleotide sequence from coordinate 23217291 to 23327884 of a lambda locus found on a human chromosome 22.

113. The vertebrate or cell according to any one of aspects 109 to 112, wherein the transgenic locus is a heavy chain locus and the human antibody gene segments are between the 3'-most endogenous JH gene segment (eg, JH4 in a mouse genome) and endogenous Cmu.

114. The vertebrate or cell according to any one of aspects 109 to 113, wherein the genome is homozygous for said transgenic locus.

115. A mouse or mouse cell or a rat or rat cell according to any one of aspects 109 to 114.

116. A method of making a non-human vertebrate cell (optionally a mouse or rat cell), the method comprising
    (a) providing a non-human ES cell whose genome comprises an endogenous antibody chain locus comprising endogenous antibody variable region gene segments and an endogenous antibody constant region; and
    (b) making a transgenic antibody chain locus by inserting into said endogenous locus a DNA sequences comprising a plurality of human antibody variable region gene segments between said endogenous antibody variable region gene segments and said endogenous constant region, so that the human antibody variable region gene segments are operably connected upstream of the endogenous constant region,
    whereby a non-human vertebrate ES cell is produced that is capable of giving rise to a progeny cell in which endogenous antibody expression is inactivated and wherein the progeny is capable of expressing antibodies comprising human variable regions; and
    (c) optionally differentiating said ES cell into said progeny cell or a non-human vertebrate (eg, mouse or rat) comprising said progeny cell.

117. The method according to aspect 116, wherein said plurality of human antibody gene segments comprises at least 11 human V segments.

118. The method according to aspect 116 or 117, wherein said plurality of human antibody gene segments comprises at least 6 human J segments.

119. The method according to aspect 116, 117 or 118, wherein a human nucleotide sequence is inserted in step (b), the nucleotide sequence comprising said antibody gene segments, wherein the nucleotide sequence is at least 110 kb.

120. The method according to any one of aspects 110 to 113, wherein the endogenous locus is a heavy chain locus and the human antibody gene segments are between the 3'-most endogenous JH gene segment and endogenous Cmu.

121. The method according to any one of aspects 116 to 120, wherein the progeny cell is homozygous for said transgenic locus.

In one embodiment of the method of aspect 116, the method comprises inactivating the genome for expression of endogenous heavy and kappa (and optionally also lambda) chains.

In one embodiment of the method of aspect 116, in part (b) said DNA sequence comprises human VH, D and JH gene segments or human VL and JL gene segments (eg, Vκ and Jκ gene segments). In an example, the DNA comprises a landing pad having a selectable marker, eg, a HPRT gene, neomycin resistance gene or a puromycin resistance gene; and/or a promoter.

In one embodiment, in part (b) of aspect 116 the endogenous gene segments are the entire endogenous VDJ region of a heavy chain locus and/or the endogenous constant region is a Cmu or Cgamma.

In one embodiment, in part (b) of aspect 116 the endogenous gene segments are the entire endogenous VJ region of a kappa chain locus and/or the endogenous constant region is a Ckappa In one embodiment, in part (b) of aspect 116 the endogenous gene segments are the entire endogenous VJ region of a lambda chain locus and/or the endogenous constant region is a Clambda.

The non-human vertebrate cell can be a hybridoma, B-cell, ES cell or an IPS cell. When the cell is an ES cell or IPS cell, the endogenous antibody chain expression is inactivated following differentiation of the cell into a progeny B-cell (eg, in a B-cell in a non-human vertebrate).

The invention further provides:—

The method according to aspect 116, wherein said inserted DNA sequence comprises a human nucleotide sequence comprising said human antibody gene segments, wherein the nucleotide sequence is at least 110, 130, 150, 170, 190, 210, 230, 250, 270 or 290 kb. In an embodiment, the nucleotide sequence corresponds to a stretch of DNA sequence of human chromosome 14, comprising the gene segments and intervening sequences in germline configuration, eg, at least a sequence corresponding to the nucleotide sequence from coordinate 106328951 to coordinate 106601551 of a human chromosome 14, eg, a sequence in the GRCH37/hg19 sequence database.

The method according to aspect 116, wherein the transgenic locus is a light chain kappa locus and the human antibody gene segments are between the 3'-most endogenous Jk gene segment and endogenous Ck; optionally wherein the human antibody gene segments comprise five functional human Jλ-Cλ clusters and at least one human VA gene segment, eg, at least a sequence corresponding to the nucleotide sequence from coordinate 23217291 to 23327884 of a lambda locus found on a human chromosome 22.

The method according to aspect 116, wherein, wherein the transgenic locus is a heavy chain locus and the human antibody gene segments are inserted between the 3'-most endogenous JH gene segment (eg, JH4 in a mouse genome) and endogenous Cmu.

122. The method according to any one of aspects 116 to 121, comprising making the genome of the progeny homozygous for said transgenic locus.

Isolating Antibodies from Transgenic Non-Human Vertebrates of the Invention & Useful Antigen-Specific Antibodies of Therapeutically-Relevant Affinities 123. A method of isolating an antibody that binds a predetermined antigen, the method comprising
    (a) providing a vertebrate (optionally a mammal; optionally a mouse or rat according to any one of the above configurations, examples, embodiments or aspects;
    (b) immunising said vertebrate with said antigen (optionally wherein the antigen is an antigen of an infectious disease pathogen);
    (c) removing B lymphocytes from the vertebrate and selecting one or more B lymphocytes expressing antibodies that bind to the antigen;
    (d) optionally immortalising said selected B lymphocytes or progeny thereof, optionally by producing hybridomas therefrom; and
    (e) isolating an antibody (eg, and IgG-type antibody) expressed by the B lymphocytes.
124. The method of aspect 123, comprising the step of isolating from said B lymphocytes nucleic acid encoding said antibody that binds said antigen; optionally exchanging the heavy chain constant region nucleotide sequence of the antibody with a nucleotide sequence encoding a human or humanised heavy chain constant region and optionally affinity maturing the variable region of said antibody; and optionally inserting said nucleic acid into an expression vector and optionally a host.
125. The method of aspect 123 or 124, further comprising making a mutant or derivative of the antibody produced by the method of aspect 122 or 123.

As demonstrated by the examples below, the non-human vertebrates of the invention are able to produce antigen-specific antibodies of sub-50 nM affinity with human sequences in their CDR3 regions. Thus, the invention further provides:—

126. An antibody or fragment (eg, a Fab or $Fab_2$) thereof comprising variable regions that specifically bind a predetermined antigen with a sub-50 nM affinity (optionally sub-40, 30, 20, 10, 1, 0.1 or 0.01 nM) as determined by surface plasmon resonance, wherein the antibody is isolated from a non-human vertebrate (optionally a mammal; optionally a mouse or rat) according to any one of the above configurations, examples, embodiments or aspects and comprises heavy chain CDR3s (as defined by Kabat) encoded by a rearranged VDJ of said vertebrate, wherein the VDJ is the product of rearrangement in vivo of a human JH gene segment of a heavy chain locus of said vertebrate with D (optionally a human D gene segment of said locus) and VH gene segments.

In one embodiment, the surface plasmon resonance (SPR) is carried out at 25° C. In another embodiment, the SPR is carried out at 37° C.

In one embodiment, the SPR is carried out at physiological pH, such as about pH7 or at pH7.6 (eg, using Hepes buffered saline at pH7.6 (also referred to as HBS-EP)).

In one embodiment, the SPR is carried out at a physiological salt level, eg, 150 mM NaCl.

In one embodiment, the SPR is carried out at a detergent level of no greater than 0.05% by volume, eg, in the presence of P20 (polysorbate 20; eg, Tween-20™) at 0.05% and EDTA at 3 mM.

In one example, the SPR is carried out at 25° C. or 37° C. in a buffer at pH7.6, 150 mM NaCl, 0.05% detergent (eg, P20) and 3 mM EDTA. The buffer can contain 10 mM Hepes. In one example, the SPR is carried out at 25° C. or 37° C. in HBS-EP. HBS-EP is available from Teknova Inc (California; catalogue number H8022).

In an example, the affinity of the antibody is determined using SPR by
1. Coupling anti-mouse (or other relevant non-human vertebrate) IgG (eg, Biacore BR-1008-38) to a biosensor chip (eg, GLM chip) such as by primary amine coupling;
2. Exposing the anti-mouse IgG (non-human vertebrate antibody) to a test IgG antibody to capture test antibody on the chip;
3. Passing the test antigen over the chip's capture surface at 1024 nM, 256 nM, 64 nM, 16 nM, 4 nM with a 0 nM (i.e. buffer alone); and
4. And determining the affinity of binding of test antibody to test antigen using surface plasmon resonance, eg, under an SPR condition discussed above (eg, at 25° C. in physiological buffer). SPR can be carried out using any standard SPR apparatus, such as by Biacore™ or using the ProteOn XPR36™ (Bio-Rad®).

Regeneration of the capture surface can be carried out with 10 mM glycine at pH1.7. This removes the captured antibody and allows the surface to be used for another interaction. The binding data can be fitted to 1:1 model inherent using standard techniques, eg, using a model inherent to the ProteOn XPR36™ analysis software.

The invention also relates to an scFv, diabody or other antibody fragment comprising a VH and VL domain from an antibody or fragment of aspect 126 (optionally following affinity maturation, eg, by phage display).

In one embodiment, the antigen is a serpin, eg, ovalbumin, antithrombin or antitrypsin. Serpins are a group of proteins with similar structures that were first identified as a set of proteins able to inhibit proteases. The acronym serpin was originally coined because many serpins inhibit chymotrypsin-like serine proteases (serine protease inhibitors). The first members of the serpin superfamily to be extensively studied were the human plasma proteins antithrombin and antitrypsin, which play key roles in controlling blood coagulation and inflammation, respectively. Initially, research focused upon their role in human disease: antithrombin deficiency results in thrombosis and antitrypsin deficiency causes emphysema. In 1980 Hunt and Dayhoff made the surprising discovery that both these molecules share significant amino acid sequence similarity to the major protein in chicken egg white, ovalbumin, and they proposed a new protein superfamily.

127. An antibody or fragment that is identical to an antibody of aspect 126 or a derivative thereof (optionally a derivative whose constant regions are human and/or an affinity matured derivative) that specifically binds said antigen with a sub-50 nM affinity as determined by surface plasmon resonance.
128. A pharmaceutical composition comprising an antibody or fragment of aspect 126 or 127 and a pharmaceutically-acceptable diluent, excipient or carrier.
129. A nucleotide sequence encoding a heavy chain variable region of an antibody or fragment of aspect 126 or 127, optionally as part of a vector (eg, an expression vector).
130. The nucleotide sequence of aspect 129, wherein the sequence is a cDNA derived from a B-cell of the vertebrate from which the antibody of aspect 126 is isolated, or is identical to such a cDNA.
131. An isolated host cell (eg, a hybridoma or a CHO cell or a HEK293 cell) comprising a nucleotide sequence according to aspect 129 or 130.

132. A method of isolating an antibody that binds a predetermined antigen, the method comprising
   (a) providing a vertebrate (optionally a mammal; optionally a mouse or rat according to any one of the above configurations, examples, embodiments or aspects;
   (b) immunising said vertebrate with said antigen;
   (c) removing B lymphocytes from the vertebrate and selecting a B lymphocyte expressing an antibody that binds to the antigen with sub-nM affinity, wherein the antibody is according to aspect 126;
   (d) optionally immortalising said selected B lymphocyte or progeny thereof, optionally by producing hybridomas therefrom; and
   (e) isolating an antibody (eg, and IgG-type antibody) expressed by the B lymphocyte.

133. The method of aspect 132, comprising the step of isolating from said B lymphocyte nucleic acid encoding said antibody that binds said antigen; optionally exchanging the heavy chain constant region nucleotide sequence of the antibody with a nucleotide sequence encoding a human or humanised heavy chain constant region and optionally affinity maturing the variable region of said antibody; and optionally inserting said nucleic acid into an expression vector and optionally a host.

134. The method of aspect 132 or 133, further comprising making a mutant or derivative of the antibody produced by the method of aspect 132 or 133.

Inactivation by Inversion of Endogenous VDJ to Genome Desert Regions

135. A mouse or mouse cell comprising inverted endogenous heavy chain gene segments (eg, VH, D and JH, such as the entire endogenous heavy chain VDJ region) that are immediately 3' of position 119753123, 119659458 or 120918606 on an endogenous mouse chromosome 12, wherein the mouse comprises a transgenic heavy chain locus comprising a plurality of human VH gene segments, a plurality of human D segments and a plurality of human JH segments operably connected upstream of an endogenous constant region (eg, C mu) so that the mouse or cell (optionally following differentiation into a B-cell) is capable of expressing an antibody comprising a variable region comprising sequences derived from the human gene segments.

136. The mouse or cell of aspect 135, wherein the genome of the mouse or cell is homozygous for said chromosome 12.

137. A cassette for inversion and inactivation of endogenous non-human vertebrate (eg, mouse or rat) antibody chain gene segments, the segments being part of an antibody chain locus sequence on a chromosome of a non-human vertebrate (eg, mouse or rat) cell (eg, ES cell) wherein the sequence is flanked at its 3' end by a site-specific recombination site (eg, lox, rox or frt), the cassette comprising a nucleotide sequence encoding an expressible label or selectable marker and a compatible site-specific recombination site (eg, lox, rox or frt) flanked by a 5' and a 3' homology arm, wherein the homology arms correspond to or are homologous to adjacent stretches of sequence in the cell genome on a different chromosome or on said chromosome at least 10 mb away from the endogenous gene segments.

138. A cassette for inversion and inactivation of endogenous mouse antibody heavy chain gene segments, the segments being part of a heavy chain locus sequence on chromosome 12 of a mouse cell (eg, ES cell) wherein the sequence is flanked at its 3' end by a site-specific recombination site (eg, lox, rox or frt), the cassette comprising a nucleotide sequence encoding an expressible label or selectable marker and a compatible site-specific recombination site (eg, lox, rox or frt) flanked by a 5' and a 3' homology arm, wherein (i) the 5' homology arm is mouse chromosome 12 DNA from coordinate 119753124 to coordinate 119757104 and the 3' homology arm is mouse chromosome 12 DNA from coordinate 119749288 to 119753123; (ii) the 5' homology arm is mouse chromosome 12 DNA from coordinate 119659459 to coordinate 119663126 and the 3' homology arm is mouse chromosome 12 DNA from coordinate 119656536 to 119659458; or (iii) the 5' homology arm is mouse chromosome 12 DNA from coordinate 120918607 to coordinate 120921930 and the 3' homology arm is mouse chromosome 12 DNA from coordinate 120915475 to 120918606.

139. A method of inactivating gene segments of an endogenous antibody locus, the method comprising
   (i) Providing a non-human vertebrate cell (eg, an ES cell, eg, a mouse ES cell) whose genome comprises an antibody chain locus comprising endogenous variable region gene segments;
   (ii) Targeting a site-specific recombination site to flank the 3' of the 3'-most of said endogenous gene segments;
   (iii) Targeting a second site-specific recombination site at least 10 mb away from said endogenous gene segments, the second site being compatible with the first site inverted with respect to the first site;
   (iv) Expressing a recombinase compatible with said sites to effect site-specific recombination between said sites, thereby inverting and moving said gene segments away from said locus, wherein the endogenous gene segments are inactivated; and
   (v) Optionally developing the cell into a progeny cell or vertebrate (eg, mouse or rat) whose genome is homozygous for the inversion.

140. A mouse or mouse cell whose genome comprises an inversion of a chromosome 12, wherein the inversion comprises inverted endogenous heavy chain gene segments (eg, VH, D and JH, such as the entire endogenous heavy chain VDJ region); wherein the mouse comprises a transgenic heavy chain locus comprising a plurality of human VH gene segments, a plurality of human D segments and a plurality of human JH segments operably connected upstream of an endogenous constant region (eg, C mu) so that the mouse or cell (optionally following differentiation into a B-cell) is capable of expressing an antibody comprising a variable region comprising sequences derived from the human gene segments; and wherein the inversion is (i) an inversion of mouse chromosome 12 from coordinate 119753123 to coordinate 114666436; (ii) an inversion of mouse chromosome 12 from coordinate 119659458 to coordinate 114666436; or (iii) an inversion of mouse chromosome 12 from coordinate 12091806 to coordinate 114666436.

Other Aspects Include:

A method for producing an antibody specific to a desired antigen the method comprising immunizing a non-human mammal as disclosed herein with the desired antigen and recovering the antibody or a cell producing the antibody.

A method for producing a fully humanised antibody comprising immunizing a non-human mammal as disclosed herein and then replacing the non-human mammal constant region of an antibody specifically reactive with the antigen with a human constant region, suitably by engineering of the nucleic acid encoding the antibody.

A method, cell or mammal as disclosed herein wherein a human coding region DNA sequence is in a functional arrangement with a non-human mammal control sequence, such that transcription of the DNA is controlled by the non-human mammal control sequence. In one aspect the human coding region V, D or J region is in a functional arrangement with a mouse promoter sequence.

The invention also relates to a humanised antibody produced according to any methods disclosed herein and use of a humanised antibody so produced in medicine.

BRIEF DESCRIPTION OF THE FIGURES

FIG. 39 illustrates Distribution of JH Usage Within Each VHs FIG. 40 illustrates Distribution of DH Usage Within Each VHs FIG. 49 illustrates that the S1$^{inv1}$ mouse shows a similar usage of both D and $J_H$ gene segments to human FIG. 54A-FIG. 54D illustrate normal IgH isotypes in transgenic mice (H1) immunised with 100 µg Cholera Toxin B subunit. FIG. 55A and FIG. 55B illustrate normal IgH isotypes and serum levels are obtained in transgenic H1 and S1 animals, respectively, of the invention following immunisation with antigens

SEQUENCES

Figure 1:
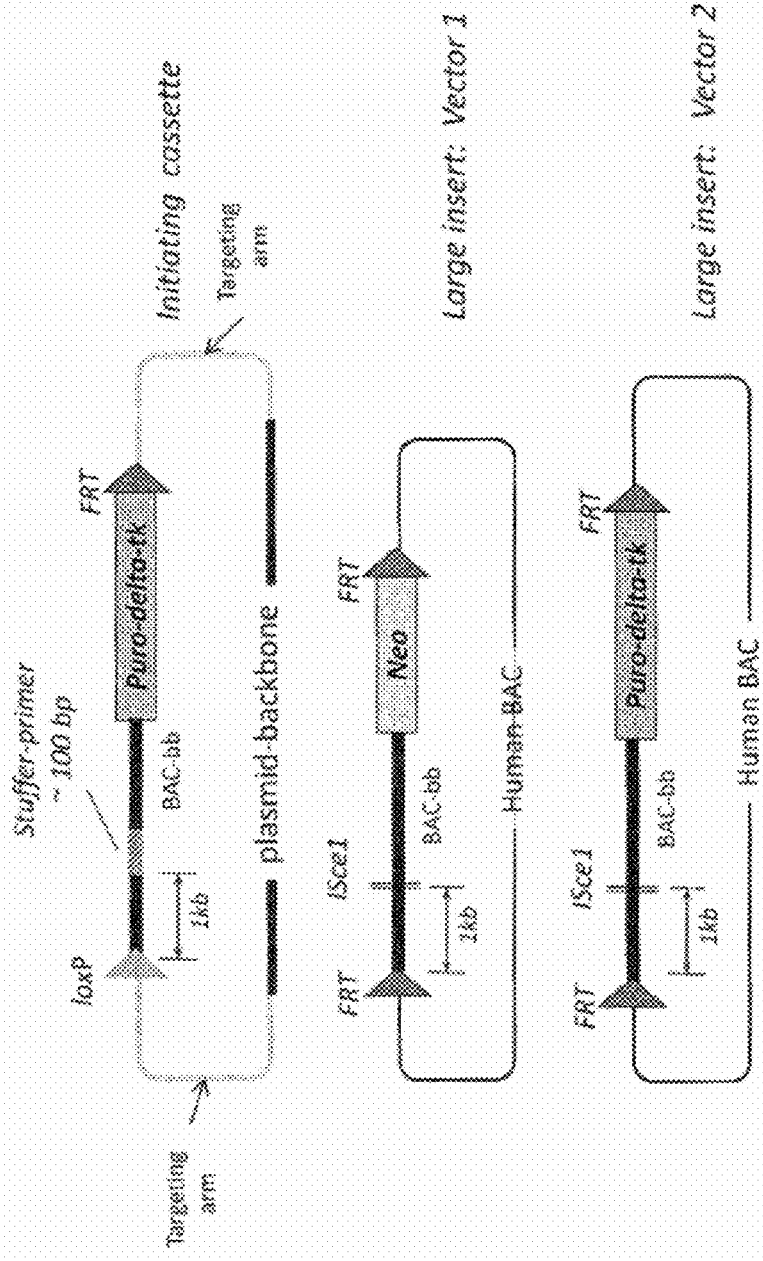
FIGS. 1-8 show an iterative process for insertion of a series of human BACs into a mouse Ig locus

SEQ ID No 1 is a Rat switch sequence
SEQ ID No 2 is a landing pad targeting vector (long version)
SEQ ID No 3 is a landing pad targeting vector (shorter version)
SEQ ID No 4 is the mouse strain 129 switch
SEQ ID No 5 is the mouse strain C57 switch
SEQ ID No 6 is the 5' homology arm of a landing pad
SEQ ID No 7 is oligo HV2-5
SEQ ID No 8 is oligo HV4-4
SEQ ID No 9 is oligo HV1-3
SEQ ID No 10 is oligo HV1-2
SEQ ID No 11 is oligo HV6-1
SEQ ID No 12 is oligo Cµ
SEQ ID No 13 is oligo KV1-9
SEQ ID No 14 is oligo KV1-8
SEQ ID No 15 is oligo KV1-6
SEQ ID No 16 is oligo KV1-5
SEQ ID No 17 is oligo Cκ
SEQ ID Nos 18-20 are rat switch sequences
SEQ ID No 21 is $X_1X_2$ T F G Q, where $X_1X_2$=PR, RT, or PW
SEQ ID No 22 is $X_1X_2$ T F G Q G T K V E I K R A D A, where $X_1X_2$=PR, RT, or PW;
SEQ ID No 23 is $X_3X_4$ T F G Q, where $X_3X_4$=PR or PW
SEQ ID No 24 is $X_3X_4$ T F G Q G T K V E I K R A D A, where $X_3X_4$=PR or PW
SEQ ID No 25 is Primer E1554
SEQ ID No 26 is Primer E1555
SEQ ID No 27 is Primer ELP1352_Cγ1
SEQ ID No 28 is Primer ELP1353_Cγ2b
SEQ ID No 29 is Primer ELP1354_Cγ2a
SEQ ID No 30 is Primer ELP1356_VH4-4
SEQ ID No 31 is Primer ELP1357_VH1-2,3
SEQ ID No 32 is Primer ELP1358_VH6-1
SEQ ID No 33 is Primer mIgG1_2 rev
SEQ ID No 34 is Primer mIgG2b rev
SEQ ID No 35 is Primer mIgG2a_2 rev
SEQ ID No 36 is Primer mCH1 unirev SEQ ID No 37 is Primer mCH1 unirev_2

SEQ ID Nos 38-45 are CDRH3 sequences

SEQ ID Nos 46-50 is 3, 4, 5, 6 or more (up to 82) repeats of GGGCT

SEQ ID NOs 51-55 are heavy chain CDR1 sequences against CTB (cloned and reference)

SEQ ID NOs 56-60 are heavy chain CDR2 sequences against CTB (cloned and reference)

SEQ ID NOs 61-63 are heavy chain CDR3 sequences against CTB (cloned and reference)

SEQ ID NOs 64-68 are J Region sequences against CTB (cloned and reference)

DETAILED DESCRIPTION OF THE INVENTION

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps The term "or combinations thereof" as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As a source of antibody gene segment sequences, the skilled person will also be aware of the following available databases and resources (including updates thereof) the contents of which are incorporated herein by reference:

The Kabat Database (G. Johnson and T. T. Wu, 2002; World Wide Web (www) kabatdatabase.com). Created by E. A. Kabat and T. T. Wu in 1966, the Kabat database publishes aligned sequences of antibodies, T-cell receptors, major histocompatibility complex (MHC) class I and II molecules, and other proteins of immunological interest. A searchable interface is provided by the SeqhuntII tool, and a range of utilities is available for sequence alignment, sequence subgroup classification, and the generation of variability plots. See also Kabat, E. A., Wu, T. T., Perry, H., Gottesman, K., and Foeller, C. (1991) Sequences of Proteins of Immunological Interest, 5th ed., NIH Publication No. 91-3242, Bethesda, Md., which is incorporated herein by reference, in particular with reference to human gene segments for use in the present invention.

KabatMan (A. C. R. Martin, 2002; World Wide Web (www) bioinf.org.uk/abs/simkab.html). This is a web interface to make simple queries to the Kabat sequence database.

IMGT (the International ImMunoGeneTics Information System®; M.-P. Lefranc, 2002; World Wide Web (www) imgt.cines.fr). IMGT is an integrated information system that specializes in antibodies, T cell receptors, and MHC molecules of all vertebrate species. It provides a common portal to standardized data that include nucleotide and protein sequences, oligonucleotide primers, gene maps, genetic polymorphisms, specificities, and two-dimensional (2D) and three-dimensional (3D) structures. IMGT includes three sequence databases (IMGT/LIGM-DB, IMGT/MHC-DB, IMGT/PRIMERDB), one genome database (IMGT/GENE-DB), one 3D structure database (IMGT/3Dstructure-DB), and a range of web resources ("IMGT Marie-Paule page") and interactive tools.

V-BASE (I. M. Tomlinson, 2002; World Wide Web (www) mrc-cpe.cam.ac.uk/vbase). V-BASE is a comprehensive directory of all human antibody germline variable region sequences compiled from more than one thousand published sequences. It includes a version of the alignment software DNAPLOT (developed by Hans-Helmar Althaus and Werner Müller) that allows the assignment of rearranged antibody V genes to their closest germline gene segments.

Antibodies—Structure and Sequence (A. C. R. Martin, 2002; World Wide Web (www) bioinf.org.uk/abs). This page summarizes useful information on antibody structure and sequence. It provides a query interface to the Kabat antibody sequence data, general information on antibodies, crystal structures, and links to other antibody-related information. It also distributes an automated summary of all antibody structures deposited in the Protein Databank (PDB). Of particular interest is a thorough description and comparison of the various numbering schemes for antibody variable regions.

AAAAA (A Ho's Amazing Atlas of Antibody Anatomy; A. Honegger, 2001; World Wide Web (www) unizh.ch/~antibody). This resource includes tools for structural analysis, modeling, and engineering. It adopts a unifying scheme for comprehensive structural alignment of antibody and T-cell-receptor sequences, and includes Excel macros for antibody analysis and graphical representation.

WAM (Web Antibody Modeling; N. Whitelegg and A. R. Rees, 2001; World Wide Web (www) antibody.bath.ac.uk). Hosted by the Centre for Protein Analysis and Design at the University of Bath, United Kingdom. Based on the AbM package (formerly marketed by Oxford Molecular) to construct 3D models of antibody Fv sequences using a combination of established theoretical methods, this site also includes the latest antibody structural information.

Mike's Immunoglobulin Structure/Function Page (M. R. Clark, 2001; World Wide Web (www) path.cam.ac.uk/~mrc7/mikeimages.html) These pages provide educational materials on immunoglobulin structure and function, and are illustrated by many colour images, models, and animations. Additional information is available on antibody humanization and Mike Clark's Therapeutic Antibody Human Homology Project, which aims to correlate clinical efficacy and anti-immunoglobulin responses with variable region sequences of therapeutic antibodies.

The Antibody Resource Page (The Antibody Resource Page, 2000; World Wide Web (www) antibodyresource-.com). This site describes itself as the "complete guide to antibody research and suppliers." Links to amino acid sequencing tools, nucleotide antibody sequencing tools, and hybridoma/cell-culture databases are provided.

Humanization bY Design (J. Saldanha, 2000; World Wide Web (www) people.cryst.bbk.ac.uk/~ubcg07s). This resource provides an overview on antibody humanization technology. The most useful feature is a searchable database (by sequence and text) of more than 40 published humanized antibodies including information on design issues, framework choice, framework back-mutations, and binding affinity of the humanized constructs.

See also Antibody Engineering Methods and Protocols, Ed. Benny K C Lo, *Methods in Molecular Biology™*, Human Press. Also at World Wide Web (www) blogsua.com/pdf/antibody-engineering-methods-and-protocolsantibody-engineering-methods-and-protocols.pdf Any part of this disclosure may be read in combination with any other part of the disclosure, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The following examples are put forth so as to provide those of ordinary skill in the art with a complete disclosure and description of how to make and use the invention, and are not intended to limit the scope of what the inventors regard as their invention.

EXAMPLES

Example 1

BAC Recombineering

Overall Strategy:

A mouse model of the invention can be achieved by inserting ~960 kb of the human heavy chain locus containing all the V, D and J-regions upstream of the mouse constant region and 473 kb of the human kappa region upstream of the mouse constant region. Alternatively, or in tandem, the human lambda region is inserted upstream of the mouse constant region. This insertion is achieved by gene targeting in ES cells using techniques well known in the art.

High fidelity insertion of intact V-D-J regions into each locus in their native (wild-type) configuration is suitably achieved by insertion of human bacterial artificial chromosomes (BACs) into the locus. Suitably the BACs are trimmed so that in the final locus no sequence is duplicated or lost compared to the original. Such trimming can be carried out by recombineering.

The relevant human BACs, suitably trimmed covering these loci are on average 90 kb in size.

In one approach the full complement of human D and J-elements as well as seven or eight human V-regions are covered by the first BACs to be inserted in the experimental insertion scheme described below. The first BACs to be inserted in the IgH and IgK loci may contain the following V-regions. IgH: V6-1, VII-1-1, V1-2, VIII-2-1, V1-3, V4-4, V2-5 and IgK: V4-1, V5-2, V7-3, V2-4, V1-5, V1-6, V3-7, V1-8.

Suitably the performance of each locus is assessed after the first BAC insertion using chimaeric mice and also after each subsequent BAC addition. See below for detailed description of this performance test.

Nine additional BAC insertions will be required for the IgH locus and five for IgK to provide the full complement of human V-regions covering all 0.96 Mb and 0.473 Mb of the IgH and IgK loci, respectively.

Not all BACs retain their wild-type configuration when inserted into the ES cell genome. Thus, high density genomic arrays were deployed to screen ES cells to identify those with intact BAC insertions (Barrett, M. T., Scheffer, A., Ben-Dor, A., Sampas, N., Lipson, D., Kincaid, R., Tsang, P., Curry, B., Baird, K., Meltzer, P. S., et al. (2004). Comparative genomic hybridization using oligonucleotide microarrays and total genomic DNA. Proceedings of the National Academy of Sciences of the United States of America 101, 17765-17770.). This screen also enables one to identify and select against ES clones in which the ES cell genome is compromised and thus not able to populate the germ line of chimeric animals. Other suitable genomic tools to facilitate this assessment include sequencing and PCR verification.

Thus in one aspect the correct BAC structure is confirmed before moving to the next step.

It is implicit from the description above that in order to completely engineer the loci with 90 kb BACs, it is necessary to perform a minimum of 10 targeting steps for IgH and 5 steps for the IgK. Mice with an IgL locus can be generated in a similar manner to the IgK locus. Additional steps are required to remove the selection markers required to support gene targeting. Since these manipulations are being performed in ES cells in a step-wise manner, in one aspect germ line transmission capacity is retained throughout this process.

Maintaining the performance of the ES cell clones through multiple rounds of manipulation without the need to test the germ line potential of the ES cell line at every step may be important in the present invention. The cell lines currently in use for the KOMP and EUCOMM global knockout projects have been modified twice prior to their use for this project and their germ line transmission rates are unchanged from the parental cells (these lines are publicly available, see World Wide Web (www) komp.org and World Wide Web (www) eucomm.org). This cell line, called JM8, can generate 100% ES cell-derived mice under published culture conditions (Pettitt, S. J., Liang, Q., Rairdan, X. Y., Moran, J. L., Prosser, H. M., Beier, D. R., Lloyd, K. C., Bradley, A., and Skarnes, W. C. (2009). Agouti C57BL/6N embryonic stem cells for mouse genetic resources. Nature Methods.). These cells have demonstrated ability to reproducibly contribute to somatic and germ line tissue of chimaeric animals using standard mouse ES cell culture conditions. This capability can be found with cells cultured on a standard feeder cell line (SNL) and even feeder-free, grown only on gelatine-coated tissue culture plates. One particular sub-line, JM8A3, maintained the ability to populate the germ line of chimeras after several serial rounds of sub-cloning. Extensive genetic manipulation via, for example, homologous recombination—as would be the case in the present invention—cannot compromise the pluripotency of the cells. The ability to generate chimeras with such high percentage of ES cell-derived tissue has other advantages. First, high levels of chimerism correlates with germ line transmission potential and provide a surrogate assay for germ line transmission while only taking 5 to 6 weeks. Second, since these mice are 100% ES cell derived the engineered loci can be directly tested, removing the delay caused by breeding. Testing the integrity of the new Ig loci is possible in the chimera since the host embryo will be derived from animals that are mutant for the RAG-1 gene as described in the next section.

Another cell line that may be used is an HPRT-ve cell line, such as AB2.1, as disclosed in Ramirez-Solis R, Liu P and Bradley A, "Chromosome engineering in mice," Nature, 1995; 378; 6558; 720-4.

RAG-1 Complementation:

While many clones will generate 100% ES derived mice some will not. Thus, at every step mice are generated in a RAG-1-deficient background. This provides mice with 100% ES-derived B- and T-cells which can be used directly for immunization and antibody production. Cells having a RAG-2 deficient background, or a combined RAG-1/RAG-2 deficient background may be used, or equivalent mutations in which mice produce only ES cell-derived B cells and/or T cells.

In order that only the human-mouse IgH or IgK loci are active in these mice, the human-mouse IgH and IgK loci can be engineered in a cell line in which one allele of the IgH or IgK locus has already been inactivated. Alternatively the inactivation of the host Ig locus, such as the IgH or IgK locus, can be carried out after insertion.

Figure 19:
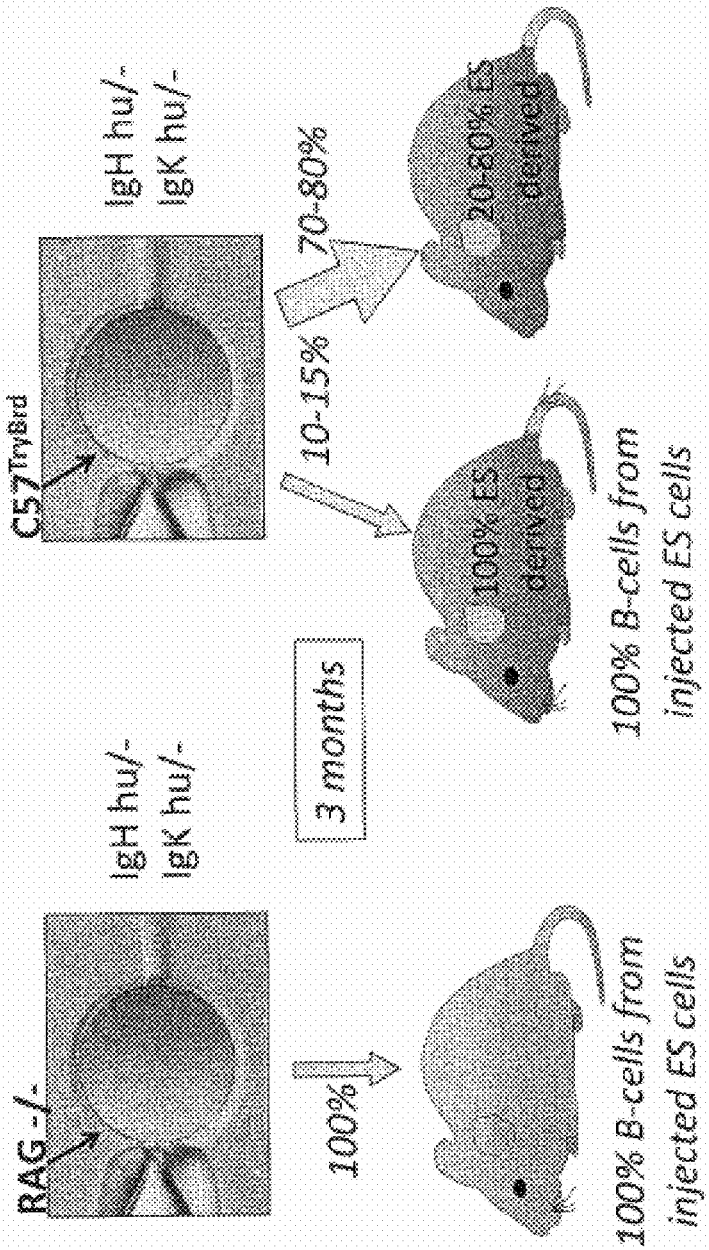
FIGS. 19 and 20 show the principles behind antibody generation in chimaeric mice
Figure 20:
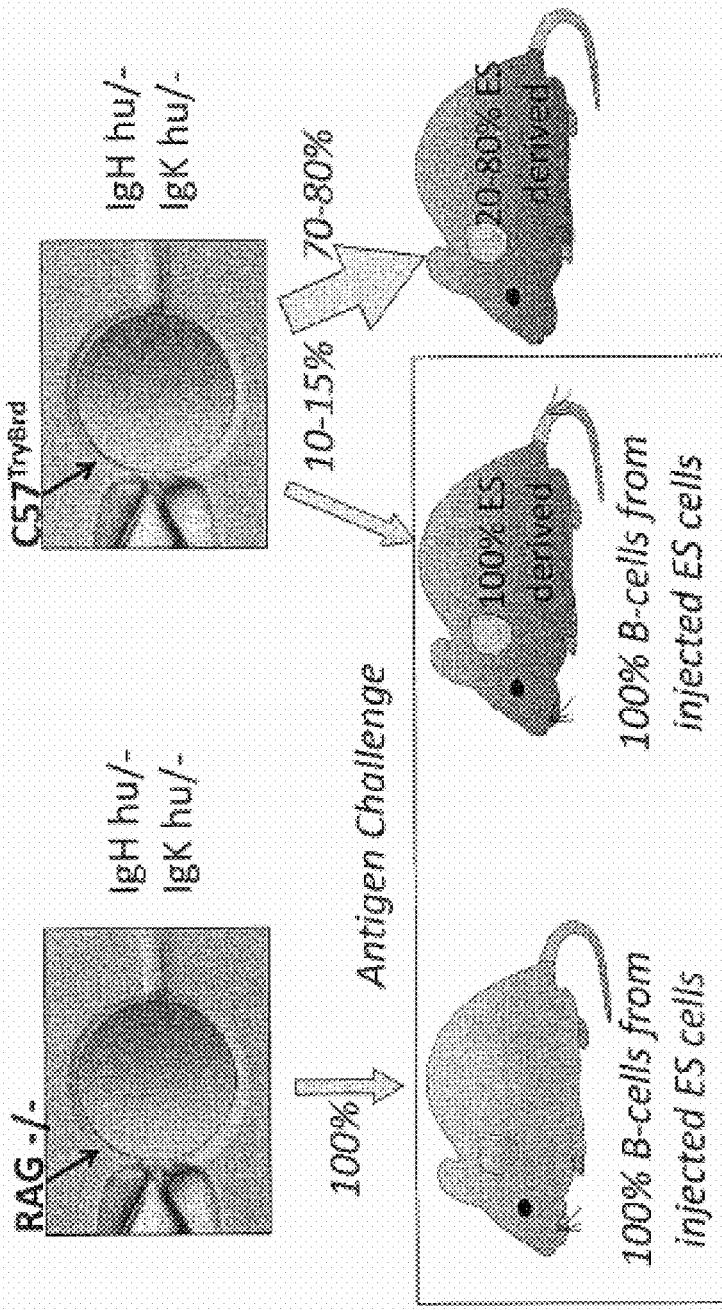
Figure 21:
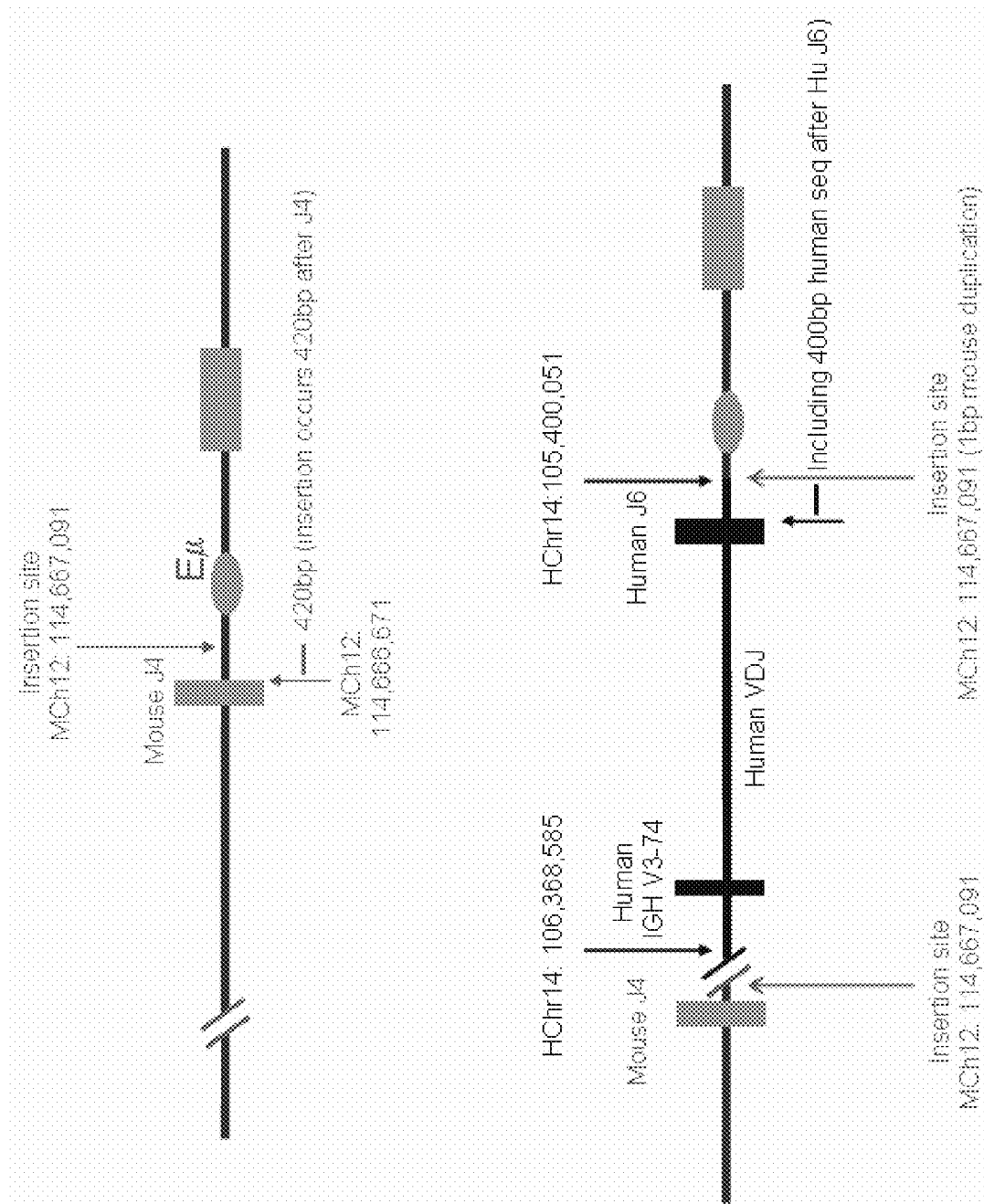
FIG. 21 shows a possible insertion site for the human DNA in a mouse chromosome FIGS. 22-26 disclose an alternative iterative process for insertion of a series of human BACs into a mouse Ig locus

Mouse strains that have the RAG-1 gene mutated are immunodeficient as they have no mature B- or T-lymphocytes (U.S. Pat. No. 5,859,307). T- and B-lymphocytes only differentiate if proper V(D)J recombination occurs. Since RAG-1 is an enzyme that is crucial for this recombination, mice lacking RAG-1 are immunodeficient. If host embryos are genetically RAG-1 homozygous mutant, a chimera produced by injecting such an embryo will not be able to produce antibodies if the animal's lymphoid tissues are derived from the host embryo. However, JM8 cells and AB2.1 cells, for example, generally contribute in excess of 80% of the somatic tissues of the chimeric animal and would therefore usually populate the lymphoid tissue. JM8 cells have wild-type RAG-1 activity and therefore antibodies produced in the chimeric animal would be encoded by the engineered JM8 ES cell genome only. Therefore, the chimeric animal can be challenged with an antigen by immunization and subsequently produce antibodies to that antigen. This allows one skilled in the art to test the performance of the engineered human/mouse IgH and IgK loci as described in the present invention. See FIGS. 19 and 20.

One skilled in the art would use the chimeric animal as described to determine the extent of antibody diversity (see e.g. Harlow, E. & Lane, D. 1998, 5$^{th}$ edition, *Antibodies: A Laboratory Manual*, Cold Spring Harbor Lab. Press, Plainview, N.Y.). For example, the existence in the chimeric animal's serum of certain antibody epitopes could be ascertained by binding to specific anti-idiotype antiserum, for example, in an ELISA assay. One skilled in the art could also sequence the genomes of B-cell clones derived from the chimeric animal and compare said sequence to wild-type sequence to ascertain the level of hypermutation, such hypermutation indicative of normal antibody maturation.

One skilled in the art would also use said chimeric animal to examine antibody function wherein said antibodies are encoded from the engineered Ig loci (see e.g. Harlow, E. & Lane, D. 1998, 5$^{th}$ edition, Antibodies: A Laboratory Manual, Cold Spring Harbor Lab. Press, Plainview, N.Y.). For example, antisera could be tested for binding an antigen, said antigen used to immunize the chimeric animal. Such a measurement could be made by an ELISA assay. Alternatively, one skilled in the art could test for neutralization of the antigen by addition of the antisera collected from the appropriately immunized chimeric animal.

It is well known to those skilled in the art that positive outcomes for any of these tests demonstrate the ability of the engineered Ig loci, the subject of the instant invention, to encode antibodies with human variable regions and mouse constant regions, said antibodies capable of functioning in the manner of wild-type antibodies.

Experimental Techniques:

Recombineering for the production of vectors for use in homologous recombination in ES cells is disclosed in, for example, WO9929837 and WO0104288, and the techniques are well known in the art. In one aspect the recombineering of the human DNA takes place using BACs as a source of said human DNA. Human BAC DNA will be isolated using QIAGEN®, BAC purification kit. The backbone of each human BAC will be modified using recombineering to the exact same or similar configuration as the BAC already inserted into the mouse IgH region. The genomic insert of each human BAC will be trimmed using recombineering so that once the BACs are inserted, a seamless contiguous part of the human V(D)J genomic region will form at the mouse IgH or IgK locus. BAC DNA transfection by electroporation and genotyping will be performed accordingly to standard protocols (Prosser, R M., Rzadzinska, A. K., Steel, K. P., and Bradley, A. (2008). "Mosaic complementation demonstrates a regulatory role for myosin VIIa in actin dynamics of stereocilia." Molecular and Cellular Biology 28, 1702-1712; Ramirez-Solis, R., Davis, A. C., and Bradley, A. (1993). "Gene targeting in embryonic stem cells." Methods in Enzymology 225, 855-878.). Recombineering will be performed using the procedures and reagents developed by Pentao Liu and Don Court's laboratories (Chan, W., Costantino, N., Li, R., Lee, S. C., Su, Q., Melvin, D., Court, D. L., and Liu, P. (2007). "A recombineering based approach for high-throughput conditional knockout targeting vector construction." Nucleic Acids Research 35, e64).

These and other techniques for gene targeting and recombination of BAC-derived chromosomal fragments into a non-human mammal genome, such as a mouse are well-known in the art and are disclosed in, for example, in World Wide Web (www) eucomm.org/information/targeting and World Wide Web (www) eucomm.org/information/publications.

Cell culture of C57BL/6N-derived cell lines, such as the JM8 male ES cells will follow standard techniques. The JM8 ES cells have been shown to be competent in extensively contributing to somatic tissues and to the germline, and are being used for large mouse mutagenesis programs at the Sanger Institute such as EUCOMM and KOMP (Pettitt, S. J., Liang, Q., Rairdan, X. Y., Moran, J. L., Prosser, H. M., Beier, D. R., Lloyd, K. C., Bradley, A., and Skarnes, W. C. (2009). "Agouti C57BL/6N embryonic stem cells for mouse genetic resources." Nature Methods.). JM8 ES cells ($1.0 \times 10^7$) will be electroporated (500 µF, 230V; Bio-Rad®) with 10 µg I-SceI linearized human BAC DNA. The transfectants will be selected with either Puromycin (3 µg/ml) or G418 (150 µg/ml). The selection will begin either 24 hours (with G418) or 48 hours (with Puromycin) post electroporation and proceed for 5 days. 10 µg linearized human BAC DNA can yield up to 500 Puromycin or G418 resistant ES cell colonies. The antibiotic resistant ES cell colonies will be picked into 96-well cell culture plates for genotyping to identify the targeted clones.

Once targeted mouse ES cell clones are identified, they will be analyzed by array Comparative Genomic Hybridization (CGH) for total genome integrity (Chung, Y. J., Jonkers, J., Kitson, H., Fiegler, H., Humphray, S., Scott, C., Hunt, S., Yu, Y., Nishijima, I., Velds, A., et al. (2004). "A whole-genome mouse BAC microarray with 1-Mb resolution for analysis of DNA copy number changes by array comparative genomic hybridization." Genome research 14, 188-196. and Liang, Q., Conte, N., Skarnes, W. C., and Bradley, A. (2008). "Extensive genomic copy number variation in embryonic stem cells." Proceedings of the National Academy of Sciences of the United States of America 105, 17453-17456.). ES cells that have abnormal genomes do not contribute to the germline of the chimeric mice efficiently. BAC integrity will be examined by PCR-amplifying each known functional V gene in the BAC. For example, in one approach the first human BAC chosen for the IgH locus has 6 functional V genes. To confirm the integrity of this BAC for the presence of these 6 IGH V genes, at least 14 pairs of PCR primers will be designed and used to PCR-amplify genomic DNA from the targeted ES cells. The human wild-type size and sequence of these fragments will ensure that the inserted BAC has not been rearranged.

More detailed CGH will also confirm the integrity of the inserted BACs. For example, one skilled in the art could use an oligo aCGH platform, which is developed by Agilent Technologies, Inc. This platform not only enables one to study genome-wide DNA copy number variation at high resolution (Barrett, M. T., Scheffer, A., Ben-Dor, A., Sampas, N., Lipson, D., Kincaid, R., Tsang, P., Curry, B., Baird, K., Meltzer, P. S., et al. (2004). "Comparative genomic hybridization using oligonucleotide microarrays and total genomic DNA." Proceedings of the National Academy of Sciences of the United States of America 101, 17765-17770.), but permit examination of a specific genome region using custom designed arrays. Comparing the traditional aCGH techniques which rely on cDNA probes or whole BAC probes, the 60-mer oligonucleotides probes can ensure specific hybridization and high sensitivity and precision that is needed in order to detect the engineered chromosome alterations that were made. For example, oligos designed to hybridize at regular intervals along the entire length of the inserted BAC would detect even quite short deletions, insertions or other rearrangements. Also, this platform provides the greatest flexibility for customized microarray designs. The targeted ES cell genomic DNA and normal human individual genomic DNA will be labelled separately with dyes and hybridized to the array. Arrays slides will be scanned using an Aglient Technologies DNA microarray scanner. Reciprocal fluorescence intensities of dye Cy5 and dye Cy3 on each array image and the log 2 ratio values will be extracted by using Bluefuse software (Bluegnome). Spots with inconsistent fluorescence patterns ("confidence"<0.29 or "quality"=0) will be excluded before normalizing all log 2 ratio values. Within an experiment, Log 2 ratio between −0.29 and +0.29 for the signal from any oligo probe are regarded as no copy number change. The log 2 ratio threshold for "Duplication" is usually >0.29999, and for deletion is <0.29999.

Once the first human BAC is inserted into the mouse IgH locus and confirmed to be in its intact, native configuration, the FRT-flanked BAC backbone will be excised by using Flp site-specific recombinase. If regular Flp-catalyzed FRT recombination is not high enough, one can use Flo, an improved version of Flpo recombinase which in certain tests is 3-4 times more efficient than the original Flp in ES cells. After the BAC backbone is excised, ES cells will become sensitive to Puromycin (or G418) and resistant to FIAU (for loss of the TK cassette). The excision events will be further characterized by PCR amplification of the junction fragment using human genomic DNA primers. These FRT-flanked BAC backbone-free ES cells will be used for the next round of human BAC insertion and for blastocyst injection.

Targeting of the genome of an ES cell to produce a transgenic mouse may be carried out using a protocol as explained by reference to the attached FIGS. 1-18.

FIG. 1 illustrates three basic backbone vectors; an initiating cassette and 2 large insert vectors 1 and 2 respectively. The initiating cassette comprises sequences homologous to the desired site of insertion into the mouse genome, those sites flanking a selectable marker and stuffer primer sequence for PCR based genotyping to confirm correct insertion of BACs. The Stuffer-primer sequence provides the basis for genotyping each BAC addition step. This sequence is considered to provide a robust well validated sequence template for PCR primer and may be located at the ISceI site, ideally ~1 kb from the BAC insert.

The large insert vectors comprise human DNA on plasmids with selectable markers and a unique restriction site for linearisation of the plasmid to aid in homologous recombination into the genome of the ES cell.

Figure 2:
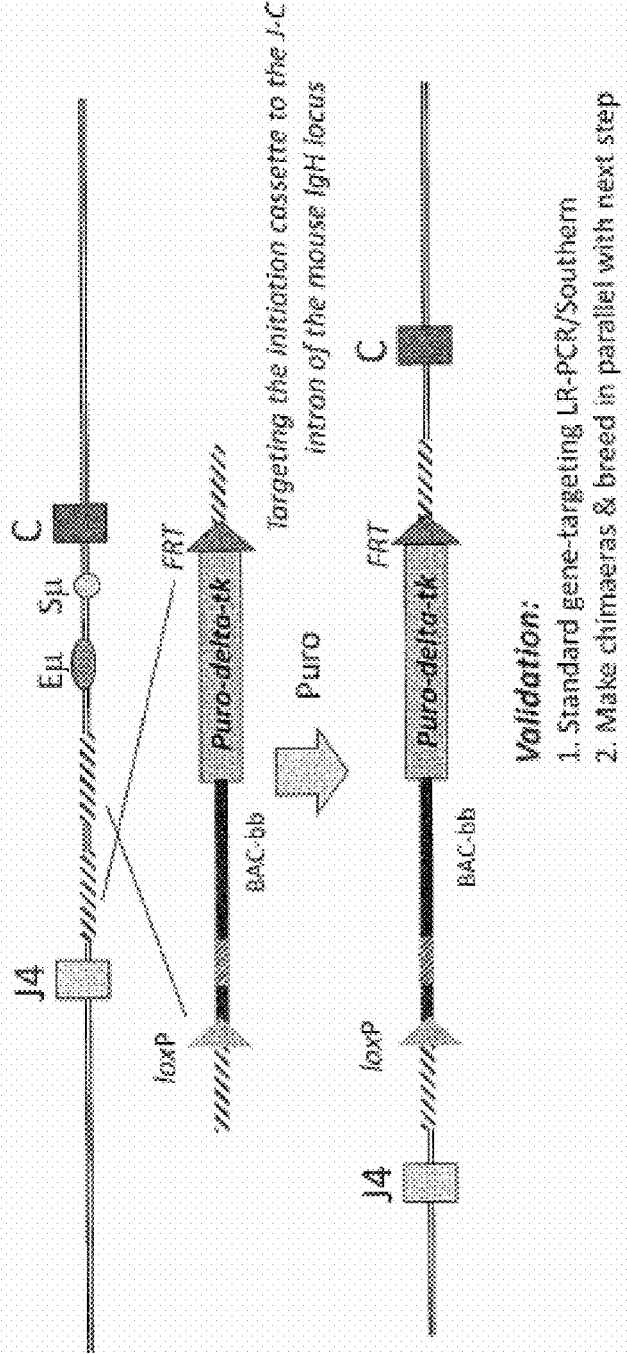

FIG. 2 illustrates insertion of an initiating cassette into the mouse genome by Homologous recombination between the mouse J4 and C alpha exons. Puromycin selection allows identification of ES cells with insertion of the cassette. pu(Delta)tk is a bifunctional fusion protein between puromycin N-acetyltransferase (Puro) and a truncated version of herpes simplex virus type 1 thymidine kinase (DeltaTk). Murine embryonic stem (ES) cells transfected with pu(Delta)tk become resistant to puromycin and sensitive to 1-(−2-deoxy-2-fluoro-1-beta-D-arabino-furanosyl)-5-iodouracil (FIAU). Unlike other HSV1 tk transgenes, puDeltatk is readily transmitted through the male germ line. Thus pu(Delta)tk is a convenient positive/negative selectable marker that can be widely used in many ES cell applications.

Figure 3:
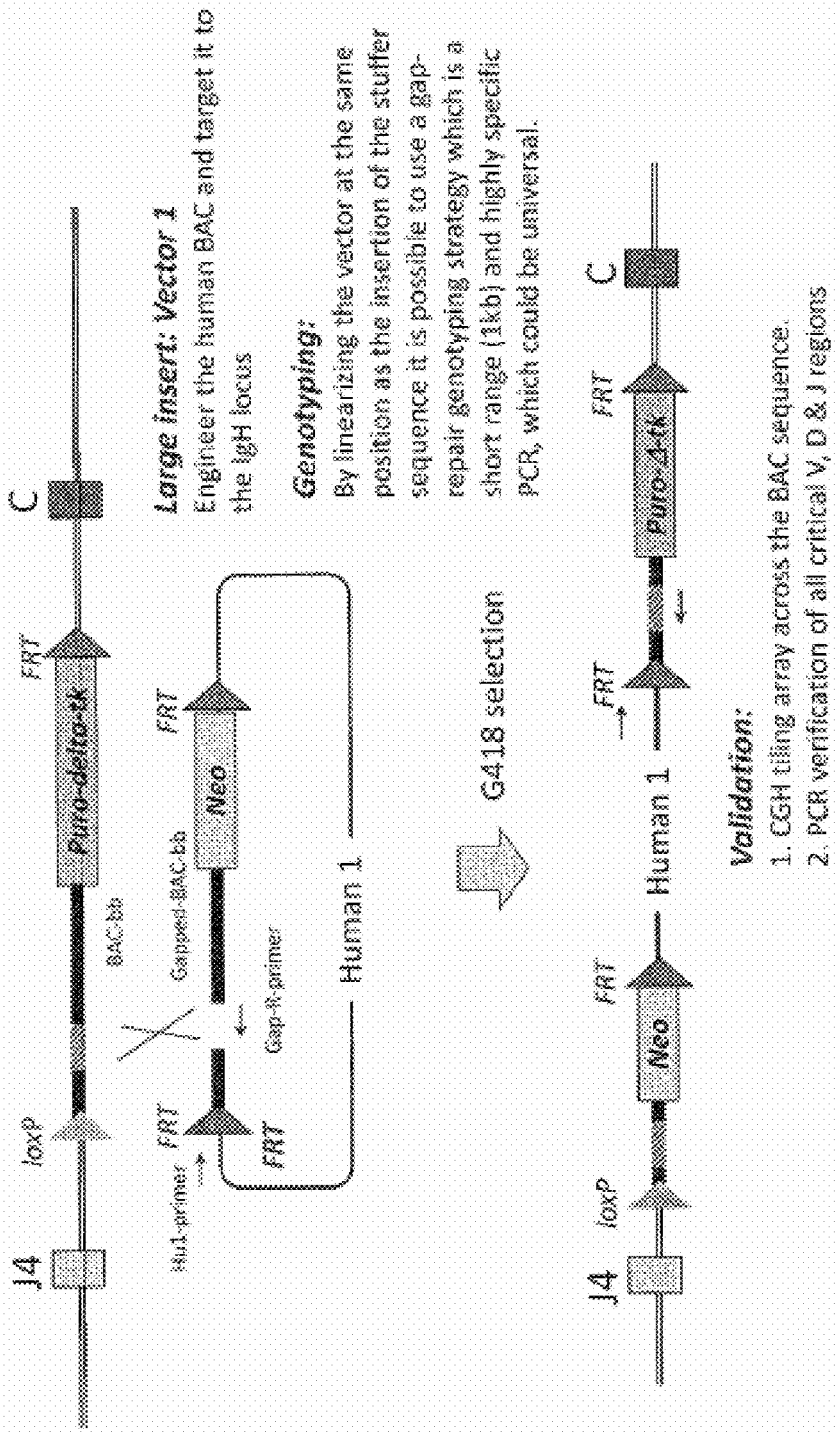

FIG. 3 illustrates targeting of the large insert vector 1 to the mouse ES cell genome. Linearisation of the vector is made at the same position as the stuffer primer sequence which allows for a gap repair genotyping strategy, well known in the art—see Zheng et al NAR 1999, Vol 27, 11, 2354-2360. In essence, random insertion of the targeting vector into the genome will not 'repair' the gap whereas a homologous recombination event will repair the gap. Juxtaposition of appropriate PCR primer sequences allows colonies to be screened individually for a positive PCR fragment indicating proper insertion. Positive selection using G418 allows for identification of mouse ES cells containing the neo selection marker. PCR verification can be made of all critical V, D and J regions. Array comparative genomic hybridization can be used to validate the BAC structure.

Figure 4:
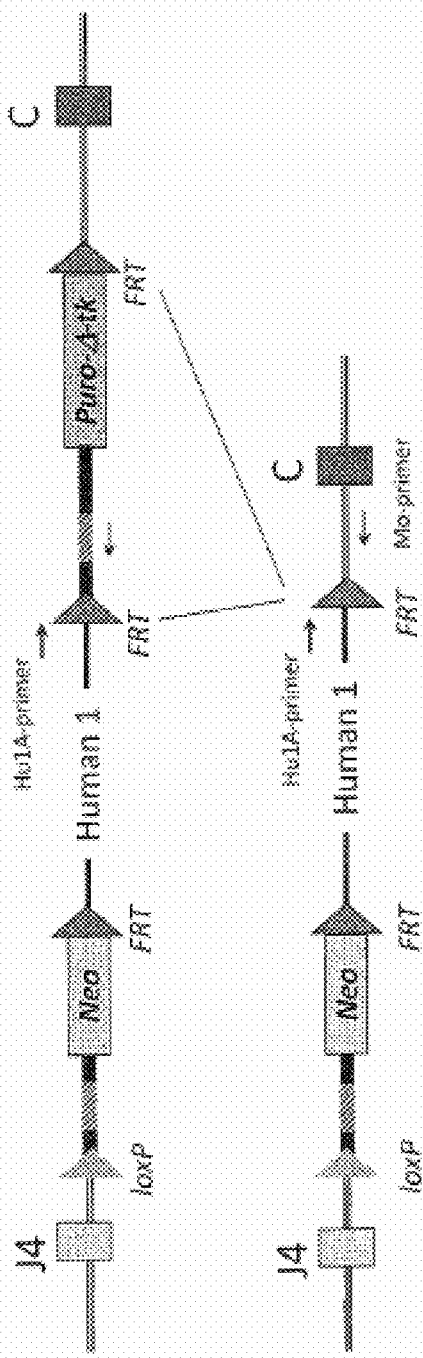

FIG. 4 illustrates the puro-delta-tk cassette and the BAC plasmid backbone is deleted using Flpe and select in FIAU.

Since Flpe works inefficiently in mouse ES cells (5% deletion with transient Flpe expression), it is expected that in most cases, the recombination occurs between the two FRT sites flanking the BAC backbone. Flpo can also be tested to find out the recombination efficiency between two FRT sites that are 10 kb away.

Given that the FRT deletion step is selectable it is possible to pool FIAU resistant clones and proceed immediately to the next step in parallel with clonal analysis. Alternatively it may be desirable to show by short range PCR that the human sequences are now adjacent to those of the mouse as shown (Hu-primer 1 and Mo-primer)

At this stage a 200 kb human locus will have been inserted.

Figure 5:
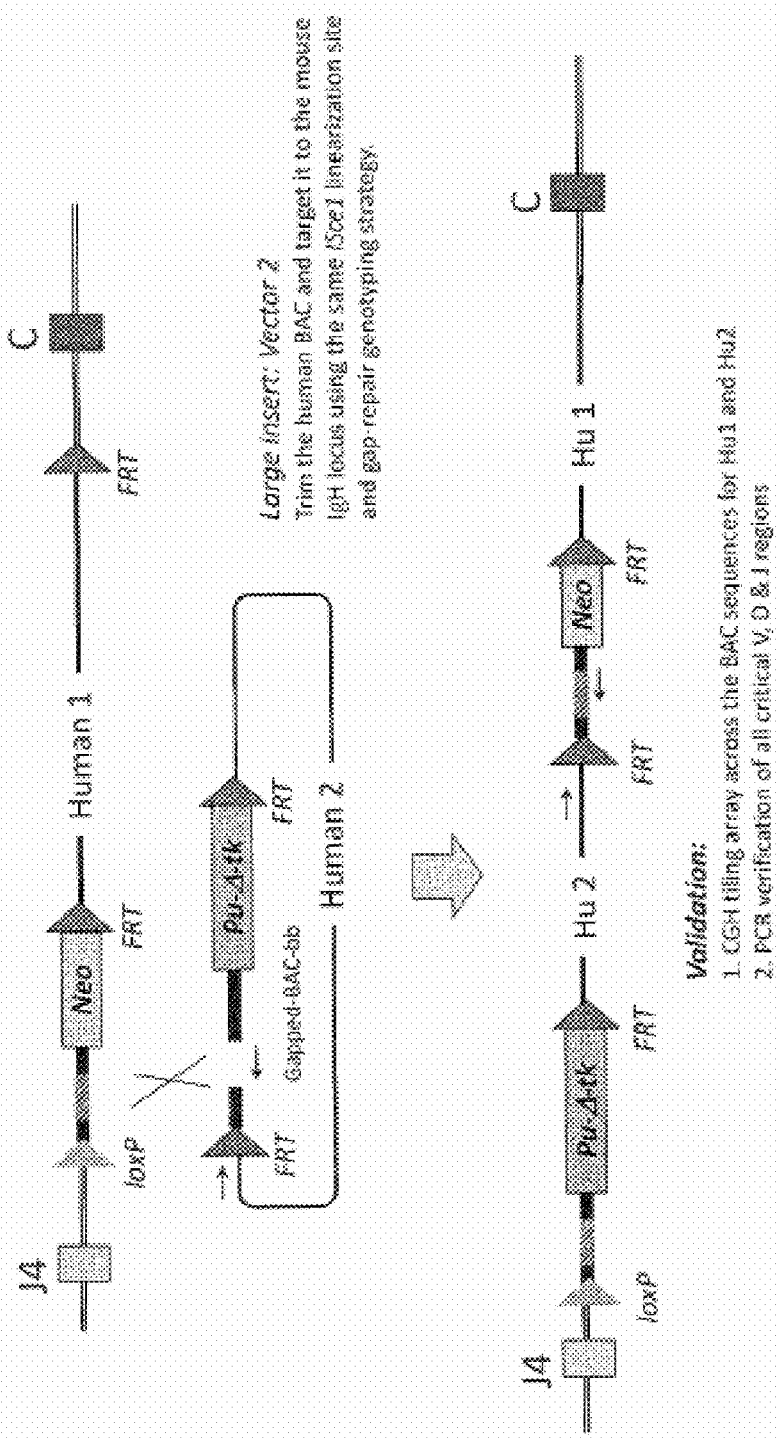

FIG. 5 illustrates a second large insert vector is targeted into the ES cell chromosome. The human BAC is targeted to the mouse IgH locus using the same initiation cassette insertion followed by IScel BAC linearization, BAC targeting to the initiation cassette and gap-repair genotyping strategy. Verification of the BAC insertion is carried out as before.

Figure 6:
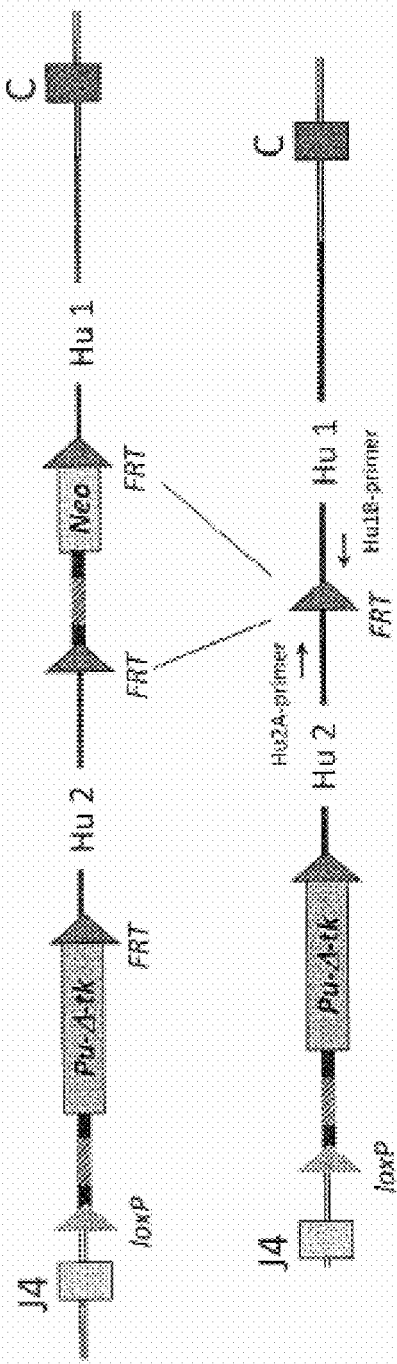

FIG. 6 illustrates the FRTY flanked BAC backbone of large insert vector 2 and the neo marker are deleted via Flpo. Note that this is not selectable, thus it will be necessary for clonal analysis at this point. This will enable confirmation of the juxtaposition of the human 2 insert with human 1 and other validation efforts.

At this stage a ~200 kb human locus will have been inserted.

Figure 7:
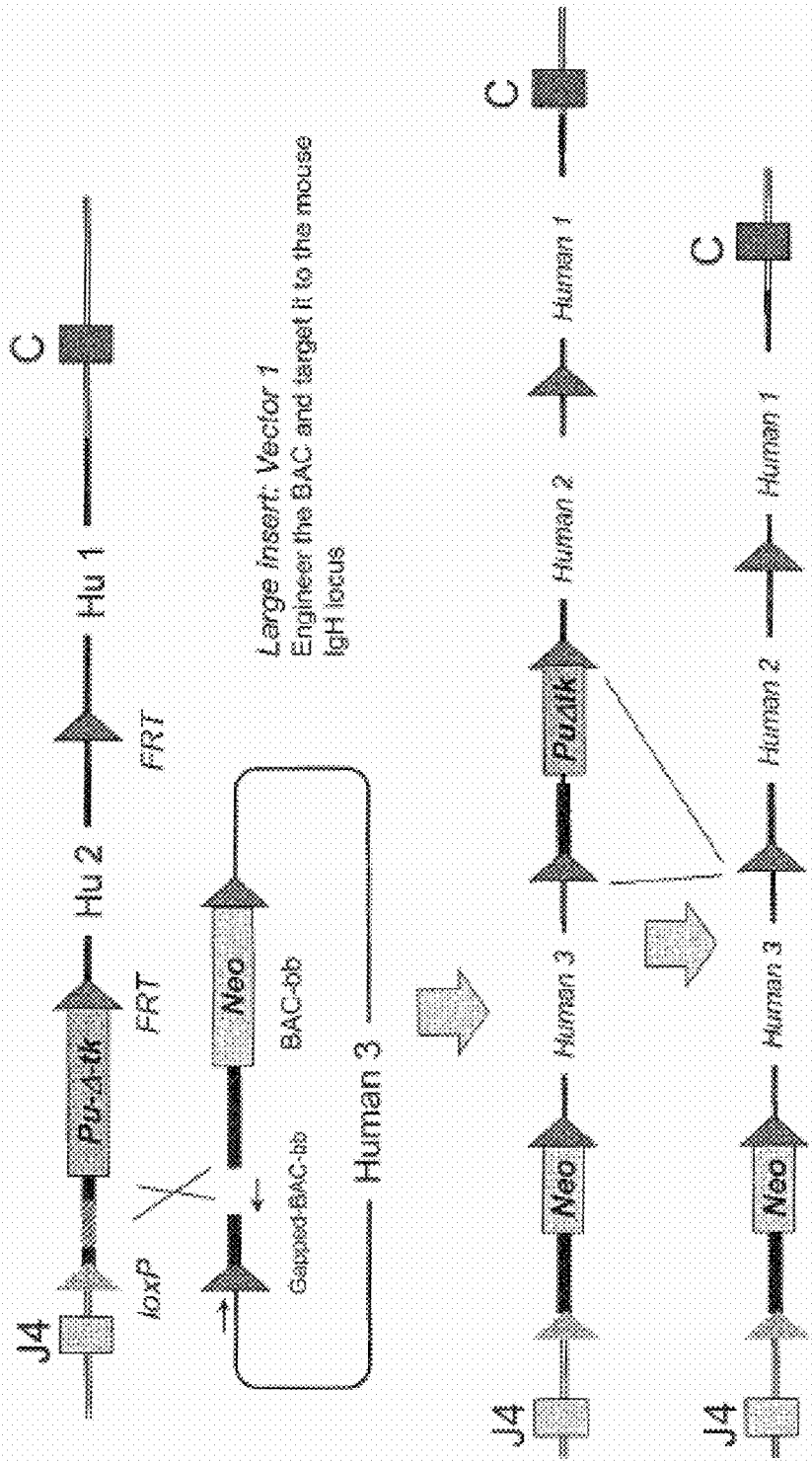

FIG. 7 illustrates the next large insert vector targeted to the mouse IgH locus. The pu-delta TK cassette is then removed, as for FIG. 4. The process can be repeated to incorporate other BACs.

Figure 8:
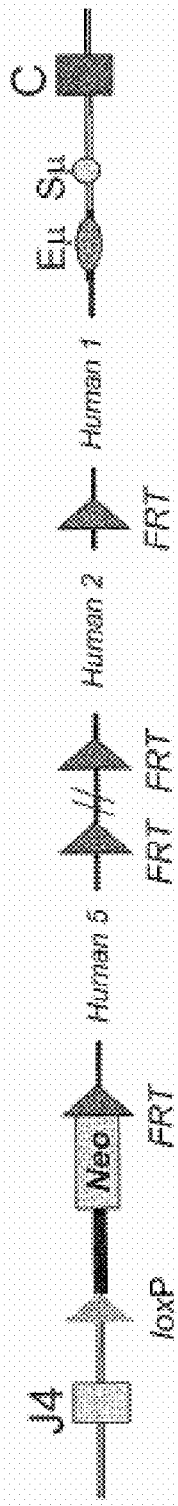
Figure 9:
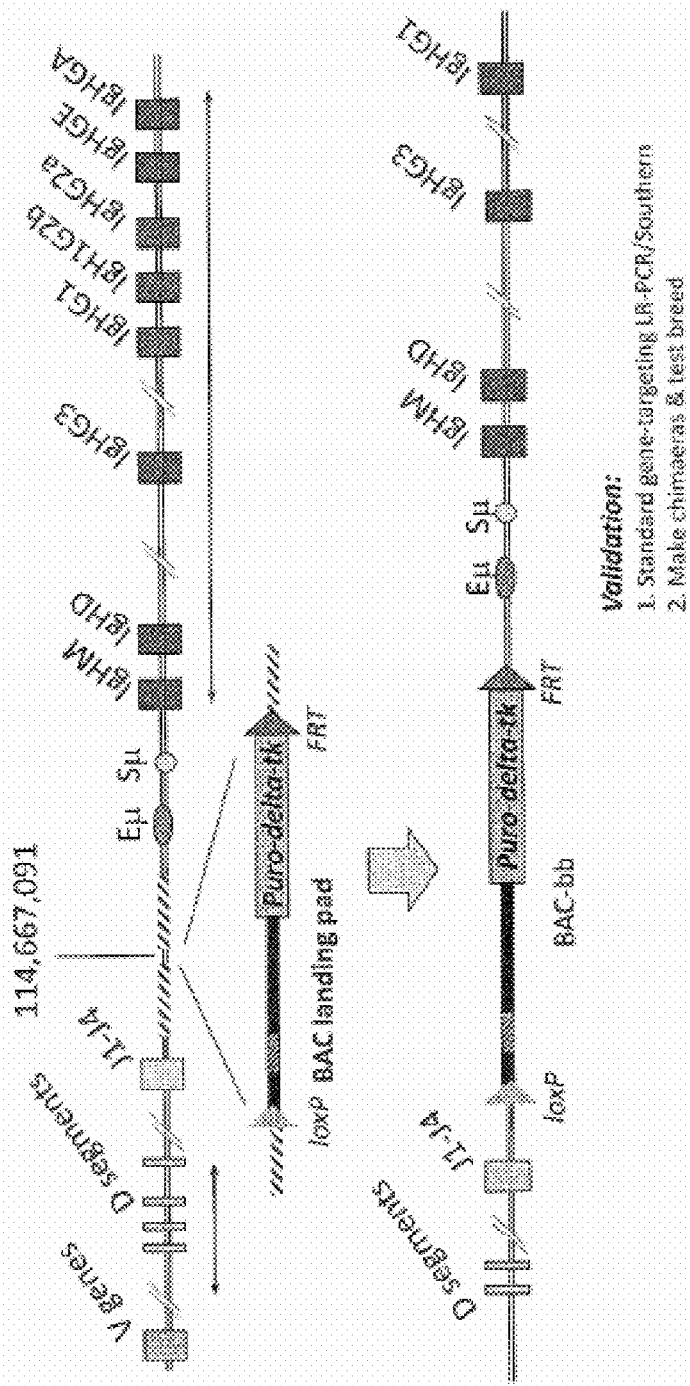
FIGS. 9-18 show in more detail the process of FIGS. 1-8 for the IgH and kappa locus
Figure 10:
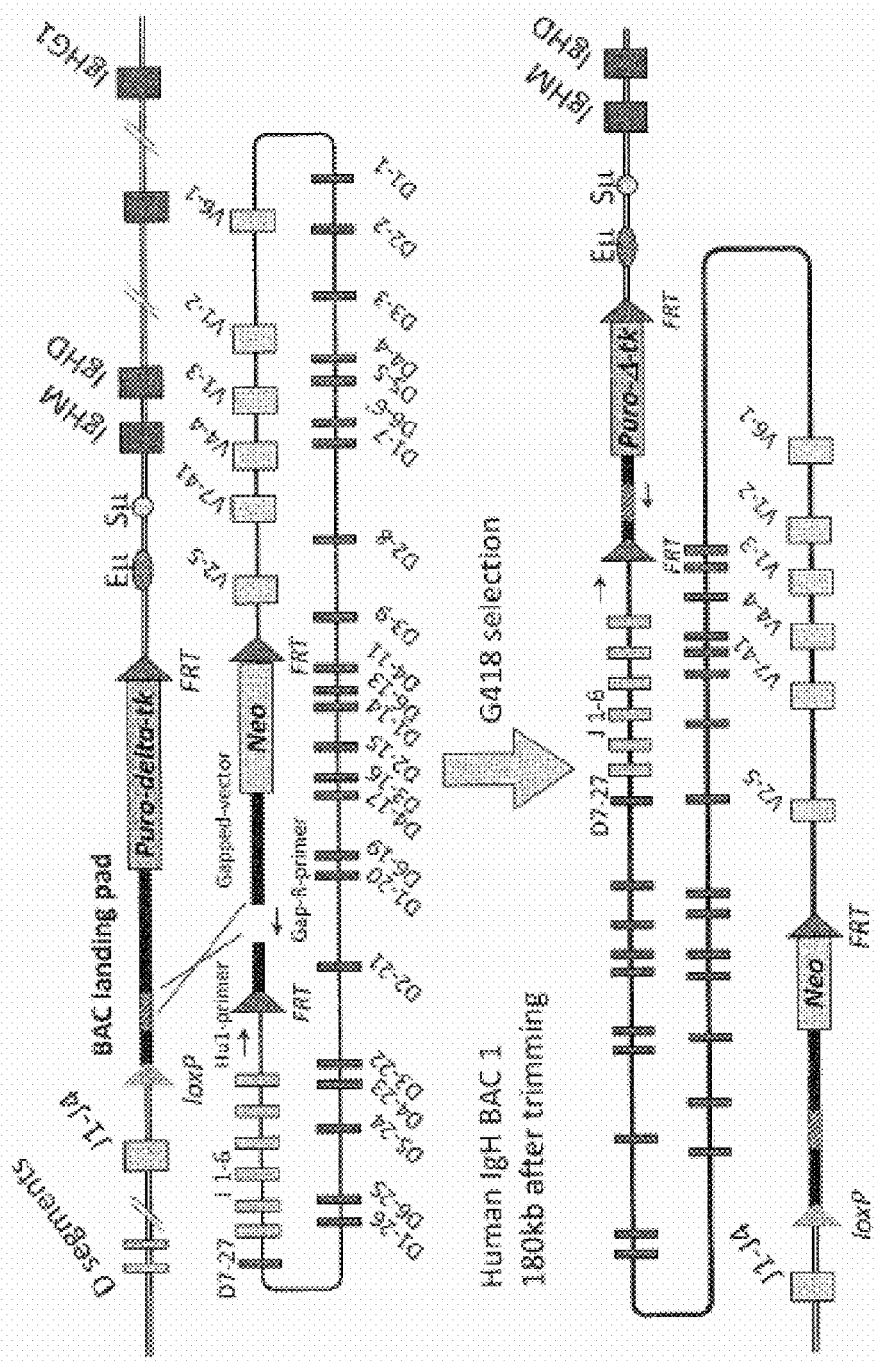
Figure 11:
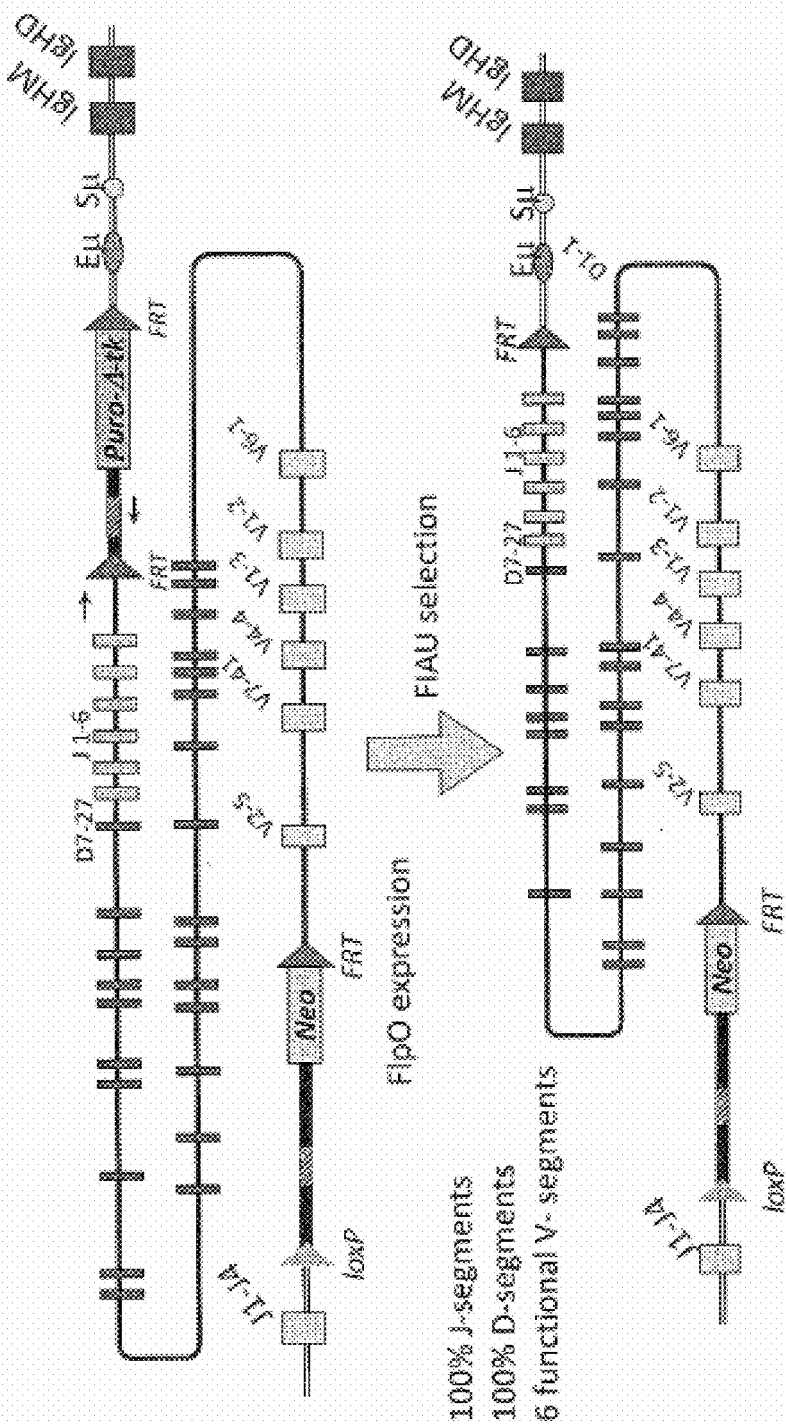
Figure 12:
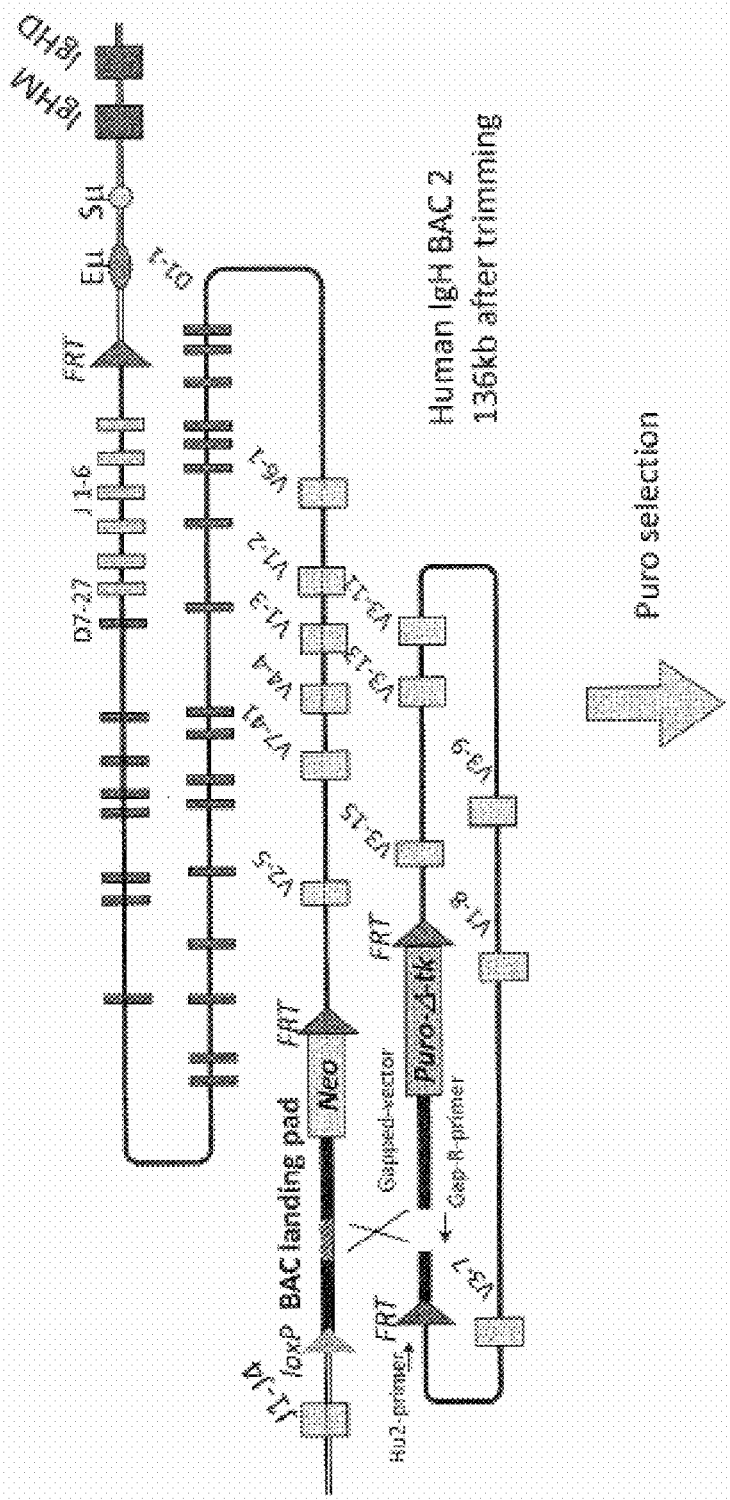
Figure 13:
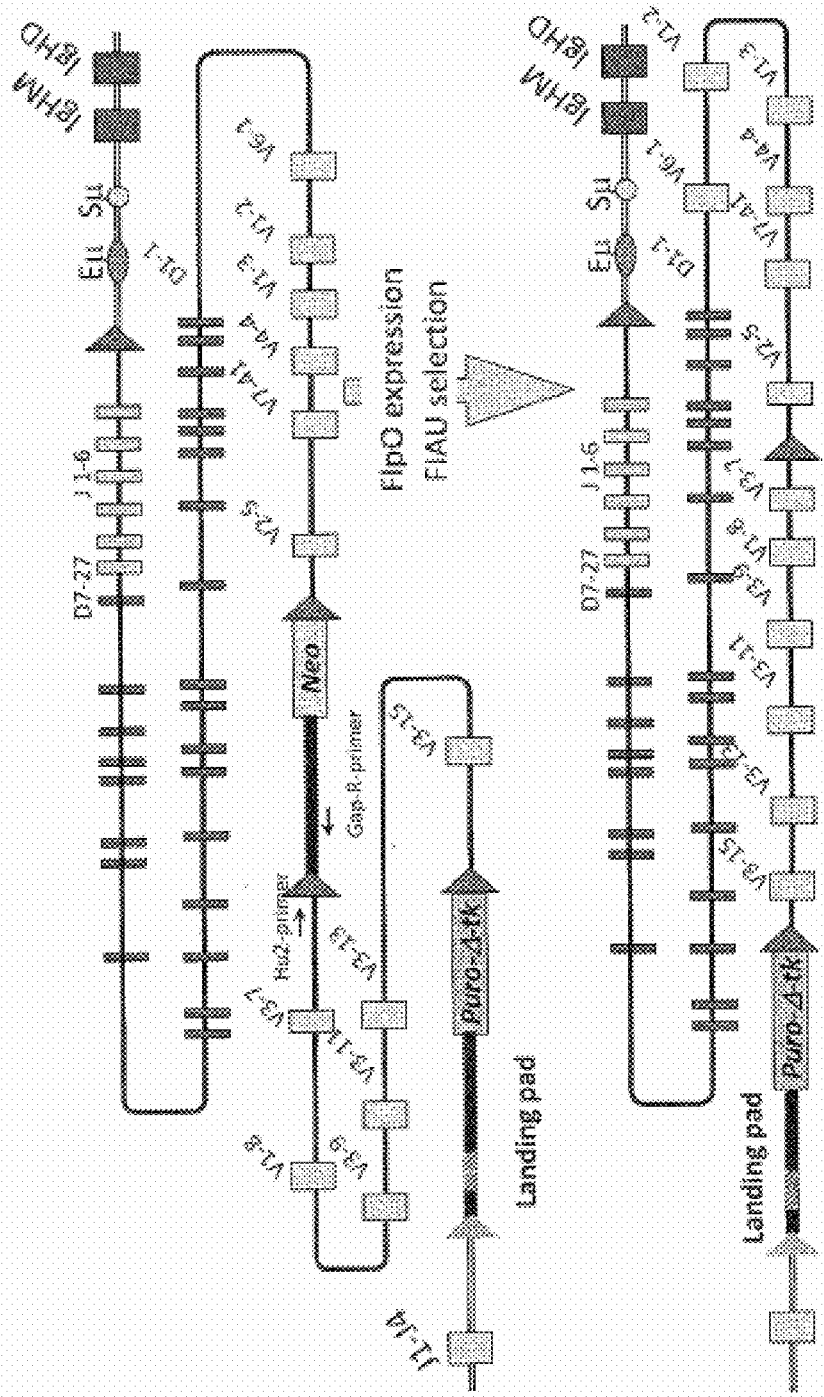
Figure 14:
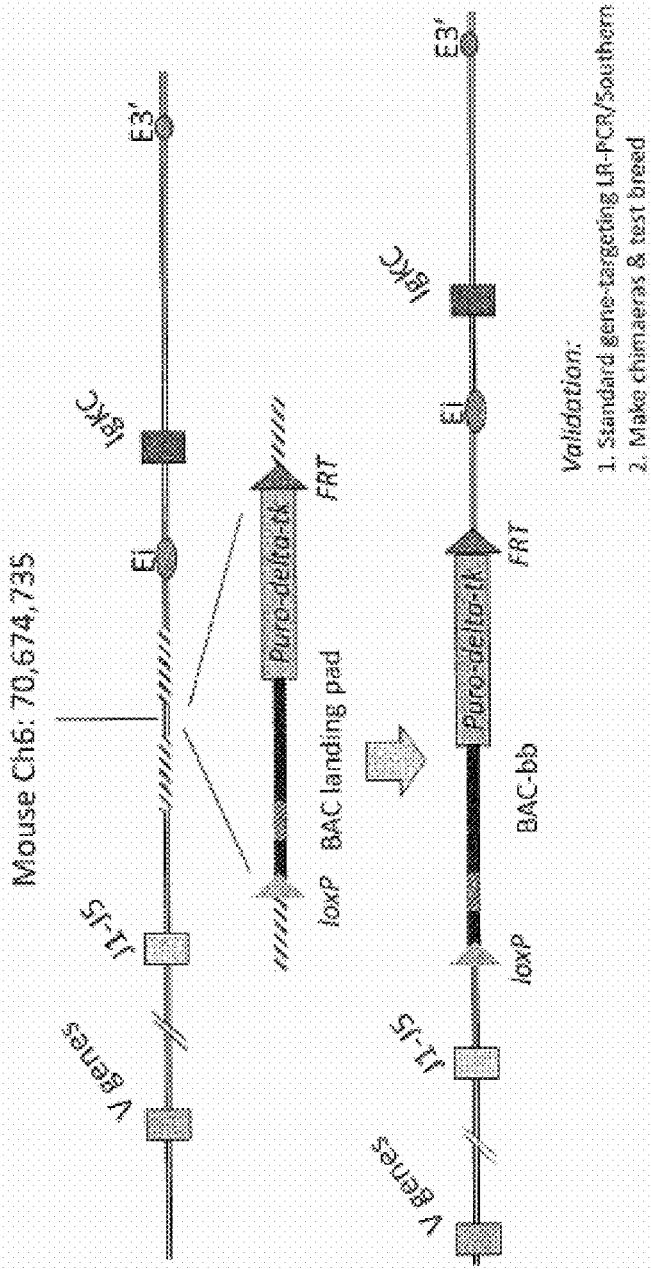
Figure 15:
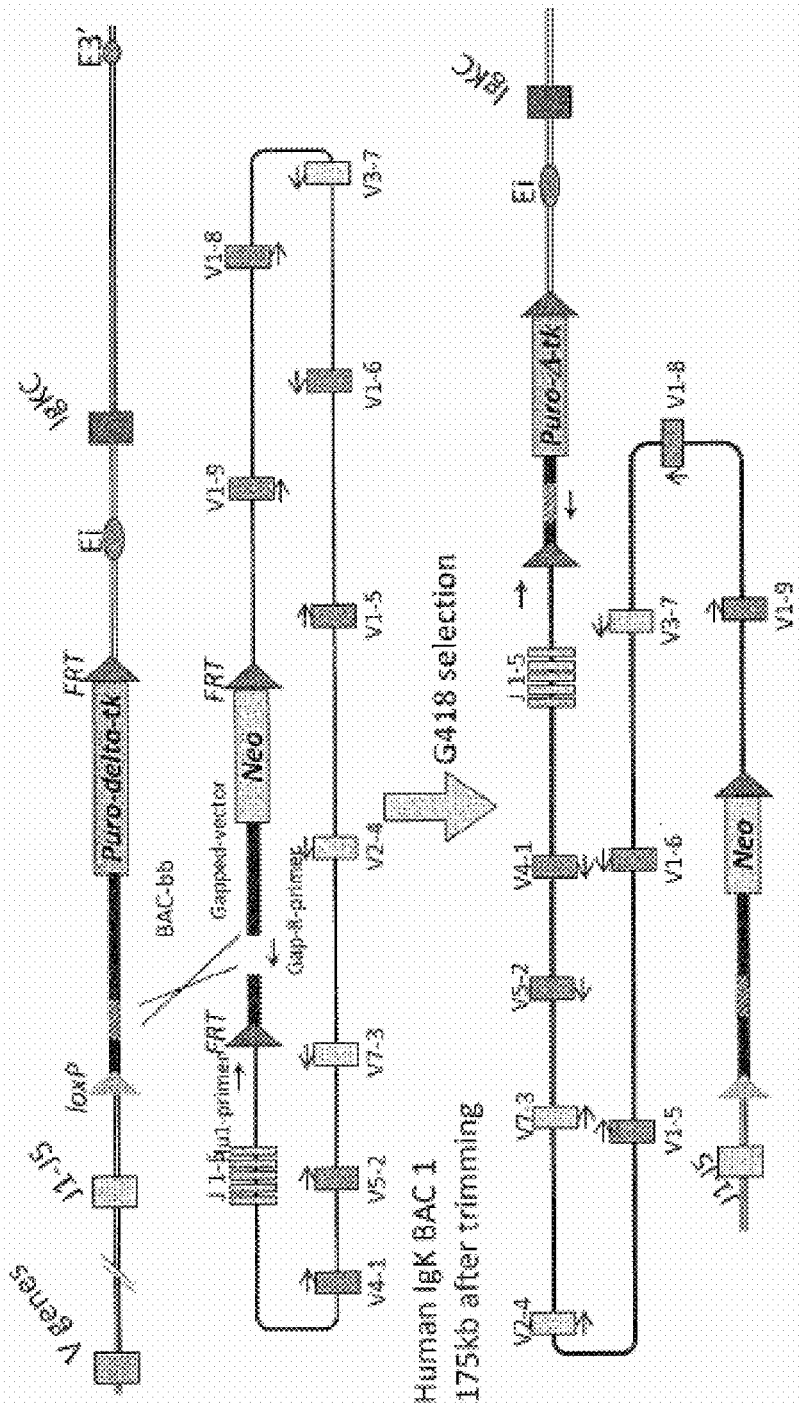
Figure 16:
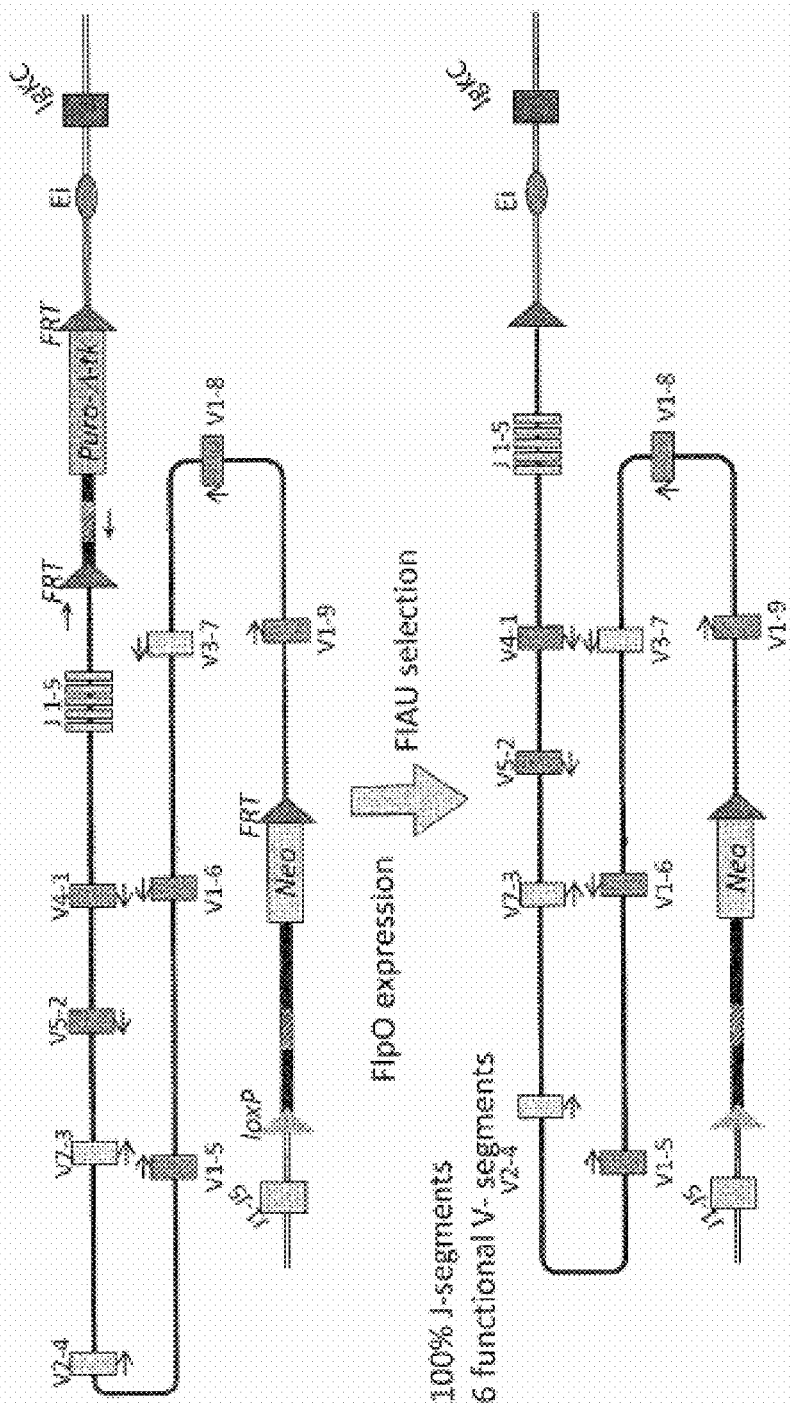
Figure 17:
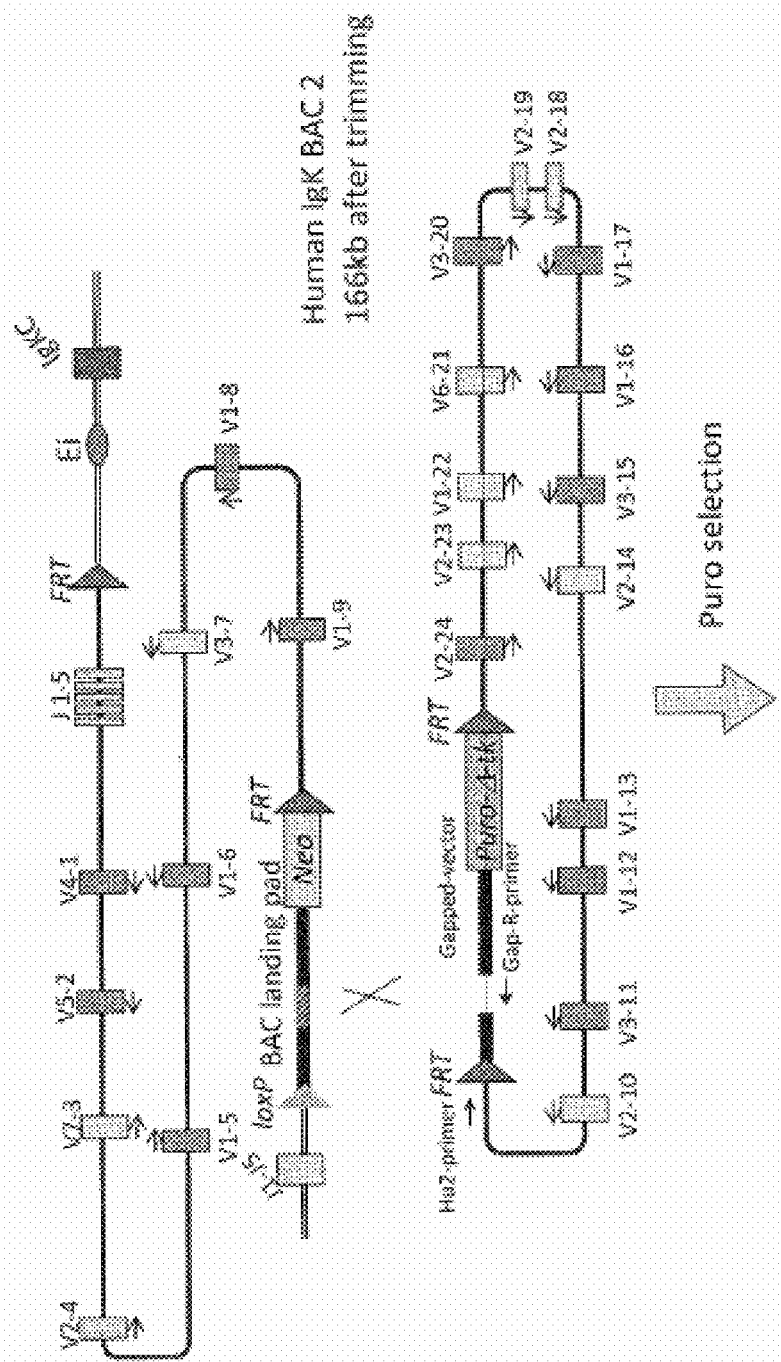
Figure 18:
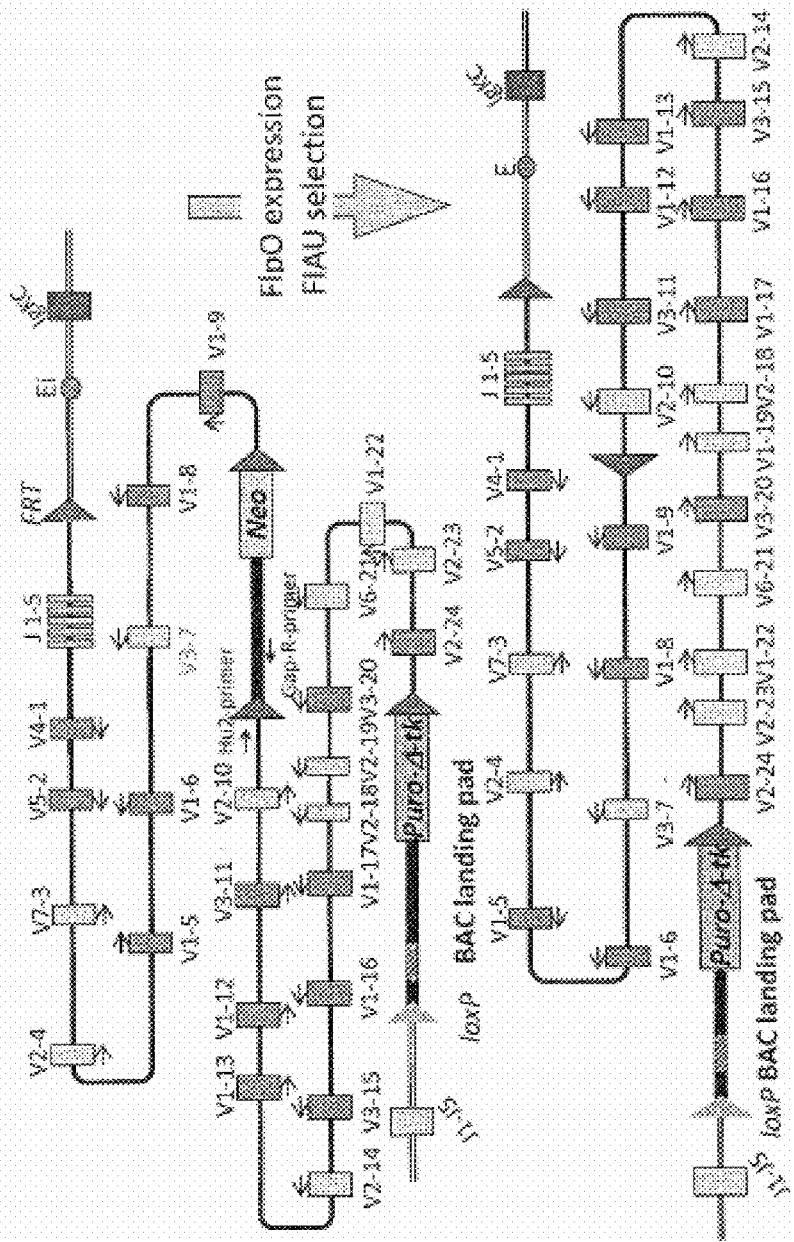

FIG. 8 illustrates the final predicted ES cell construct.

FIGS. 9-18 provide a further level of detail of this process.

Example 2

Site-Specific Recombination

In a further method of the invention site specific recombination can also be employed. Site-specific recombination (SSR) has been widely used in the last 20-years for the integration of transgenes into defined chromosomal loci. SSR involves recombination between homologous DNA sequences.

The first generation of SSR-based chromosomal targeting involved recombination between (i) a single recombination target site (RT) such as loxP or FRT in a transfected plasmid with (ii) a chromosomal RT site provided by a previous integration. A major problem with this approach is that insertion events are rare since excision is always more efficient than insertion. A second generation of SSR called RMCE (recombinase-mediated cassette exchange) was introduced by Schlake and Bode in 1994 (Schlake, T.; J. Bode (1994). "Use of mutated FLP-recognition-target-(FRT-) sites for the exchange of expression cassettes at defined chromosomal loci". Biochemistry 33: 12746-12751). Their method is based on using two heterospecific and incompatible RTs in the transfected plasmid which can recombine with compatible RT sites on the chromosome resulting in the swap of one piece of DNA for another—or a cassette exchange. This approach has been successfully exploited in a variety of efficient chromosomal targeting, including integration of BAC inserts of greater than 50 kb (Wallace, H. A. C. et al. (2007). "Manipulating the mouse genome to engineering precise functional syntenic replacements with human sequence". Cell 128: 197-209; Prosser, H. M. et al. (2008). "Mosaic complementation demonstrates a regulatory role for myosin Vila in actin dynamics of Stereocilia". Mol. Cell. Biol. 28: 1702-12).

The largest insert size of a BAC is about 300-kb and therefore this places an upper limit on cassette size for RMCE.

In the present invention a new SSR-based technique called sequential RMCE (SRMCE) was used, which allows continuous insertion of BAC inserts into the same locus.

The method comprises the steps of 1 insertion of DNA forming an initiation cassette (also called a landing pad herein) into the genome of a cell;

2 insertion of a first DNA fragment into the insertion site, the first DNA fragment comprising a first portion of a human DNA and a first vector portion containing a first selectable marker or generating a selectable marker upon insertion;

3 removal of part of the vector DNA;

4 insertion of a second DNA fragment into the vector portion of the first DNA fragment, the second DNA fragment containing a second portion of human DNA and a second vector portion, the second vector portion containing a second selectable marker, or generating a second selectable marker upon insertion;

5 removal of any vector DNA to allow the first and second human DNA fragments to form a contiguous sequence; and 6 iteration of the steps of insertion of a part of the human V(D)J DNA and vector DNA removal, as necessary, to produce a cell with all or part of the human VDJ or VJ region sufficient to be capable of generating a chimaeric antibody in conjunction with a host constant region, wherein the insertion of at least one DNA fragment uses site specific recombination.

Figure 22:
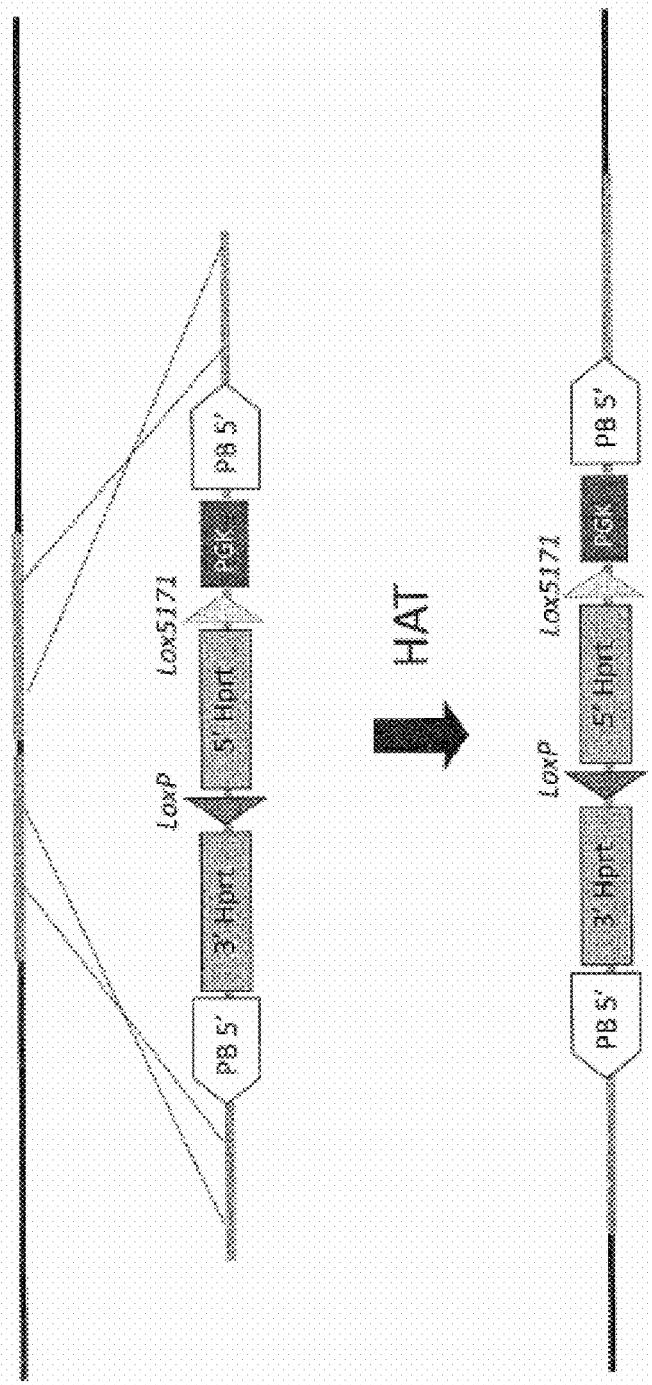

In one specific aspect the approach utilizes three heterospecific and incompatible loxP sites. The method is comprised of the steps as follows, and illustrated in FIGS. 22-26:

1. Targeting a landing pad into the defined locus. An entry vector containing an HPRT mini-gene flanked by inverted piggyBac (PB) ITRs is targeted into defined region (for example: a region between IGHJ and Eμ or IGKJ and Eκ or IGLC1 and Eλ3-1) to serve as a landing pad for BAC targeting. The HPRT mini-gene is comprised of two synthetic exons and associated intron. The 5' HPRT exon is flanked by two heterospecific and incompatible loxP sites (one wild-type and the other a mutated site, lox5171) in inverted orientation to each other (FIG. 22). These two loxP sites provide recombination sites for the BAC insertion through RMCE.

Figure 23:
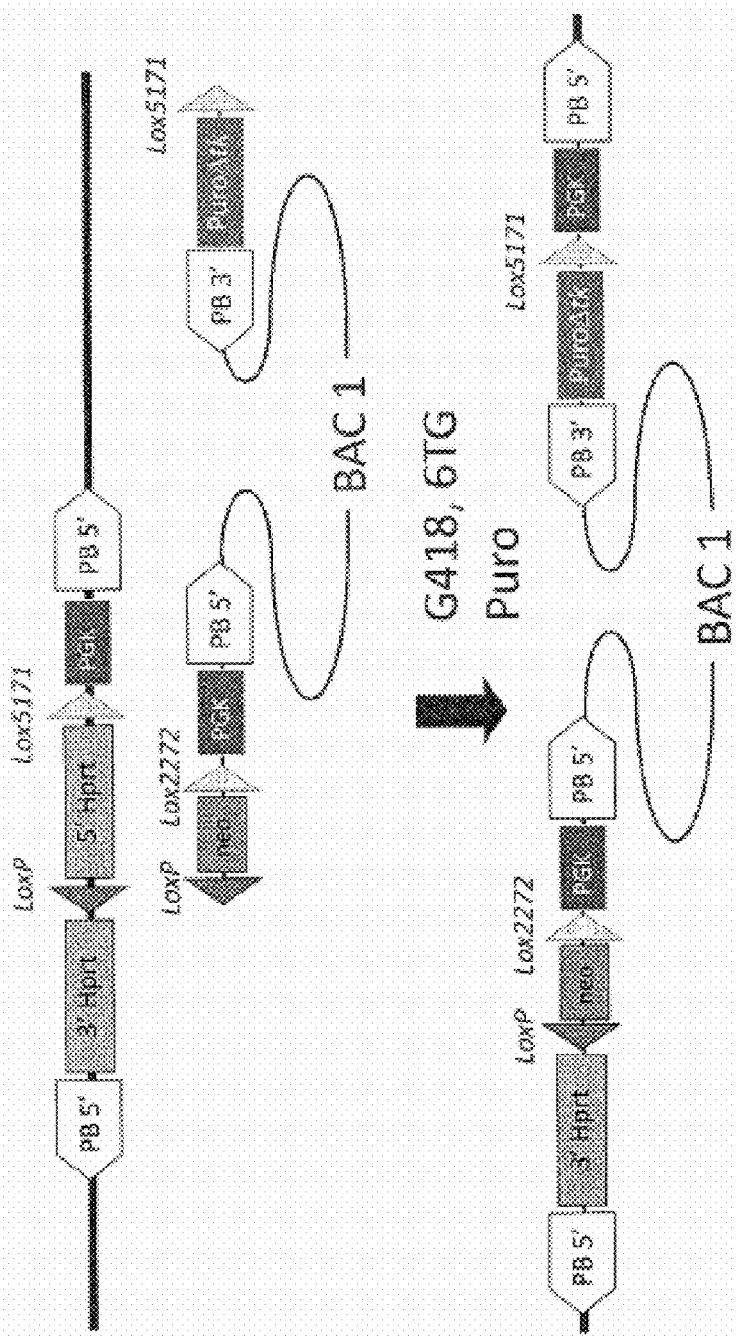

2. Insertion of the 1$^{st}$ modified BAC into the targeted landing pad. The 1$^{st}$ BAC has a length of DNA to be inserted into the genome flanked by engineered modifications. The 5' modification (loxP-neo gene-lox2272-PGK promoter-PB 5'LTR) and 3' modification (PB3'LTR-puroΔTK gene-lox5171) is depicted in FIG. 23 along with the relative orientations of the lox sites and PB LTRs. With transient CRE expression from a co-electroporated vector, the DNA sequence would be inserted into the defined locus through RMCE. The cells in which a correct insertion has occurred can be selected as follows: (i) Puromycin-resistance (the puroΔTK gene has acquired a promoter—"PGK"—from the landing pad), (ii) 6TG-resistance (the HPRT mini-gene has been disrupted), and (iii) G418-resistance (selects for any insertion via the 5' region PGK-neo arrangement). Any combination of these selection regimes can be used. G418- and 6TG-resistance select for correct events on the 5' end while puro-resistance selects for correct events on the 3' end.
3. Curing (removing) the 3' modification of the $1^{st}$ insertion. A properly inserted $1^{st}$ BAC results the 3' end having a puroΔTK gene flanked by inverted PB LTRs (FIG. 24)—essentially a proper transposon structure. This transposon can then be removed by the transient expression of the piggyBac transposase (from an electroporated vector). Cells with the correct excision event can be selected by FIAU resistance—ie, no thymidine kinase activity from the puroΔTK gene. This completely removes the 3' modification leaving no trace nucleotides.
4. Insertion of a $2^{nd}$ modified BAC into the 5' end of $1^{st}$ insertion. The $2^{nd}$ BAC has a length of DNA to be inserted into the genome (usually intended to be contiguous with the DNA inserted with the $1^{st}$ BAC) flanked by engineered modifications. The 5' modification (loxP-HPRT mini gene 5' portion-lox5171-PGK promoter-PB5'LTR) and 3' modification (PB3'LTR-puroΔTK-lox2272) is depicted in FIG. 25 along with the relative orientations of the lox sites and PB LTRs. With transient CRE expression from a co-electroporated vector, the DNA sequence would be inserted into the defined locus through RMCE. The cells in which a correct insertion has occurred can be selected as follows: (i) HAT-resistance (the HPRT mini-gene is reconstituted by a correct insertion event, ie: the 5' and 3' exon structures are brought together), and (ii) puromycin-resistance (puroΔTK gene has acquired a promoter—"PGK"—from the landing pad).
5. Curing (removing) the 3' modification of the $2^{nd}$ insertion. A properly inserted $2^{nd}$ BAC results the 3' end having a puroΔTK gene flanked by inverted PB LTRs (FIG. 26)—essentially a proper transposon structure, exactly analogous to the consequence of a successful $1^{st}$ BAC insertion. And therefore this transposon can likewise be removed by the transient expression of the piggyBac transposase (from an electroporated vector). Cells with the correct excision event can be selected by FIAU resistance—ie, no thymidine kinase activity from the puroΔTK gene. This completely removes the 3' modification leaving no trace nucleotides.
6. After curing of the 3' modification of the $2^{nd}$ BAC insertion, the landing pad becomes identical to the original. This entire process, steps 2 through 5, can be repeated multiple times to build up a large insertion into the genome. When complete, there are no residual nucleotides remaining other than the desired insertion.

Figure 27:
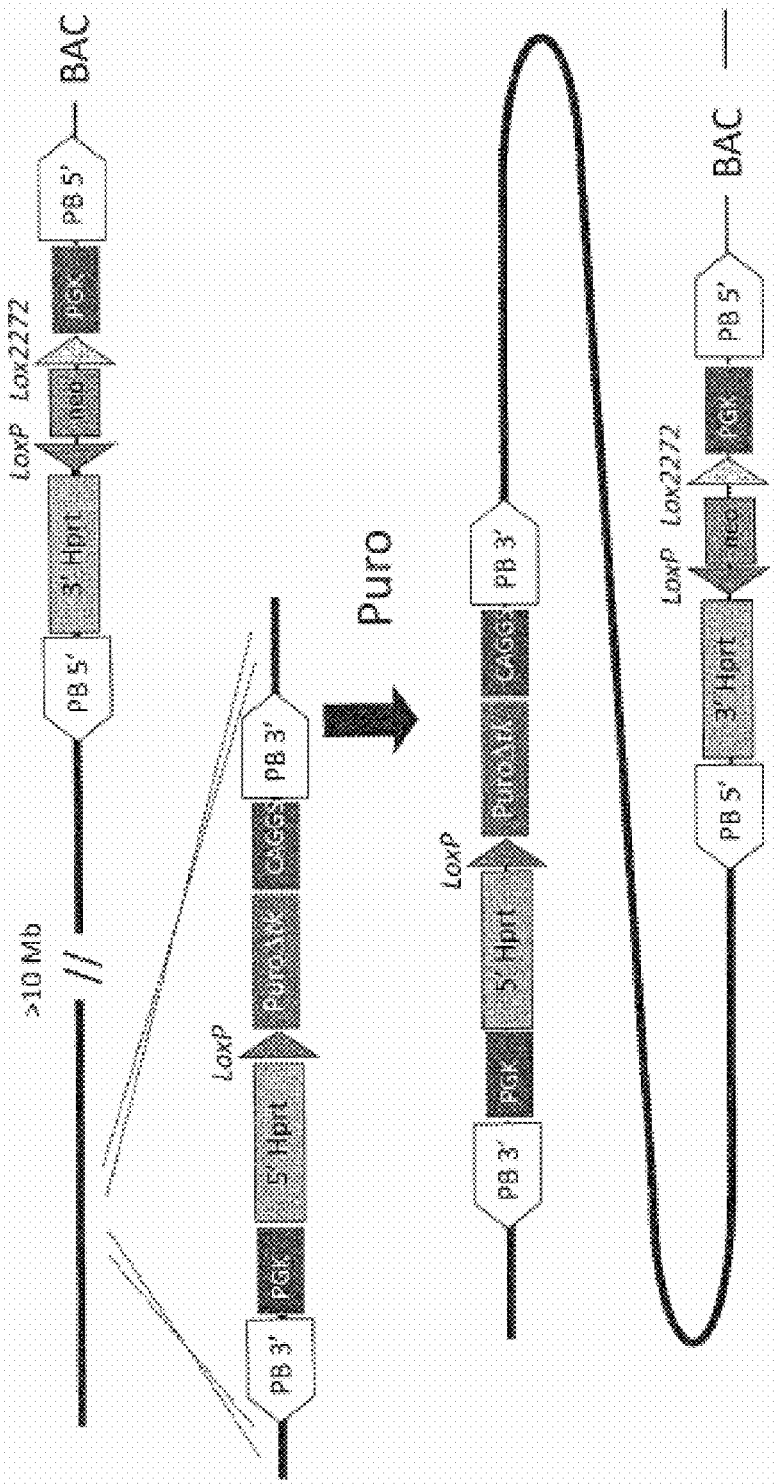
FIGS. 27-29 illustrate a mechanism for inversion of the host VDJ region
Figure 28:
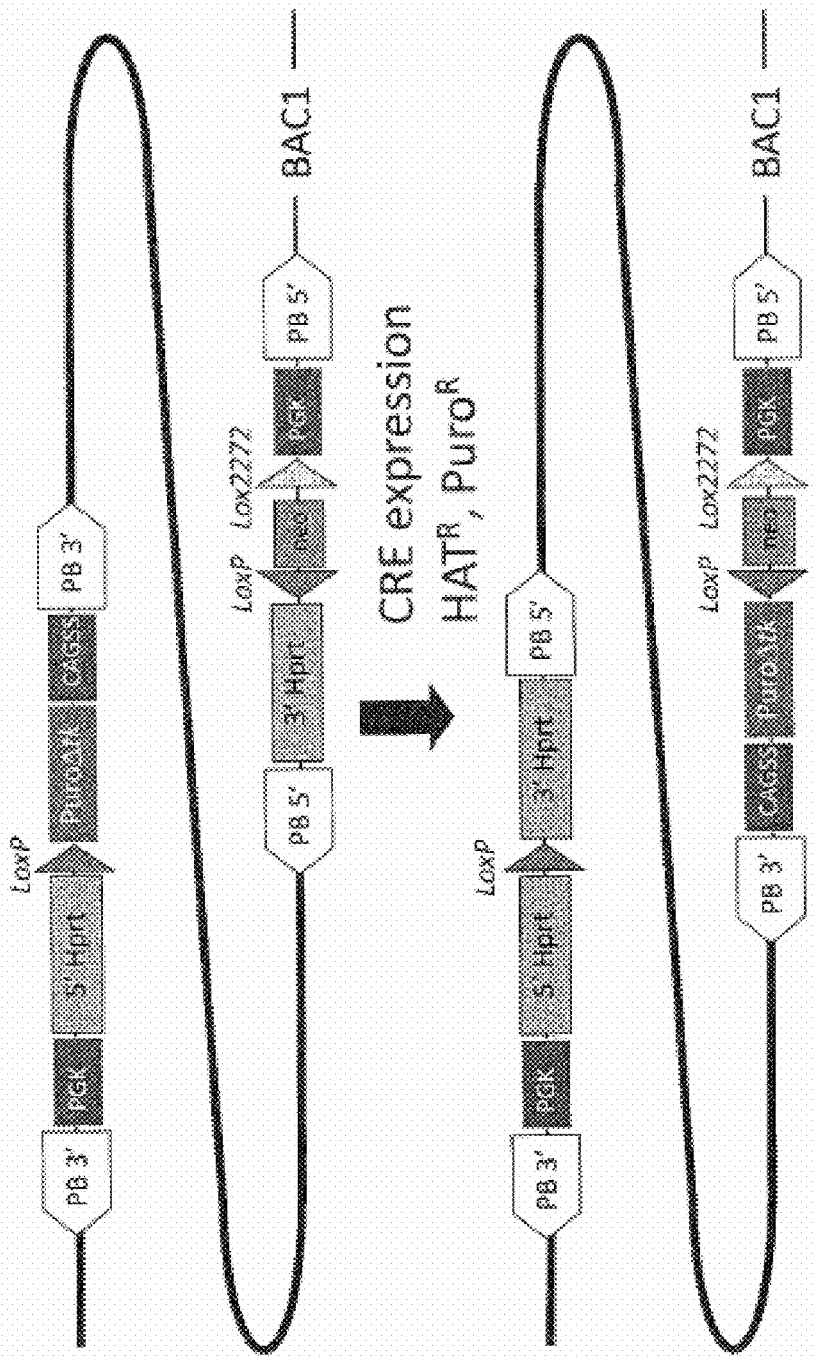
Figure 29:
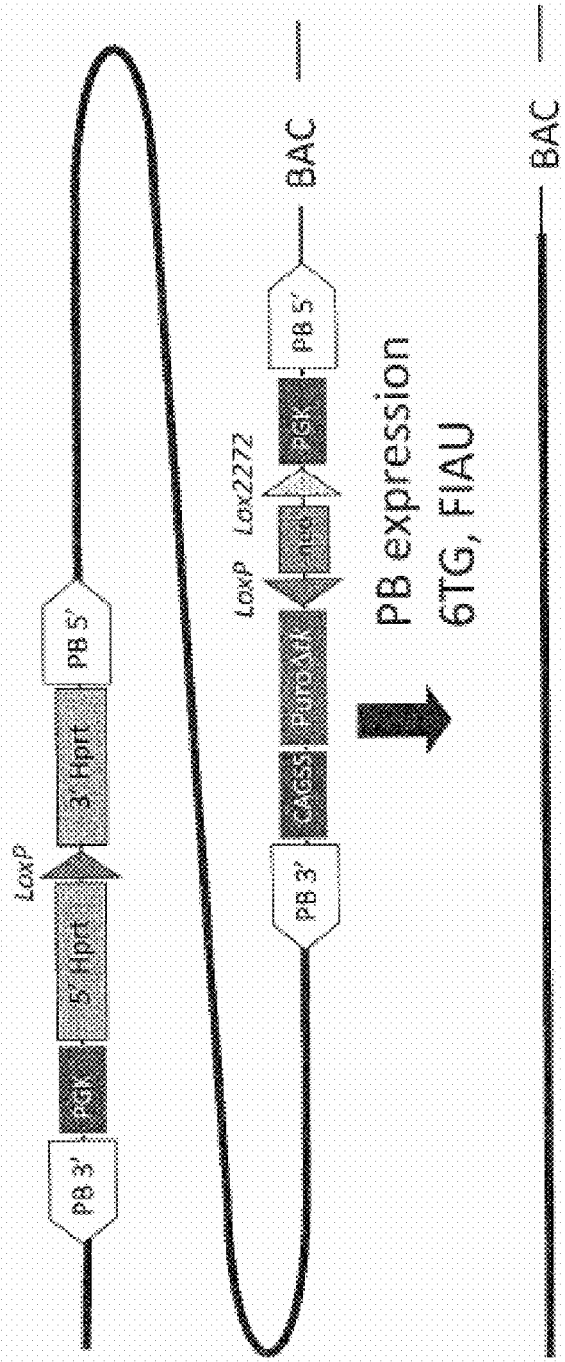

With the insertion of an odd number of BACs into the Ig loci, the endogenous VDJ or VJ sequences can be inactivated through an inversion via chromosomal engineering as follows (see FIGS. 27-29):
1. Targeting a "flip-over" cassette into a 5' region 10 to 40 megabases away from the endogenous VDJ or VJ. The flip-over vector (PB3'LTR-PGK promoter-HPRT mini gene 5' portion-loxP-puroΔTK-CAGGS promoter-PB3'LTR) is depicted in FIG. 27 along with the relative orientations of the lox sites and PB LTRs.
2. Transient CRE expression will result in recombination between the loxP site in the "flip-over" cassette and the loxP site in the 5' modification. This 5' modification is as described in Steps 2 and 3 above—essentially the modification resulting from insertion of an odd number of BACs, after the 3' modification has been cured. The loxP sites are inverted relative to one another and therefore the described recombination event results in an inversion as depicted in FIG. 28. Cells with the correct inversion will be HAT-resistance since the HPRT mini-gene is reconstituted by a correct inversion.
3. A correct inversion also leaves two transposon structures flanking the "flip-over" cassette and the 5' modification. Both can be excised with transient piggyBAC transposase expression, leaving no remnant of either modification (FIG. 29). Cells with the correct excisions can be selected as follows: (i) 6TG-resistance (the HPRT mini-gene is deleted) and (ii) FIAU-resistance (the puroΔTK gene is deleted). An inversion as described in the Ig loci would move the endogenous IGH-VDJ or IGK-VJ region away from the Eμ or Eκ enhancer region, respectively, and lead to inactivation of the endogenous IGH-VDJ or IGK-VJ regions.

The methods of insertion of the invention suitably provide one or more of:
Selection at both 5' and 3' ends of the inserted DNA fragment;
Efficient curing of the 3' modification, preferably by transposase mediated DNA excision;
Inactivation of endogenous IGH or IGK activity through an inversion; and
Excision of modifications, leaving no nucleotide traces remaining in the chromosome.

Example 3

Insertion of a Test Vector into the Genome at a Defined Location

Figure 30:
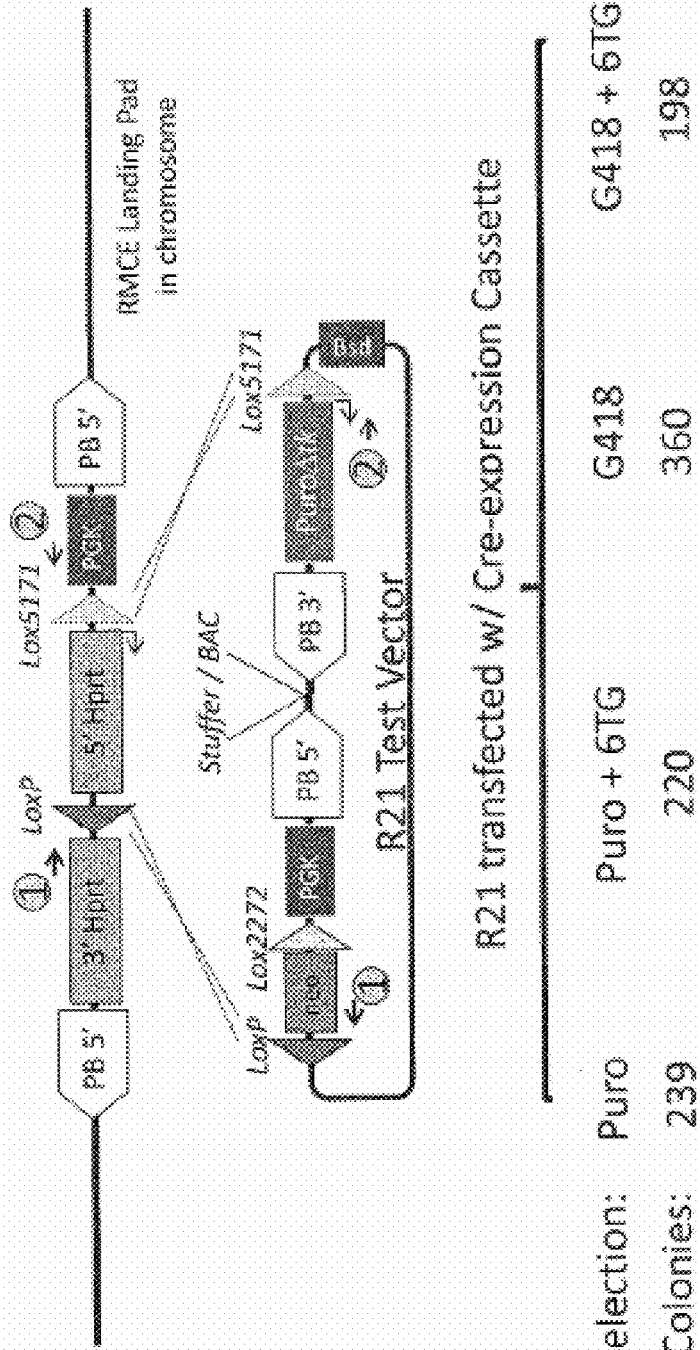
FIG. 30 illustrates proof of principle for insertion of a plasmid using an RMCE approach

Proof of concept of the approach is disclosed in FIG. 30. In FIG. 30 a landing pad as shown in FIG. 22 was inserted into the genome of a mouse by homologous recombination, followed by insertion of the R21 plasmid into that landing pad via cre-mediated site specific recombination. The insertion event generated a number of general insertion events, 360 G418 resistant colonies, of which ~220 were inserted into the desired locus, as demonstrated by disruption of the HRPT minilocus.

Figure 31:
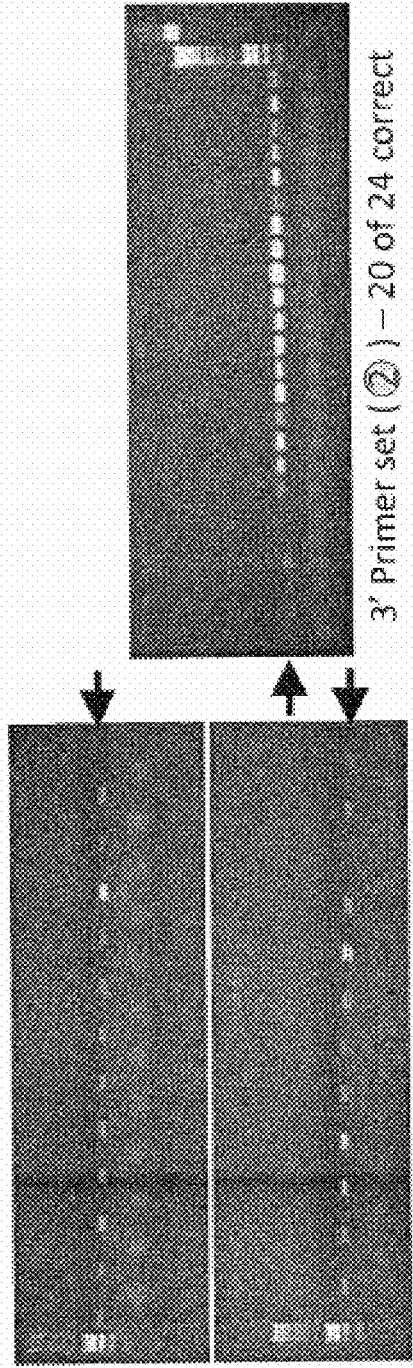
FIG. 31 illustrates sequential RMCE-Integration into Landing Pad

The R21 vector mimics the $1^{st}$ BAC insertion vector at the 5' and 3' ends, including all selection elements and recombinase target sites. In place of BAC sequences, there is a small 'stuffer' sequence. This vector will both test all the principals designed in the invention and allow easy testing of the results in that PCR across the stuffer is feasible and therefore allows both ends of the insertion to be easily tested. R21 was co-electroporated with a cre-expressing vector into the ES cells harbouring the landing pad in the IGH locus. Four sets of transformed cells were transfected in parallel and then placed under different selection regimes as indicated in FIG. 30. G418 selection (neo gene expression) resulted in the largest number of colonies due to there being no requirement for specific landing-pad integration. Any integration of R21 into the genome will provide neo expression leading to G418-resistance. Puro selection resulted in a similar colony number to Puro+6TG or G418+6TG, suggesting that the stringency of Puro selection is due to the PuroΔTK lacking a promoter in the vector. Puro expression is only acquired when an integration occurs near a promoter element—in this design most likely specifically in the landing pad. These conclusions are supported by the results from junction PCR which is shown in FIG. 31.

Figure 32:
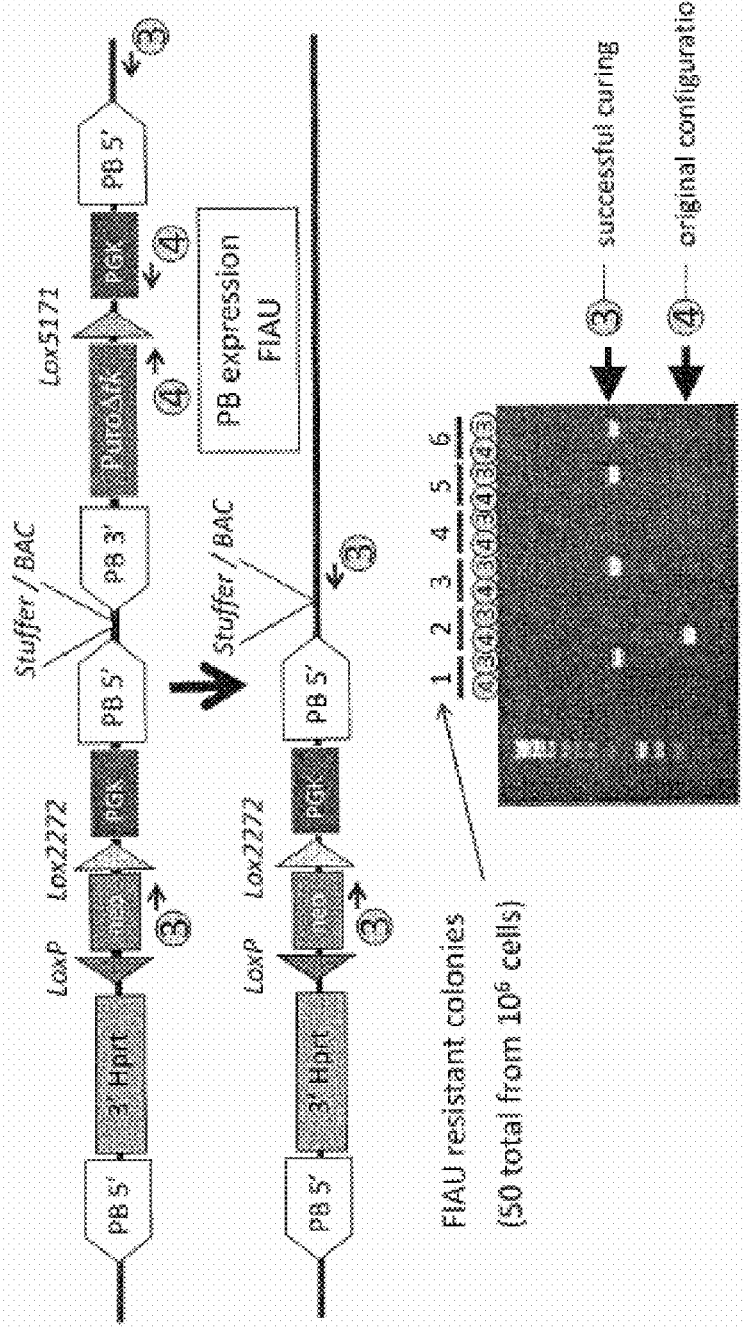
FIG. 32 illustrates confirmation of Successful Insertion into Landing Pad

The next step in the invention is to 'cure' the 3' end of the integrated BAC vector, leaving a seamless transition between the insertion and the flanking genome. This curing was demonstrated by expanding an individual clone from above (R21 inserted into the landing pad) and expressing piggyBac recombinase in this clone via transfection of an expressing plasmid. FIAU was used to select colonies in which the 3' modification was excised—ie, through loss of the 'PGK-puroΔTK' element between the piggyBac terminal repeats. Fifty such clones resulted from a transfection of $10^6$ cells; of these six were tested for the expected genomic structure. Successful curing resulted in positive PCR between the primer set labelled "3" in FIG. 32. Of the 6 clones, 4 had correct excisions, 1 clone remained in the original configuration and 1 other had a deletion.

These data demonstrate iterative insertion of DNA into a landing pad at a defined genomic locus using the approaches outlined above.

Example 4

Insertion of Large Parts of the Human IG Loci into Defined Positions in the Mouse Genome Example 3 demonstrated that the design of the claimed invention was capable of providing for the insertion of a test vector into the genome at a defined location, in this case the R21 vector into the mouse IGH locus. The use of the appropriate selection media and the expression of cre-recombinase resulted in a genomic alteration with the predicted structure.

The same design elements described in this invention were built into the 5' and 3' ends of a BAC insert. Said insert comprised human sequences from the IGH locus and was approximately 166-kb. This engineered BAC was electroporated along with a cre-expressing plasmid DNA into mouse ES cells harbouring the landing pad at the mouse IGH locus. The transfected cell population was grown in puro-containing media to select for appropriate insertion events.

Figure 33:
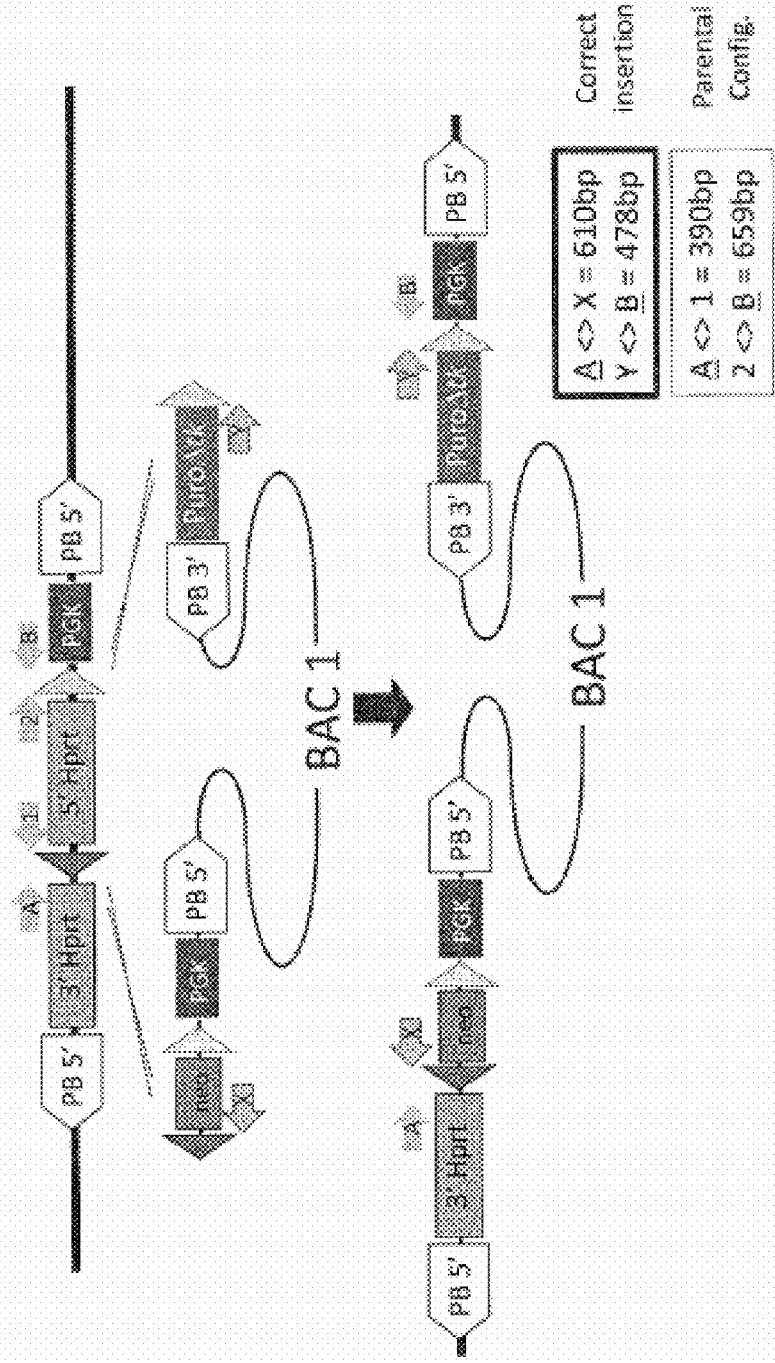
FIG. 33 illustrates PCR Confirmation of 3' End Curing
Figure 34:
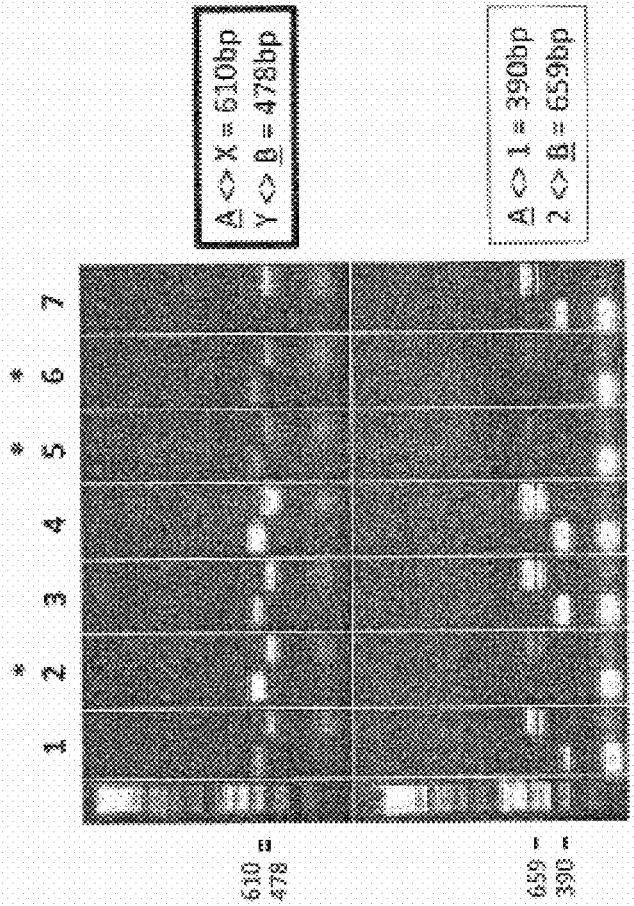
FIG. 34 illustrates insertion of BAC#1 and PCR Diagnostics

Seven resulting clones were isolated and further analysed. The expected recombination event and resulting structure are depicted in FIG. 33. Based upon data from the R21 experiment outlined in Example 3, a stringent selection for correct clones was expected when the transfected population was selected in puro-containing media. This is because the puro-coding region requires a promoter element and this is preferentially supplied by the landing pad after recombination. Accordingly, the majority of the 7 isolated clones had inserted correctly into the genome at the landing pad as determined by the diagnostic PCR. The primers for diagnosing a correct insertion are depicted in FIG. 33. Correct junctions are present in the genome if a 610-bp fragment is amplified between primers 'A' and 'X' and a 478-bp fragment is amplified between primers 'Y' and 'B' (FIGS. 33 and 34). Note that there are amplified fragments between 'A' and '1' primers and '2' and 'B' primers indicating the presence of parental genome (that is, the landing pad alone). These result from parental cells present internally in the cell colonies under puro-selection that escape the selection due to the geometry of a colony. After passaging the colony through puro-containing media, these parental junction fragments disappear indicating that the parental cells are removed from the population. In addition, all the clones were shown to be resistant to 6-TG as expected if the HPRT gene is inactivated by the correct insertion event.

These data indicate that the disclosed strategy for inserting large parts of the human IG loci into defined positions in the mouse genome will enable the construction of a mouse with a plurality of the variable regions of human IG regions upstream of the mouse constant regions as described.

Example 5

Inserted Loci are Functional in Terms of Gene Rearrangement, Junctional Diversity as Well as Expression Bacterial artificial chromosomes (BACs) were created, wherein the BACs had inserts of human Ig gene segments (human V, D and/or J gene segments). Using methods described herein, landing pads were used in a method to construct chimaeric Ig loci in mouse embryonic stem cells (ES cells), such that chimaeric IgH and IgK loci were provided in which human gene segments are functionally inserted upstream of endogenous constant regions. To test if the human IgH-VDJ or IgK-VJ gene segments in the chimaera mice derived from human BAC-inserted ES cell clones appropriately rearrange and express, RT-PCR was performed for the RNA samples of white blood cells from those mice with the primer pairs of human variable (V) region and mouse constant (C) region. The sequences of oligos are shown as follows (Table 1). Each V oligo is paired with C oligo (HV with Cμ; KV with Cκ) for PCR reaction.

TABLE 1

| Oligo | Sequence |
| --- | --- |
| HV2-5 | AGATCACCTTGAAGGAGTCTGGTCC (SEQ ID NO 7) |
| HV4-4 | TGGTGAAGCCTTCGGAGACCCTGTC (SEQ ID NO 8) |
| HV1-3 | CACTAGCTATGCTATGCATTGGGTG (SEQ ID NO 9) |
| HV1-2 | ATGGATCAACCCTAACAGTGGTGGC (SEQ ID NO 10) |
| HV6-1 | GGAAGGACATACTACAGGTCCAAGT (SEQ ID NO 11) |
| Cμ | TAGGTACTTGCCCCCTGTCCTCAGT (SEQ ID NO 12) |
| KV1-9 | AGCCCAGTGTGTTCCGTACAGCCTG (SEQ ID NO 13) |
| KV1-8 | ATCCTCATTCTCTGCATCTACAGGA (SEQ ID NO 14) |
| KV1-6 | GGTAAGGATGGAGAACACTGGCAGT (SEQ ID NO 15) |
| KV1-5 | TTAGTAGCTGGTTGGCCTGGTATCA (SEQ ID NO 16) |
| Cκ | CTTTGCTGTCCTGATCAGTCCAACT (SEQ ID NO 17) |

Using the one-step formulation of SuperScript™ III One-Step RT-PCR System with Platinum® Taq High Fidelity (Invitrogen™; World Wide Web (www) invitrogen.com/site/us/en/home/References/protocols/nucleic-acid-amplification-and-expression-profiling/per-protocol/superscript-3-one-step-rt-per-system-with-platinum-taq-high-fidelity.html#prot3), both cDNA synthesis and PCR amplification were achieved in a single tube using gene-specific primers and target RNAs.

The RT-PCR results showed most of the human IGH-VDJ or IGK-VJ gene segments appropriately rearrange and express in the chimaera mice. To investigate the details about the diversity generated from VDJ/VJ rearrangement, those specific RT-PCR fragments were cloned into a common vector for sequencing.

Figure 35:
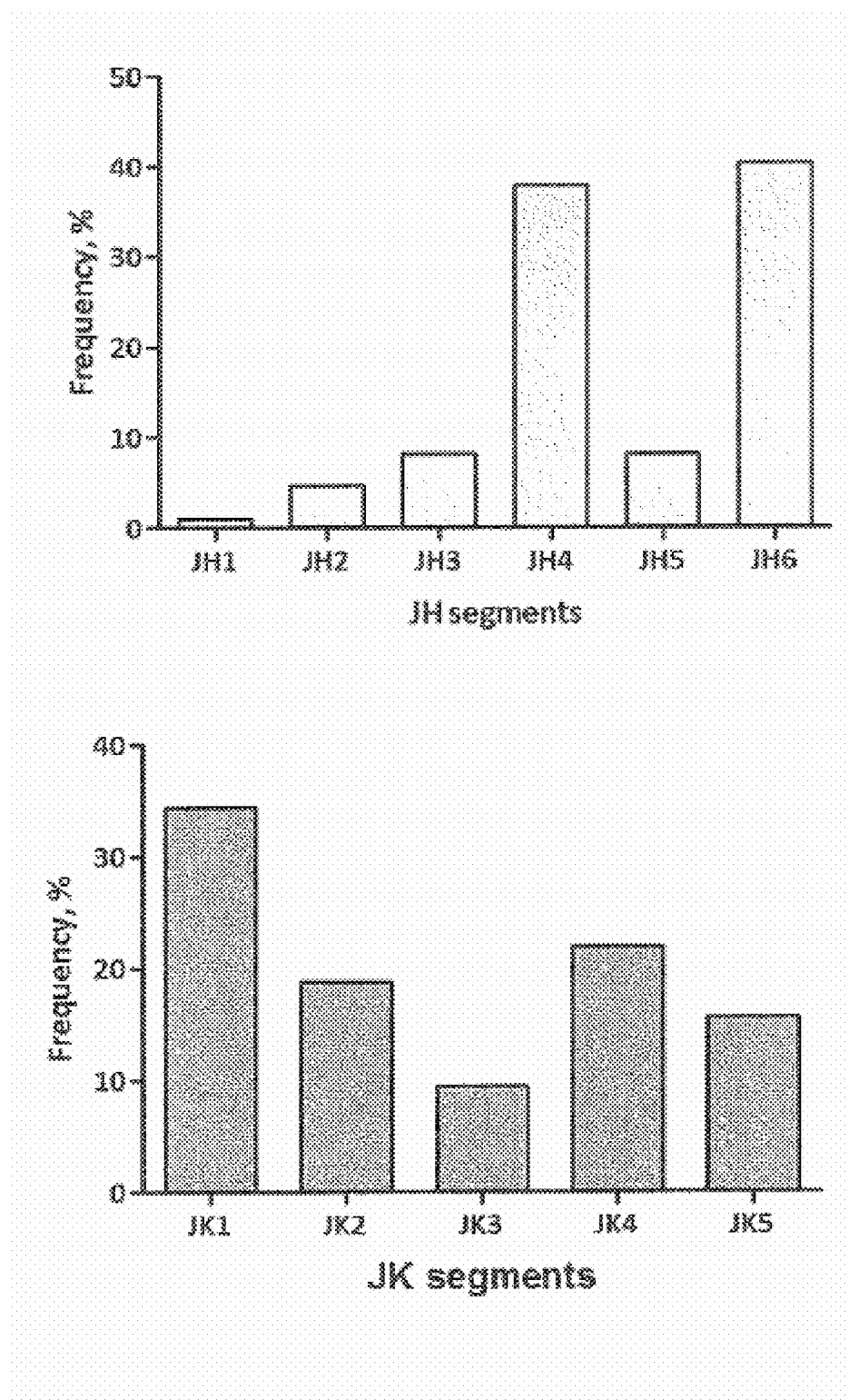
FIG. 35 illustrates JH and JK usage
Figure 36:
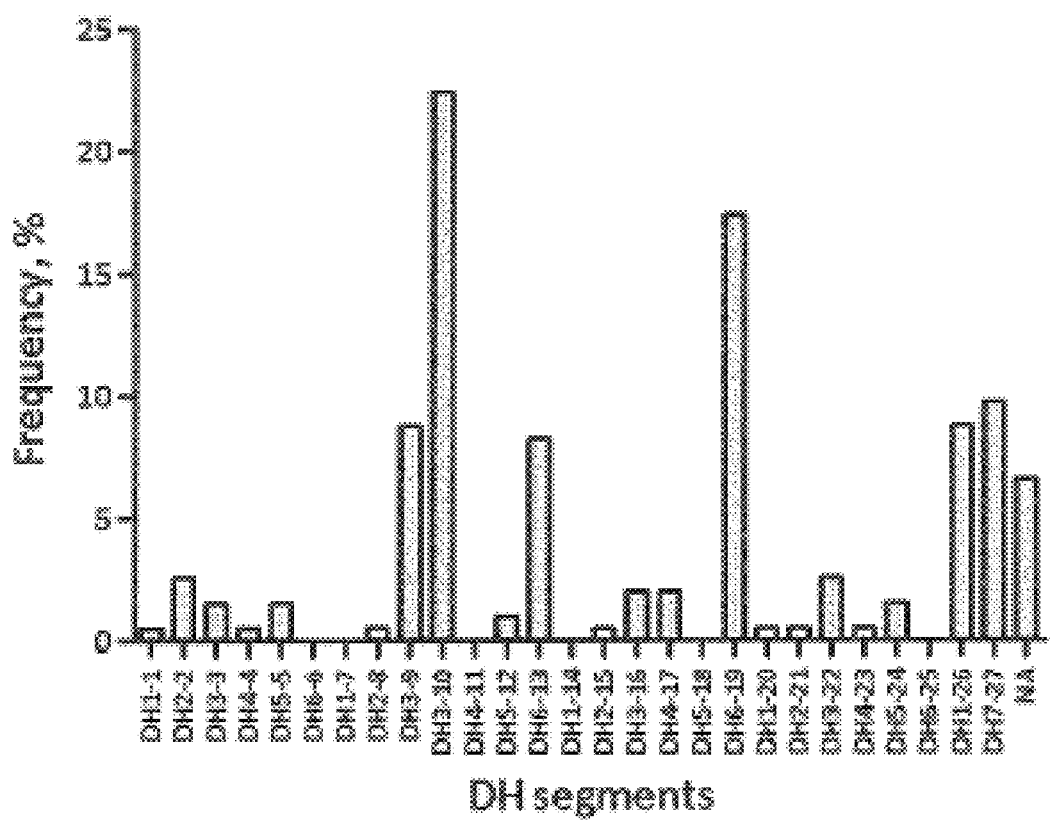
FIG. 36 illustrates DH usage
Figure 37:
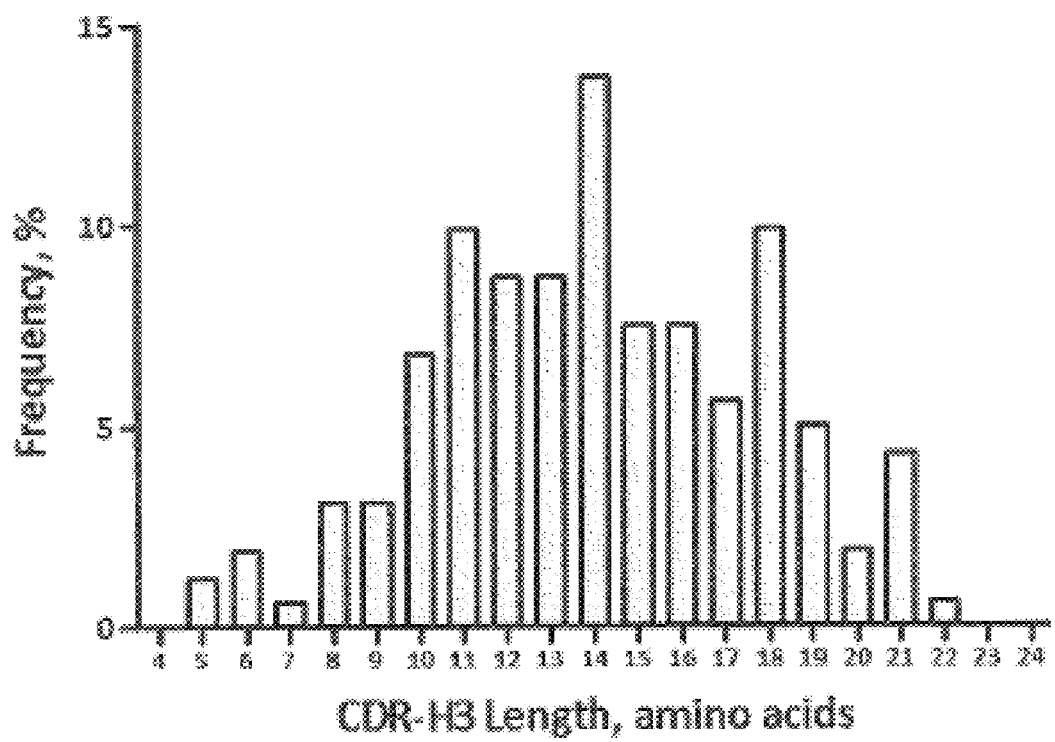
FIG. 37 illustrates the distribution of CDR-H3 length in human VDJCµ transcripts from chimera mice
Figure 38:
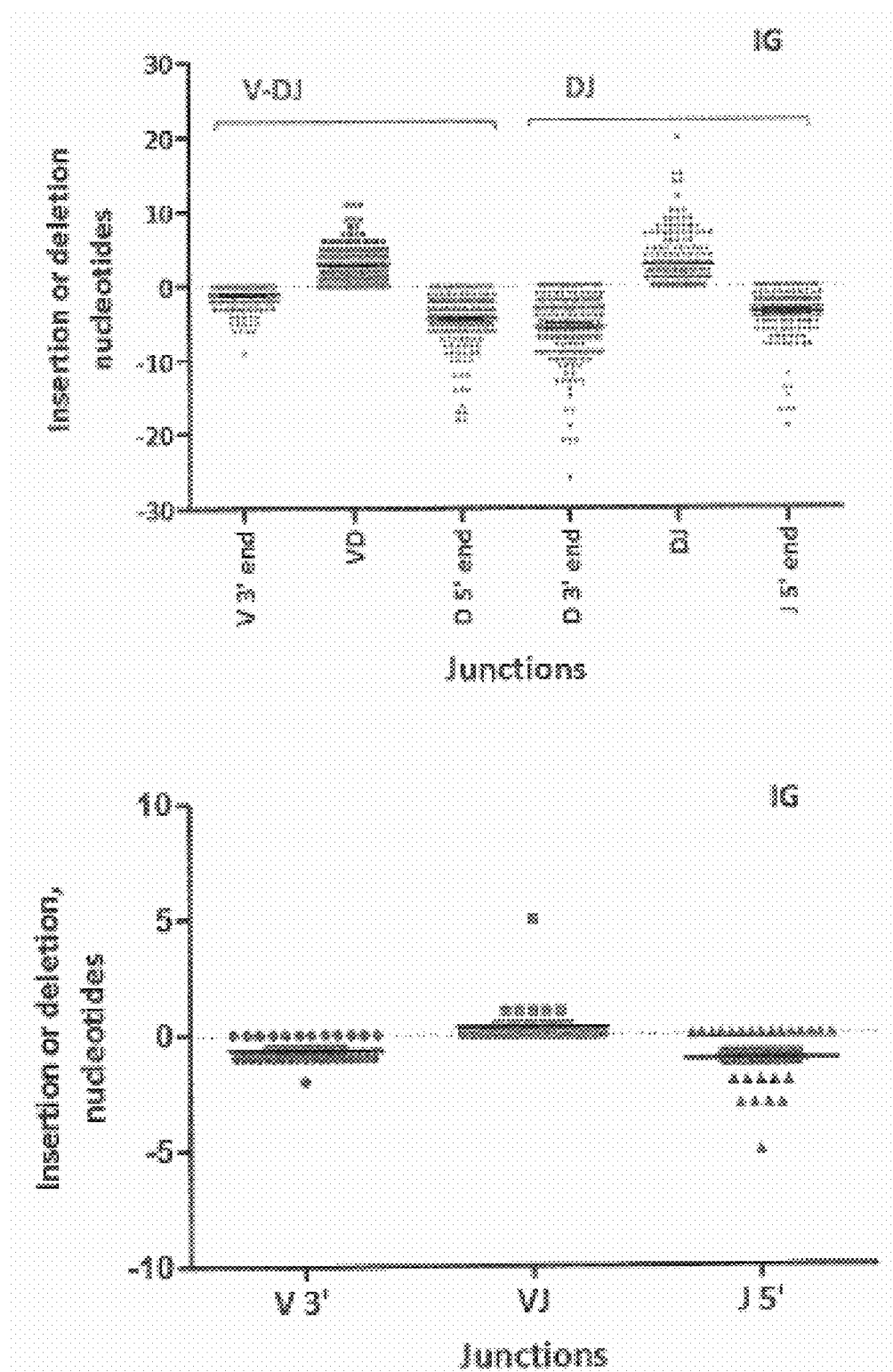
FIG. 38 illustrates the distribution of nucleotide numbers of deletion and insertion in IGH-VDI or IGK-VJ junctions

Sequencing results indicate that JH, DH, and JK usages (FIG. 35 and FIG. 36) are similar to human results. In addition, the results from the IGH-VDJCμ transcripts show that the range and mean of CDR-H3 length (FIG. 37) are similar to that observed in human. The junctional diversity generated from exonuclease and nucleotide addition activities (FIG. 38) was also observed. The IGH rearrangement possessed a higher frequency of these activities compared to the IGK one. These data suggest that the inserted loci are functional in terms of gene rearrangement, junctional diversity as well as expression.

Example 6

Productive VJ Rearrangement and Somatic Hypermutation can be Obtained

Figure 41:
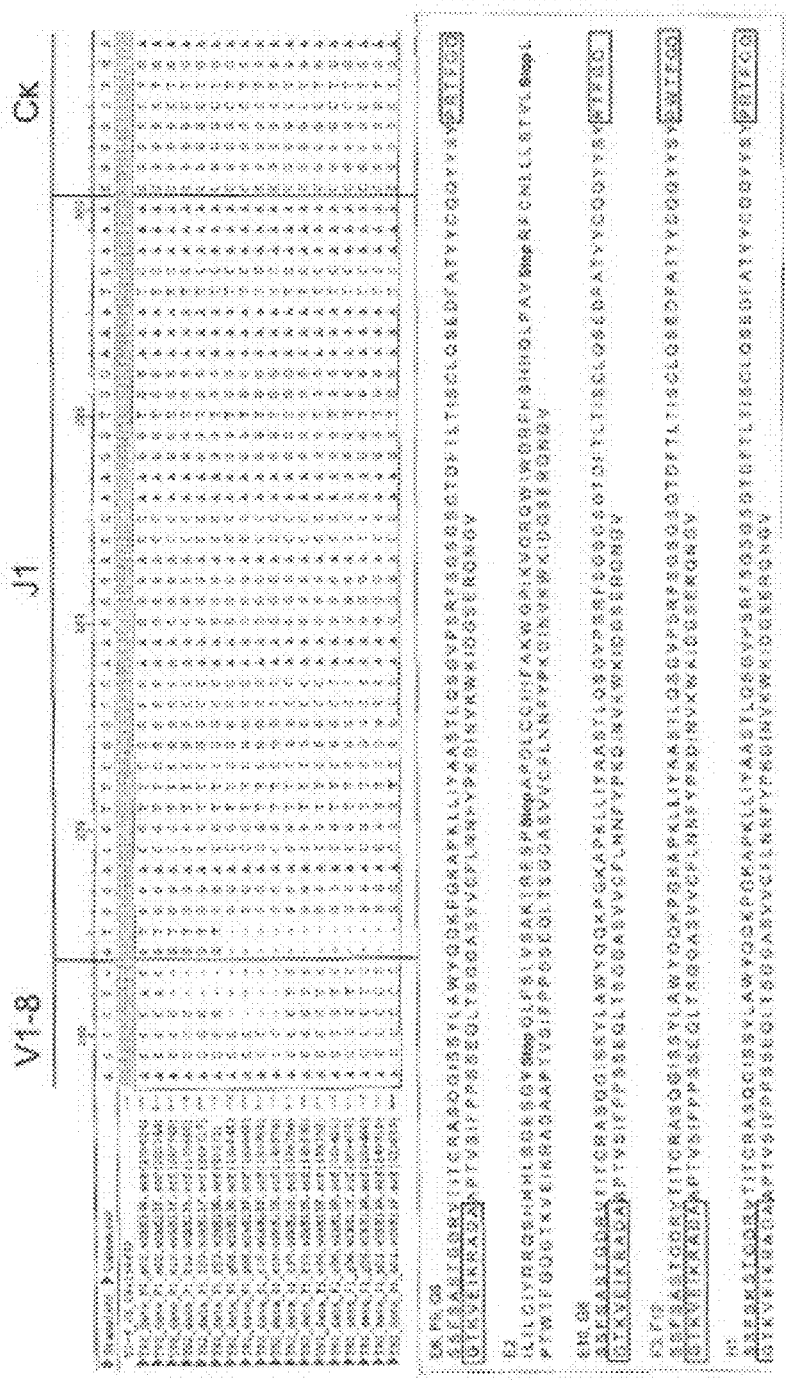
FIG. 41 illustrates Nucleotide Gain or Loss at VJ Joints Generates IGK Variants
Figure 42:
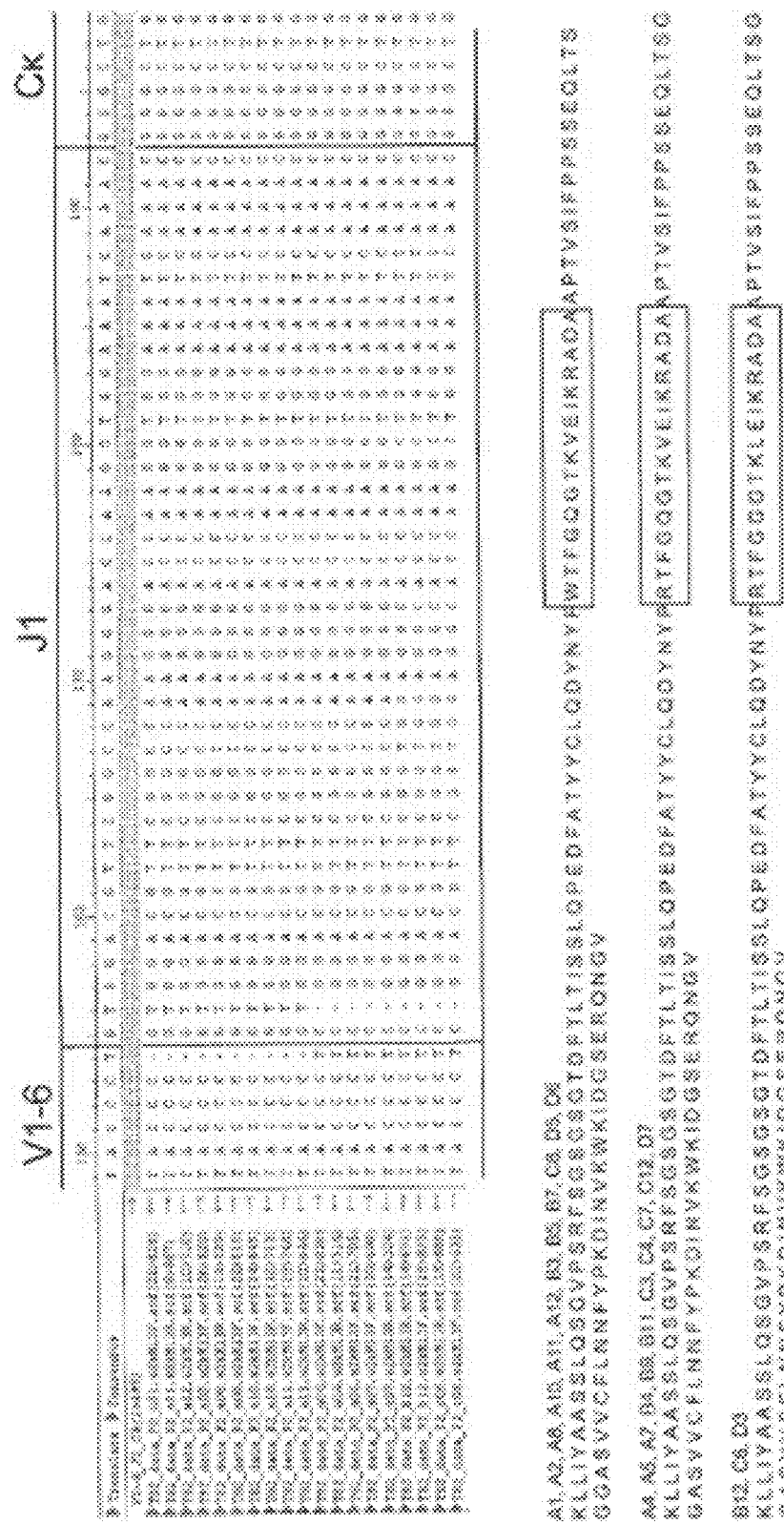
FIG. 42 illustrates Hypermutaion in J Regions Generates IGK Variants
Figure 43:
FIG. 43 illustrates Joint Diversity Produces Functional CDS

FIG. 41 shows an analysis of kappa mRNA from mice B-cells bearing rearranged VJ, the VJ having been rearranged from human germline kappa V1-8 and J1, and demonstrates that both that productive VJ rearrangement and somatic hypermutation can be obtained, the latter as seen from the changes in antibodies encoded by mRNA with respect to the germline sequences. The same is displayed for V1-6 and J1 in FIG. 42. Importantly, the recombination eliminates stop codons that are encoded by the combination of (unmutated) human germline gene segments, thereby allowing for antibody-encoding mRNA sequences. FIG. 43 demonstrates that inserted human kappa V1-5 J1 and V1-5 J4 can produce functional coding sequences in vivo and junctional diversity.

Example 7

Figure 44:
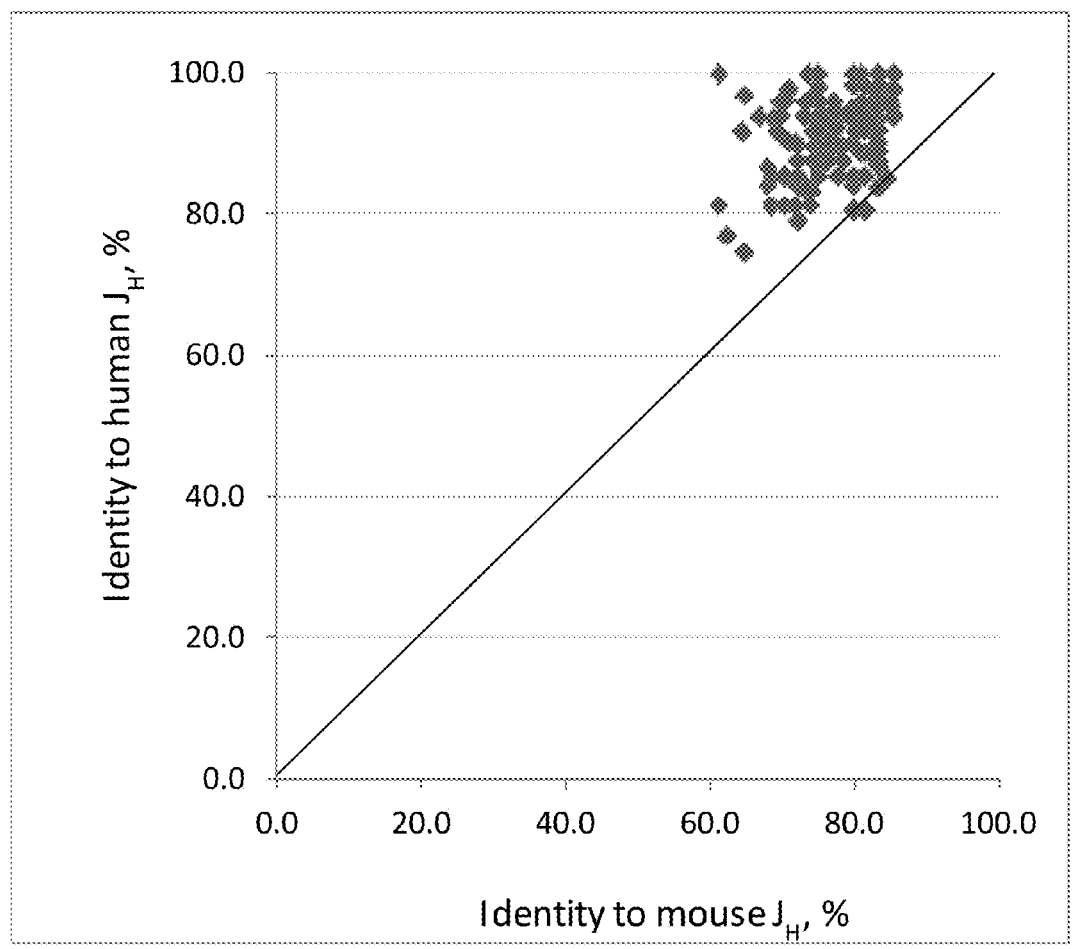
FIG. 44 illustrates a plot of identity of $J_H$ gene segment use a 5'-RACE Cµ-specific library generated from the splenic B lymphocytes of transgenic mice according to the invention in which endogenous gene segment use has been inactivated by inversion

Inactivation of Use of Endogenous IGHV Gene Segments for Expressed Rearranged Heavy Chain by Inversion Introduction A 5'-RACE Cμ-specific library was generated from the splenic B lymphocytes of transgenic mice, denoted S1 mice. These mice comprise transgenic heavy chain loci, each locus containing the six most 3' functional human $V_H$ gene segments ($V_H$2-5, 7-4-1, 4-4, 1-3, 1-2, 6-1), and all the human D and $J_H$ gene segments inserted into the endogenous heavy chain locus between endogenous IGHJ4 and Eμ (mouse chromosome 12: between coordinates 114666435 and 114666436). The human DNA was obtained from a bacterial artificial chromosome (BAC) containing the sequence of human chromosome 14 from coordinate 106328951 to coordinate 106494908. Further details on the construction of transgenic antibody loci using sRMCE is given elsewhere herein and in WO2011004192 (which is incorporated herein by reference). 4×96-well plates of clones were randomly picked for sequencing to determine the usage of the gene segments. All detected immunoglobulin heavy chains were rearranged from mouse $V_H$ or human $V_H$ with human D-$J_H$. No mouse D and $J_H$ segments were detected in rearranged products (FIG. 44).

This result indicates that insertion of human $V_H$-D-$J_H$ gene segments into an endogenous locus between the last endogenous J region (in this case, $J_H$4) and the Eμ enhancer effectively inactivates the use of endogenous D and $J_H$ gene segments for expressed rearranged immunoglobulin heavy chains.

Figure 45:
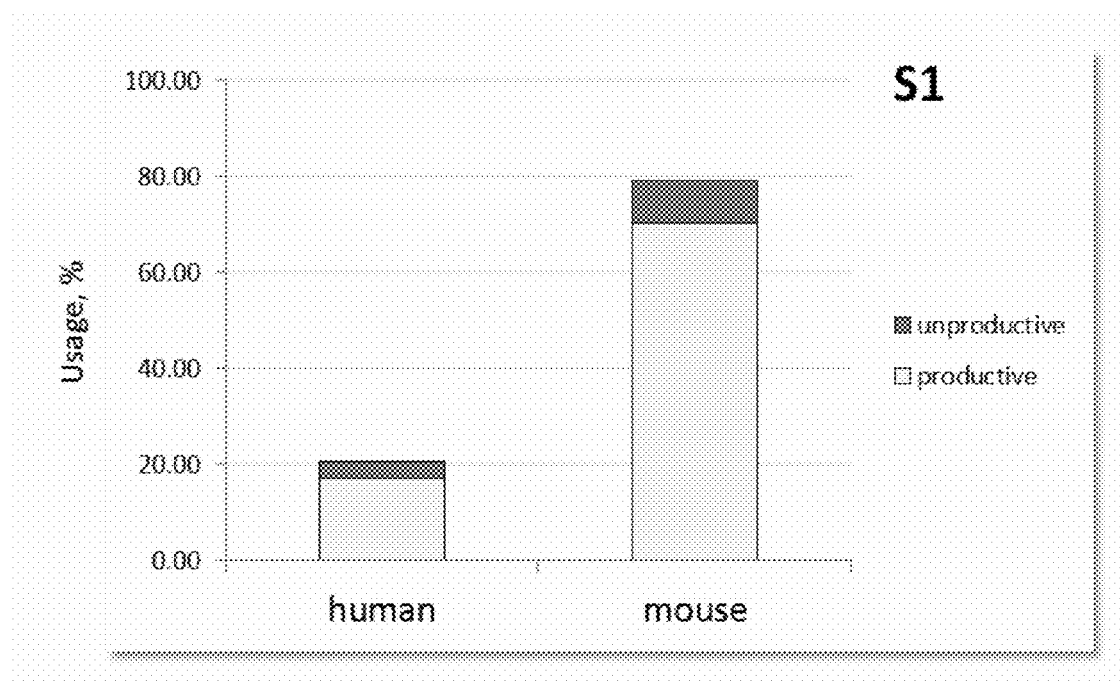
FIG. 45 illustrates the ratio of mouse $V_H$ to human $V_H$ usage as determined from antibody sequences from splenic B lymphocytes of transgenic mice according to the invention in which endogenous gene segment use has been inactivated by inversion

The ratio of mouse $V_H$ to human $V_H$ usage was around 3 to 1 (FIG. 45). To completely eliminate mouse $V_H$ use for antibody generation, the endogenous mouse $V_H$-D-$J_H$ was inverted and moved to a distant region of the same chromosome. The rearrangement of mouse $V_H$s to human D-$J_H$ segments was totally blocked by effects of inversion and distance from the heavy chain locus.

Figure 46:
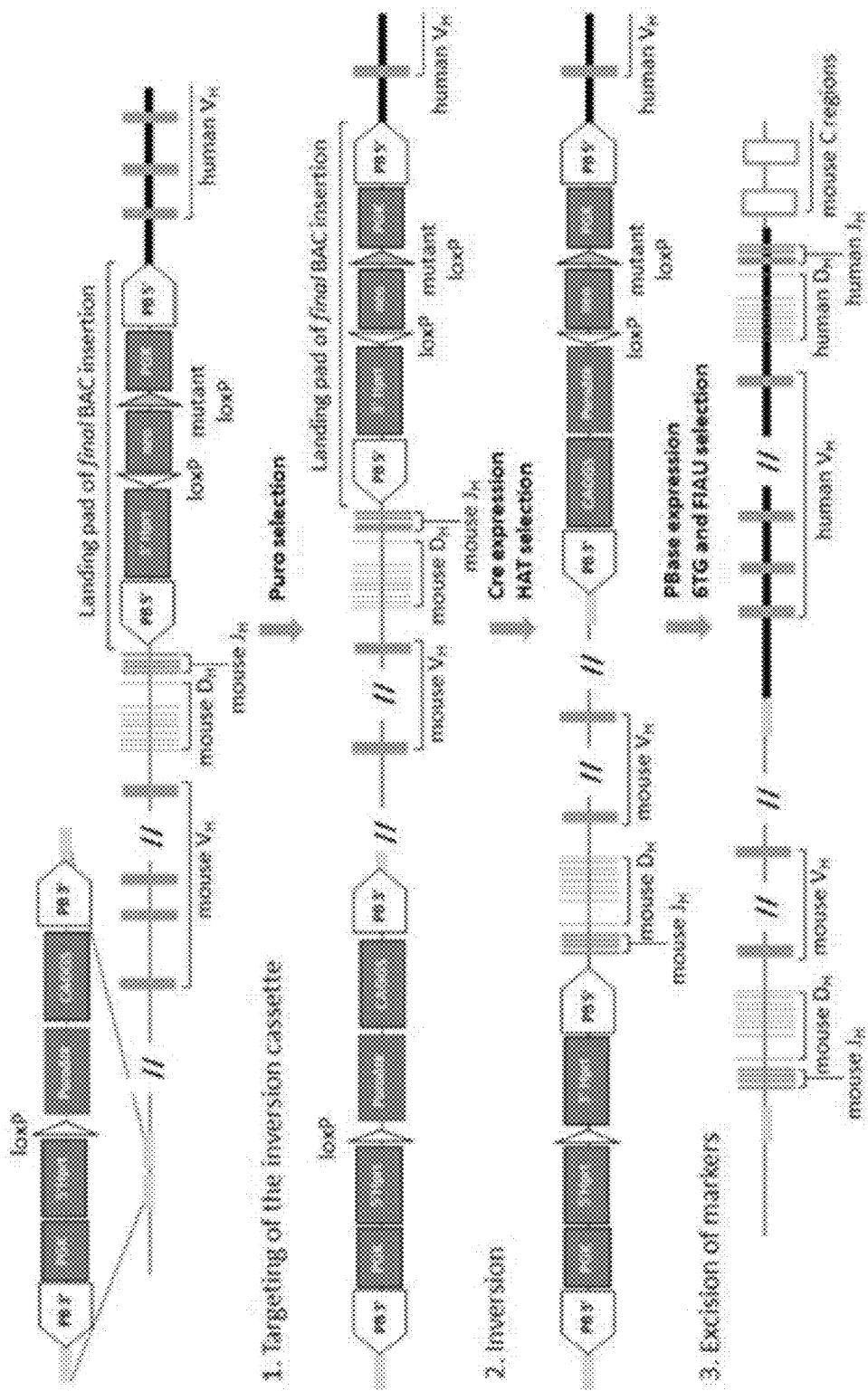
FIG. 46 illustrates inversion strategy schematic

The inversion strategy included three steps: (a) targeting of an inversion cassette, (b) inversion of endogenous VDJ and (c) excision of markers (FIG. 46).

(a) Targeting of the Inversion Cassette:

The inversion cassette consists of four components: a CAGGS promoter-driven puromycin-resistant-delta-thymidine kinase (puroΔtk) gene, a 5' HPRT gene segment under the PGK promoter control, a loxP site between them and inversely oriented to another loxP site already in the heavy chain locus, and two flanking piggyback LTRs (PB3'LTRs). The inversion targeting cassette was inserted to a region that is 5' and distant to the endogenous IGH locus at chromosome 12 as shown in FIG. 46. The targeted ES clones were identified and confirmed by PCR.

(b) Inversion:

Following the insertion, transient expression of cre from a transfected plasmid resulted in inversion of a section of chromosome 12 fragment including the endogenous $V_H$-D-$J_H$ locus and intervening sequences through recombination of two inverted loxP sites, ie, those in the inversion cassette and the landing pad for the BAC insertion respectively. The invertants were selected by HAT and confirmed by junction PCRs cross the two recombined loxP sites.

(c) Excision of Markers:

The inversion rearranged the relative orientation of the PB3'LTRs from the inversion cassette and PB5'LTR from the landing pad to generate two piggyBac transposon structures flanking the inverted region. With transient expression of piggyBac transposase (PBase), these two transposons were excised from the chromosome (and thus the mouse cell genome). The cured ES clones were selected by 1-(−2-deoxy-2-fluoro-1-b-D-arabinofuranosyl)-5-iodouracil (FIAU) and 6TG, and confirmed by junction PCRs cross the excised regions.

Methods

Tissue Culture:

The procedures for ES cell culture, electroporation and drug selection have been described previously (Ramirez-Solis, R., A. C. Davis, and A. Bradley. 1993. Gene targeting in mouse embryonic stem cells. Methods Enzymol. 225: 855-878).

Figure 47:
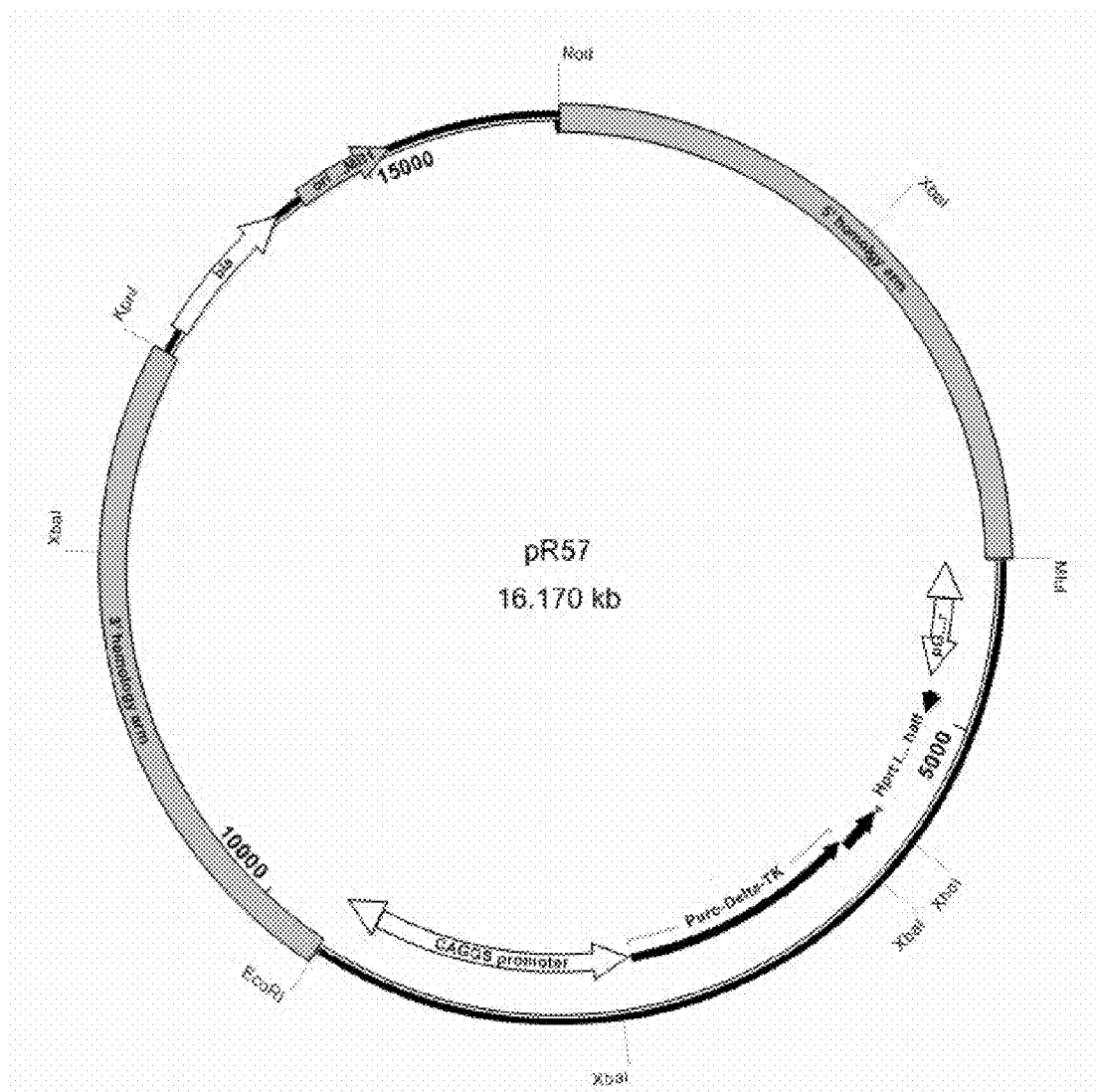
FIG. 47 illustrates targeting construct R57 for inversion

Targeting of the Locus for Inversion:

Briefly, 51 cell line (S1.11.1) was cultured in M15 medium (Knockout™ DMEM supplemented with 15% fetal bovine serum, 2 mM glutamine, antibiotics, and 0.1 mM 2-mercaptoethonal). Targeting construct R57 (FIG. 47) was linearized outside the region of homology by NotI. A total of 20 μg of the linearized construct was electroporated into 51 cell lines (AB2.1-derived) with a Bio-Rad® Gene Pulser™, and 107 cells were plated onto three 90-mm-diameter SNL76/7 feeder plates containing M15 medium. At 24 h after electroporation, M15 containing puromycin (3 μg of the active ingredient per ml) was added to each 90-mm-diameter plate, and the cells were maintained under selection for 9 days. 96 puromycin-resistant clones were then picked and expanded in 96-well plates. The targeting events were identified by long-range PCR.

Figure 48:
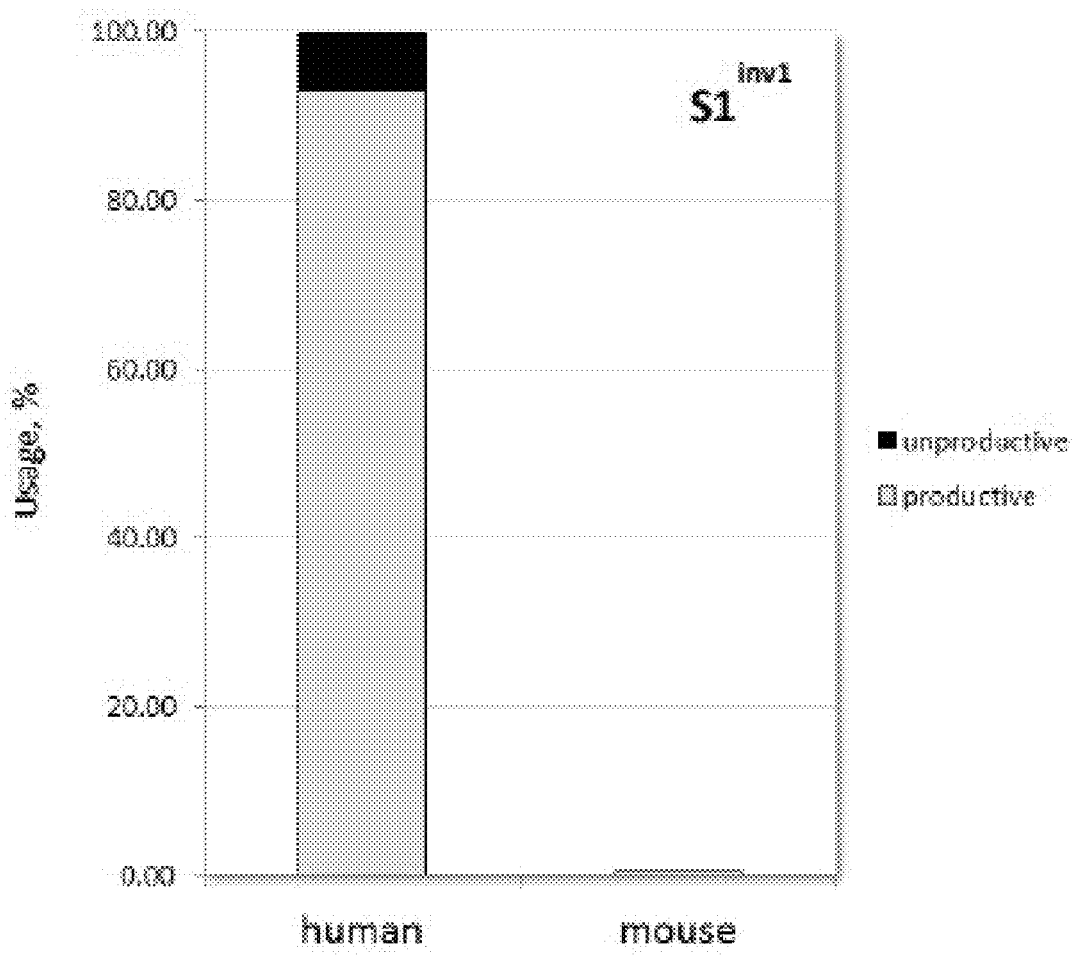
FIG. 48 illustrates sequence analysis from a Cµ-specific 5'-RACE library of splenic B lymphocytes of S1$^{inv1}$ (one human IGH BAC (ie, multiple human VH, all functional human D and JH) with an inverted endogenous IGH locus) mouse shows that practically all the transcripts came from rearranged human $V_H$-D-$J_H$ gene segments

Cre-loxP Mediated Inversion:

12 positive clones were pooled together and cultured in a 6-well tissue culture plate with M15 medium. The cells were transfected with 10 μg of pCAGGS-Cre plasmid for the inversion of mouse endogenous locus and then plated onto three 90-mm-diameter SNL76/7 feeder plates containing M15 medium. At 24 h after electroporation, M15 containing 1×HAT (hypoxanthine-aminopterin-thymidine) was added to each 90-mm-diameter plate, and the cells were maintained under selection for 7 days and then treated with 1×HT (hypoxanthine-thymidine) for 2 days. 48 HAT resistant colonies were picked and genotyped by PCR amplification of the junctions after Cre-loxP mediated inversion.
HyPBase-Mediated Marker Excision:

12 positive clones were pooled together and cultured in 6-well tissue culture plate using M15 medium. The cells were transfected with 5 µg of HyPBase plasmid to activate the PB transposon LTRs flanking two selection markers (Hprt-mini gene and PGK-puroΔtk gene) and plated onto one 90-mm-diameter SNL76/7 feeder plates containing M15 medium. At 72 h after electroporation, a serial dilution of the cells was then plated onto three 90-mm-diameter SNL76/7 feeder plates containing M15 supplemented with 1-(−2-deoxy-2-fluoro-1-b-D-arabinofuranosyl)-5-iodouracil (FIAU). Cells were maintained under selection for 10 days, and FIAU-resistant colonies were counted, picked, and expanded in 96-well plates. Positive clones were identified by PCR amplification of the junctions after excision of the selection markers. Positive clones were then expanded for blastocyst microinjection.
Generation of Chimera and Breeding:

Mouse chimaeras were generated by microinjection of ES cells into C57/BL6 blastocysts and transfered into pseudopregnant recipients. Male chimaeras were test-crossed with C57/BL6 mice. Agouti F1 offspring were genotyped by S1 3' junction PCR. Test-cross positive heterozygotes were further intercrossed to generate homozygotes.
Determination of VH-D-JH Usage by Rapid Amplification of 5'-cDNA Ends (5' RACE) PCR:

Total RNA was extracted from the spleen of S1inv1 mouse (KMSF30.1d) with TRIzol® Reagent (Invitrogen™, Life Technologies Ltd™) and treated with DNase I. Rapid amplification of 5'-cDNA ends (5' RACE) PCR was performed using 573' RACE kit (2nd Generation, Roche) following the protocol supplied by the manufacturer. The first-strand cDNA was synthesised using primer E1554 (5'-ATGACTTCAGTGTTGTTCTGGTAG-3'; SEQ ID No 25) which is located at the mouse endogenous Cµ region. The synthesised first cDNA strand was purified using High Pure PCR Product Purification Kit (Roche). Poly(A) tail was added following the protocol supplied with the 5'/3' RACE kit (2nd Generation, Roche). The 5' end of the $V_H$-D-$J_H$ rearranged transcript was amplified by nested PCR with forward primers Oligo dT, which is included in the kit, and nested Cµ-specific reverse primers E1555 (5'-CACCAGAT-TCTTATCAGAC-3'; SEQ ID No 26). Following reaction, the 5' RACE PCR product was checked on a 1% agarose gel and purified using QIAquick® Gel Extraction Kit (QIAGEN) as the protocol supplied with the kit, then cloned into pDrive vector using QIAGEN PCR Cloning Kit (QIAGEN) for sequencing analysis.
Results The sequence analysis from a Cµ-specific 5'-RACE library of splenic B lymphocytes of S1$^{inv1}$ (one human IGH BAC (ie, multiple human VH, all functional human D and JH) with an inverted endogenous IGH locus version 1) mouse shows that practically all the transcripts came from rearranged human $V_H$-D-$J_H$ gene segments (FIG. 48). Mouse $V_H$ usage was rarely detected (0.4%), and no mouse D and $J_H$ usage was detected. Human $V_H$ usage was 99.6% and only human D and $J_H$ were used; it was hypothesized that the rare mouse $V_H$ usage was due to trans-switching with another chromosome and not due to use of moue $V_H$ from the inverted sequences. The inversion resulted in complete inactivation of the endogenous $V_H$ use.

This Result Indicates that Inversion is an Effective Way to Inactivate the Rearrangement of Endogenous $V_H$ Gene Segments.

The S1$^{inv1}$ mouse also shows a similar usage of both D and $J_H$ gene segments to human (FIG. 49) (Link, J M et al. Mol. Immunol. 2005. 42, 943-955). Thus, a mouse was produced that comprises a transgenic heavy chain locus that expresses heavy chains comprising human variable regions, but no mouse variable regions, and furthermore the human variable regions demonstrated a normal, human sequence distribution corresponding to human D and J usage observed in humans.

Example 8

Inactivation of Use of Endogenous IGHV Gene Segments for Expressed Rearranged Heavy Chain by Insertion of Human IgH Genomic DNA Introduction Insertion of human BACs with $V_H$-D-$J_H$ gene segments into an endogenous mouse heavy chain locus between $J_H$4 and Eµ in chromosome 12 allows human $V_H$-D-$J_H$ gene segments to effectively use mouse Eµ and 3' enhancers and rearrange to generate chimeric antibody with human variable region and mouse constant region. Meanwhile, the endogenous $V_H$-D-$J_H$ gene segments are pushed away from endogenous enhancers and constant regions. This distance effect results in inactivation of mouse D and $J_H$ use for expressed rearranged antibody products. As the distance increases by stepwise BAC insertion, it is expected that the mouse VH usage would be significantly reduced.
Results Insertion of human DNA from a 1$^{st}$ human BAC (BAC comprising a the sequence of mouse Chromosome 14 from coordinate 106328951 to coordinate 106494908; containing six most 3' functional $V_H$ gene segments ($V_H$2-5, 7-4-1, 4-4, 1-3, 1-2, 6-1), and all the human D and $J_H$ gene segments) into the heavy chain endogenous locus of a AB2.1 ES cell genome between endogenous IGHJ4 and Eµ (at mouse chromosome 12: between coordinates 114666435 and 114666436) effectively inactivates the use of endogenous D and $J_H$ gene segments for expressed rearranged immunoglobulin heavy chain (FIG. 44). The rearranged transcripts with mouse $V_H$ gene segments are reduced in the resulting S1 mouse. The proportion of transcripts using mouse $V_H$ is around 75% of all observed sequences (FIG. 45).

Figure 24:
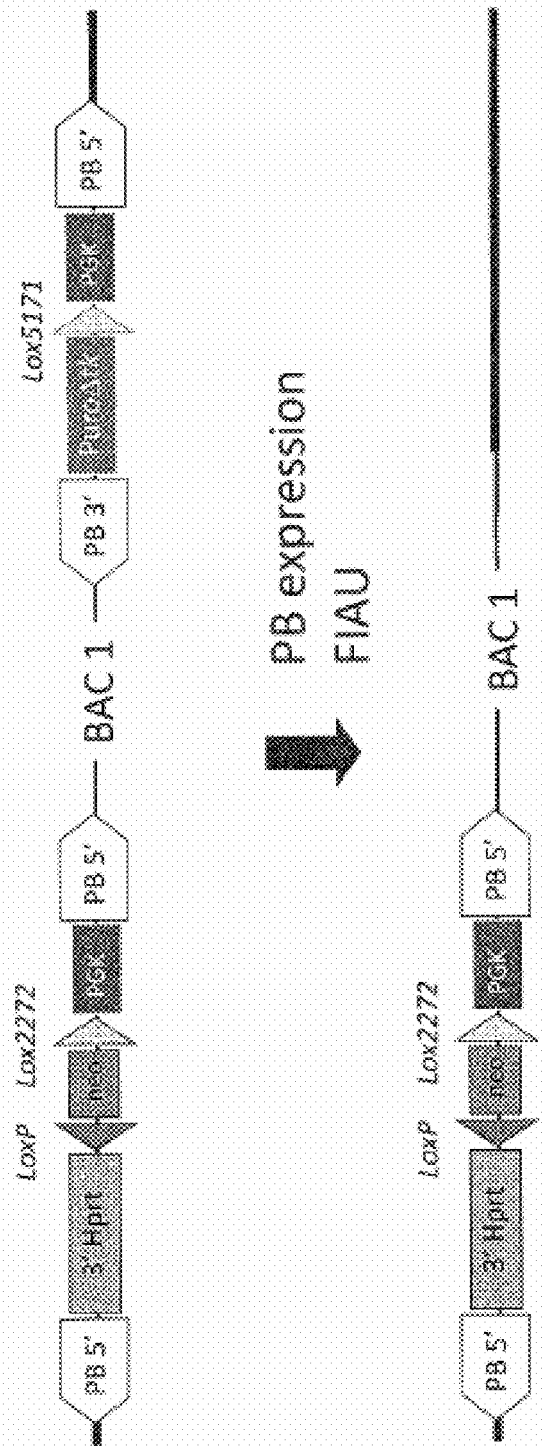
Figure 25:
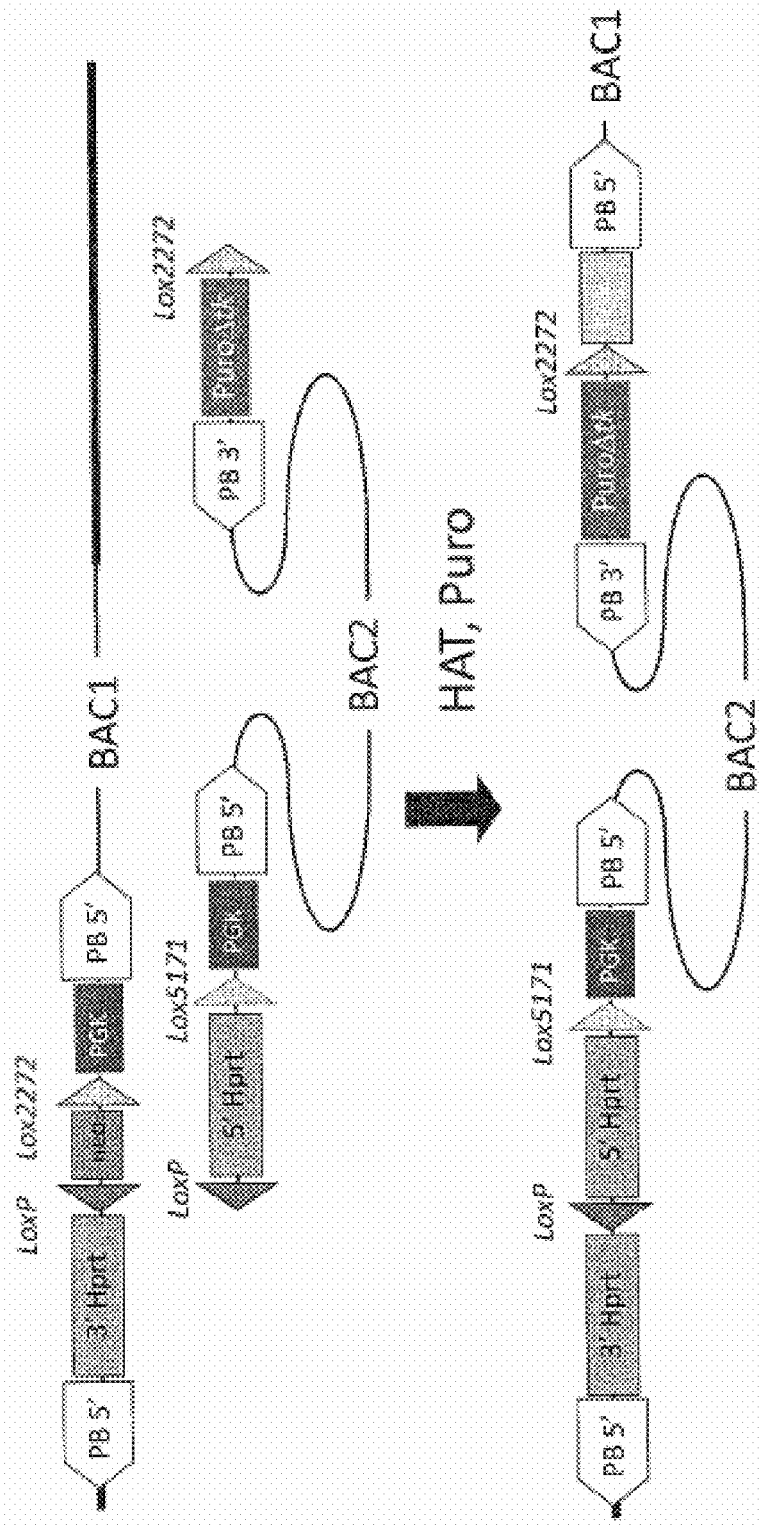
Figure 26:
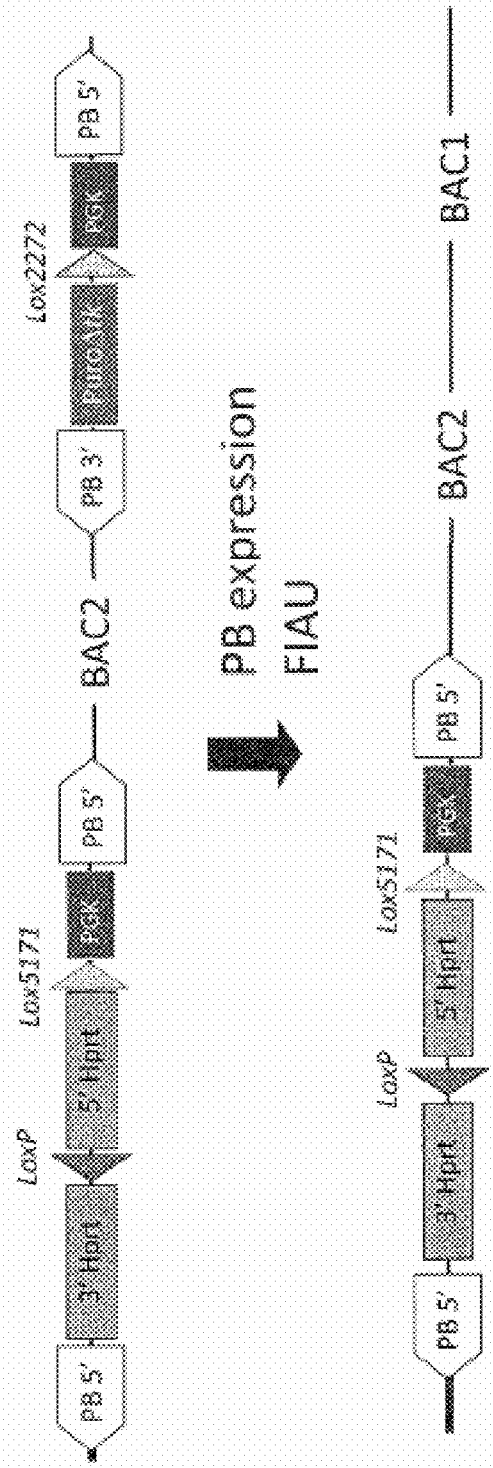
Figure 50:
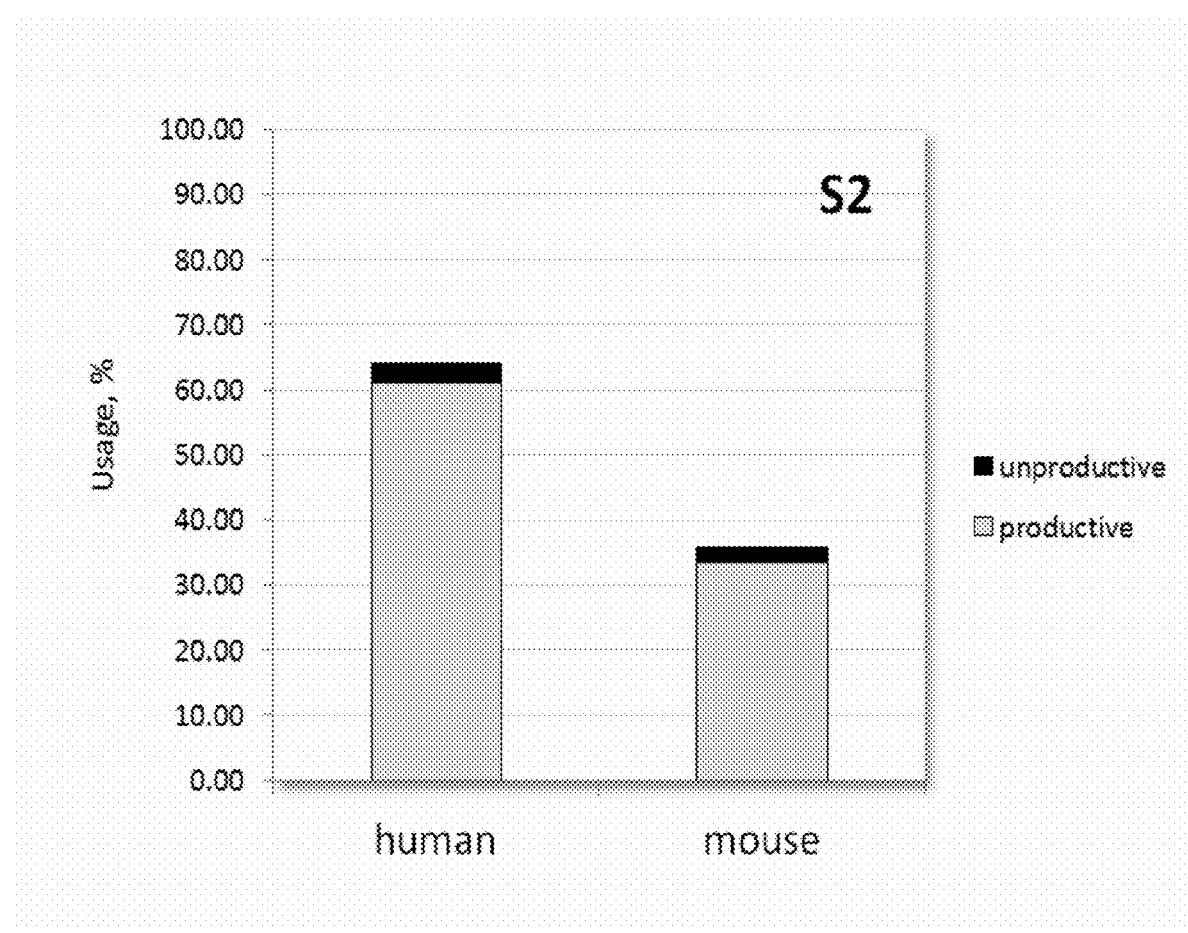
FIG. 50 illustrates that mouse $V_H$ usage is further significantly reduced following insertion of the 2$^{nd}$ human BAC into the endogenous heavy chain locus

Following the 1$^{st}$ BAC DNA insertion, human DNA from a 2$^{nd}$ human BAC (Chr14: 106494909-106601551) (BAC comprising a the sequence of mouse Chromosome 14 from coordinate 106494909 to coordinate 106601551; containing 5 more functional VH gene segments ($V_H$3-13, 3-11, 3-9, 1-8, 3-7)) was inserted into the landing pad left behind after curing following the 1$^{st}$ BAC insertion (see, eg, FIG. 24). The mouse $V_H$ usage is further significantly reduced following this insertion of the 2$^{nd}$ BAC into the locus. The proportion of transcripts using mouse VH was further reduced to 35% of all observed sequences (FIG. 50).

This result indicate that the endogenous $V_H$-D-$J_H$ gene segments could be inactivated (ie, not used for expressed rearranged heavy chains) through insertion of human VDJ sequences from one or more BACs. As the distance increases by stepwise BAC insertion, it is expected that the mouse VH usage would be significantly reduced.

Example 9

Normal Class Switch and Hypermutation in Transgenic Mice of the Invention

Introduction

The B cell arm of the immune system has evolved to produce high affinity, antigen-specific antibodies in response to antigenic challenge. Antibodies are generated in B lymphocytes by a process of gene rearrangement in which variable (V), diversity (D; for the IGH locus) and joining (J) gene segments are recombined, transcribed and spliced to a Cμ (for IGH) or a Cκ or Cλ (for IGL) constant region gene segment to form an IgM antibody. Depending on the stage of B cell development, IgM is either located on the cell surface or secreted. The recombination process generates a primary antibody repertoire with sufficient germ line diversity to bind a wide range of antigens. However, it is usually not large enough to provide the high affinity antibodies that are required for an effective immune response to an antigen such as an infectious agent. Therefore, the immune system adopts a two-stage diversification process to increase diversity further. When challenged with antigens, B cells undergo selection and maturation by a process called somatic mutation. B cells expressing antibodies which bind to antigen undergo multiple rounds of diversification, clonal expansion and antigen selection in the germinal centres (GCs) of the secondary lymphoid organs. During this process, the rearranged variable regions of the immunoglobulin genes acquire somatic hypermutation through nucleotide substitution, addition or deletion. This stepwise process creates a secondary repertoire from the weak binders selected originally from the primary repertoire and combines rapid proliferation of antigen-reactive B cells with intense selection for quality of binding, eventually giving rise to high affinity antibodies with broad epitope coverage. During this process, antibodies undergo class switching in which the Cμ constant region is replaced by Cγ, Cα or Cε to produce respectively IgG, A or E classes of antibody with different effector functions.

Insertion of 1$^{st}$ human BAC (Chr14: 106328951-106494908) containing six most 3' functional $V_H$ gene segments ($V_H$2-5, 7-4-1, 4-4, 1-3, 1-2, 6-1), and all the D and $J_H$ gene segments into the locus between endogenous IGHJ4 and Eμ (Chr12: 114666435 and 114666436) produces transgenic mice that generate chimeric immunoglobulin heavy chains containing human variable and mouse constant regions. This result demonstrates that human immunoglobulin gene segments are able to be rearranged and expressed in mice. Here, RT-PCR experiments and sequence analysis were performed to further demonstrate that immunized transgenic mice have proper class switch and hypermutation for generated antibodies.

Methods

RT-PCR and Sequence Analysis:

Wild type or S1 chimera mice at 6-8 weeks of age were primed by intraperitoneal injection of 10$^6$ sheep RBCs suspended in phosphate buffer saline (PBS). The immunized mice were boosted twice with the same amount of sheep RBCs two and four weeks after priming. Four days after the last boost, peripheral blood cells were collected from the immunized mice. Total RNA was isolated from peripheral blood cells with TRIzol® reagent (Invitrogen™) and treated with DNase I. Reverse transcription polymerase chain reaction (RT-PCR) was performed using SuperScript® III First-Strand Synthesis System (Invitrogen™) following the protocol supplied by the manufacturer. The 1st strand cDNA was synthesized with the specific Cγ primers (Cγ1, Cγ2a, Cγ2b), following by PCR with specific human V primers (VH1-2, 3, VH4-4, VH6-1) and Cγ primers (Table 2). Following reaction, the RT-PCR product was checked on a 1% agarose gel and purified using QIAquick® Gel Extraction Kit (QIAGEN) as the protocol supplied with the kit, then cloned into pDrive vector using QIAGEN PCR Cloning Kit (QIAGEN) for sequencing analysis.

TABLE 2

| | | |
|---|---|---|
| ELP1352_Cγ1 | 5'-AGAGCGGCCGCTGGGCAACGTTGCAGGTGACGGTC-3' | SEQ ID No 27 |
| ELP1353_Cγ2b | 5'-AGAGCGGCCGCTTTGTCCACCGTGGTGCTGCTGG-3' | SEQ ID No 28 |
| ELP1354_Cγ2a | 5'-AGAGCGGCCGCACATTGCAGGTGATGGACTGGC-3' | SEQ ID No 29 |
| ELP1356_VH4-4 | 5'-AGGACGCGTGAAACACCTGTGGTTCTTCCTCCTGC-3' | SEQ ID No 30 |
| ELP1357_VH1-2,3 | 5'-AGGACGCGTCACCATGGACTGGACCTGGAGGAT-3' | SEQ ID No 31 |
| ELP1358_VH6-1 | 5'-AGGACGCGTATGTCTGTCTCCTTCCTCATCTTCC-3' | SEQ ID No 32 |

Results

Figure 51:
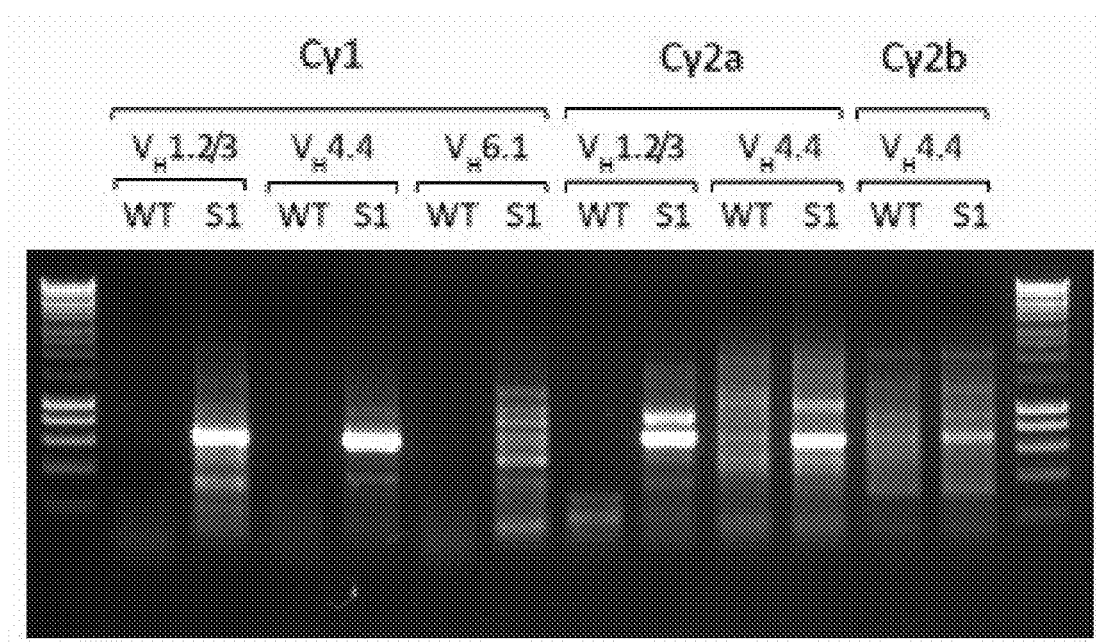
FIG. 51 illustrates a gel showing that normal class-switching (to IgG-type) was observed in transcripts from mice of the invention. The rearranged transcripts were detected using RT-PCR with human VH-specific and mouse Cγ-specific primers for amplification from peripheral blood cells of immunized transgenic mice
Figure 52:
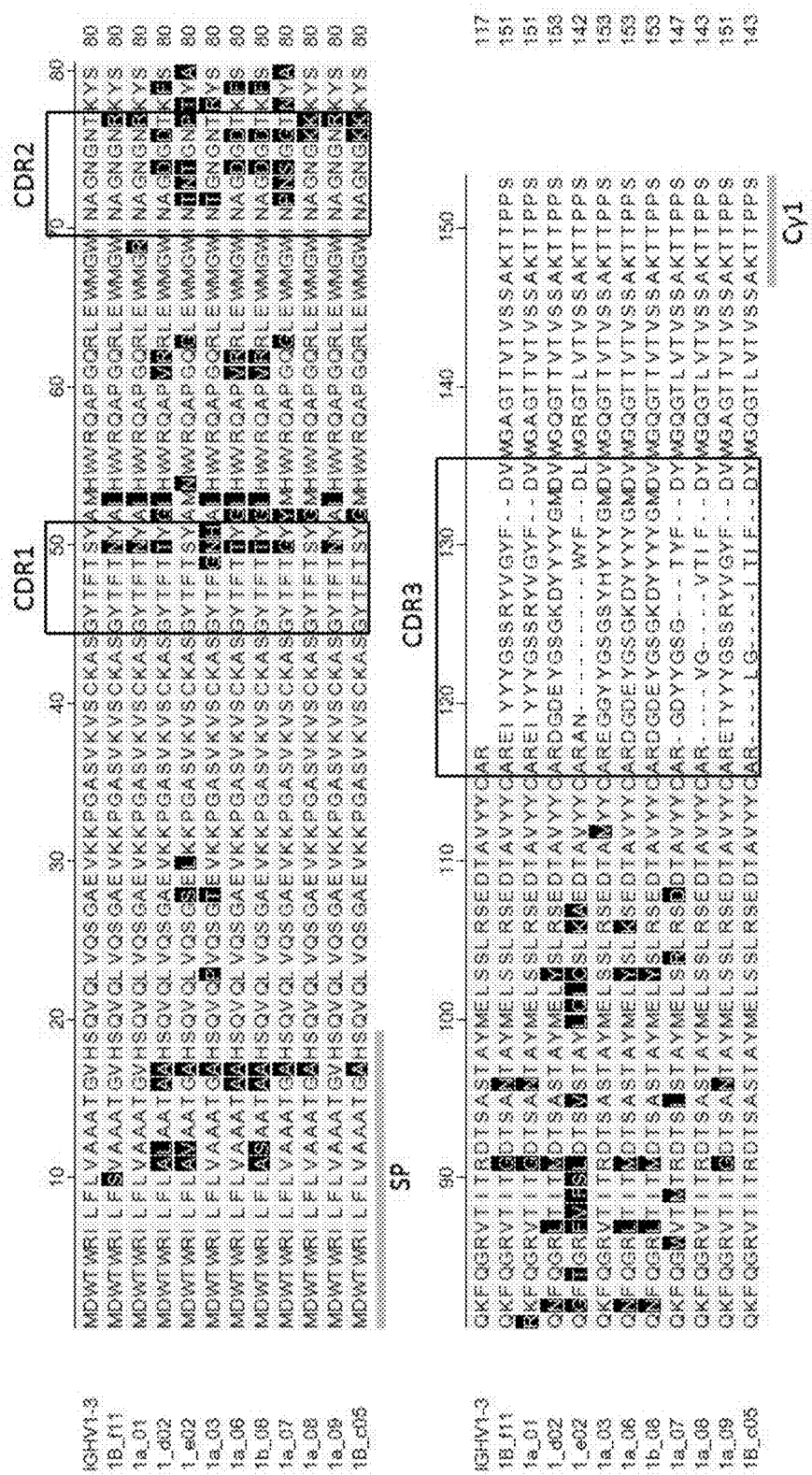
FIG. 52 illustrates sequence analysis amplified fragments demonstrate hypermutation occurred within the human variable regions of these IGγ chains from mice of the invention

The rearranged transcripts were detected using RT-PCR with human VH-specific and mouse Cγ-specific primers for amplification from peripheral blood cells of immunized transgenic mice (FIG. 51). Further sequence analysis of these amplified fragments demonstrated hypermutation happened within the human variable regions of these IGγ chains (FIG. 52). These results indicate that loci of the invention comprising insertion of human IGH BAC containing $V_H$, D and $J_H$ gene segments into the locus between endogenous IGHJ4 and Eμ regions has normal class switching and hypermutation functionality (IgM to IgG) following antigen challenge.

Example 10

Normal B Cell Compartments in Transgenic Mice of the Invention

Introduction

In mice, about 2×10$^7$ bone marrow immature B cells are produced daily. Among them, only 10-20% of these cells survive to exit the bone marrow and enter the spleen. The immature splenic B cell population is divided into two distinct subsets: transitional 1 (T1) and transitional 2 (T2) B cells. In vivo experiments indicate that T1 cells give rise to T2 cells, whereas T2 cells can further differentiate into mature (M) B cells. In contrast to immature B cells (3-4 days old), mature B cells are long-lived (15-20 weeks old) and are ready to respond to antigens (Pillai S et al; Immunol. Reviews. 2004. 197: 206-218). Thus, the component of mature B cell population is directly linked to the efficiency of humoral immune response.

The T1, T2 and M cell populations can be categorized by their cell surface IgM and IgD levels. A normal phenotype of splenic B cell compartment is required to mount a robust immune response.

Methods

Flow Cytometric Analysis of Mature B Lymphocytes:

To obtain a single cell suspension from spleen, the spleens of mice listed below were gently passaged through a 30 µm cell strainer. Single cells were resuspended in PBS supplemented with 3% heat inactivated foetal calf serum (FCS; Gibco®). The following antibodies were used for staining:

Antibody against B220/CD45R conjugated with allophycocyanin (APC) (eBioscience, clone RA3-6B2), antibody against IgD receptor conjugated with phycoerythrin (PE) (eBioscience, clone 11-26) and IgM receptor conjugated with fluorescein isothiocyanate (FITC) (eBioscience, clone 11/41).

$5 \times 10^6$ cells were used for each staining. To each vial containing splenocytes a cocktail of antibodies was added consisting of: IgD (PE) (eBioscience, clone 11-26), IgM (FITC) and B220/CD45R (APC). Cells were incubated at 6° C. for 15 minutes, washed to remove excess of unbound antibodies and analysed using a fluorescence-activated cell sorting (FACS) analyser from Miltenyi Biotech. B-cells were gated as $B220^+IgM^+IgD^-$ for T1 population, $B220^+IgM^+IgD^+$ for T2 population and $B220^+IgM^-IgD^+$ for M population. Percentage of cells was calculated using gating system.

Results

Four different genotypes of mice were generated:—

Wild type (WT);

A transgenic mouse homozygous for a heavy chain transgene comprising insertion of the $1^{st}$ BAC human DNA noted above in which there are 6 human VH, all functional human D and JH gene segments (S1/S1);

A transgenic mouse homozygous for a heavy chain transgene comprising insertion of a human VH, all functional human D and JH gene segments (H1/H1); and A transgenic mouse homozygous for a kappa chain transgene comprising insertion of 6 functional human Vκ and 5 functional Jκ gene segments (K1/K1).

Figure 53:
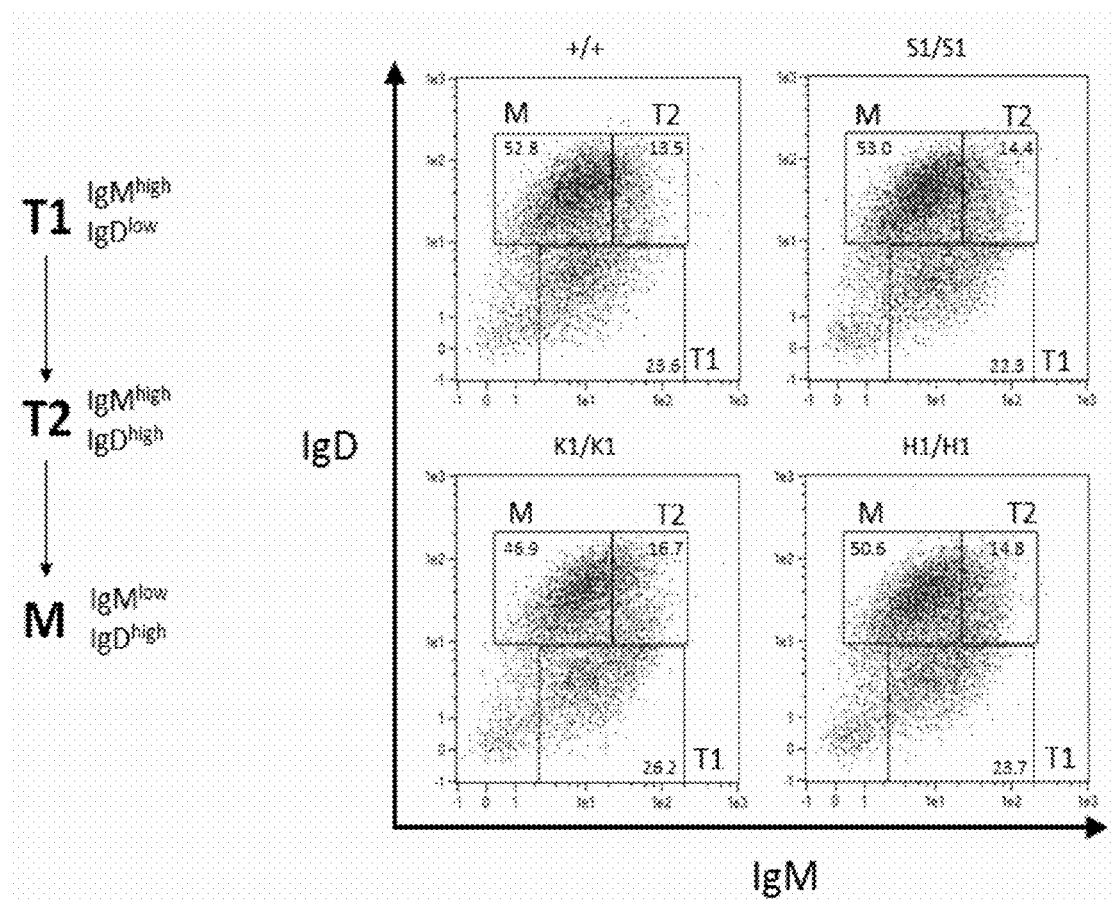
FIG. 53 illustrates Flow cytometric analysis showing normal B-cell compartments in transgenic mice of the invention
Figure 54E:
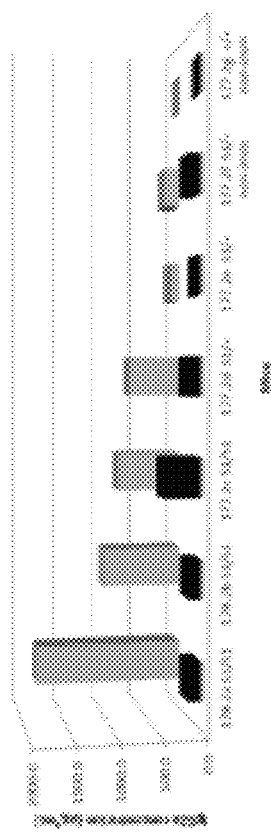
FIG. 54E-FIG. 54H illustrate normal IgH isotypes in transgenic mice (S1) immunised with 100 µg Cholera Toxin B subunit.
Figure 54F:
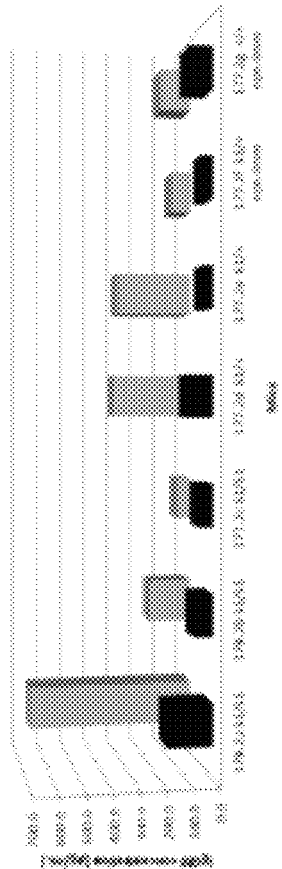
Figure 54G:
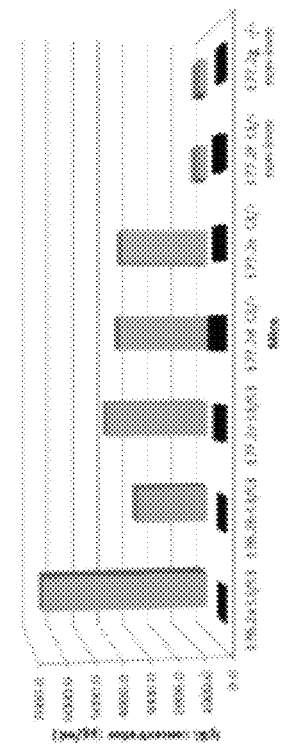
Figure 54H:
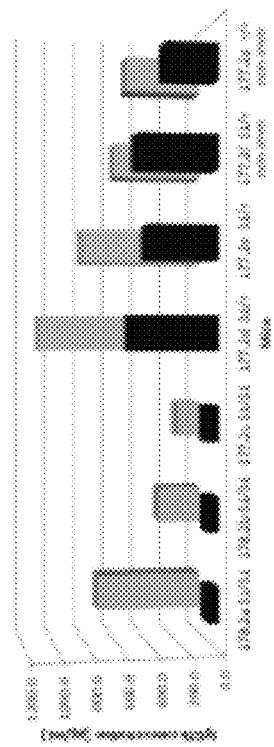

Spleens from these naïve mice were collected and analysed for their B cell compartments. The number and percentages of T1, T2 and M cells among those mice are similar (FIG. 53), indicating that genetic manipulation of endogenous IG loci in transgenic mice according to the invention do not compromise their B cell development. These data help to establish that animals according to the invention provide a robust platform for antibody discovery.

Example 11

Normal IgH Isotypes & Serum Levels in Transgenic Animals of the Invention

Figure 55B:
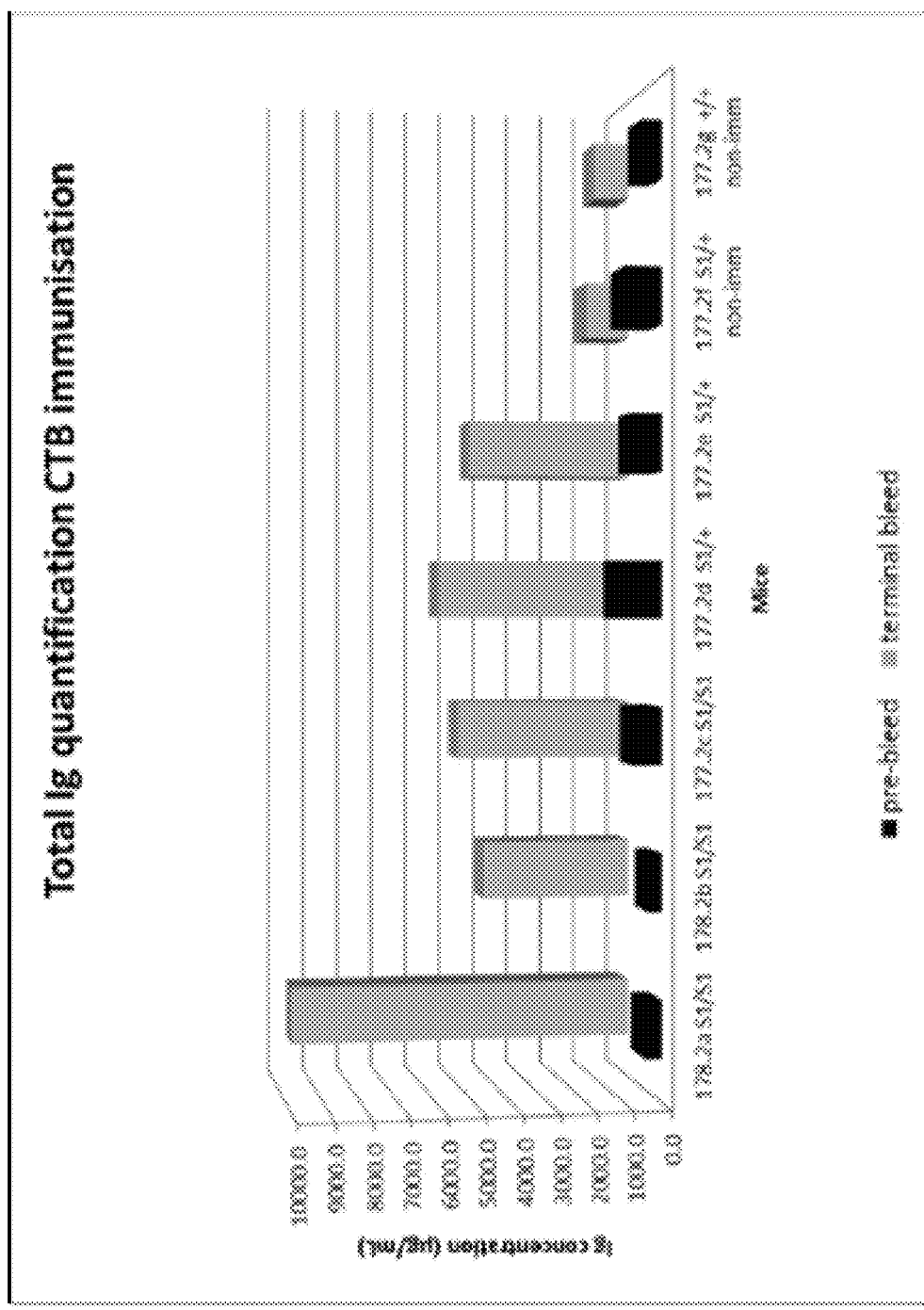

Transgenic mice (H1) carrying all human JH, all human DH and human Vh2-5 under control of a rat switch region or mice (S1) carrying all human JH, all human DH and human Vh2-5, Vh7-41, Vh4-4, Vh1-3, Vh1-2 and Vh6-1 under control of a mouse switch region were immunised with 100 µg Cholera Toxin B subunit (CTB; Sigma-Aldrich® C9903) emulsified in Complete Freund's Adjuvant CFA; Sigma-Aldrich® F 5881). At least three animals were injected sc or ip and then boosted with 25 µg antigen in Incomplete Freund's Adjuvant (IFA; Sigma-Aldrich® F 5506) at (i) 14 days and 21 days or (ii) 28 days after priming. Blood was taken before priming at day "−1" (pre-bleeds) and on the day the spleens were taken (usually 4d after last boost). Serum was analysed by ELISA using an antigen independent assessment of Ig isotypes. This assay detects total serum antibodies of all species. Specific detection for mouse IgG1, IgG2a, IgG2b and IgM was used ((Anti-mouse IgG1 HRP AbD Serotec STAR132P, Anti-mouse IgG2a HRP AbD Serotec STAR133P, Anti-mouse IgG2b HRP AbD Serotec STAR134P, Anti-mouse IgM HRP Abcam® ab97230) and concentrations were read off a standard curve produced for each isotype using polyclonal isotype controls (IgG1, Kappa murine myeloma Sigma-Aldrich® M9269, IgG2a, Kappa murine myeloma Sigma-Aldrich® M9144, IgG2b, Kappa from murine myeloma Sigma-Aldrich® M8894, IgM, Kappa from murine myeloma Sigma-Aldrich® M3795). Results (FIGS. 54 & 55 for H1 homozygous and S1 homozygous and heterozygous mice) showed that even with these relatively short immunisation regimes mice showed an increase in overall IgG levels after immunisation over pre-bleeds. In cases where control mice (+/+) not carrying any human immunoglobulin genes were included and immunised, these mice showed comparable changes in total observed Ig levels (FIG. 54). Individual isotype levels were more variable between animals possibly showing various stages of class switching. IgM levels never exceeded 800 µg/ml whereas IgG levels reached more than 6 mg/ml in some animals. Non-immunised controls showed no such increases in switched isotype Ig levels.

These results demonstrate that mice comprising multiple human VDJ gene segments under the control of a rat Sµ rat or mouse switch are able to undergo productive recombination and class switching in response to antigen challenge and that the mice produce antibody levels that are broadly comparable to unmodified mice The transgenic mice are able to produce antibodies of each of the IgG1, IgG2a, IgG2b and IgM isotypes after immunisation. Titers for CTB-specific Ig in pre-bleeds and terminal bleeds were determined and all immunised animals showed at CTB-specific titres of at least 1/100 000.

Example 12

Generation of Anti-Ovalbumin Antibodies with Sub-50 nm Affinities from Animals of the Invention Transgenic mice carrying all human JH, all human DH and human Vh2-5 under control of a rat Sµ switch region were immunised with 25 µg ovalbumin (OVA; Sigma-Aldrich® A7641) in Sigma-Aldrich® adjuvant (Sigma Adjuvant System® S6322) ip and then boosted with the same amount of OVA in adjuvant at day 14 and day 21. Spleenocytes were taken 4 days later and fused using 1 ml polyethyleneglycol (PEG Average MW1450; Sigma-Aldrich® P7306) with a myeloma line. Fused hybridoma cells were plated on 5 96-well plates and after selection with hypoxanthine-aminopterin-thymidine (HAT) wells tested for expression of OVA-specific antibodies by ELISA. Clones positive by ELISA were re-tested by surface plasmon resonance (SPR) and binding kinetics determined using the ProteOn™ XPR36 (Bio-Rad®). Briefly, anti-mouse IgG (GE Biacore™ BR-1008-38) was coupled to a GLM biosensor chip by primary amine coupling, this was used to capture the antibodies to be tested directly from tissue culture supernatants. Ovalbumin was used as the analyte and passed over the captured antibody surface at 1024 nM, 256 nM, 64 nM, 16 nM, 4 nM with a 0 nM (i.e. buffer alone) used to double reference the binding data. Regeneration of the anti-mouse IgG capture surface was by 10 mM glycine pH1.7, this removed the captured antibody and allowed the surface to be used for another interaction. The binding data was fitted to 1:1 model inherent to the ProteOn™ XPR36 analysis software. The run was carried out 1×HBS-EP (10 mM Hepes, 150 mM NaCl, 3 mM EDTA, 0.05% polysorbate, pH7.6 (Teknova H8022)) used as running buffer and carried out at 25° C.

For 8 positive clones, heavy chain V-regions were recovered by RT-PCR (Access RT-PCR System, A1250, Promega) using forward primers specific for Ig signal sequences (Wardemann et al Science 301, 1374 (2003)) and the following reverse primers for the constant regions of mouse IgG (Table 3):

TABLE 3

| Primer Name | Sequence | bp | |
|---|---|---|---|
| mIgG1_2 rev | GGGGCCAGTGGATAGACAGAT | 21 | SEQ ID No 33 |
| mIgG2b rev | CAGTGGATAGACTGATGG | 18 | SEQ ID No 34 |
| mIgG2a_2 rev | CAGTGGATAGACCGATGG | 21 | SEQ ID No 35 |
| mCH1 unirev | KCAGGGGCCAGTGGATAGAC | 20 | SEQ ID No 36 |
| mCH1 unirev_2 | TARCCYTTGACMAGGCATCC | 20 | SEQ ID No 37 |

RT-PCR products were either directly sequenced using the same primer pairs or cloned in to TA plasmids (TOPO® TA Cloning® Kit for Sequencing, K4595-40, Invitrogen™) and submitted for plasmid sequencing. Results (Table 4, below) show that CDRH3 sequences had variable CDRs except for two identical clones (16C9 and 20B5) that also had near identical KD kinetic values. The determined equilibrium binding constant KD ranged from 0.38 nM to 40.60 nM, as determined by SPR at 25° C.

These results demonstrate that mice comprising multiple human VDJ gene segments under the control of a rat Cμ switch are able to undergo productive recombination and produce high affinity antigen-specific antibodies whose CDR3 regions have sequences encoded by human gene segments (human JH was separately identified by V-Quest, IMGT).

TABLE 4

| KD [nM] | clone code | CDR3 and FR4 (underlined) according to Kabat definition | |
|---|---|---|---|
| 0.38 | 16C9 | QEVINYYYYGMDV<u>WGQGTTVTVSS</u> | SEQ ID No 38 |
| 0.52 | 20B5 | QEVINYYYYGMDV<u>WGQGTTVTVSS</u> | SEQ ID No 39 |
| 5.89 | 19F4 | LEMATINYYYYGMDV<u>WGQGTMVTVSS</u> | SEQ ID No 40 |
| 39.70 | 19E1 | QEFGNYYYYGMDV<u>WGQGTTVTVSS</u> | SEQ ID No 41 |
| 3.10 | 19G8 | QEDGNPYYFGMDF<u>WGQGTTVTVSS</u> | SEQ ID No 42 |
| 8.95 | 20H10 | GSSYYYDGMDV<u>WGQGTTVTVSS</u> | SEQ ID No 43 |
| 4.46 | 18D10 | LENDYGYYYYGMDV<u>WGQGTTVTVSS</u> | SEQ ID No 44 |
| 40.60 | 16F2 | RGGLSPLYGMDV<u>WGQGTTVTVSS</u> | SEQ ID No 45 |

Example 13

Generation of Anti-Cholera Toxin B Antibodies with Human Vh Regions from Animals of the Invention Transgenic mice carrying all human JH, all human DH and human Vh2-5, Vh7-41, Vh4-4, Vh1-3, Vh1-2 and Vh6-1 under control of a mouse Sμ switch region were immunised and fused as described in Example 11. Fused hybridoma cells were plated on 5 96-well plates and after selection with hypoxanthine-aminopterin-thymidine (HAT) or G418 (Gibco® Cat No 10131-027, Lot 503317) and wells tested for expression of CTB-specific antibodies by ELISA. Clones positive by ELISA were re-tested by surface plasmon resonance SPR and binding kinetics determined using the ProteOn XPR36™ (Bio-Rad®).

Briefly, anti-mouse IgG (GE Biacore™ BR-1008-38) was coupled to a GLM biosensor chip by primary amine coupling, this was used to capture the antibodies to be tested directly from tissue culture supernatants. Cholera toxin B was used as analyte and passed over the captured antibody surface at 256 nM, 64 nM, 16 nM, 4 nM and 1 nM, with a 0 nM (i.e. buffer alone) used to double reference the binding data. Regeneration of the anti-mouse IgG capture surface was by 10 mM glycine pH1.7, this removed the captured antibody and allowed the surface to be used for another interaction. The binding data was fitted to 1:1 model inherent to the ProteOn XPR36™ analysis software. The run was carried out 1×HBS-EP (10 mM Hepes, 150 mM NaCl, 3 mM EDTA, 0.05% polysorbate, pH7.6 (Teknova H8022)) used as running buffer and carried out at 37° C.

From the clones initially identified by ELISA, binding to CTB was confirmed by SPR. However, due to the pentameric nature of the cholera toxin B, the majority of fits to the 1:1 model were poor and the equilibrium binding constant KDs could not be accurately determined. Where fits were acceptable, equilibrium binding constant KDs determined ranged from 0.21 nM to 309 nM but due to the pentameric nature of cholera toxin B these are likely to be the result of multimeric interactions and therefore apparent affinities with possible avidity components.

Clones identified by SPR for binding to CTB were subjected to RT-PCR as described in Example 12 to recover the Vh regions. RT-PCR products were directly sequenced using the same primer pairs. Results were obtained for only 14 clones presumably because the human primers described in Wardemann et al were not designed to amplify mouse Vh regions and therefore may have failed to amplify certain mouse Vh classes. Results showed that 3 of the 14 CTB-specific recovered heavy chain V-region sequences were human V, D and J regions as identified by V-Quest, IMGT (Table 5).

TABLE 5

Alignment of heavy chain CDRs and J-region of 3 clones identified as binding to CTB and preferentially matching with human reference sequences from IMGT database; note that the KD values given here are apparent values due to the avidity of the CTB-antibody interaction

| Vh region | Clone Name | Sequence (Kabat definitions) | | | | KD [nM] |
|---|---|---|---|---|---|---|
| | | CDR1 | CDR2 | CDR3 | J-regions | |
| IGHV4-4*02 | — | SSNWWS (SEQ ID NO 51) | EIYHSGSTNYNPSLKS (SEQ ID NO 56) | n/a | IGHJ2*01 YWYFDLWGRGTLVTVSS (SEQ ID NO 64) | — |
| | 12D10 | SGNWWS (SEQ ID NO 52) | EIYHSGNTNYNPSLKS (SEQ ID NO 57) | GPLTGEKYYFDL (SEQ ID NO 61) | -YYFDLWGRGTLVTVSS (SEQ ID NO 65) | 0..27 |
| | 1283 | RSNWWS (SEQ ID NO 53) | EIYHSGSTNYNPSLKS (SEQ ID NO 58) | IGDWYFDL (SEQ ID NO 62) | -WYFDLWGRGTLVTVSS (SEQ ID NO 66) | 0.85 |
| IGHV6-1*01 | — | SNSAAWN (SEQ ID NO 54) | RTYYRSKWYND YAVSVKS (SEQ ID NO 59) | n/a | IGHJ3*01 DAFDVWGQGTMVTVSS (SEQ ID NO 67) | — |
| | 4A12 | SNSAAWN (SEQ ID NO 55) | RTYYRSKWYND YKVSVKS (SEQ ID NO 60) | EGSHSGSGWYLDAFDI (SEQ ID NO 63) | DAFDIWGQGTKVTVSS (SEQ ID NO 68) | 1.61 |

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The invention claimed is:

1. A transgenic mouse having a germline with a homozygous immunoglobulin heavy chain (IgH) locus comprising unrearranged human IgH variable region gene segments comprising Vs, Ds and Js at an endogenous locus operatively linked to an IgH constant (C) region comprising an endogenous C segment at an IgH locus;

wherein said homozygous IgH locus comprises in 5' to 3' transcriptional orientation said unrearranged human Vs, Ds and Js comprising a 3' JH gene segment, a human/mouse chimeric DNA junction, an enhancer, and said operatively linked C region;

wherein said homozygous chimeric IgH locus comprises a chimeric J/C intron comprising human DNA downstream of and naturally contiguous with said 3' JH gene segment, said human DNA being contiguous with mouse J/C intronic DNA upstream of said enhancer, and wherein said human DNA joins said mouse J/C intronic DNA at said human/mouse chimeric junction within said J/C intron, wherein DNA between said 3' human JH segment and said human/mouse chimeric DNA junction is less than 2 kb, said germline comprising all or part of mouse IgH variable region DNA; wherein said homozygous IgH locus of said mouse is capable of undergoing V, D, J joining; wherein said transgenic mouse is capable, upon stimulation with antigen, of producing antibody comprising a chimeric Ig heavy chain comprising a human IgH variable region; and wherein said transgenic mouse is capable of breeding with a second transgenic mouse, said second transgenic mouse having a germline with a homozygous IgH locus comprising unrearranged human IgH variable region gene segments operatively linked to an IgH constant (C) region comprising an endogenous C segment of an IgH locus to provide subsequent generation mice, wherein a said subsequent generation mouse comprises:

(a) in its germline an homozygous IgH locus comprising unrearranged human IgH variable region gene segments operatively linked to an IgH constant (C) region comprising an endogenous C segment of an IgH locus, and (b) in its germline all or part of mouse IgH variable region DNA; and (c) wherein said IgH locus of said subsequent generation mouse is capable of undergoing V, D, J joining;

(d) wherein said subsequent generation mouse is capable, upon stimulation with antigen, of producing antibody comprising a chimeric Ig heavy chain comprising a human IgH variable region; and (e) is capable of breeding with a mouse having a germline with a homozygous IgH locus comprising unrearranged human IgH variable region gene segments operatively linked to an IgH constant (C) region comprising an endogenous C segment of an IgH locus to provide further subsequent generation mice.

2. The mouse of claim 1, wherein said mouse J/C intronic DNA at said human/mouse chimeric junction and upstream of said enhancer comprises 129 mouse strain DNA, and wherein said enhancer is a mouse 129 strain µ enhancer.

3. The transgenic mouse of claim 1, wherein DNA between said 3' human JH gene segment and said human/mouse chimeric DNA junction is less than 1 kb.

4. The mouse of claim 1, wherein said C gene segment comprises a mouse Cµ segment.

5. The transgenic mouse of claim 1, wherein said all or part of said mouse IgH variable region DNA is away from its native position in an IgH locus.

6. The transgenic mouse of claim 5, wherein said all or part of said mouse IgH variable region DNA is inverted with respect to its native chromosomal orientation and upstream of said human variable region gene segments.

7. The transgenic mouse of claim 2, wherein said unrearranged human VH gene segments are in the place of endogenous mouse Ig VH region segment(s) upstream of said enhancer.

8. The transgenic mouse of claim 2, wherein said unrearranged human DH gene segments are in the place of endogenous mouse Ig DH gene segment(s) upstream of said enhancer.

9. The transgenic mouse of claim 2, wherein said unrearranged human JH gene segments are in the place of endogenous mouse Ig JH gene segment(s) upstream of said enhancer.

10. The transgenic mouse of claim 1, wherein said human DNA contiguous with said human 3' JH gene segment comprises 400 base pairs of human JC intron DNA.

* * * * *